United States Patent
Huang et al.

(10) Patent No.: US 9,434,942 B2
(45) Date of Patent: *Sep. 6, 2016

(54) SMALL INTERFERING RNAS WITH TARGET-SPECIFIC SEED SEQUENCES

(75) Inventors: Xiang Huang, Research Triangle Park, NC (US); Thomas McNeill, Frisco, TX (US); Mike Schweiner, Research Triangle Park, NC (US)

(73) Assignee: Syngenta Participations, AG, Basel (CH)

( * ) Notice: Subject to any disclaimer, the term of this patent is extended or adjusted under 35 U.S.C. 154(b) by 215 days.

This patent is subject to a terminal disclaimer.

(21) Appl. No.: 13/980,714

(22) PCT Filed: Feb. 14, 2012

(86) PCT No.: PCT/US2012/025004

§ 371 (c)(1),
(2), (4) Date: Aug. 23, 2013

(87) PCT Pub. No.: WO2012/112512

PCT Pub. Date: Aug. 23, 2012

(65) Prior Publication Data

US 2013/0333070 A1    Dec. 12, 2013

Related U.S. Application Data

(60) Provisional application No. 61/442,765, filed on Feb. 14, 2011.

(51) Int. Cl.
C12N 15/113 (2010.01)
C12Q 1/68 (2006.01)

(52) U.S. Cl.
CPC ........... *C12N 15/113* (2013.01); *C12Q 1/6888* (2013.01); *C12Q 1/6895* (2013.01); *C12N 2310/113* (2013.01); *C12N 2330/31* (2013.01); *C12Q 2600/13* (2013.01); *C12Q 2600/178* (2013.01)

(58) Field of Classification Search
None
See application file for complete search history.

(56) References Cited

U.S. PATENT DOCUMENTS

| 7,723,568 | B2 * | 5/2010 | Lutfiyya ............ C12N 15/8216 435/320.1 |
| 7,868,149 | B2 * | 1/2011 | Boukharov .......... C07K 14/415 435/6.13 |
| 2002/0099171 | A1 | 7/2002 | De Robertis et al. |
| 2005/0153317 | A1 | 7/2005 | De Nise et al. |
| 2006/0185027 | A1 * | 8/2006 | Bartel et al. .................... 800/14 |
| 2007/0083334 | A1 | 4/2007 | Mintz et al. |
| 2008/0009012 | A1 * | 1/2008 | Birmingham et al. ........... 435/6 |
| 2009/0013434 | A1 * | 1/2009 | Huang et al. ................. 800/279 |
| 2010/0175153 | A1 | 7/2010 | Guo et al. |

FOREIGN PATENT DOCUMENTS

| WO | 2006073727 | 7/2006 |
| WO | 2012058266 | 5/2012 |
| WO | 2012078949 | 6/2012 |

OTHER PUBLICATIONS

Bartel, 2009, Cell, 136:215-233.*
Schwab et al., "Highly specific gene silencing by artificial MicroRNAs in Arabidopsis," The Plant Cell, 2006, vol. 18, p. 1121-1133.
Lewis et al., Conserved seed pairing, often flanked by adenosines, indicates that thousands of human genes are MicroRNA targets; (2005); Cell 120:15-20.
Kulcheski et al., "Identification of novel soybean microRNAs involved in abiotic and biotic stresses," BMC Genomics, 2011, 12; p. 1-17.
Genbank Accession No. EF210138, Glycine max ethylene receptor (ETR1) gene, complete cds, Jan. 8, 2007, from the Internet, May 22, 2012, http://www.ncbi.nlm.nih.gov/nuccore/EF210138., pp. 1-2.
International Search Report dated Jun. 7, 2012 for International Patent Application No. PCT/US12/25004.
International Preliminary Report on Patentability dated Mar. 12, 2014 for International Patent Application No. PCT/US12/025004.
Bartel et al., MicroRNAs: Target recognition and regulatory functions, Cell 136, 2009, p. 215-233.
Alvarez et al., Endogenous and synthetic microRNAs stimulate simultaneous, efficient, and localized regulation of multiple targets in diverse species, The Plant Cell Review, 2006, 18, p. 1134-1151.
Saxena et al., "Small RNAs with imperfect match to endogenous mRNA repress translation," The Journal of Biological Chemistry, 2003, 278(45); p. 44312-44319.

* cited by examiner

*Primary Examiner* — Jason Deveau Rosen
(74) *Attorney, Agent, or Firm* — Christopher Leming

(57) ABSTRACT

Disclosed are methods for design and synthesis of siRNA libraries, siRNA libraries produced thereby, siRNA molecules, and uses thereof.

3 Claims, No Drawings

SEQUENCE LISTING

```
<160> NUMBER OF SEQ ID NOS: 60

<210> SEQ ID NO 1
<211> LENGTH: 21
<212> TYPE: RNA
<213> ORGANISM: Artificial Sequence
<220> FEATURE:
<223> OTHER INFORMATION: siRNA0043

<400> SEQUENCE: 1
uaacuuauug uugaucuggu u                                                 21

<210> SEQ ID NO 2
<211> LENGTH: 21
<212> TYPE: RNA
<213> ORGANISM: Artificial Sequence
<220> FEATURE:
<223> OTHER INFORMATION: siRNA0046

<400> SEQUENCE: 2
uaacuucuug uugaucuggu u                                                 21

<210> SEQ ID NO 3
<211> LENGTH: 21
<212> TYPE: RNA
<213> ORGANISM: Artificial Sequence
<220> FEATURE:
<223> OTHER INFORMATION: siRNA0097

<400> SEQUENCE: 3
uaaguucaug uugaucuggu u                                                 21

<210> SEQ ID NO 4
<211> LENGTH: 21
<212> TYPE: RNA
<213> ORGANISM: Artificial Sequence
<220> FEATURE:
<223> OTHER INFORMATION: siRNA0145

<400> SEQUENCE: 4
uagcuugaug uugaucuggu u                                                 21
```

```
<210> SEQ ID NO 5
<211> LENGTH: 21
<212> TYPE: RNA
<213> ORGANISM: Artificial Sequence
<220> FEATURE:
<223> OTHER INFORMATION: siRNA0192

<400> SEQUENCE: 5
uagguuggug uugaucuggu u                                                 21

<210> SEQ ID NO 6
<211> LENGTH: 21
<212> TYPE: RNA
<213> ORGANISM: Artificial Sequence
<220> FEATURE:
<223> OTHER INFORMATION: siRNA0243

<400> SEQUENCE: 6
uaucuucgug uugaucuggu u                                                 21

<210> SEQ ID NO 7
<211> LENGTH: 21
<212> TYPE: RNA
<213> ORGANISM: Artificial Sequence
<220> FEATURE:
<223> OTHER INFORMATION: siRNA0309

<400> SEQUENCE: 7
ugacaggaug uugaucuggu u                                                 21

<210> SEQ ID NO 8
<211> LENGTH: 21
<212> TYPE: RNA
<213> ORGANISM: Artificial Sequence
<220> FEATURE:
<223> OTHER INFORMATION: siRNA0382

<400> SEQUENCE: 8
ugaggucaug uugaucuggu u                                                 21

<210> SEQ ID NO 9
<211> LENGTH: 21
<212> TYPE: RNA
<213> ORGANISM: Artificial Sequence
<220> FEATURE:
<223> OTHER INFORMATION: siRNA0423

<400> SEQUENCE: 9
ugguauggug uugaucuggu u                                                 21

<210> SEQ ID NO 10
<211> LENGTH: 21
<212> TYPE: RNA
<213> ORGANISM: Artificial Sequence
<220> FEATURE:
<223> OTHER INFORMATION: siRNA0458

<400> SEQUENCE: 10
ugggaucuug uugaucuggu u                                                 21

<210> SEQ ID NO 11
<211> LENGTH: 21
<212> TYPE: RNA
<213> ORGANISM: Artificial Sequence
<220> FEATURE:
<223> OTHER INFORMATION: siRNA0483
```

```
<400> SEQUENCE: 11
ugucagauug uugaucuggu u                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA0514

<400> SEQUENCE: 12
ugucgugaug uugaucuggu u                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA0531

<400> SEQUENCE: 13
ugucuucgug uugaucuggu u                                              21

<210> SEQ ID NO 14
<211> LENGTH: 21
<212> TYPE: RNA
<213> ORGANISM: Artificial Sequence
<220> FEATURE:
<223> OTHER INFORMATION: siRNA0569

<400> SEQUENCE: 14
ugugugauug uugaucuggu u                                              21

<210> SEQ ID NO 15
<211> LENGTH: 21
<212> TYPE: RNA
<213> ORGANISM: Artificial Sequence
<220> FEATURE:
<223> OTHER INFORMATION: si-rps23-1

<400> SEQUENCE: 15
uucucggaaa uugcgcuucu u                                              21

<210> SEQ ID NO 16
<211> LENGTH: 97
<212> TYPE: DNA
<213> ORGANISM: Artificial Sequence
<220> FEATURE:
<223> OTHER INFORMATION: amiRNA0043

<400> SEQUENCE: 16
agctccttgt taacttattg ttgatctggc aagtctcttg gatctcaaat gccactgaac      60
cctttgccag atcaagtata agttacaaca cgggttt                              97

<210> SEQ ID NO 17
<211> LENGTH: 97
<212> TYPE: DNA
<213> ORGANISM: Artificial Sequence
<220> FEATURE:
<223> OTHER INFORMATION: amiRNA0046

<400> SEQUENCE: 17
agctccttgt taacttcttg ttgatctggc aagtctcttg gatctcaaat gccactgaac      60
cctttgccag atcaagtaga agttacaaca cgggttt                              97
```

<210> SEQ ID NO 18
<211> LENGTH: 97
<212> TYPE: DNA
<213> ORGANISM: Artificial Sequence
<220> FEATURE:
<223> OTHER INFORMATION: amiRNA0097

<400> SEQUENCE: 18
agctccttgt taagttcatg ttgatctggc aagtctcttg gatctcaaat gccactgaac    60
cctttgccag atcaagttga acttacaaca cgggttt    97

<210> SEQ ID NO 19
<211> LENGTH: 97
<212> TYPE: DNA
<213> ORGANISM: Artificial Sequence
<220> FEATURE:
<223> OTHER INFORMATION: amiRNA0145

<400> SEQUENCE: 19
agctccttgt tagcttgatg ttgatctggc aagtctcttg gatctcaaat gccactgaac    60
cctttgccag atcaagttca agctacaaca cgggttt    97

<210> SEQ ID NO 20
<211> LENGTH: 97
<212> TYPE: DNA
<213> ORGANISM: Artificial Sequence
<220> FEATURE:
<223> OTHER INFORMATION: amiRNA0192

<400> SEQUENCE: 20
agctccttgt taggttggtg ttgatctggc aagtctcttg gatctcaaat gccactgaac    60
cctttgccag atcaagtcca acctacaaca cgggttt    97

<210> SEQ ID NO 21
<211> LENGTH: 97
<212> TYPE: DNA
<213> ORGANISM: Artificial Sequence
<220> FEATURE:
<223> OTHER INFORMATION: amiRNA0243

<400> SEQUENCE: 21
agctccttgt tatcttcgtg ttgatctggc aagtctcttg gatctcaaat gccactgaac    60
cctttgccag atcaagtcga agatacaaca cgggttt    97

<210> SEQ ID NO 22
<211> LENGTH: 97
<212> TYPE: DNA
<213> ORGANISM: Artificial Sequence
<220> FEATURE:
<223> OTHER INFORMATION: amiRNA0309

<400> SEQUENCE: 22
agctccttgt tgacaggatg ttgatctggc aagtctcttg gatctcaaat gccactgaac    60
cctttgccag atcaagttcc tgtcacaaca cgggttt    97

<210> SEQ ID NO 23
<211> LENGTH: 97
<212> TYPE: DNA
<213> ORGANISM: Artificial Sequence
<220> FEATURE:
<223> OTHER INFORMATION: amiRNA0382

```
<400> SEQUENCE: 23
agctccttgt tgaggtcatg ttgatctggc aagtctcttg gatctcaaat gccactgaac    60
cctttgccag atcaagttga cctcacaaca cgggttt                             97

<210> SEQ ID NO 24
<211> LENGTH: 97
<212> TYPE: DNA
<213> ORGANISM: Artificial Sequence
<220> FEATURE:
<223> OTHER INFORMATION: amiRNA0423

<400> SEQUENCE: 24
agctccttgt tggtatggtg ttgatctggc aagtctcttg gatctcaaat gccactgaac    60
cctttgccag atcaagtcca taccacaaca cgggttt                             97

<210> SEQ ID NO 25
<211> LENGTH: 97
<212> TYPE: DNA
<213> ORGANISM: Artificial Sequence
<220> FEATURE:
<223> OTHER INFORMATION: amiRNA0458

<400> SEQUENCE: 25
agctccttgt tgggatcttg ttgatctggc aagtctcttg gatctcaaat gccactgaac    60
cctttgccag atcaacaaga tcccacaaca cgggttt                             97

<210> SEQ ID NO 26
<211> LENGTH: 97
<212> TYPE: DNA
<213> ORGANISM: Artificial Sequence
<220> FEATURE:
<223> OTHER INFORMATION: amiRNA0483

<400> SEQUENCE: 26
agctccttgt tgtcagattg ttgatctggc aagtctcttg gatctcaaat gccactgaac    60
cctttgccag atcaagtatc tgacacaaca cgggttt                             97

<210> SEQ ID NO 27
<211> LENGTH: 97
<212> TYPE: DNA
<213> ORGANISM: Artificial Sequence
<220> FEATURE:
<223> OTHER INFORMATION: amiRNA0514

<400> SEQUENCE: 27
agctccttgt tgtcgtgatg ttgatctggc aagtctcttg gatctcaaat gccactgaac    60
cctttgccag atcaagttca cgacacaaca cgggttt                             97

<210> SEQ ID NO 28
<211> LENGTH: 97
<212> TYPE: DNA
<213> ORGANISM: Artificial Sequence
<220> FEATURE:
<223> OTHER INFORMATION: amiRNA0531

<400> SEQUENCE: 28
agctccttgt tgtcttcgtg ttgatctggc aagtctcttg gatctcaaat gccactgaac    60
cctttgccag atcaagtcga agacacaaca cgggttt                             97

<210> SEQ ID NO 29
<211> LENGTH: 97
```

```
<212> TYPE: DNA
<213> ORGANISM: Artificial Sequence
<220> FEATURE:
<223> OTHER INFORMATION: amiRNA0569

<400> SEQUENCE: 29
agctccttgt tgtgtgattg ttgatctggc aagtctcttg gatctcaaat gccactgaac    60
cctttgccag atcaacaatc acacacaaca cgggttt                             97

<210> SEQ ID NO 30
<211> LENGTH: 97
<212> TYPE: DNA
<213> ORGANISM: Artificial Sequence
<220> FEATURE:
<223> OTHER INFORMATION: aMIR164-rps23-1

<400> SEQUENCE: 30
agctccttgt ttctcggaaa ttgcgcttcc aagtctcttg gatctcaaat gccactgaac    60
cctttggaag cgcaaaatcc gagaacaaca cgggttt                             97

<210> SEQ ID NO 31
<211> LENGTH: 10509
<212> TYPE: DNA
<213> ORGANISM: Artificial Sequence
<220> FEATURE:
<223> OTHER INFORMATION: pKS49 (amiR0043)

<400> SEQUENCE: 31
taattcctgt ggttggcatg cacatacaaa tggacgaacg gataaacctt ttcacgccct    60
tttaaatatc cgattattct aataaacgct ctttttctctt aggtttaccc gccaatatat   120
cctgtcaaac actgatagtt taaactgaag gcgggaaacg acaatctgat catgagcgga   180
gaattaaggg agtcacgtta tgacccccgc cgatgacgcg ggacaagccg ttttacgttt    240
ggaactgaca gaaccgcaac gctgcaggaa ttggccgcag cggccattta aatcaattgg    300
gcgcgtacgt agcactagtg aattccggac ccaagctttg gcagacaaag tggcagacat    360
actgtcccac aaatgaagat ggaatctgta aagaaaaacg cgtgaaataa tgcgtctgac    420
aaaggttagg tcggctgcct ttaatcaata ccaaagtggt ccctaccacg atggaaaaac    480
tgtgcagtcg gtttggcttt ttctgacgaa caaataagat tcgtggccga caggtggggg    540
tccaccatgt gaaggcatct tcagactcca ataatgagc aatgacgtaa gggcttacga    600 ataagtaag ggtagtttgg gaaatgtcca ctcacccgtc agtctataaa tacttagccc   660
ctccctcatt gttaagggag caaaatctca gagagatagt cctagagaga gaaagagagc    720
aagtagccta gaagtggatc tccaccatgg cccagtccaa gcacggcctg accaaggaga    780
tgaccatgaa gtaccgcatg gagggctgcg tggacggcca caagttcgtg atcaccggcg    840
agggcatcgg ctacccccttc aagggcaagc aggccatcaa cctgtgcgtg gtggagggcg    900
gccccttgcc cttcgccgag gacatccttgt ccgccgcctt catgtacggc aaccgcgtgt    960
tcaccgagta cccccaggac atcgtcgact acttcaagaa ctcctgcccc gccggctaca   1020
cctgggaccg ctccttcctg ttcgaggacg gcgccgtgtg catctgcaac gccgacatca   1080
ccgtgagcgt ggaggagaac tgcatgtacc acgagtccaa gttctacggc gtgaacttcc   1140
ccgccgacgg ccccgtgatg aagaagatga ccgacaactg ggagccctcc tgcgagaaga   1200
tcatccccgt gcccaagcag ggcatcttga agggcgacgt gagcatgtac ctgctgctga   1260
aggacggtgg ccgcttgcgc tgccagttcg acaccgtgta caaggccaag tccgtgcccc    1320
```

```
gcaagatgcc cgactggcac ttcatccagc acaagctgac ccgcgaggac cgcagcgacg    1380
ccaagaacca gaagtggcac ctgaccgagc acgccatcgc ctccggctcc gccttgccct    1440
gctctagatc cccgaatttc cccgatcgtt caaacatttg gcaataaagt ttcttaagat    1500
tgaatcctgt tgccggtctt gcgatgatta tcatataatt tctgttgaat tacgttaagc    1560
atgtaataat taacatgtaa tgcatgacgt tatttatgag atgggttttt atgattagag    1620
tcccgcaatt atacatttaa tacgcgatag aaaacaaaat atagcgcgca aactaggata    1680
aattatcgcg cgcggtgtca tctatgttac tagatcgcgg accctcatga gcggagaatt    1740
aagggagtca cgttatgacc cccgccgatg acgcgggaca gccgttttta cgtttggaac    1800
tgacagaacc gcaacgaagc tttggcagac aaagtggcag acatactgtc ccacaaatga    1860
agatggaatc tgtaaaagaa aacgcgtgaa ataatgcgtc tgacaaaggt taggtcggct    1920
gcctttaatc aataccaaag tggtccctac cacgatggaa aaactgtgca gtcggtttgg    1980 cttttttctga cgaacaaata agattcgtgg ccgacaggtg ggggtccacc atgtgaaggc    2040
atcttcagac tccaataatg gagcaatgac gtaagggctt acgaaataag taagggtagt    2100
ttgggaaatg tccactcacc cgtcagtcta taaatactta gcccctccct cattgttaag    2160
ggagcaaaat ctcagagaga tagtcctaga gagagaaaga gagcaagtag cctagaagtg    2220
gatccagctc cttgttaact tattgttgat ctggcaagtc tcttggatct caaatgccac    2280 tgaaccctttt gccagatcaa gtataagtta caacacgggt ttgagctctt catatgacga    2340
tcgttcaaac atttggcaat aaagtttctt aagattgaat cctgttgccg gtcttgcgat    2400
gattatcata taatttctgt tgaattacgt taagcatgta ataattaaca tgtaatgcat    2460
gacgttattt atgagatggg ttttatgat tagagtcccg caattataca tttaatacgc    2520
gatagaaaac aaaatatagc gcgcaaacta ggataaatta tcgcgcgcgg tgtcatctat    2580
gttactagat cgcggaccga agcttgcatg cctgcaggtc gactctagag gatccggagc    2640
caagtctcat aaacgccatt gtggaagaaa gtcttgagtt ggtggtaatg taacagagta    2700
gtaagaacag agaagagaga gagtgtgaga tacatgaatt gtcgggcaac aaaaatcctg    2760
aacatcttat tttagcaaag agaaagagtt ccgagtctgt agcagaagag tgaggagaaa    2820
tttaagctct tggacttgtg aattgttccg cctcttgaat acttcttcaa tcctcatata    2880
ttcttcttct atgttacctg aaaaccggca tttaatctcg cgggtttatt ccggttcaac    2940 atttttttg ttttgagtta ttatctgggc ttaataacgc aggcctgaaa taaattcaag    3000
gcccaactgt ttttttttt aagaagttgc tgttaaaaaa aaaaaaggg aattaacaac    3060 aacaacaaaa aaagataaag aaaataataa caattacttt aattgtagac taaaaaaaca    3120
tagattttat catgaaaaaa agagaaaaga aataaaaact tggatcaaaa aaaaaacata    3180
cagatcttct aattattaac ttttcttaaa aattaggtcc ttttttccaa caattaggtt    3240
tagagttttg gaattaaacc aaaaagattg ttctaaaaaa tactcaaatt tggtagataa    3300
gtttccttat tttaattagt caatggtaga actttttttt tcttttcttt attagagtag    3360
attagaatct tttatgccaa gtattgataa attaaatcaa gaagataaac tatcataatc    3420
aacatgaaat taaagaaaaa atctcatata gtattagt attctctata tatattatga    3480
ttgcttattc ttaatgggtt gggttaacca agacatagtc ttaatggaaa gaatcttttt    3540 tgaactttt ccttattgat taaattcttc tatagaaaag aaagaaatta tttgaggaaa    3600
agtatataca aaagaaaaa tagaaaaatg tcagtgaagc agatgtaatg gatgacctaa    3660
tccaaccacc accataggat gtttctactt gagtcggtct tttaaaaacg cacggtggaa    3720
```

```
aatatgacac gtatcatatg attccttcct ttagtttcgt gataataatc ctcaactgat   3780
atcttccttt ttttgttttg gctaaagata ttttattctc attaatagaa aagacggttt   3840
tgggcttttg gtttgcgata taaagaagac cttcgtgtgg aagataataa ttcatccttt   3900
cgtcttttc tgactcttca atctctccca aagcctaaag cgatctctgc aaatctctcg    3960
cgactctctc tttcaaggta tattttctga ttcttttgt ttttgattcg tatctgatct    4020
ccaattttg ttatgtggat tattgaatct tttgtataaa ttgcttttga caatattgtt    4080
cgtttcgtca atccagcttc taaattttgt cctgattact aagatatcga ttcgtagtgt   4140
ttacatctgt gtaatttctt gcttgattgt gaaattagga ttttcaagga cgatctattc   4200
aattttgtg ttttctttgt tcgattctct ctgttttagg tttcttatgt ttagatccgt    4260
ttctctttgg tgttgttttg atttctctta cggcttttga tttggtatat gttcgctgat   4320
tggtttctac ttgttctatt gttttatttc aggtggatcc caccatgtct ccggagagga   4380
gaccagttga gattaggcca gctacagcag ctgatatggc cgcggtttgt gatatcgtta   4440
accattacat tgagacgtct acagtgaact ttaggacaga gccacaaaca ccacaagagt   4500
ggattgatga tctagagagg ttgcaagata gatacccttg gttggttgct gaggttgagg   4560
gtgttgtggc tggtattgct tacgctgggc cctggaaggc taggaacgct tacgattgga   4620
cagttgagag tactgtttac gtgtcacata ggcatcaaag gttgggccta ggatctacat   4680
tgtacacaca tttgcttaag tctatggagg cgcaaggttt taagtctgtg gttgctgtta   4740
taggccttcc aaacgatcca tctgttaggt tgcatgaggc tttgggatac acagcccggg   4800
gtacattgcg cgcagctgga tacaagcatg gtggatggca tgatgttggt ttttggcaaa   4860
gggattttga gttgccagct cctccaaggc cagttaggcc agttacccag atatgagtcg   4920
agctctagat ccccgaattt ccccgatcgt tcaaacattt ggcaataaag tttcttaaga   4980
ttgaatcctg ttgccggtct tgcgatgatt atcatataat ttctgttgaa ttacgttaag   5040
catgtaataa ttaacatgta atgcatgacg ttatttatga gatgggtttt tatgattaga   5100
gtcccgcaat tatacatttta atacgcgata gaaaacaaaa tatagcgcgc aaactaggat   5160
aaattatcgc gcgcggtgtc atctatgtta ctagatcggg aattgggtac catgcccggg   5220
cggccagcat ggccgtatcc gcaatgtgtt attaagttgt ctaagcgtca atttgtttac   5280
accacaatat atcctgccac cagccagcca acagctcccc gaccggcagc tcggcacaaa   5340
atcaccactc gatacaggca gcccatcaga attaattctc atgtttgaca gcttatcatc   5400
gactgcacgt tgcaccaatg cttctggcgt caggcagcca tcggaagctg tggtatggct   5460
gtgcaggtcg taaatcactg cataattcgt gtcgctcaag gcgcactccc gttctggata   5520
atgttttttg cgccgacatc ataacggttc tggcaaatat tctgaaatga gctgttgaca   5580
attaatcatc cggctcgtat aatgtgtgga attgtgagcg gataacaatt tcacacagga   5640
aacagaccat gagggaagcg ttgatcgccg aagtatcgac tcaactatca gaggtagttg   5700
gcgtcatcga gcgccatctc gaaccgacgt tgctggccgt acatttgtac ggctccgcag   5760
tggatggcgg cctgaagcca cacagtgata ttgatttgct ggttacggtg accgtaaggc   5820
ttgatgaaac aacgcggcga gctttgatca acgacctttt ggaaacttcg gcttcccctg   5880
gagagagcga gattctccgc gctgtagaag tcaccattgt tgtgcacgac gacatcattc   5940
cgtggcgtta tccagctaag cgcgaactgc aatttggaga atggcagcgc aatgacattc   6000
ttgcaggtat cttcgagcca gccacgatcg acattgatct ggctatcttg ctgacaaaag   6060
```

```
caagagaaca tagcgttgcc ttggtaggtc cagcggcgga ggaactcttt gatccggttc    6120
ctgaacagga tctatttgag gcgctaaatg aaaccttaac gctatggaac tcgccgcccg    6180
actgggctgg cgatgagcga aatgtagtgc ttacgttgtc ccgcatttgg tacagcgcag    6240
taaccggcaa aatcgcgccg aaggatgtcg ctgccgactg gcaatggag cgcctgccgg     6300
cccagtatca gcccgtcata cttgaagcta ggcaggctta tcttggacaa gaagatcgct    6360
tggcctcgcg cgcagatcag ttggaagaat ttgttcacta cgtgaaaggc gagatcacca    6420
aagtagtcgg caaataaagc tctagtggat ctccgtaccc ccggggatc tggctcgcgg     6480
cggacgcacg acgccggggc gagaccatag gcgatctcct aaatcaatag tagctgtaac    6540
ctcgaagcgt ttcacttgta acaacgattg agaattttttg tcataaaatt gaaatacttg   6600
gttcgcattt ttgtcatccg cggtcagccg caattctgac gaactgccca tttagctgga    6660
gatgattgta catccttcac gtgaaaattt ctcaagcgct gtgaacaagg gttcagattt    6720
tagattgaaa ggtgagccgt tgaaacacgt tcttcttgtc gatgacgacg tcgctatgcg    6780
gcatcttatt attgaatacc ttacgatcca cgccttcaaa gtgaccgcgg tagccgacag    6840
cacccagttc acaagagtac tctcttccgc gacggtcgat gtcgtggttg ttgatctaga    6900
tttaggtcgt gaagatgggc tcgagatcgt tcgtaatctg gcggcaaagt ctgatattcc    6960
aatcataatt atcagtggcg accgccttga ggagacggat aaagttgttg cactcgagct    7020
aggagcaagt gattttatcg ctaagccgtt cagtatcaga gagtttctag cacgcattcg    7080
ggttgccttg cgcgtgcgcc ccaacgttgt ccgctccaaa gaccgacggt ctttttgttt    7140
tactgactgg acacttaatc tcaggcaacg tcgcttgatg tccgaagctg gcggtgaggt    7200
gaaacttacg gcaggtgagt tcaatcttct cctcgcgttt ttagagaaac cccgcgacgt    7260
tctatcgcgc gagcaacttc tcattgccag tcgagtacgc gacgaggagg tttatgacag    7320
gagtatagat gttctcattt tgaggctgcg ccgcaaactt gaggcagatc cgtcaagccc    7380
tcaactgata aaaacagcaa gaggtgccgg ttatttctttt gacgcggacg tgcaggtttc    7440
gcacgggggg acgatggcag cctgagccaa ttcccagatc cccgaggaat cggcgtgagc    7500
ggtcgcaaac catccggccc ggtacaaatc ggcgcggcgc tgggtgatga cctggtggag    7560
aagttgaagg ccgcgcaggc cgcccagcgg caacgcatcg aggcagaagc acgccccggt    7620
gaatcgtggc aagcggccgc tgatcgaatc cgcaaagaat cccggcaacc gccggcagcc    7680
ggtgcgccgt cgattaggaa gccgcccaag ggcgacgagc aaccagattt tttcgttccg    7740
atgctctatg acgtgggcac ccgcgatagt cgcagcatca tggacgtggc cgttttccgt    7800
ctgtcgaagc gtgaccgacg agctggcgag gtgatccgct acgagcttcc agacgggcac    7860
gtagaggttt ccgcagggcc ggccggcatg ccagtgtgt gggattacga cctggtactg     7920
atggcggttt cccatctaac cgaatccatg aaccgatacc gggaagggaa gggagacaag    7980
cccggccgcg tgttccgtcc acacgttgcg gacgtactca agttctgccg gcgagccgat    8040
ggcggaaagc agaaagacga cctggtagaa acctgcattc ggttaaacac cacgcacgtt    8100
gccatgcagc gtacgaagaa ggccaagaac ggccgcctgg tgacggtatc cgagggtgaa    8160
gccttgatta gccgctacaa gatcgtaaag agcgaaaccg gcggccgga gtacatcgag     8220
atcgagctag ctgattggat gtaccgcgag atcacagaag gcaagaaccc ggacgtgctg    8280
acggttcacc ccgattactt tttgatcgat cccggcatcg gccgttttct ctaccgcctg    8340
gcacgccgcg ccgcaggcaa ggcagaagcc agatggttgt tcaagacgat ctacgaacgc    8400
agtggcagcg ccggagagtt caagaagttc tgtttcaccg tgcgcaagct gatcgggtca    8460
```

```
aatgacctgc cggagtacga tttgaaggag gaggcggggc aggctggccc gatcctagtc    8520
atgcgctacc gcaacctgat cgagggcgaa gcatccgccg gttcctaatg tacggagcag    8580
atgctagggc aaattgccct agcagggaaa aaggtcgaa aaggtctctt tcctgtggat     8640
agcacgtaca ttgggaaccc aaagccgtac attgggaacc ggaacccgta cattgggaac    8700
ccaaagccgt acattgggaa ccggtcacac atgtaagtga ctgatataaa agagaaaaaa    8760
ggcgattttt ccgcctaaaa ctctttaaaa cttattaaaa ctcttaaaac ccgcctggcc    8820
tgtgcataac tgtctggcca gcgcacagcc gaagagctgc aaaaagcgcc tacccttcgg    8880
tcgctgcgct ccctacgccc cgccgcttcg cgtcggccta cgcggccgc tggccgctca     8940 aaaatggctg gcctacggcc aggcaatcta ccagggcgcg acaagccgc gccgtcgcca     9000 ctcgaccgcc ggcgctgagg tctgcctcgt gaagaaggtg ttgctgactc ataccaggcc    9060
tgaatcgccc catcatccag ccagaaagtg agggagccac ggttgatgag agctttgttg    9120
taggtggacc agttggtgat tttgaacttt tgctttgcca cggaacggtc tgcgttgtcg    9180
ggaagatgcg tgatctgatc cttcaactca gcaaaagttc gatttattca acaaagccgc    9240
cgtcccgtca agtcagcgta atgctctgcc agtgttacaa ccaattaacc aattctgatt    9300
agaaaaactc atcgagcatc aaatgaaact gcaatttatt catatcagga ttatcaatac    9360 catattttg aaaaagccgt ttctgtaatg aaggagaaaa ctcaccgagg cagttccata     9420
ggatggcaag atcctggtat cggtctgcga ttccgactcg tccaacatca atacaaccta    9480
ttaatttccc ctcgtcaaaa ataaggttat caagtgagaa atcaccatga gtgacgactg    9540
aatccggtga gaatggcaaa agctctgcat taatgaatcg gccaacgcgc ggggagaggc    9600
ggtttgcgta ttgggcgctc ttccgcttcc tcgctcactg actcgctgcg ctcggtcgtt    9660
cggctgcggc gagcggtatc agctcactca aaggcggtaa tacggttatc cacagaatca    9720
ggggataacg caggaaagaa catgtgagca aaaggccagc aaaaggccag gaaccgtaaa    9780
aaggccgcgt tgctggcgtt tttccatagg ctccgccccc ctgacgagca tcacaaaaat    9840
cgacgctcaa gtcagaggtg gcgaaacccg acaggactat aaagatacca ggcgtttccc    9900
cctggaagct ccctcgtgcg ctctcctgtt ccgaccctgc cgcttaccgg atacctgtcc    9960
gcctttctcc cttcgggaag cgtggcgctt tctcatagct cacgctgtag gtatctcagt   10020
tcggtgtagg tcgttcgctc caagctgggc tgtgtgcacg aaccccccgt tcagcccgac   10080
cgctgcgcct tatccggtaa ctatcgtctt gagtccaacc cggtaagaca cgacttatcg   10140
ccactggcag cagccactgg taacaggatt agcagagcga ggtatgtagg cggtgctaca   10200
gagttcttga agtggtggcc taactacggc tacactagaa gaacagtatt tggtatctgc   10260
gctctgctga agccagttac cttcggaaaa agagttggta gctcttgatc cggcaaacaa   10320
accaccgctg gtagcggtgg tttttttgtt tgcaagcagc agattacgcg cagaaaaaaa   10380
ggatctcaag aagatccttt gatcttttct acggggtctg acgctcagtg gaacgaaaac   10440
tcacgttaag ggattttggt catgagatta tcaaaaagga tcttcaccta gatccttttg   10500
atccggaat                                                           10509
```

<210> SEQ ID NO 32
<211> LENGTH: 10509
<212> TYPE: DNA
<213> ORGANISM: Artificial Sequence
<220> FEATURE:
<223> OTHER INFORMATION: pKS50 (amiR0046)

<400> SEQUENCE: 32

```
ggaattaatt cctgtggttg gcatgcacat acaaatggac gaacggataa acctttttcac    60
gccctttaa atatccgatt attctaataa acgctctttt ctcttaggtt tacccgccaa    120
tatatcctgt caaacactga tagtttaaac tgaaggcggg aaacgacaat ctgatcatga    180
gcggagaatt aagggagtca cgttatgacc cccgccgatg acgcgggaca agccgtttta    240
cgtttggaac tgacagaacc gcaacgctgc aggaattggc cgcagcggcc atttaaatca    300
attgggcgcg tacgtagcac tagtgaattc cggacccaag ctttggcaga caaagtggca    360
gacatactgt cccacaaatg aagatggaat ctgtaaaaga aaacgcgtga ataatgcgt    420
ctgacaaagg ttaggtcggc tgcctttaat caataccaaa gtggtcccta ccacgatgga    480
aaaactgtgc agtcggtttg ctttttctg acgaacaaat aagattcgtg ccgacaggt    540
gggggtccac catgtgaagg catcttcaga ctccaataat ggagcaatga cgtaagggct    600
tacgaaataa gtaagggtag tttgggaaat gtccactcac ccgtcagtct ataaatactt    660
agcccctccc tcattgttaa gggagcaaaa tctcagagag atagtcctag agagagaaag    720
agagcaagta gcctagaagt ggatctccac catggcccag tccaagcacg cctgaccaa    780
ggagatgacc atgaagtacc gcatggaggg ctgcgtggac ggccacaagt tcgtgatcac    840
cggcgagggc atcggctacc ccttcaaggg caagcaggcc atcaacctgt gcgtggtgga    900
gggcggcccc ttgcccttcg ccgaggacat cttgtccgcc gccttcatgt acggcaaccg    960
cgtgttcacc gagtaccccc aggacatcgt cgactacttc aagaactcct gccccgccgg    1020
ctacacctgg gaccgctcct tcctgttcga ggacggcgcc gtgtgcatct gcaacgccga    1080
catcaccgtg agcgtggagg agaactgcat gtaccacgag tccaagttct acggcgtgaa    1140
cttccccgcc gacggccccg tgatgaagaa gatgaccgac aactgggagc ctcctgcga    1200
gaagatcatc cccgtgccca gcagggcat cttgaagggc gacgtgagca tgtacctgct    1260
gctgaaggac ggtggccgct tgcgctgcca gttcgacacc gtgtacaagg ccaagtccgt    1320
gccccgcaag atgcccgact ggcacttcat ccagcacaag ctgacccgcg aggaccgcag    1380
cgacgccaag aaccagaagt ggcacctgac cgagcacgcc atcgcctccg gctccgcctt    1440
gccctgctct agatccccga atttccccga tcgttcaaac atttggcaat aaagtttctt    1500
aagattgaat cctgttgccg gtcttgcgat gattatcata taatttctgt tgaattacgt    1560
taagcatgta ataattaaca tgtaatgcat gacgttattt atgagatggg ttttatgat    1620
tagagtcccg caattataca tttaatacgc gatagaaaac aaaatatagc gcgcaaacta    1680
ggataaatta tcgcgcgcgg tgtcatctat gttactagat cgcggaccct catgagcgga    1740
gaattaaggg agtcacgtta tgaccccgc cgatgacgcg ggacaagccg ttttacgttt    1800
ggaactgaca gaaccgcaac gaagctttgg cagacaaagt ggcagacata ctgtcccaca    1860
aatgaagatg gaatctgtaa agaaaacgc gtgaataat gcgtctgaca aaggttaggt    1920
cggctgcctt taatcaatac caaagtggtc cctaccacga tggaaaaact gtgcagtcgg    1980
tttggctttt tctgacgaac aaataagatt cgtggccgac aggtgggggt ccaccatgtg    2040
aaggcatctt cagactccaa taatggagca atgacgtaag gcttacgaa ataagtaagg    2100
gtagtttggg aaatgtccac tcacccgtca gtctataaat acttagcccc tcctcattg    2160
ttaagggagc aaaatctcag agagatagtc ctagagagag aaagagagca agtagcctag    2220
aagtggatcc agctccttgt taacttcttg ttgatctggc aagtctcttg gatctcaaat    2280
gccactgaac ccttttgccag atcaagtaga agttacaaca cgggtttgag ctcttcatat    2340
```

```
gacgatcgtt caaacatttg gcaataaagt ttcttaagat tgaatcctgt tgccggtctt    2400
gcgatgatta tcatataatt tctgttgaat tacgttaagc atgtaataat taacatgtaa    2460
tgcatgacgt tatttatgag atgggttttt atgattagag tcccgcaatt atacatttaa    2520
tacgcgatag aaaacaaaat atagcgcgca aactaggata aattatcgcg cgcggtgtca    2580
tctatgttac tagatcgcgg accgaagctt gcatgcctgc aggtcgactc tagaggatcc    2640
ggagccaagt ctcataaacg ccattgtgga agaaagtctt gagttggtgg taatgtaaca    2700
gagtagtaag aacagagaag agagagagtg tgagatacat gaattgtcgg gcaacaaaaa    2760
tcctgaacat cttattttag caaagagaaa gagttccgag tctgtagcag aagagtgagg    2820
agaaatttaa gctcttggac ttgtgaattg ttccgcctct tgaatacttc ttcaatcctc    2880
atatattctt cttctatgtt acctgaaaac cggcatttaa tctcgcgggt ttattccggt    2940
tcaacatttt ttttgttttg agttattatc tgggcttaat aacgcaggcc tgaaataaat    3000
tcaaggccca actgtttttt tttttaagaa gttgctgtta aaaaaaaaaa aagggaatta    3060
acaacaacaa caaaaaaaga taaagaaaat aataacaatt actttaattg tagactaaaa    3120
aaacatagat tttatcatga aaaaagaga aagaaataa aaacttggat caaaaaaaaa    3180
acatacagat cttctaatta ttaacttttc ttaaaaatta ggtccttttt cccaacaatt    3240
aggtttagag ttttggaatt aaaccaaaaa gattgttcta aaaaatactc aaatttggta    3300
gataagtttc cttattttaa ttagtcaatg gtagatactt ttttttcttt tctttattag    3360
agtagattag aatctttat gccaagtatt gataaattaa atcaagaaga taaactatca    3420
taatcaacat gaaattaaaa gaaaaatctc atatatagta ttagtattct ctatatatat    3480
tatgattgct tattcttaat gggttgggtt aaccaagaca tagtcttaat ggaaagaatc    3540
ttttttgaac tttttcctta ttgattaaat tcttctatag aaaagaaaga aattatttga    3600
ggaaaagtat atacaaaaag aaaaatagaa aaatgtcagt gaagcagatg taatggatga    3660
cctaatccaa ccaccaccat aggatgtttc tacttgagtc ggtcttttaa aaacgcacgg    3720
tggaaaatat gacacgtatc atatgattcc ttcctttagt ttcgtgataa taatcctcaa    3780
ctgatatctt ccttttttg ttttggctaa agatatttta ttctcattaa tagaaaagac    3840
ggttttgggc ttttgtttg cgatataaag aagaccttcg tgtggaagat aataattcat    3900
cctttcgtct ttttctgact cttcaatctc tcccaaagcc taaagcgatc tctgcaaatc    3960
tctcgcgact ctctctttca aggtatattt tctgattctt tttgttttg attcgtatct    4020 gatctccaat ttttgttatg tggattattg aatcttttgt ataaattgct tttgacaata    4080
ttgttcgttt cgtcaatcca gcttctaaat tttgtcctga ttactaagat atcgattcgt    4140
agtgtttaca tctgtgtaat ttcttgcttg attgtgaaat taggattttc aaggacgatc    4200
tattcaattt ttgtgttttc tttgttcgat tctctctgtt ttaggtttct tatgtttaga    4260
tccgtttctc tttggtgttg ttttgatttc tcttacggct tttgatttgg tatatgttcg    4320
ctgattggtt tctacttgtt ctattgtttt atttcaggtg gatcccacca tgtctccgga    4380
gaggagacca gttgagatta ggccagctac agcagctgat atggccgcgg tttgtgatat    4440
cgttaaccat tacattgaga cgtctacagt gaactttagg acagagccac aaacaccaca    4500
agagtggatt gatgatctag agaggttgca agatagatac ccttggttgg ttgctgaggt    4560
tgagggtgtt gtggctggta ttgcttacgc tgggccctgg aaggctagga acgcttacga    4620
ttggacagtt gagagtactg tttacgtgtc acataggcat caaaggttgg gcctaggatc    4680
```

```
tacattgtac acacatttgc ttaagtctat ggaggcgcaa ggttttaagt ctgtggttgc   4740
tgttataggc cttccaaacg atccatctgt taggttgcat gaggctttgg gatacacagc   4800
ccggggtaca ttgcgcgcag ctggatacaa gcatggtgga tggcatgatg ttggtttttg   4860
gcaaagggat tttgagttgc cagctcctcc aaggccagtt aggccagtta cccagatatg   4920
agtcgagctc tagatccccg aatttccccg atcgttcaaa catttggcaa taaagtttct   4980
taagattgaa tcctgttgcc ggtcttgcga tgattatcat ataatttctg ttgaattacg   5040
ttaagcatgt aataattaac atgtaatgca tgacgttatt tatgagatgg gtttttatga   5100
ttagagtccc gcaattatac atttaatacg cgatagaaaa caaatatag cgcgcaaact    5160 aggataaatt atcgcgcgcg gtgtcatcta tgttactaga tcgggaattg ggtaccatgc   5220
ccgggcggcc agcatggccg tatccgcaat gtgttattaa gttgtctaag cgtcaatttg   5280
tttacaccac aatatatcct gccaccagcc agcaacagc tccccgaccg gcagctcggc    5340
acaaaatcac cactcgatac aggcagccca tcagaattaa ttctcatgtt tgacagctta   5400
tcatcgactg cacggtgcac caatgcttct ggcgtcaggc agccatcgga agctgtggta   5460
tggctgtgca ggtcgtaaat cactgcataa ttcgtgtcgc tcaaggcgca ctcccgttct   5520
ggataatgtt ttttgcgccg acatcataac ggttctggca aatattctga atgagctgt    5580 tgacaattaa tcatccggct cgtataatgt gtggaattgt gagcggataa caatttcaca   5640
caggaaacag accatgaggg aagcgttgat cgccgaagta tcgactcaac tatcagaggt   5700
agttggcgtc atcgagcgcc atctcgaacc gacgttgctg gccgtacatt tgtacggctc   5760
cgcagtggat ggcggcctga agccacacag tgatattgat tgctggtta cggtgaccgt    5820 aaggcttgat gaaacaacgc ggcgagcttt gatcaacgac cttttggaaa cttcggcttc   5880
ccctggagag agcgagattc tccgcgctgt agaagtcacc attgttgtgc acgacgacat   5940
cattccgtgg cgttatccag ctaagcgcga actgcaattt ggagaatggc agcgcaatga   6000
cattcttgca ggtatcttcg agccagccac gatcgacatt gatctggcta tcttgctgac   6060
aaaagcaaga gaacatagcg ttgccttggt aggtccagcg gcggaggaac tctttgatcc   6120
ggttcctgaa caggatctat ttgaggcgct aaatgaaacc ttaacgctat ggaactcgcc   6180
gcccgactgg gctggcgatg agcgaaatgt agtgcttacg ttgtcccgca tttggtacag   6240
cgcagtaacc ggcaaaatcg cgccgaagga tgtcgctgcc gactgggcaa tggagcgcct   6300
gccggcccag tatcagcccg tcatacttga agctaggcag gcttatcttg acaagaaga   6360 tcgcttggcc tcgcgcgcag atcagttgga agaatttgtt cactacgtga aaggcgagat   6420
caccaaagta gtcggcaaat aaagctctag tggatctccg taccccgggg ggatctggct   6480
cgcggcggac gcacgacgcc ggggcgagac cataggcgat ctcctaaatc aatagtagct   6540
gtaacctcga agcgtttcac ttgtaacaac gattgagaat ttttgtcata aaattgaaat   6600
acttggttcg catttttgtc atccgcggtc agccgcaatt ctgacgaact gcccatttag   6660
ctggagatga ttgtacatcc ttcacgtgaa aatttctcaa cgctgtgaa caagggttca    6720 gatttagat tgaaaggtga gccgttgaaa cacgttcttc ttgtcgatga cgacgtcgct    6780
atgcggcatc ttattattga ataccttacg atccacgcct tcaaagtgac gcggtagcc    6840 gacagcaccc agttcacaag agtactctct tccgcgacgg tcgatgtcgt ggttgttgat   6900
ctagatttag gtcgtgaaga tgggctcgag atcgttcgta atctggcggc aaagtctgat   6960
attccaatca taattatcag tggcgaccgc cttgaggaga cggataaagt tgttgcactc   7020
gagctaggag caagtgattt tatcgctaag ccgttcagta tcagagagtt tctagcacgc   7080
```

```
attcgggttg ccttgcgcgt gcgcccaac gttgtccgct ccaaagaccg acggtctttt    7140
tgttttactg actggacact taatctcagg caacgtcgct tgatgtccga agctggcggt    7200
gaggtgaaac ttacggcagg tgagttcaat cttctcctcg cgttttttaga gaaacccgc    7260 gacgttctat cgcgcgagca acttctcatt gccagtcgag tacgcgacga ggaggtttat    7320
gacaggagta tagatgttct cattttgagg ctgcgccgca aacttgaggc agatccgtca    7380
agccctcaac tgataaaaac agcaagaggt gccggttatt tctttgacgc ggacgtgcag    7440
gtttcgcacg gggggacgat ggcagcctga gccaattccc agatccccga ggaatcggcg    7500
tgagcggtcg caaaccatcc ggcccggtac aaatcggcgc ggcgctgggt gatgacctgg    7560
tggagaagtt gaaggccgcg caggccgccc agcggcaacg catcgaggca gaagcacgcc    7620
ccggtgaatc gtggcaagcg gccgctgatc gaatccgcaa agaatcccgg caaccgccgg    7680
cagccggtgc gccgtcgatt aggaagccgc ccaagggcga cgagcaacca gatttttttcg   7740 ttccgatgct ctatgacgtg gcacccgcg atagtcgcag catcatggac gtggccgttt     7800
tccgtctgtc gaagcgtgac cgacgagctg gcgaggtgat ccgctacgag cttccagacg    7860
ggcacgtaga ggtttccgca gggccggccg gcatggccag tgtgtgggat tacgacctgg    7920
tactgatggc ggtttcccat ctaaccgaat ccatgaaccg ataccgggaa gggaagggag    7980
acaagcccgg ccgcgtgttc cgtccacacg ttgcggacgt actcaagttc tgccggcgag    8040
ccgatggcgg aaagcagaaa gacgacctgg tagaaacctg cattcggtta aacaccacgc    8100
acgttgccat gcagcgtacg aagaaggcca agaacggccg cctggtgacg gtatccgagg    8160
gtgaagcctt gattagccgc tacaagatcg taaagagcga aaccgggcgg ccggagtaca    8220
tcgagatcga gctagctgat tggatgtacc gcgagatcac agaaggcaag aacccggacg    8280
tgctgacggt tcaccccgat tacttttttga tcgatcccgg catcggccgt tttctctacc    8340
gcctggcacg ccgcgccgca ggcaaggcag aagccagatg gttgttcaag acgatctacg    8400
aacgcagtgg cagcgccgga gagttcaaga agttctgttt caccgtgcgc aagctgatcg    8460
ggtcaaatga cctgccggag tacgatttga aggaggaggc ggggcaggct ggcccgatcc    8520
tagtcatgcg ctaccgcaac ctgatcgagg gcgaagcatc cgccggttcc taatgtacgg    8580
agcagatgct agggcaaatt gccctagcag gggaaaaagg tcgaaaaggt ctctttcctg    8640
tggatagcac gtacattggg aacccaaagc cgtacattgg gaaccggaac ccgtacattg    8700
ggaacccaaa gccgtacatt gggaaccggt cacacatgta agtgactgat ataaaagaga    8760
aaaaaggcga ttttttccgcc taaaactctt taaaacttat taaaactctt aaaacccgcc    8820
tggcctgtgc ataactgtct ggccagcgca cagccgaaga gctgcaaaaa gcgcctaccc    8880
ttcggtcgct gcgctcccta cgccccgccg cttcgcgtcg gcctatcgcg gccgctggcc    8940
gctcaaaaat ggctggccta cggccaggca atctaccagg gcgcggacaa gccgcgccgt    9000
cgccactcga ccgccggcgc tgaggtctgc ctcgtgaaga aggtgttgct gactcatacc    9060
aggcctgaat cgccccatca tccagccaga aagtgaggga gccacggttg atgagagctt    9120
tgttgtaggt ggaccagttg gtgattttga acttttgctt tgccacggaa cggtctgcgt    9180
tgtcgggaag atgcgtgatc tgatccttca actcagcaaa agttcgattt attcaacaaa    9240
gccgccgtcc cgtcaagtca gcgtaatgct ctgccagtgt tacaaccaat taaccaattc    9300
tgattagaaa aactcatcga gcatcaaatg aaactgcaat ttattcatat caggattatc    9360
aataccatat ttttgaaaaa gccgtttctg taatgaagga gaaaactcac cgaggcagtt    9420
```

```
ccataggatg gcaagatcct ggtatcggtc tgcgattccg actcgtccaa catcaataca    9480
acctattaat ttcccctcgt caaaaataag gttatcaagt gagaaatcac catgagtgac    9540
gactgaatcc ggtgagaatg gcaaaagctc tgcattaatg aatcggccaa cgcgcgggga    9600
gaggcggttt gcgtattggg cgctcttccg cttcctcgct cactgactcg ctgcgctcgg    9660
tcgttcggct gcggcgagcg gtatcagctc actcaaaggc ggtaatacgg ttatccacag    9720
aatcagggga taacgcagga agaacatgt gagcaaaagg ccagcaaaag gccaggaacc    9780
gtaaaaaggc cgcgttgctg gcgtttttcc ataggctccg ccccctgac gagcatcaca    9840 aaaatcgacg ctcaagtcag aggtggcgaa acccgacagg actataaaga taccaggcgt    9900 ttcccctgg aagctccctc gtgcgctctc ctgttccgac cctgccgctt accggatacc    9960
tgtccgcctt tctcccttcg ggaagcgtgg cgctttctca tagctcacgc tgtaggtatc   10020
tcagttcggt gtaggtcgtt cgctccaagc tgggctgtgt gcacgaaccc cccgttcagc   10080
ccgaccgctg cgccttatcc ggtaactatc gtcttgagtc caacccggta agacacgact   10140
tatcgccact ggcagcagcc actggtaaca ggattagcag agcgaggtat gtaggcggtg   10200
ctacagagtt cttgaagtgg tggcctaact acggctacac tagaagaaca gtatttggta   10260
tctgcgctct gctgaagcca gttaccttcg gaaaaagagt tggtagctct tgatccggca   10320
aacaaaccac cgctggtagc ggtggttttt tgtttgcaa gcagcagatt acgcgcagaa   10380
aaaaaggatc tcaagaagat cctttgatct tttctacggg gtctgacgct cagtggaacg   10440
aaaactcacg ttaagggatt ttggtcatga gattatcaaa aaggatcttc acctagatcc   10500
ttttgatcc                                                          10509

<210> SEQ ID NO 33
<211> LENGTH: 10509
<212> TYPE: DNA
<213> ORGANISM: Artificial Sequence
<220> FEATURE:
<223> OTHER INFORMATION: pKS100 (amiR0097)

<400> SEQUENCE: 33
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg     240
aactgacaga accgcaacgc tgcaggaatt ggccgcagcg gccatttaaa tcaattgggc     300
gcgtacgtag cactagtgaa ttccggaccc aagctttggc agacaaagtg gcagacatac     360
tgtcccacaa atgaagatgg aatctgtaaa agaaacgcg tgaaataatg cgtctgacaa     420
aggttaggtc ggctgccttt aatcaatacc aaagtggtcc ctaccacgat ggaaaaactg     480
tgcagtcggt ttggcttttt ctgacgaaca ataagattc gtggccgaca ggtgggggtc     540
caccatgtga aggcatcttc agactccaat aatggagcaa tgacgtaagg gcttacgaaa     600
taagtaaggg tagtttggga aatgtccact cacccgtcag tctataaata cttagcccct     660
ccctcattgt taagggagca aaatctcaga gagatagtcc tagagagaga aagagagcaa     720
gtagcctaga agtggatctc caccatggcc cagtccaagc acggcctgac caaggagatg     780
accatgaagt accgcatgga gggctgcgtg gacggccaca agttcgtgat caccggcgag     840
ggcatcggct accccttcaa gggcaagcag gccatcaacc tgtgcgtggt ggagggcggc     900
cccttgccct tcgccgagga catcttgtcc gccgccttca tgtacggcaa ccgcgtgttc     960
```

```
accgagtacc cccaggacat cgtcgactac ttcaagaact cctgccccgc cggctacacc   1020
tgggaccgct ccttcctgtt cgaggacggc gccgtgtgca tctgcaacgc cgacatcacc   1080
gtgagcgtgg aggagaactg catgtaccac gagtccaagt tctacggcgt gaacttcccc   1140
gccgacggcc ccgtgatgaa gaagatgacc gacaactggg agccctcctg cgagaagatc   1200
atccccgtgc ccaagcaggg catcttgaag ggcgacgtga gcatgtacct gctgctgaag   1260
gacggtggcc gcttgcgctg ccagttcgac accgtgtaca aggccaagtc cgtgccccgc   1320
aagatgcccg actggcactt catccagcac aagctgaccc gcgaggaccg cagcgacgcc   1380
aagaaccaga gtggcaccct gaccgagcac gccatcgcct ccggctccgc cttgccctgc   1440
tctagatccc cgaatttccc cgatcgttca acatttggc aataaagttt cttaagattg   1500
aatcctgttg ccggtcttgc gatgattatc atataattc tgttgaatta cgttaagcat   1560
gtaataatta acatgtaatg catgacgtta tttatgagat gggtttttat gattagagtc   1620
ccgcaattat acatttaata cgcgatagaa acaaaatat agcgcgcaaa ctaggataaa   1680
ttatcgcgcg cggtgtcatc tatgttacta gatcgcggac cctcatgagc ggagaattaa   1740
gggagtcacg ttatgacccc cgccgatgac gcgggacaag ccgttttacg tttggaactg   1800
acagaaccgc aacgaagctt tggcagacaa gtggcagac atactgtccc acaaatgaag   1860
atggaatctg taaagaaaa cgcgtgaaat aatgcgtctg acaaaggtta ggtcggctgc   1920
ctttaatcaa taccaaagtg gtccctacca cgatggaaaa actgtgcagt cggtttggct   1980
ttttctgacg aacaaataag attcgtggcc gacaggtggg ggtccaccat gtgaaggcat   2040
cttcagactc caataatgga gcaatgacgt aagggcttac gaaataagta agggtagttt   2100
gggaaatgtc cactcacccg tcagtctata aatacttagc ccctccctca ttgttaaggg   2160
agcaaaatct cagagagata gtcctagaga gagaaagaga gcaagtagcc tagaagtgga   2220
tccagctcct tgttaagttc atgttgatct ggcaagtctc ttggatctca aatgccactg   2280 aacccttgc cagatcaagt tgaacttaca acacgggttt gagctcttca tatgacgatc   2340
gttcaaacat ttggcaataa agtttcttaa gattgaatcc tgttgccggt cttgcgatga   2400
ttatcatata atttctgttg aattacgtta agcatgtaat aattaacatg taatgcatga   2460
cgttatttat gagatgggtt tttatgatta gagtcccgca attatacatt taatacgcga   2520
tagaaaacaa aatatagcgc gcaaactagg ataaattatc gcgcgcggtg tcatctatgt   2580
tactagatcg cggaccgaag cttgcatgcc tgcaggtcga ctctagagga tccggagcca   2640
agtctcataa acgccattgt ggaagaaagt cttgagttgg tggtaatgta acagagtagt   2700
aagaacagag aagagagaga gtgtgagata catgaattgt cgggcaacaa aaatcctgaa   2760
catcttattt tagcaaagag aaagagttcc gagtctgtag cagaagagtg aggagaaatt   2820
taagctcttg gacttgtgaa ttgttccgcc tcttgaatac ttcttcaatc ctcatatatt   2880
cttcttctat gttacctgaa aaccggcatt aatctcgcg ggtttattcc ggttcaacat   2940 ttttttttgtt ttgagttatt atctgggctt aataacgcag gcctgaaata aattcaaggc   3000
ccaactgttt ttttttttaa gaagttgctg ttaaaaaaaa aaaagggaa ttaacaacaa   3060 caacaaaaa agataaagaa aataataaca attactttaa ttgtagacta aaaaaacata   3120
gattttatca tgaaaaaag agaaaagaaa taaaaacttg gatcaaaaaa aaaacataca   3180
gatcttctaa ttattaactt ttcttaaaaa ttaggtcctt tttcccaaca attaggttta   3240
gagttttgga attaaaccaa aaagattgtt ctaaaaaata ctcaaatttg gtagataagt   3300
```

```
ttccttattt taattagtca atggtagata ctttttttc ttttctttat tagagtagat      3360
tagaatcttt tatgccaagt attgataaat taaatcaaga agataaaacta tcataatcaa     3420 catgaaatta aaagaaaaat ctcatatata gtattagtat tctctatata tattatgatt     3480
gcttattctt aatgggttgg gttaaccaag acatagtctt aatggaaaga atctttttg      3540 aacttttcc ttattgatta aattcttcta tagaaaagaa agaaattatt tgaggaaaag      3600
tatatacaaa aagaaaaata gaaaatgtc agtgaagcag atgtaatgga tgacctaatc     3660
caaccaccac cataggatgt ttctacttga gtcggtcttt taaaaacgca cggtggaaaa     3720
tatgacacgt atcatatgat tccttccttt agtttcgtga taataatcct caactgatat    3780
cttccttttt ttgttttggc taaagatatt ttattctcat aatagaaaaa gacggttttg    3840
ggcttttggt ttgcgatata aagaagacct tcgtgtggaa gataataatt catccttcg     3900 tcttttctg actcttcaat ctctcccaaa gcctaaagcg atctctgcaa atctctcgcg     3960
actctctctt tcaaggtata ttttctgatt ctttttgttt ttgattcgta tctgatctcc    4020 aattttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200
tttttgtgtt ttcttttgttc gattctctct gttttaggtt tcttatgttt agatccgttt   4260
ctctttggtg ttgtttttgat ttctcttacg gcttttgatt tggtatatgt tcgctgattg   4320
gtttctactt gttctattgt tttatttcag gtggatccca ccatgtctcc ggagaggaga    4380
ccagttgaga ttaggccagc tacagcagct gatatggccg cggtttgtga tatcgttaac    4440
cattacattg agacgtctac agtgaacttt aggacagagc cacaaacacc acaagagtgg    4500
attgatgatc tagagaggtt gcaagataga taccttggt tggttgctga ggttgagggt     4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac     5280 cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
```

```
gtcatcgagc gccatctcga accgacgttg ctggccgtac atttgtacgg ctccgcagtg   5760
gatggcggcc tgaagccaca cagtgatatt gatttgctgg ttacggtgac cgtaaggctt   5820
gatgaaacaa cgcggcgagc tttgatcaac gaccttttgg aaacttcggc ttcccctgga   5880
gagagcgaga ttctccgcgc tgtagaagtc accattgttg tgcacgacga catcattccg   5940
tggcgttatc cagctaagcg cgaactgcaa tttggagaat ggcagcgcaa tgacattctt   6000
gcaggtatct tcgagccagc cacgatcgac attgatctgg ctatcttgct gacaaaagca   6060
agagaacata gcgttgcctt ggtaggtcca gcggcggagg aactctttga tccggttcct   6120
gaacaggatc tatttgaggc gctaaatgaa accttaacgc tatggaactc gccgcccgac   6180
tgggctggcg atgagcgaaa tgtagtgctt acgttgtccc gcatttggta cagcgcagta   6240
accggcaaaa tcgcgccgaa ggatgtcgct gccgactggg caatggagcg cctgccggcc   6300
cagtatcagc ccgtcatact tgaagctagg caggcttatc ttggacaaga agatcgcttg   6360
gcctcgcgcg cagatcagtt ggaagaattt gttcactacg tgaaaggcga gatcaccaaa   6420
gtagtcggca aataaagctc tagtggatct ccgtaccccc gggggatctg gctcgcggcg   6480
gacgcacgac gccggggcga gaccataggc gatctcctaa atcaatagta gctgtaacct   6540
cgaagcgttt cacttgtaac aacgattgag aattttgtc ataaaattga aatacttggt   6600
tcgcattttt gtcatccgcg gtcagccgca attctgacga actgcccatt tagctggaga   6660
tgattgtaca tccttcacgt gaaaatttct caagcgctgt gaacaagggt tcagatttta   6720
gattgaaagg tgagccgttg aaacacgttc ttcttgtcga tgacgacgtc gctatgcggc   6780
atcttattat tgaatacctt acgatccacg ccttcaaagt gaccgcggta gccgacagca   6840
cccagttcac aagagtactc tcttccgcga cggtcgatgt cgtggttgtt gatctagatt   6900
taggtcgtga agatgggctc gagatcgttc gtaatctggc ggcaaagtct gatattccaa   6960
tcataattat cagtggcgac cgccttgagg agacggataa agttgttgca ctcgagctag   7020
gagcaagtga ttttatcgct aagccgttca gtatcagaga gtttctagca cgcattcggg   7080
ttgccttgcg cgtgcgcccc aacgttgtcc gctccaaaga ccgacggtct ttttgtttta   7140
ctgactggac acttaatctc aggcaacgtc gcttgatgtc cgaagctggc ggtgaggtga   7200
aacttacggc aggtgagttc aatcttctcc tcgcgttttt agagaaaccc cgcgacgttc   7260
tatcgcgcga gcaacttctc attgccagtc gagtacgcga cgaggaggtt tatgacagga   7320
gtatagatgt tctcattttg aggctgcgcc gcaaacttga ggcagatccg tcaagccctc   7380
aactgataaa aacagcaaga ggtgccggtt atttctttga cgcggacgtg caggtttcgc   7440 acgggggac gatggcagcc tgagccaatt cccagatccc cgaggaatcg gcgtgagcgg   7500
tcgcaaacca tccggcccgg tacaaatcgg cgcggcgctg ggtgatgacc tggtggagaa   7560
gttgaaggcc gcgcaggccg cccagcggca acgcatcgag gcagaagcac gccccggtga   7620
atcgtggcaa gcgccgcctg atcgaatccg caaagaatcc cggcaaccgc cggcagccgg   7680
tgcgccgtcg attaggaagc cgcccaaggg cgacgagcaa ccagattttt tcgttccgat   7740
gctctatgac gtgggcaccc gcgatagtcg cagcatcatg gacgtggccg ttttccgtct   7800
gtcgaagcgt gaccgacgag ctggcgaggt gatccgctac gagcttccag acgggcacgt   7860
agaggtttcc gcaggccgg ccggcatggc cagtgtgtgg gattacgacc tggtactgat   7920 ggcggttttcc catctaaccg aatccatgaa ccgataccgg gaagggaagg agacaagcc   7980 cggccgcgtg ttccgtccac acgttgcgga cgtactcaag ttctgccggc gagccgatgg   8040
```

```
cggaaagcag aaagacgacc tggtagaaac ctgcattcgg ttaaacacca cgcacgttgc    8100
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760 cgattttcc gcctaaaact ctttaaaact tattaaaact cttaaacccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacggccag gcaatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccag ttggtgattt tgaactttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tatttttgaa aaagccgttt ctgtaatgaa ggagaaaact caccgaggca gttccatagg    9420
atggcaagat cctggtatcg gtctgcgatt ccgactcgtc aacatcaat acaacctatt    9480 aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc    10020
ggtgtaggtc gttcgctcca agctgggctg tgtgcacgaa ccccccgttc agcccgaccg    10080
ctgcgcctta tccggtaact atcgtcttga gtccaacccg gtaagacacg acttatcgcc    10140
actggcagca gccactggta acaggattag cagagcgagg tatgtaggcg gtgctacaga    10200
gttcttgaag tggtggccta actacggcta cactagaaga acagtatttg gtatctgcgc    10260
tctgctgaag ccagttacct tcggaaaaag agttggtagc tcttgatccg gcaaacaaac    10320
caccgctggt agcggtggtt tttttgtttg caagcagcag attacgcgca gaaaaaaagg    10380
atctcaagaa gatcctttga tcttttctac ggggtctgac gctcagtgga acgaaaactc    10440
```

```
                                                 -continued acgttaaggg attttggtca tgagattatc aaaaaggatc ttcacctaga tccttttgat    10500
ccggaatta                                                           10509

<210> SEQ ID NO 34
<211> LENGTH: 10509
<212> TYPE: DNA
<213> ORGANISM: Artificial Sequence
<220> FEATURE:
<223> OTHER INFORMATION: pKS101 (amiR0145)

<400> SEQUENCE: 34
attcctgtgg ttggcatgca catacaaatg gacgaacgga taaaccttt cacgcccttt      60 taaatatccg attattctaa taaacgctct tttctcttag gtttacccgc caatatatcc    120
tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccatttaaa tcaattgggc    300
gcgtacgtag cactagtgaa ttccggaccc aagctttggc agacaaagtg gcagacatac    360
tgtcccacaa atgaagatgg aatctgtaaa agaaaacgcg tgaaataatg cgtctgacaa    420
aggttaggtc ggctgccttt aatcaatacc aaagtggtcc ctaccacgat ggaaaaactg    480
tgcagtcggt ttggcttttt ctgacgaaca aataagattc gtggccgaca ggtgggggtc    540
caccatgtga aggcatcttc agactccaat aatggagcaa tgacgtaagg gcttacgaaa    600
taagtaaggg tagtttggga aatgtccact cacccgtcag tctataaata cttagcccct    660
ccctcattgt taagggagca aaatctcaga gagatagtcc tagagagaga aagagagcaa    720
gtagcctaga agtggatctc caccatggcc cagtccaagc acggcctgac caaggagatg    780
accatgaagt accgcatgga gggctgcgtg gacggccaca agttcgtgat caccggcgag    840
ggcatcggct accccttcaa gggcaagcag gccatcaacc tgtgcgtggt ggagggcggc    900
cccttgccct tcgccgagga catcttgtcc gccgccttca tgtacggcaa ccgcgtgttc    960
accgagtacc cccaggacat cgtcgactac ttcaagaact cctgccccgc cggctacacc    1020
tgggaccgct ccttcctgtt cgaggacggg gccgtgtgca tctgcaacgc cgacatcacc    1080
gtgagcgtgg aggagaactg catgtaccac gagtccaagt tctacggcgt gaacttcccc    1140
gccgacggcc ccgtgatgaa gaagatgacc gacaactggg agccctcctg cgagaagatc    1200
atccccgtgc ccaagcaggg catcttgaag ggcgacgtga gcatgtacct gctgctgaag    1260
gacggtggcc gcttgcgctg ccagttcgac accgtgtaca aggccaagtc cgtgccccgc    1320
aagatgcccg actggcactt catccagcac aagctgaccc gcgaggaccg cagcgacgcc    1380
aagaaccaga gtggcacctg accgagcac gccatcgcct ccggctccgc cttgccctgc    1440
tctagatccc cgaatttccc cgatcgttca acatttggc aataaagttt cttaagattg     1500
aatcctgttg ccgtcttgc gatgattatc atataatttc tgttgaatta cgttaagcat    1560
gtaataatta acatgtaatg catgacgtta tttatgagat gggtttttat gattagagtc    1620
ccgcaattat acatttaata cgcgatagaa aacaaaatat agcgcgcaaa ctaggataaa    1680
ttatcgcgcg cggtgtcatc tatgttacta gatcgcggac cctcatgagc ggagaattaa    1740
gggagtcacg ttatgacccc cgccgatgac gcgggacaag ccgttttacg tttggaactg    1800
acagaaccgc aacgaagctt tggcagacaa agtggcagac atactgtccc acaaatgaag    1860
atggaatctg taaaagaaaa cgcgtgaaat aatgcgtctg acaaaggtta ggtcggctgc    1920
```

```
ctttaatcaa taccaaagtg gtccctacca cgatggaaaa actgtgcagt cggtttggct    1980
ttttctgacg aacaaataag attcgtggcc gacaggtggg ggtccaccat gtgaaggcat    2040
cttcagactc caataatgga gcaatgacgt aagggcttac gaaataagta agggtagttt    2100
gggaaatgtc cactcacccg tcagtctata aatacttagc ccctccctca ttgttaaggg    2160
agcaaaatct cagagagata gtcctagaga gagaaagaga gcaagtagcc tagaagtgga    2220
tccagctcct tgttagcttg atgttgatct ggcaagtctc ttggatctca aatgccactg    2280
aacccttcgc cagatcaagt tcaagctaca acacgggttt gagctcttca tatgacgatc    2340
gttcaaacat ttggcaataa agtttcttaa gattgaatcc tgttgccggt cttgcgatga    2400
ttatcatata atttctgttg aattacgtta agcatgtaat aattaacatg taatgcatga    2460
cgttatttat gagatgggtt tttatgatta gagtcccgca attatacatt taatacgcga    2520
tagaaaacaa aatatagcgc gcaaactagg ataaattatc gcgcgcggtg tcatctatgt    2580
tactagatcg cggaccgaag cttgcatgcc tgcaggtcga ctctagagga tccggagcca    2640
agtctcataa acgccattgt ggaagaaagt cttgagttgg tggtaatgta acagagtagt    2700
aagaacagag aagagagaga gtgtgagata catgaattgt cgggcaacaa aaatcctgaa    2760
catcttattt tagcaaagag aaagagttcc gagtctgtag cagaagagtg aggagaaatt    2820
taagctcttg gacttgtgaa ttgttccgcc tcttgaatac ttcttcaatc ctcatatatt    2880
cttcttctat gttacctgaa aaccggcatt taatctcgcg ggtttattcc ggttcaacat    2940
ttttttgtt ttgagttatt atctgggctt aataacgcag gcctgaaata aattcaaggc    3000
ccaactgttt tttttttaa gaagttgctg ttaaaaaaaa aaaagggaa ttaacaacaa    3060
caacaaaaaa agataaagaa aataataaca attactttaa ttgtagacta aaaaaacata    3120
gatttttatca tgaaaaaaag agaaaagaaa taaaaacttg gatcaaaaaa aaaacataca    3180
gatcttctaa ttattaactt ttcttaaaaa ttaggtcctt tttcccaaca attaggttta    3240
gagttttgga attaaaccaa aaagattgtt ctaaaaaata ctcaaatttg gtagataagt    3300
ttccttattt taattagtca atggtagata cttttttttc ttttctttat tagagtagat    3360
tagaatcttt tatgccaagt attgataaat taaatcaaga agataaaacta tcataatcaa    3420
catgaaatta aaagaaaaat ctcatatata gtattagtat tctctatata tattatgatt    3480
gcttattctt aatgggttgg gttaaccaag acatagtctt aatggaaaga atctttttg    3540
aacttttttcc ttattgatta aattcttcta tagaaaagaa agaaattatt tgaggaaaag    3600
tatatacaaa aagaaaaata gaaaaatgtc agtgaagcag atgtaatgga tgacctaatc    3660
caaccaccac cataggatgt ttctacttga gtcggtcttt taaaaacgca cggtggaaaa    3720
tatgacacgt atcatatgat tccttccttt agtttcgtga taataatcct caactgatat    3780
cttccttttt ttgttttggc taaagatatt ttattctcat taatagaaaa gacggttttg    3840
ggcttttggt ttgcgatata aagaagacct tcgtgtggaa gataataatt catcctttcg    3900
tctttttctg actcttcaat ctctcccaaa gcctaaagcg atctctgcaa atctctcgcg    3960
actctctctt tcaaggtata ttttctgatt cttttttgttt ttgattcgta tctgatctcc    4020
aattttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200
tttttgtgtt tctttgttc gattctctct gttttaggtt tcttatgttt agatccgttt    4260
ctctttggtg ttgttttgat ttctcttacg gcttttgatt tggtatatgt tcgctgattg    4320
```

```
gtttctactt gttctattgt tttatttcag gtggatccca ccatgtctcc ggagaggaga    4380
ccagttgaga ttaggccagc tacagcagct gatatggccg cggtttgtga tatcgttaac    4440
cattacattg agacgtctac agtgaacttt aggacagagc cacaaacacc acaagagtgg    4500
attgatgatc tagagaggtt gcaagataga tacccttggt tggttgctga ggttgagggt    4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac    5280 cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
gacgcacgac gccggggcga gaccataggc gatctcctaa atcaatagta gctgtaacct    6540
cgaagcgttt cacttgtaac aacgattgag aatttttgtc ataaaattga aatacttggt    6600
tcgcattttt gtcatccgcg gtcagccgca attctgacga actgcccatt tagctggaga    6660
```

```
tgattgtaca tccttcacgt gaaaatttct caagcgctgt gaacaagggt tcagatttta   6720
gattgaaagg tgagccgttg aaacacgttc ttcttgtcga tgacgacgtc gctatgcggc   6780
atcttattat tgaataccct acgatccacg ccttcaaagt gaccgcggta gccgacagca   6840
cccagttcac aagagtactc tcttccgcga cggtcgatgt cgtggttgtt gatctagatt   6900
taggtcgtga agatgggctc gagatcgttc gtaatctggc ggcaaagtct gatattccaa   6960
tcataattat cagtggcgac cgccttgagg agacggataa agttgttgca ctcgagctag   7020
gagcaagtga ttttatcgct aagccgttca gtatcagaga gtttctagca cgcattcggg   7080
ttgccttgcg cgtgcgcccc aacgttgtcc gctccaaaga ccgacggtct ttttgtttta   7140
ctgactggac acttaatctc aggcaacgtc gcttgatgtc cgaagctggc ggtgaggtga   7200
aacttacggc aggtgagttc aatcttctcc tcgcgttttt agagaaaccc cgcgacgttc   7260
tatcgcgcga gcaacttctc attgccagtc gagtacgcga cgaggaggtt tatgacagga   7320
gtatagatgt tctcattttg aggctgcgcc gcaaacttga ggcagatccg tcaagccctc   7380
aactgataaa aacagcaaga ggtgccggtt atttctttga cgcggacgtg caggtttcgc   7440 acgggggac gatggcagcc tgagccaatt cccagatccc cgaggaatcg gcgtgagcgg   7500
tcgcaaacca tccggcccgg tacaaatcgg cgcggcgctg ggtgatgacc tggtggagaa   7560
gttgaaggcc gcgcaggccg cccagcggca acgcatcgag gcagaagcac gccccggtga   7620
atcgtggcaa gcgccgctg atcgaatccg caaagaatcc cggcaaccgc cggcagccgg   7680
tgcgccgtcg attaggaagc cgcccaaggg cgacgagcaa ccagattttt tcgttccgat   7740
gctctatgac gtgggcaccc gcgatagtcg cagcatcatg gacgtggccg ttttccgtct   7800
gtcgaagcgt gaccgacgag ctggcgaggt gatccgctac gagcttccag acgggcacgt   7860
agaggtttcc gcagggccgg ccggcatggc cagtgtgtgg gattacgacc tggtactgat   7920 ggcggttcc catctaaccg aatccatgaa ccgataccgg gaagggaagg gagacaagcc   7980
cggccgcgtg ttccgtccac acgttgcgga cgtactcaag ttctgccggc gagccgatgg   8040
cggaaagcag aaagacgacc tggtagaaac ctgcattcgg ttaaacacca cgcacgttgc   8100
catgcagcgt acgaagaagg ccaagaacgg ccgcctggtg acggtatccg agggtgaagc   8160
cttgattagc cgctacaaga tcgtaaagag cgaaaccggg cggccggagt acatcgagat   8220
cgagctagct gattggatgt accgcgagat cacagaaggc aagaacccgg acgtgctgac   8280
ggttcacccc gattactttt tgatcgatcc cggcatcggc cgttttctct accgcctggc   8340
acgccgcgcc gcaggcaagg cagaagccag atggttgttc aagacgatct acgaacgcag   8400
tggcagcgcc ggagagttca agaagttctg tttcaccgtg cgcaagctga tcgggtcaaa   8460
tgacctgccg gagtacgatt tgaaggagga ggcggggcag gctggcccga tcctagtcat   8520
gcgctaccgc aacctgatcg agggcgaagc atccgccggt tcctaatgta cggagcagat   8580
gctagggcaa attgccctag caggggaaaa aggtcgaaaa ggtctctttc ctgtggatag   8640
cacgtacatt gggaacccaa agccgtacat tgggaaccgg aacccgtaca ttgggaaccc   8700
aaagccgtac attgggaacc ggtcacacat gtaagtgact gatataaaag agaaaaaagg   8760
cgatttttcc gcctaaaact cttaaaaact tattaaaact cttaaaaccc gcctggcctg   8820
tgcataactg tctggccagc gcacagccga agagctgcaa aaagcgccta cccttcggtc   8880
gctgcgctcc ctacgccccg ccgcttcgcg tcggcctatc gcggccgctg gccgctcaaa   8940
aatggctggc ctacgccag gcaatctacc agggcgcgga caagccgcgc cgtcgccact   9000
cgaccgccgg cgctgaggtc tgcctcgtga agaaggtgtt gctgactcat accaggcctg   9060
```

```
aatcgcccca tcatccagcc agaaagtgag ggagccacgg ttgatgagag ctttgttgta    9120
ggtggaccag ttggtgattt tgaacttttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360 tattttgaa aaagccgttt ctgtaatgaa ggagaaaact caccgaggca gttccatagg     9420
atggcaagat cctggtatcg gtctgcgatt ccgactcgtc caacatcaat acaacctatt    9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc    10020
ggtgtaggtc gttcgctcca agctgggctg tgtgcacgaa ccccccgttc agcccgaccg    10080
ctgcgcctta tccggtaact atcgtcttga gtccaacccg gtaagacacg acttatcgcc    10140
actggcagca gccactggta acaggattag cagagcgagg tatgtaggcg gtgctacaga    10200
gttcttgaag tggtggccta actacggcta cactagaaga acagtatttg gtatctgcgc    10260
tctgctgaag ccagttacct tcggaaaaag agttggtagc tcttgatccg gcaaacaaac    10320
caccgctggt agcggtggtt tttttgtttg caagcagcag attacgcgca gaaaaaaagg    10380
atctcaagaa gatcctttga tcttttctac ggggtctgac gctcagtgga acgaaaactc    10440
acgttaaggg attttggtca tgagattatc aaaaaggatc ttcacctaga tccttttgat    10500
ccggaatta                                                           10509
```

<210> SEQ ID NO 35
<211> LENGTH: 10509
<212> TYPE: DNA
<213> ORGANISM: Artificial Sequence
<220> FEATURE:
<223> OTHER INFORMATION: pKS102 (amiR0192)

<400> SEQUENCE: 35

```
attcctgtgg ttggcatgca catacaaatg gacgaacgga taaacctttt cacgcccttt      60
taaatatccg attattctaa taaacgctct tttctcttag gtttaccgc caatatatcc       120 tgtcaaacac tgatagttta aactgaaggc gggaaacgac aatctgatca tgagcggaga     180
attaagggag tcacgttatg acccccgccg atgacgcggg acaagccgtt ttacgtttgg     240
aactgacaga accgcaacgc tgcaggaatt ggccgcagcg gccatttaaa tcaattgggc     300
gcgtacgtag cactagtgaa ttccggaccc aagcttggc agacaaagtg gcagacatac      360
tgtcccacaa atgaagatgg aatctgtaaa agaaaacgcg tgaaataatg cgtctgacaa     420
aggttaggtc ggctgccttt aatcaatacc aaagtggtcc ctaccacgat ggaaaaactg    480
tgcagtcggt ttggcttttt ctgacgaaca aataagattc gtggccgaca ggtggggtc      540
```

-continued

```
caccatgtga aggcatcttc agactccaat aatggagcaa tgacgtaagg gcttacgaaa    600
taagtaaggg tagtttggga aatgtccact cacccgtcag tctataaata cttagcccct    660
ccctcattgt taagggagca aaatctcaga gagatagtcc tagagagaga aagagagcaa    720
gtagcctaga agtggatctc caccatggcc cagtccaagc acggcctgac caaggagatg    780
accatgaagt accgcatgga gggctgcgtg gacggccaca agttcgtgat caccggcgag    840
ggcatcggct accccttcaa gggcaagcag gccatcaacc tgtgcgtggt ggagggcggc    900
cccttgccct tcgccgagga catcttgtcc gccgccttca tgtacggcaa ccgcgtgttc    960
accgagtacc cccaggacat cgtcgactac ttcaagaact cctgccccgc cggctacacc   1020
tgggaccgct ccttcctgtt cgaggacggc gccgtgtgca tctgcaacgc cgacatcacc   1080
gtgagcgtgg aggagaactg catgtaccac gagtccaagt tctacggcgt gaacttcccc   1140
gccgacggcc ccgtgatgaa gaagatgacc gacaactggg agccctcctg cgagaagatc   1200
atccccgtgc ccaagcaggg catcttgaag ggcgacgtga gcatgtacct gctgctgaag   1260
gacggtggcc gcttgcgctg ccagttcgac accgtgtaca aggccaagtc cgtgccccgc   1320
aagatgcccg actggcactt catccagcac aagctgaccc gcgaggaccg cagcgacgcc   1380
aagaaccaga agtggcacct gaccgagcac gccatcgcct ccggctccgc cttgccctgc   1440
tctagatccc cgaatttccc cgatcgttca acatttggc aataaagttt cttaagattg   1500
aatcctgttg ccggtcttgc gatgattatc atataatttc tgttgaatta cgttaagcat   1560
gtaataatta acatgtaatg catgacgtta tttatgagat gggttttat gattagagtc   1620
ccgcaattat acatttaata cgcgatagaa acaaaatat agcgcgcaaa ctaggataaa   1680
ttatcgcgcg cggtgtcatc tatgttacta gatcgcggac cctcatgagc ggagaattaa   1740
gggagtcacg ttatgacccc cgccgatgac gcgggacaag ccgttttacg tttgaactg    1800
acagaaccgc aacgaagctt tggcagacaa agtggcagac atactgtccc acaaatgaag   1860
atggaatctg taaagaaaa cgcgtgaaat aatgcgtctg acaaaggtta ggtcggctgc    1920
ctttaatcaa taccaaagtg gtccctacca cgatggaaaa actgtgcagt cggtttggct   1980
ttttctgacg aacaaataag attcgtggcc gacaggtggg ggtccaccat gtgaaggcat   2040
cttcagactc caataatgga gcaatgacgt aagggcttac gaaataagta agggtagttt   2100
gggaaatgtc cactcacccg tcagtctata aatacttagc ccctccctca ttgttaaggg   2160
agcaaaatct cagagagata gtcctagaga gagaaagaga gcaagtagcc tagaagtgga   2220
tccagctcct tgttaggttg gtgttgatct ggcaagtctc ttggatctca aatgccactg   2280
aacccttgc cagatcaagt ccaacctaca acacgggttt gagctcttca tatgacgatc    2340
gttcaaacat ttggcaataa agtttcttaa gattgaatcc tgttgccggt cttgcgatga   2400
ttatcatata atttctgttg aattacgtta agcatgtaat aattaacatg taatgcatga   2460
cgttatttat gagatgggtt tttatgatta gagtcccgca attatacatt taatacgcga   2520
tagaaaacaa aatatagcgc gcaaactagg ataaattatc gcgcgcggtg tcatctatgt   2580
tactagatcg cggaccgaag cttgcatgcc tgcaggtcga ctctagagga tccggagcca   2640
agtctcataa acgccattgt ggaagaaagt cttgagttgg tggtaatgta acagagtagt   2700
aagaacagag aagagagaga gtgtgagata catgaattgt cgggcaacaa aaatcctgaa   2760
catcttattt tagcaaagag aaagagttcc gagtctgtag cagaagagtg aggagaaatt   2820
taagctcttg gacttgtgaa ttgttccgcc tcttgaatac ttcttcaatc ctcatatatt   2880
cttcttctat gttacctgaa aaccggcatt taatctcgcg ggtttattcc ggttcaacat   2940
```

```
ttttttttgtt ttgagttatt atctgggctt aataacgcag gcctgaaata aattcaaggc    3000
ccaactgttt ttttttttaa gaagttgctg ttaaaaaaaa aaaagggaa ttaacaacaa     3060 caacaaaaaa agataaagaa ataataaca attactttaa ttgtagacta aaaaaacata    3120
gattttatca tgaaaaaaag agaaaagaaa taaaaacttg gatcaaaaaa aaaacataca    3180
gatcttctaa ttattaactt ttcttaaaaa ttaggtcctt tttcccaaca attaggttta    3240
gagttttgga attaaaccaa aaagattgtt ctaaaaaata ctcaaatttg gtagataagt    3300
ttccttattt taattagtca atggtagata cttttttttc ttttctttat tagagtagat    3360
tagaatcttt tatgccaagt attgataaat taaatcaaga agataaacta tcataatcaa    3420
catgaaatta aaagaaaaat ctcatatata gtattagtat tctctatata tattatgatt    3480
gcttattctt aatgggttgg gttaaccaag acatagtctt aatggaaaga atctttttg     3540 aactttttcc ttattgatta aattcttcta tagaaaagaa agaaattatt tgaggaaaag    3600
tatatacaaa aagaaaaata gaaaaatgtc agtgaagcag atgtaatgga tgacctaatc    3660
caaccaccac cataggatgt ttctacttga gtcggtcttt taaaaacgca cggtggaaaa    3720
tatgacacgt atcatatgat tccttccttt agtttcgtga taataatcct caactgatat    3780 cttcctttt ttgttttggc taaagatatt ttattctcat taatagaaaa gacggttttg     3840
ggcttttggt ttgcgatata aagaagacct tcgtgtggaa gataataatt catcctttcg    3900 tcttttctg actcttcaat ctctcccaaa gcctaaagcg atctctgcaa atctctcgcg     3960
actctctctt tcaaggtata ttttctgatt cttttttgttt ttgattcgta tctgatctcc   4020
aatttttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200
tttttgtgtt ttcttttgttc gattctctct gttttaggtt tcttatgttt agatccgttt    4260
ctctttggtg ttgttttgat ttctcttacg gcttttgatt tggtatatgt tcgctgattg   4320
gtttctactt gttctattgt tttatttcag gtggatccca ccatgtctcc ggagaggaga    4380
ccagttgaga ttaggccagc tacagcagct gatatgccg cggtttgtga tatcgttaac     4440
cattacattg agacgtctac agtgaacttt aggacagagc cacaaacacc acaagagtgg    4500
attgatgatc tagagaggtt gcaagataga taccccttggt tggttgctga ggttgagggt   4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat ttgtttacac    5280
```

```
cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata cgcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatgagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
gacgcacgac gccggggcga gaccataggc gatctcctaa atcaatagta gctgtaacct    6540
cgaagcgttt cacttgtaac aacgattgag aattttttgtc ataaaattga aatacttggt    6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaacacgttc ttcttgtcga tgacgacgtc gctatgcggc    6780
atcttattat tgaataccct acgatccacg ccttcaaagt gaccgcggta gccgacagca    6840
cccagttcac aagagtactc tcttccgcga cggtcgatgt cgtggttgtt gatctagatt    6900
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga ttttatcgct aagccgttca gtatcagaga gtttctagca cgcattcggg    7080
ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttctttga cgcggacgtg caggtttcgc    7440
acgggggac gatggcagcc tgagccaatt cccagatccc cgaggaatcg gcgtgagcgg    7500
tcgcaaacca tccggcccgg tacaaatcgg cgcggcgctg ggtgatgacc tggtggagaa    7560
gttgaaggcc gcgcaggccg cccagcggca acgcatcgag gcagaagcac gccccggtga    7620
atcgtggcaa gcggccgctg atcgaatccg caaagaatcc cggcaaccgc cggcagccgg    7680
```

-continued

```
tgcgccgtcg attaggaagc cgcccaaggg cgacgagcaa ccagattttt tcgttccgat    7740
gctctatgac gtgggcaccc gcgatagtcg cagcatcatg gacgtggccg ttttccgtct    7800
gtcgaagcgt gaccgacgag ctggcgaggt gatccgctac gagcttccag acgggcacgt    7860
agaggtttcc gcagggccgg ccggcatggc cagtgtgtgg gattacgacc tggtactgat    7920
ggcggtttcc catctaaccg aatccatgaa ccgataccgg gaagggaagg gagacaagcc    7980
cggccgcgtg ttccgtccac acgttgcgga cgtactcaag ttctgccggc gagccgatgg    8040
cggaaagcag aaagacgacc tggtagaaac ctgcattcgg ttaaacacca cgcacgttgc    8100
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760
cgatttttcc gcctaaaact ctttaaaact tattaaaact cttaaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacgccagg caatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccag ttggtgattt tgaacttttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tatttttgaa aaagccgttt ctgtaatgaa ggagaaaact caccgaggca gttccatagg    9420
atggcaagat cctggtatcg gtctgcgatt ccgactcgtc caacatcaat acaacctatt    9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960 cttctccct tcgggaagcg tggcgctttc tcatagctca cgctgtaggt atctcagttc   10020
```

```
ggtgtaggtc gttcgctcca agctgggctg tgtgcacgaa ccccccgttc agcccgaccg   10080
ctgcgcctta tccggtaact atcgtcttga gtccaacccg gtaagacacg acttatcgcc   10140
actggcagca gccactggta acaggattag cagagcgagg tatgtaggcg gtgctacaga   10200
gttcttgaag tggtggccta actacggcta cactagaaga acagtatttg gtatctgcgc   10260
tctgctgaag ccagttacct tcggaaaaag agttggtagc tcttgatccg gcaaacaaac   10320
caccgctggt agcggtggtt ttttgtttg caagcagcag attacgcgca gaaaaaaagg   10380
atctcaagaa gatcctttga tcttttctac ggggtctgac gctcagtgga acgaaaactc   10440
acgttaaggg attttggtca tgagattatc aaaaaggatc ttcacctaga tccttttgat   10500
ccggaatta                                                           10509

<210> SEQ ID NO 36
<211> LENGTH: 10509
<212> TYPE: DNA
<213> ORGANISM: Artificial Sequence
<220> FEATURE:
<223> OTHER INFORMATION: pKS105 (amiR0243)

<400> SEQUENCE: 36
attcctgtgg ttggcatgca catacaaatg gacgaacgga taaacctttt cacgccctttt   60 taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg acccccgccg atgacgcggg acaagccgtt ttacgtttgg   240
aactgacaga accgcaacgc tgcaggaatt ggccgcagcg ccatttaaa tcaattgggc   300 gcgtacgtag cactagtgaa ttccggaccc aagctttggc agacaaagtg gcagacatac   360
tgtcccacaa atgaagatgg aatctgtaaa agaaaacgcg tgaaataatg cgtctgacaa   420
aggttaggtc ggctgccttt aatcaatacc aaagtggtcc ctaccacgat ggaaaaactg   480
tgcagtcggt ttggcttttt ctgacgaaca aataagattc gtggccgaca ggtgggggtc   540
caccatgtga aggcatcttc agactccaat aatggagcaa tgacgtaagg gcttacgaaa   600
taagtaaggg tagtttggga aatgtccact cacccgtcag tctataaata cttagccccct   660 ccctcattgt taagggagca aaatctcaga gagatagtcc tagagagaga aagagagcaa   720
gtagcctaga agtggatctc caccatggcc cagtccaagc acggcctgac caaggagatg   780
accatgaagt accgcatgga gggctgcgtg gacggccaca gttcgtgat caccggcgag   840 ggcatcggct acccttcaa gggcaagcag gccatcaacc tgtgcgtggt ggagggcggc   900
cccttgccct cgccgagga catcttgtcc gccgccttca tgtacggcaa ccgcgtgttc   960
accgagtacc cccaggacat cgtcgactac ttcaagaact cctgccccgc cggctacacc   1020
tgggaccgct ccttcctgtt cgaggacggc gccgtgtgca tctgcaacgc cgacatcacc   1080
gtgagcgtgg aggagaactg catgtaccac gagtccaagt tctacggcgt gaacttcccc   1140
gccgacggcc ccgtgatgaa gaagatgacc gacaactggg agccctcctg cgagaagatc   1200
atccccgtgc ccaagcaggg catcttgaag ggcgacgtga gcatgtacct gctgctgaag   1260
gacggtggcc gcttgcgctg ccagttcgac accgtgtaca aggccaagtc cgtgcccgc    1320 aagatgcccg actggcactt catccagcac aagctgaccc gcgaggaccg cagcgacgcc   1380
aagaaccaga agtggcacct gaccgagcac gccatcgcct ccggctccgc cttgccctgc   1440
tctagatccc cgaatttccc cgatcgttca aacatttggc aataaagttt cttaagattg   1500
aatcctgttg ccggtcttgc gatgattatc atataatttc tgttgaatta cgttaagcat   1560
```

-continued

```
gtaataatta acatgtaatg catgacgtta tttatgagat gggtttttat gattagagtc    1620
ccgcaattat acatttaata cgcgatagaa aacaaaatat agcgcgcaaa ctaggataaa    1680
ttatcgcgcg cggtgtcatc tatgttacta gatcgcggac cctcatgagc ggagaattaa    1740
gggagtcacg ttatgacccc cgccgatgac gcgggacaag ccgttttacg tttggaactg    1800
acagaaccgc aacgaagctt tggcagacaa agtggcagac atactgtccc acaaatgaag    1860
atggaatctg taaagaaaaa cgcgtgaaat aatgcgtctg acaaaggtta ggtcggctgc    1920
ctttaatcaa taccaaagtg gtccctacca cgatggaaaa actgtgcagt cggtttggct    1980
ttttctgacg aacaaataag attcgtggcc gacaggtggg ggtccaccat gtgaaggcat    2040
cttcagactc caataatgga gcaatgacgt aagggcttac gaaataagta agggtagttt    2100
gggaaatgtc cactcacccg tcagtctata aatacttagc ccctccctca ttgttaaggg    2160
agcaaaatct cagagagata gtcctagaga gagaaagaga gcaagtagcc tagaagtgga    2220
tccagctcct tgttatcttc gtgttgatct ggcaagtctc ttggatctca aatgccactg    2280
aacccttgc cagatcaagt cgaagataca acacgggttt gagctcttca tatgacgatc    2340
gttcaaacat ttggcaataa agtttcttaa gattgaatcc tgttgccggt cttgcgatga    2400
ttatcatata atttctgttg aattacgtta agcatgtaat aattaacatg taatgcatga    2460
cgttatttat gagatgggtt tttatgatta gagtcccgca attatacatt taatacgcga    2520
tagaaaacaa aatatagcgc gcaaactagg ataaattatc gcgcgcggtg tcatctatgt    2580
tactagatcg cggaccgaag cttgcatgcc tgcaggtcga ctctagagga tccggagcca    2640
agtctcataa acgccattgt ggaagaaagt cttgagttgg tggtaatgta acagagtagt    2700
aagaacagag aagagagaga gtgtgagata catgaattgt cgggcaacaa aaatcctgaa    2760
catcttattt tagcaaagag aaagagttcc gagtctgtag cagaagagtg aggagaaatt    2820
taagctcttg gacttgtgaa ttgttccgcc tcttgaatac ttcttcaatc ctcatatatt    2880
cttcttctat gttacctgaa aaccggcatt taatctcgcg ggtttattcc ggttcaacat    2940
ttttttttgtt ttgagttatt atctgggctt aataacgcag gcctgaaata aattcaaggc    3000
ccaactgttt ttttttttaa gaagttgctg ttaaaaaaaa aaaagggaa ttaacaacaa    3060
caacaaaaaa agataaagaa aataataaca attactttaa ttgtagacta aaaaaacata    3120
gattttatca tgaaaaaaag agaaagaaa taaaaacttg gatcaaaaaa aaaacataca    3180
gatcttctaa ttattaactt ttcttaaaaa ttaggtcctt tttcccaaca attaggttta    3240
gagttttgga attaaaccaa aaagattgtt ctaaaaaata ctcaaatttg gtagataagt    3300
ttccttattt taattagtca atggtagata ctttttttttc ttttctttat tagagtagat    3360
tagaatcttt tatgccaagt attgataaat taaatcaaga agataaaacta tcataatcaa    3420
catgaaatta aaagaaaaat ctcatatata gtattagtat tctctatata tattatgatt    3480
gcttattctt aatgggttgg gttaaccaag acatagtctt aatggaaaga atcttttttg    3540
aacttttttcc ttattgatta aattcttcta tagaaaagaa agaaattatt tgaggaaaag    3600
tatatacaaa aagaaaaata gaaaaatgtc agtgaagcag atgtaatgga tgacctaatc    3660
caaccaccac cataggatgt ttctacttga gtcggtcttt taaaaacgca cggtggaaaa    3720
tatgacacgt atcatatgat tccttccttt agtttcgtga taataatcct caactgatat    3780
cttccttttt ttgttttggc taaagatatt ttattctcat taatagaaaa gacggttttg    3840
ggcttttggt ttgcgatata aagaagacct tcgtgtggaa gataataatt catcctttcg    3900
```

```
tcttttctg actcttcaat ctctcccaaa gcctaaagcg atctctgcaa atctctcgcg    3960
actctctctt tcaaggtata ttttctgatt cttttgttt ttgattcgta tctgatctcc    4020 aattttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200
tttttgtgtt ttcttttgttc gattctctct gttttaggtt tcttatgttt agatccgttt    4260
ctctttggtg ttgttttgat ttctcttacg gcttttgatt tggtatatgt tcgctgattg    4320
gtttctactt gttctattgt tttatttcag gtggatccca ccatgtctcc ggagaggaga    4380
ccagttgaga ttaggccagc tacagcagct gatatggccg cggtttgtga tatcgttaac    4440
cattacattg agacgtctac agtgaacttt aggacagagc cacaaacacc acaagagtgg    4500
attgatgatc tagagaggtt gcaagataga taccccttggt tggttgctga ggttgagggt    4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggttttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac    5280 cacaatatat cctgccacca gccagccaac agctcccgga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaattc acacaggaaa    5640 cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
```

```
cagtatcagc ccgtcatact tgaagctagg caggcttatc ttggacaaga agatcgcttg   6360
gcctcgcgcg cagatcagtt ggaagaattt gttcactacg tgaaaggcga gatcaccaaa   6420
gtagtcggca aataaagctc tagtggatct ccgtacccccc ggggatctg ctcgcggcg   6480 gacgcacgac gccggggcga gaccataggc gatctcctaa atcaatagta gctgtaacct   6540
cgaagcgttt cacttgtaac aacgattgag aattttttgtc ataaaattga aatacttggt   6600
tcgcattttt gtcatccgcg gtcagccgca attctgacga actgcccatt tagctggaga   6660
tgattgtaca tccttcacgt gaaaatttct caagcgctgt gaacaagggt tcagattta    6720 gattgaaagg tgagccgttg aaacacgttc ttcttgtcga tgacgacgtc gctatgcggc   6780
atcttattat tgaataccttt acgatccacg ccttcaaagt gaccgcggta gccgacagca   6840
cccagttcac aagagtactc tcttccgcga cggtcgatgc cgtggttgtt gatctagatt   6900
taggtcgtga agatgggctc gagatcgttc gtaatctggc ggcaaagtct gatattccaa   6960
tcataattat cagtggcgac cgccttgagg agacggataa agttgttgca ctcgagctag   7020
gagcaagtga ttttatcgct aagccgttca gtatcagaga gtttctagca cgcattcggg   7080
ttgccttgcg cgtgcgcccc aacgttgtcc gctccaaaga ccgacggtct ttttgttta    7140 ctgactggac acttaatctc aggcaacgtc gcttgatgtc cgaagctggc ggtgaggtga   7200
aacttacggc aggtgagttc aatcttctcc tcgcgttttt agagaaaccc cgcgacgttc   7260
tatcgcgcga gcaacttctc attgccagtc gagtacgcga cgaggaggtt tatgacagga   7320
gtatagatgt tctcattttg aggctgcgcc gcaaacttga ggcagatccg tcaagccctc   7380
aactgataaa aacagcaaga ggtgccggtt atttctttga cgcggacgtg caggtttcgc   7440 acgggggggac gatggcagcc tgagccaatt cccagatccc cgaggaatcg gcgtgagcgg   7500
tcgcaaacca tccggcccgg tacaaatcgg cgcggcgctg ggtgatgacc tggtggagaa   7560
gttgaaggcc gcgcaggccg cccagcggca acgcatcgag gcagaagcac gccccggtga   7620
atcgtggcaa gcggccgctg atcgaatccg caaagaatcc cggcaaccgc cggcagccgg   7680
tgcgccgtcg attaggaagc cgcccaaggg cgacgagcaa ccagattttt tcgttccgat   7740
gctctatgac gtgggcaccc gcgatagtcg cagcatcatg gacgtggccg tttttccgtct   7800 gtcgaagcgt gaccgacgag ctggcgaggt gatccgctac gagcttccag acgggcacgt   7860
agaggtttcc gcagggccgg ccggcatggc cagtgtgtgg gattacgacc tggtactgat   7920 ggcggttttcc catctaaccg aatccatgaa ccgataccgg gaagggaagg gagacaagcc   7980
cggccgcgtg ttccgtccac acgttgcgga cgtactcaag ttctgccggc gagccgatgg   8040
cggaaagcag aaagacgacc tggtagaaac ctgcattcgg ttaaacacca cgcacgttgc   8100
catgcagcgt acgaagaagg ccaagaacgg ccgcctggtg acggtatccg agggtgaagc   8160
cttgattagc cgctacaaga tcgtaaagag cgaaaccggg cggccggagt acatcgagat   8220
cgagctagct gattggatgt accgcgagat cacagaaggc aagaaccggg acgtgctgac   8280
ggttcacccc gattactttt tgatcgatcc cggcatcggc cgttttctct accgcctggc   8340
acgccgcgcc gcaggcaagg cagaagccag atggttgttc aagacgatct acgaacgcag   8400
tggcagcgcg ggagagttca agaagttctg tttcaccgtg cgcaagctga tcgggtcaaa   8460
tgacctgccg gagtacgatt tgaaggagga ggcggggcag gctggcccga tcctagtcat   8520
gcgctaccgc aacctgatcg agggcgaagc atccgccggt tcctaatgta cggagcagat   8580
gctagggcaa attgccctag caggggaaaa aggtcgaaaa ggtctctttc ctgtggatag   8640
```

```
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760
cgattttttcc gcctaaaact cttaaaact tattaaaact cttaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacgccag gcaatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccag ttggtgattt tgaactttg ctttgccacg aacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tattttgaa aaagccgttt ctgtaatgaa ggagaaaact caccgaggca gttccatagg    9420
atggcaagat cctggtatcg gtctgcgatt ccgactcgtc caacatcaat acaacctatt    9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc    10020
ggtgtaggtc gttcgctcca agctgggctg tgtgcacgaa ccccccgttc agcccgaccg    10080
ctgcgcctta tccggtaact atcgtcttga gtccaacccg gtaagacacg acttatcgcc    10140
actggcagca gccactggta acaggattag cagagcgagg tatgtaggcg gtgctacaga    10200
gttcttgaag tggtggccta actacggcta cactagaaga acagtatttg gtatctgcgc    10260
tctgctgaag ccagttacct tcggaaaaag agttggtagc tcttgatccg gcaaacaaac    10320
caccgctggt agcggtggtt ttttgtttg caagcagcag attacgcgca gaaaaaaagg    10380
atctcaagaa gatcctttga tcttttctac ggggtctgac gctcagtgga acgaaaactc    10440
acgttaaggg attttggtca tgagattatc aaaaaggatc ttcacctaga tccttttgat    10500
ccggaatta                                                           10509
```

<210> SEQ ID NO 37
<211> LENGTH: 10509
<212> TYPE: DNA
<213> ORGANISM: Artificial Sequence
<220> FEATURE:
<223> OTHER INFORMATION: pKS106 (amiR0309)

<400> SEQUENCE: 37

```
attcctgtgg ttggcatgca catacaaatg gacgaacgga taaacctttt cacgcccttt      60
taaatatccg attattctaa taaacgctct tttctcttag gttacccgc caatatatcc     120
tgtcaaacac tgatagttta aactgaaggc gggaaacgac aatctgatca tgagcggaga    180
```

```
attaagggag tcacgttatg accccccgccg atgacgcggg acaagccgtt ttacgtttgg    240
aactgacaga accgcaacgc tgcaggaatt ggccgcagcg gccatttaaa tcaattgggc    300
gcgtacgtag cactagtgaa ttccggaccc aagctttggc agacaaagtg gcagacatac    360
tgtcccacaa atgaagatgg aatctgtaaa agaaaacgcg tgaaataatg cgtctgacaa    420
aggttaggtc ggctgccttt aatcaatacc aaagtggtcc ctaccacgat ggaaaaactg    480
tgcagtcggt ttggctttt ctgacgaaca aataagattc gtggccgaca ggtgggggtc    540
caccatgtga aggcatcttc agactccaat aatggagcaa tgacgtaagg gcttacgaaa    600
taagtaaggg tagtttggga aatgtccact cacccgtcag tctataaata cttagcccct    660
ccctcattgt taagggagca aaatctcaga gagatagtcc tagagagaga aagagagcaa    720
gtagcctaga agtggatctc caccatggcc cagtccaagc acggcctgac caaggagatg    780
accatgaagt accgcatgga gggctgcgtg gacggccaca agttcgtgat caccggcgag    840
ggcatcggct accccttcaa gggcaagcag gccatcaacc tgtgcgtggt ggagggcggc    900
cccttgccct tcgccgagga catcttgtcc gccgccttca tgtacggcaa ccgcgtgttc    960
accgagtacc cccaggacat cgtcgactac ttcaagaact cctgccccgc cggctacacc   1020
tgggaccgct ccttcctgtt cgaggacggc gccgtgtgca tctgcaacgc cgacatcacc   1080
gtgagcgtgg aggagaactg catgtaccac gagtccaagt tctacggcgt gaacttcccc   1140
gccgacggcc ccgtgatgaa gaagatgacc gacaactggg agccctcctg cgagaagatc   1200
atccccgtgc ccaagcaggg catcttgaag gcgacgtga gcatgtacct gctgctgaag   1260
gacggtggcc gcttgcgctg ccagttcgac accgtgtaca aggccaagtc cgtgccccgc   1320
aagatgcccg actggcactt catccagcac aagctgaccc gcgaggaccg cagcgacgcc   1380
aagaaccaga agtggcacct gaccgagcac gccatcgcct ccggctccgc cttgccctgc   1440
tctagatccc cgaatttccc cgatcgttca acatttggc aataaagttt cttaagattg   1500
aatcctgttg ccggtcttgc gatgattatc atataaattc tgttgaatta cgttaagcat   1560
gtaataatta acatgtaatg catgacgtta tttatgagat gggtttttat gattagagtc   1620
ccgcaattat acatttaata cgcgatagaa acaaaatat agcgcgcaaa ctaggataaa   1680
ttatcgcgcg cggtgtcatc tatgttacta gatcgcggac cctcatgagc ggagaattaa   1740
gggagtcacg ttatgacccc cgccgatgac gcgggacaag ccgttttacg tttgaactg   1800 acagaaccgc aacgaagctt tggcagacaa agtggcagac atactgtccc acaaatgaag   1860
atggaatctg taaagaaaa cgcgtgaaat aatgcgtctg acaaaggtta ggtcggctgc   1920
ctttaatcaa taccaaagtg gtccctacca cgatggaaaa actgtgcagt cggtttggct   1980
ttttctgacg aacaaataag attcgtggcc gacaggtggg ggtccaccat gtgaaggcat   2040
cttcagactc caataatgga gcaatgacgt aagggcttac gaaataagta agggtagttt   2100
gggaaatgtc cactcacccg tcagtctata aatacttagc ccctccctca ttgttaaggg   2160
agcaaaatct cagagagata gtcctagaga gagaaagaga gcaagtagcc tagaagtgga   2220
tccagctcct tgttgacagg atgttgatct ggcaagtctc ttggatctca aatgccactg   2280
aacccttgtc cagatcaagt tcctgtcaca acacgggttt gagctcttca tatgacgatc   2340
gttcaaacat ttggcaataa agtttcttaa gattgaatcc tgttgccggt cttgcgatga   2400
ttatcatata atttctgttg aattacgtta agcatgtaat aattaacatg taatgcatga   2460
cgttatttat gagatgggtt tttatgatta gagtcccgca attatacatt taatacgcga   2520
```

```
tagaaaacaa aatatagcgc gcaaactagg ataaattatc gcgcgcggtg tcatctatgt   2580
tactagatcg cggaccgaag cttgcatgcc tgcaggtcga ctctagagga tccggagcca   2640
agtctcataa acgccattgt ggaagaaagt cttgagttgg tggtaatgta acagagtagt   2700
aagaacagag aagagagaga gtgtgagata catgaattgt cgggcaacaa aaatcctgaa   2760
catcttattt tagcaaagag aaagagttcc gagtctgtag cagaagagtg aggagaaatt   2820
taagctcttg gacttgtgaa ttgttccgcc tcttgaatac ttcttcaatc ctcatatatt   2880
cttcttctat gttacctgaa aaccggcatt taatctcgcg ggtttattcc ggttcaacat   2940 ttttttttgtt ttgagttatt atctgggctt aataacgcag gcctgaaata aattcaaggc   3000
ccaactgttt tttttttttaa gaagttgctg ttaaaaaaaa aaaagggaa ttaacaacaa   3060 caacaaaaaa agataaagaa aataataaca attactttaa ttgtagacta aaaaaacata   3120
gattttatca tgaaaaaaag agaaaagaaa taaaaacttg gatcaaaaaa aaaacataca   3180
gatcttctaa ttattaactt ttcttaaaaa ttaggtcctt tttcccaaca attaggttta   3240
gagttttgga attaaaccaa aaagattgtt ctaaaaaata ctcaaatttg gtagataagt   3300
ttccttattt taattagtca atggtagata cttttttttc ttttctttat tagagtagat   3360
tagaatcttt tatgccaagt attgataaat taaatcaaga agataaacta tcataatcaa   3420
catgaaatta aaagaaaaat ctcatatata gtattagtat tctctatata tattatgatt   3480
gcttattctt aatgggttgg gttaaccaag acatagtctt aatggaaaga atctttttttg   3540 aacttttttcc ttattgatta aattcttcta tagaaaagaa agaaattatt tgaggaaaag   3600
tatatacaaa aagaaaaata gaaaaatgtc agtgaagcag atgtaatgga tgacctaatc   3660
caaccaccac cataggatgt ttctacttga gtcggtcttt taaaaacgca cggtggaaaa   3720
tatgacacgt atcatatgat tccttccttt agtttcgtga taataatcct caactgtatat   3780 cttccttttt ttgttttggc taaagatatt ttattctcat aatagaaaaa gacggttttg   3840
ggcttttggt ttgcgatata aagaagacct tcgtgtggaa gataataatt catcctttcg   3900 tcttttttctg actcttcaat ctctcccaaa gcctaaagcg atctctgcaa atctctcgcg   3960
actctctctt tcaaggtata ttttctgatt cttttttgttt ttgattcgta tctgatctcc   4020 aattttttgtt atgtggatta ttgaatcttt tgtataaatt gcttttgaca atattgttcg   4080
tttcgtcaat ccagcttcta aattttgtcc tgattactaa gatatcgatt cgtagtgttt   4140
acatctgtgt aatttcttgc ttgattgtga aattaggatt ttcaaggacg atctattcaa   4200 ttttttgtgtt ttcttttgttc gattctctct gttttaggtt tcttatgttt agatccgttt   4260
ctctttggtg ttgttttgat ttctcttacg gcttttgatt tggtatatgt tcgctgattg   4320
gtttctactt gttctattgt tttatttcag gtggatccca ccatgtctcc ggagaggaga   4380
ccagttgaga ttaggccagc tacagcagct gatatggccg cggtttgtga tatcgttaac   4440
cattacattg agacgtctac agtgaacttt aggacagagc cacaaacacc acaagagtgg   4500
attgatgatc tagagaggtt gcaagataga taccccttggt tggttgctga ggttgagggt   4560
gttgtggctg gtattgctta cgctgggccc tggaaggcta ggaacgctta cgattggaca   4620
gttgagagta ctgtttacgt gtcacatagg catcaaaggt tgggcctagg atctacattg   4680
tacacacatt tgcttaagtc tatggaggcg caaggtttta agtctgtggt tgctgttata   4740
ggccttccaa acgatccatc tgttaggttg catgaggctt tgggatacac agcccggggt   4800
acattgcgcg cagctggata caagcatggt ggatggcatg atgttggttt ttggcaaagg   4860
gattttgagt tgccagctcc tccaaggcca gttaggccag ttacccagat atgagtcgag   4920
```

```
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac    5280 cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
gacgcacgac gccggggcga gaccataggc gatctcctaa atcaatagta gctgtaacct    6540
cgaagcgttt cacttgtaac aacgattgag aattttgtc ataaaattga aatacttggt    6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaacacgttc ttccttgtcga tgacgacgtc gctatgcggc    6780
atcttattat tgaatacctt acgatccacg ccttcaaagt gaccgcggta gccgacagca    6840
cccagttcac aagagtactc tcttccgcga cggtcgatgt cgtggttgtt gatctagatt    6900
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga ttttatcgct aagccgttca gtatcagaga gttctagca cgcattcggg    7080 ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
```

```
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttctttga cgcggacgtg caggtttcgc    7440
acgggggac gatggcagcc tgagccaatt cccagatccc cgaggaatcg gcgtgagcgg     7500
tcgcaaacca tccggcccgg tacaaatcgg cgcggcgctg ggtgatgacc tggtggagaa    7560
gttgaaggcc gcgcaggccg cccagcggca acgcatcgag gcagaagcac gccccggtga    7620
atcgtggcaa gcggccgctg atcgaatccg caaagaatcc cggcaaccgc cggcagccgg    7680
tgcgccgtcg attaggaagc cgcccaaggg cgacgagcaa ccagattttt tcgttccgat    7740
gctctatgac gtgggcaccc gcgatagtcg cagcatcatg gacgtggccg ttttccgtct    7800
gtcgaagcgt gaccgacgag ctggcgaggt gatccgctac gagcttccag acgggcacgt    7860
agaggtttcc gcagggccgg ccggcatggc cagtgtgtgg gattacgacc tggtactgat    7920
ggcggtttcc catctaaccg aatccatgaa ccgataccgg gaaggaagg gagacaagcc     7980
cggccgcgtg ttccgtccac acgttgcgga cgtactcaag ttctgccggc gagccgatgg    8040
cggaaagcag aaagacgacc tggtagaaac ctgcattcgg ttaaacacca cgcacgttgc    8100
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760
cgattttttcc gcctaaaact cttaaaact tattaaaact cttaaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacgccag gcaatctacc agggcgcgga caagccgcgc cgtcgccact    9000
cgaccgccgg cgctgaggtc tgcctcgtga agaaggtgtt gctgactcat accaggcctg    9060
aatcgccca tcatccagcc agaaagtgag ggagccacgg ttgatgagag ctttgttgta     9120
ggtggaccag ttggtgattt tgaacttttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tatttttgaa aaagccgttt ctgtaatgaa ggagaaaact caccgaggca gttccatagg    9420
atggcaagat cctggtatcg gtctgcgatt ccgactcgtc aacatcaat acaacctatt     9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
```

```
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc   10020
ggtgtaggtc gttcgctcca agctgggctg tgtgcacgaa ccccccgttc agcccgaccg   10080
ctgcgcctta tccggtaact atcgtcttga gtccaacccg gtaagacacg acttatcgcc   10140
actggcagca gccactggta acaggattag cagagcgagg tatgtaggcg gtgctacaga   10200
gttcttgaag tggtggccta actacggcta cactagaaga acagtatttg gtatctgcgc   10260
tctgctgaag ccagttacct tcggaaaaag agttggtagc tcttgatccg gcaaacaaac   10320
caccgctggt agcggtggtt tttttgtttg caagcagcag attacgcgca gaaaaaaagg   10380
atctcaagaa gatcctttga tcttttctac ggggtctgac gctcagtgga acgaaaactc   10440
acgttaaggg attttggtca tgagattatc aaaaaggatc ttcacctaga tccttttgat   10500
ccggaatta                                                            10509

<210> SEQ ID NO 38
<211> LENGTH: 10509
<212> TYPE: DNA
<213> ORGANISM: Artificial Sequence
<220> FEATURE:
<223> OTHER INFORMATION: pKS107 (amiR0382)

<400> SEQUENCE: 38
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg acccccgccg atgacgcggg acaagccgtt ttacgtttgg     240
aactgacaga accgcaacgc tgcaggaatt ggccgcagcg ccatttaaa tcaattgggc      300 gcgtacgtag cactagtgaa ttccggaccc aagctttggc agacaaagtg cagacatac      360 tgtcccacaa atgaagatgg aatctgtaaa agaaaacgcg tgaaataatg cgtctgacaa     420
aggttaggtc ggctgccttt aatcaatacc aaagtggtcc ctaccacgat ggaaaaactg     480
tgcagtcggt ttggcttttt ctgacgaaca aataagattc gtggccgaca ggtggggtc      540 caccatgtga aggcatcttc agactccaat aatggagcaa tgacgtaagg gcttacgaaa     600
taagtaaggg tagtttggga aatgtccact cacccgtcag tctataaata cttagcccct     660
ccctcattgt taagggagca aaatctcaga gagatagtcc tagagagaga aagagagcaa     720
gtagcctaga agtggatctc caccatggcc cagtccaagc acggcctgac caaggagatg     780
accatgaagt accgcatgga gggctgcgtg gacggccaca gttcgtgat caccggcgag      840 ggcatcggct accccttcaa gggcaagcag gccatcaacc tgtgcgtggt ggagggcggc     900
cccttgccct tcgccgagga catcttgtcc gccgccttca tgtacggcaa ccgcgtgttc     960
accgagtacc cccaggacat cgtcgactac ttcaagaact cctgccccgc cggctacacc    1020
tgggaccgct ccttcctgtt cgaggacggc gccgtgtgca tctgcaacgc cgacatcacc    1080
gtgagcgtgg aggagaactg catgtaccac gagtccaagt tctacggcgt gaacttcccc    1140
```

```
gccgacggcc ccgtgatgaa gaagatgacc gacaactggg agccctcctg cgagaagatc      1200
atccccgtgc ccaagcaggg catcttgaag ggcgacgtga gcatgtacct gctgctgaag      1260
gacggtggcc gcttgcgctg ccagttcgac accgtgtaca aggccaagtc cgtgccccgc      1320
aagatgcccg actggcactt catccagcac aagctgaccc gcgaggaccg cagcgacgcc      1380
aagaaccaga gtggcacct gaccgagcac gccatcgcct ccggctccgc cttgccctgc       1440
tctagatccc cgaatttccc cgatcgttca acatttggc aataaagttt cttaagattg       1500
aatcctgttg ccggtcttgc gatgattatc atataatttc tgttgaatta cgttaagcat     1560
gtaataatta acatgtaatg catgacgtta tttatgagat gggttttat gattagagtc      1620 ccgcaattat acatttaata cgcgatagaa aacaaaatat agcgcgcaaa ctaggataaa     1680
ttatcgcgcg cggtgtcatc tatgttacta gatcgcggac cctcatgagc ggagaattaa     1740
gggagtcacg ttatgacccc cgccgatgac gcgggacaag ccgttttacg tttggaactg     1800
acagaaccgc aacgaagctt tggcagacaa agtggcagac atactgtccc acaaatgaag     1860
atggaatctg taaagaaaa cgcgtgaaat aatgcgtctg acaaaggtta ggtcggctgc      1920
ctttaatcaa taccaaagtg gtccctacca cgatggaaaa actgtgcagt cggtttggct     1980 tttctgacg aacaaataag attcgtggcc gacaggtggg ggtccaccat gtgaaggcat      2040
cttcagactc caataatgga gcaatgacgt aagggcttac gaaataagta agggtagttt    2100
gggaaatgtc cactcacccg tcagtctata atacttagc ccctccctca ttgttaaggg      2160
agcaaaatct cagagagata gtcctagaga gagaaagaga gcaagtagcc tagaagtgga     2220
tccagctcct tgttgaggtc atgttgatct ggcaagtctc ttggatctca aatgccactg     2280 aacccttgc cagatcaagt tgacctcaca acacgggttt gagctcttca tatgacgatc      2340
gttcaaacat ttggcaataa agtttcttaa gattgaatcc tgttgccggt cttgcgatga     2400
ttatcatata atttctgttg aattacgtta agcatgtaat aattaacatg taatgcatga     2460
cgttatttat gagatgggtt tttatgatta gagtcccgca attatacatt taatacgcga    2520
tagaaaacaa aatatagcgc gcaaactagg ataaattatc gcgcgcggtg tcatctatgt    2580
tactagatcg cggaccgaag cttgcatgcc tgcaggtcga ctctagagga tccgagcca     2640 agtctcataa acgccattgt ggaagaaagt cttgagttgg tggtaatgta acagagtagt    2700
aagaacagag aagagagaga gtgtgagata catgaattgt cgggcaacaa aaatcctgaa    2760
catcttattt tagcaaagag aaagagttcc gagtctgtag cagaagagtg aggagaaatt    2820
taagctcttg gacttgtgaa ttgttccgcc tcttgaatac ttcttcaatc ctcatatatt    2880
cttcttctat gttacctgaa aaccggcatt taatctcgcg ggtttattcc ggttcaacat    2940 ttttttttgtt ttgagttatt atctgggctt aataacgcag gcctgaaata aattcaaggc   3000
ccaactgttt ttttttttaa gaagttgctg ttaaaaaaaa aaaagggaa ttaacaacaa      3060 caacaaaaaa agataaagaa aataataaca attactttaa ttgtagacta aaaaaacata    3120
gattttatca tgaaaaaaag agaaaagaaa taaaaacttg gatcaaaaaa aaaacataca    3180
gatcttctaa ttattaactt ttcttaaaaa ttaggtcctt tttcccaaca attaggttta    3240
gagttttgga attaaaccaa aaagattgtt ctaaaaaata ctcaaatttg gtagataagt    3300
ttccttattt taattagtca atggtagata cttttttttc ttttctttat tagagtagat    3360
tagaatcttt tatgccaagt attgataaat taaatcaaga agataaacta tcataatcaa    3420
catgaaatta aagaaaaat ctcatatata gtattagtat tctctatata tattatgatt     3480
gcttattctt aatgggttgg gttaaccaag acatagtctt aatggaaaga atcttttttg    3540
```

| | |
|---|---|
| aacttttttcc ttattgatta aattcttcta tagaaaagaa agaaattatt tgaggaaaag | 3600 |
| tatatacaaa aagaaaaata gaaaaatgtc agtgaagcag atgtaatgga tgacctaatc | 3660 |
| caaccaccac cataggatgt ttctacttga gtcggtcttt taaaaacgca cggtggaaaa | 3720 |
| tatgacacgt atcatatgat tccttccttt agtttcgtga taataatcct caactgatat | 3780 |
| cttccttttt ttgttttggc taaagatatt ttattctcat taatagaaaa gacggttttg | 3840 |
| ggcttttggt ttgcgatata aagaagacct tcgtgtggaa gataataatt catccttttcg | 3900 |
| tcttttttctg actcttcaat ctctcccaaa gcctaaagcg atctctgcaa atctctcgcg | 3960 |
| actctctctt tcaaggtata ttttctgatt cttttttgttt ttgattcgta tctgatctcc | 4020 |
| aatttttgtt atgtggatta ttgaatcttt tgtataaatt gcttttgaca atattgttcg | 4080 |
| tttcgtcaat ccagcttcta aatttttgtcc tgattactaa gatatcgatt cgtagtgttt | 4140 |
| acatctgtgt aatttcttgc ttgattgtga aattaggatt ttcaaggacg atctattcaa | 4200 |
| tttttgtgtt ttcttttgttc gattctctct gtttttaggtt tcttatgttt agatccgttt | 4260 |
| ctctttggtg ttgtttttgat ttctcttacg gcttttgatt tggtatatgt tcgctgattg | 4320 |
| gtttctactt gttctattgt tttatttcag gtggatccca ccatgtctcc ggagaggaga | 4380 |
| ccagttgaga ttaggccagc tacagcagct gatatggccg cggtttgtga tatcgttaac | 4440 |
| cattacattg agacgtctac agtgaacttt aggacagagc cacaaacacc acaagagtgg | 4500 |
| attgatgatc tagagaggtt gcaagataga tacccttggt tggttgctga ggttgagggt | 4560 |
| gttgtggctg gtattgctta cgctgggccc tggaaggcta ggaacgctta cgattggaca | 4620 |
| gttgagagta ctgtttacgt gtcacatagg catcaaaggt tgggcctagg atctacattg | 4680 |
| tacacacatt tgcttaagtc tatggaggcg caaggtttta agtctgtggt tgctgttata | 4740 |
| ggccttccaa acgatccatc tgttaggttg catgaggctt tgggatacac agcccggggt | 4800 |
| acattgcgcg cagctggata caagcatggt ggatggcatg atgttggttt ttggcaaagg | 4860 |
| gattttgagt tgccagctcc tccaaggcca gttaggccag ttacccagat atgagtcgag | 4920 |
| ctctagatcc ccgaatttcc ccgatcgttc aaacatttgg caataaagtt tcttaagatt | 4980 |
| gaatcctgtt gccggtcttg cgatgattat catataattt ctgttgaatt acgttaagca | 5040 |
| tgtaataatt aacatgtaat gcatgacgtt atttatgaga tgggttttta tgattagagt | 5100 |
| cccgcaatta tacatttaat acgcgataga aaacaaaata tagcgcgcaa actaggataa | 5160 |
| attatcgcgc gcggtgtcat ctatgttact agatcgggaa ttgggtacca tgcccgggcg | 5220 |
| gccagcatgg ccgtatccgc aatgtgttat taagttgtct aagcgtcaat ttgtttacac | 5280 |
| cacaatatat cctgccacca gccagccaac agctccccga ccggcagctc ggcacaaaat | 5340 |
| caccactcga tacaggcagc ccatcagaat taattctcat gtttgacagc ttatcatcga | 5400 |
| ctgcacggtg caccaatgct tctggcgtca ggcagccatc ggaagctgtg gtatggctgt | 5460 |
| gcaggtcgta aatcactgca taattcgtgt cgctcaaggc gcactcccgt tctggataat | 5520 |
| gttttttgcg ccgacatcat aacggttctg gcaaatattc tgaaatgagc tgttgacaat | 5580 |
| taatcatccg gctcgtataa tgtgtggaat tgtgagcgga taacaatttc acacaggaaa | 5640 |
| cagaccatga gggaagcgtt gatcgccgaa gtatcgactc aactatcaga ggtagttggc | 5700 |
| gtcatcgagc gccatctcga accgacgttg ctggccgtac atttgtacgg ctccgcagtg | 5760 |
| gatggcggcc tgaagccaca cagtgatatt gatttgctgg ttacggtgac cgtaaggctt | 5820 |
| gatgaaacaa cgcggcgagc tttgatcaac gaccttttgg aaacttcggc ttcccctgga | 5880 |

```
gagagcgaga ttctccgcgc tgtagaagtc accattgttg tgcacgacga catcattccg   5940
tggcgttatc cagctaagcg cgaactgcaa tttggagaat ggcagcgcaa tgacattctt   6000
gcaggtatct tcgagccagc cacgatcgac attgatctgg ctatcttgct gacaaaagca   6060
agagaacata gcgttgcctt ggtaggtcca gcggcggagg aactctttga tccggttcct   6120
gaacaggatc tatttgaggc gctaaatgaa accttaacgc tatggaactc gccgcccgac   6180
tgggctggcg atgagcgaaa tgtagtgctt acgttgtccc gcatttggta cagcgcagta   6240
accggcaaaa tcgcgccgaa ggatgtcgct gccgactggg caatggagcg cctgccggcc   6300
cagtatcagc ccgtcatact tgaagctagg caggcttatc ttggacaaga agatcgcttg   6360
gcctcgcgcg cagatcagtt ggaagaattt gttcactacg tgaaaggcga gatcaccaaa   6420
gtagtcggca aataaagctc tagtggatct ccgtaccccc gggggatctg gctcgcggcg   6480
gacgcacgac gccggggcga gaccataggc gatctcctaa atcaatagta gctgtaacct   6540
cgaagcgttt cacttgtaac aacgattgag aattttttgtc ataaaattga aatacttggt   6600
tcgcattttt gtcatccgcg gtcagccgca attctgacga actgcccatt tagctggaga   6660
tgattgtaca tccttcacgt gaaaatttct caagcgctgt gaacaagggt tcagatttta   6720
gattgaaagg tgagccgttg aaaacgttc ttcttgtcga tgacgacgtc gctatgcggc   6780
atcttattat tgaataccttt acgatccacg ccttcaaagt gaccgcggta gccgacagca   6840
cccagttcac aagagtactc tcttccgcga cggtcgatgt cgtggttgtt gatctagatt   6900
taggtcgtga agatgggctc gagatcgttc gtaatctggc ggcaaagtct gatattccaa   6960
tcataattat cagtggcgac cgccttgagg agacggataa agttgttgca ctcgagctag   7020
gagcaagtga ttttatcgct aagccgttca gtatcagaga gtttctagca cgcattcggg   7080
ttgccttgcg cgtgcgcccc aacgttgtcc gctccaaaga ccgacggtct ttttgttta    7140
ctgactggac acttaatctc aggcaacgtc gcttgatgtc cgaagctggc ggtgaggtga   7200
aacttacggc aggtgagttc aatcttctcc tcgcgttttt agagaaaccc cgcgacgttc   7260
tatcgcgcga gcaacttctc attgccagtc gagtacgcga cgaggaggtt tatgacagga   7320
gtatagatgt tctcattttg aggctgcgcc gcaaacttga ggcagatccg tcaagccctc   7380
aactgataaa aacagcaaga ggtgccggtt atttctttga gcgcggacgtg caggtttcgc   7440
acgggggggac gatggcagcc tgagccaatt cccagatccc cgaggaatcg gcgtgagcgg   7500
tcgcaaacca tccggcccgg tacaaatcgg cgcggcgctg ggtgatgacc tggtggagaa   7560
gttgaaggcc gcgcaggccg cccagcggca acgcatcgag gcagaagcac gccccggtga   7620
atcgtggcaa gcggccgctg atcgaatccg caaagaatcc cggcaaccgc cggcagccgg   7680
tgcgccgtcg attaggaagc cgcccaaggg cgacgagcaa ccagattttt tcgttccgat   7740
gctctatgac gtgggcaccc gcgatagtcg cagcatcatg gacgtggccg ttttccgtct   7800
gtcgaagcgt gaccgacgag ctggcgaggt gatccgctac gagcttccag acgggcacgt   7860
agaggtttcc gcagggccgg ccggcatggc cagtgtgtgg gattacgacc tggtactgat   7920
ggcggttttcc catctaaccg aatccatgaa ccgataccgg gaagggaagg gagacaagcc   7980
cggccgcgtg ttccgtccac acgttgcgga cgtactcaag ttctgccggc gagccgatgc   8040
cggaaagcag aaagacgacc tggtagaaac ctgcattcgg ttaaacacca cgcacgttgc   8100
catgcagcgt acgaagaagg ccaagaacgg ccgcctggtg acggtatccg agggtgaagc   8160
cttgattagc cgctacaaga tcgtaaagag cgaaaccggg cggccggagt acatcgagat   8220
cgagctagct gattggatgt accgcgagat cacagaaggc aagaacccgg acgtgctgac   8280
```

```
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760 cgattttttcc gcctaaaact ctttaaaact tattaaaact cttaaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacgccag gcaatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccag ttggtgattt tgaacttttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tatttttgaa aaagccgttt ctgtaatgaa ggagaaaact caccgaggca gttccatagg    9420
atggcaagat cctggtatcg gtctgcgatt ccgactcgtc caacatcaat acaacctatt    9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc   10020
ggtgtaggtc gttcgctcca agctgggctg tgtgcacgaa ccccccgttc agcccgaccg   10080
ctgcgcctta tccggtaact atcgtcttga gtccaacccg gtaagacacg acttatcgcc   10140
actggcagca gccactggta acaggattag cagagcgagg tatgtaggcg gtgctacaga   10200
gttcttgaag tggtggccta actacggcta cactagaaga acagtatttg gtatctgcgc   10260
tctgctgaag ccagttacct tcggaaaaag agttggtagc tcttgatccg gcaaacaaac   10320
caccgctggt agcggtggtt tttttgtttg caagcagcag attacgcgca gaaaaaaagg   10380
atctcaagaa gatcctttga tcttttctac ggggtctgac gctcagtgga acgaaaactc   10440
acgttaaggg attttggtca tgagattatc aaaaaggatc ttcacctaga tccttttgat   10500
ccggaatta                                                          10509
```

<210> SEQ ID NO 39

<211> LENGTH: 10509
<212> TYPE: DNA
<213> ORGANISM: Artificial Sequence
<220> FEATURE:
<223> OTHER INFORMATION: pKS62 (amiR0423)

<400> SEQUENCE: 39

| | |
|---|---|
| attcctgtgg ttggcatgca catacaaatg gacgaacgga taaacctttt cacgcccttt | 60 |
| taaatatccg attattctaa taaacgctct tttctcttag gtttacccgc caatatatcc | 120 |
| tgtcaaacac tgatagttta aactgaaggc gggaaacgac aatctgatca tgagcggaga | 180 |
| attaagggag tcacgttatg accccgccg atgacgcggg acaagccgtt ttacgtttgg | 240 |
| aactgacaga accgcaacgc tgcaggaatt ggccgcagcg gccatttaaa tcaattgggc | 300 |
| gcgtacgtag cactagtgaa ttccggaccc aagctttggc agacaaagtg gcagacatac | 360 |
| tgtcccacaa atgaagatgg aatctgtaaa agaaaacgcg tgaaataatg cgtctgacaa | 420 |
| aggttaggtc ggctgccttt aatcaatacc aaagtggtcc ctaccacgat ggaaaaactg | 480 |
| tgcagtcggt ttggcttttt ctgacgaaca ataagattc gtggccgaca ggtggggtc | 540 |
| caccatgtga aggcatcttc agactccaat aatggagcaa tgacgtaagg gcttacgaaa | 600 |
| taagtaaggg tagtttggga aatgtccact cacccgtcag tctataaata cttagcccct | 660 |
| ccctcattgt taaggagca aaatctcaga gagatagtcc tagagagaga aagagagcaa | 720 |
| gtagcctaga agtggatctc caccatggcc cagtccaagc acggcctgac caaggagatg | 780 |
| accatgaagt accgcatgga gggctgcgtg gacggccaca agttcgtgat caccggcgag | 840 |
| ggcatcggct acccttcaa gggcaagcag gccatcaacc tgtgcgtggt ggagggcggc | 900 |
| cccttgccct tcgccgagga catcttgtcc gccgccttca tgtacggcaa ccgcgtgttc | 960 |
| accgagtacc cccaggacat cgtcgactac ttcaagaact cctgccccgc cggctacacc | 1020 |
| tgggaccgct ccttcctgtt cgaggacggc gccgtgtgca tctgcaacgc cgacatcacc | 1080 |
| gtgagcgtgg aggagaactg catgtaccac gagtccaagt tctacggcgt gaacttcccc | 1140 |
| gccgacggcc ccgtgatgaa gaagatgacc gacaactggg agccctcctg cgagaagatc | 1200 |
| atccccgtgc ccaagcaggg catcttgaag ggcgacgtga gcatgtacct gctgctgaag | 1260 |
| gacggtggcc gcttgcgctg ccagttcgac accgtgtaca aggccaagtc cgtgccccgc | 1320 |
| aagatgcccg actggcactt catccagcac aagctgaccc cgcgaggaccg cagcgacgcc | 1380 |
| aagaaccaga gtggcacct gaccgagcac gccatcgcct ccggctccgc cttgccctgc | 1440 |
| tctagatccc cgaatttccc cgatcgttca acatttggc aataaagttt cttaagattg | 1500 |
| aatcctgttg ccggtcttgc gatgattatc atataatttc tgttgaatta cgttaagcat | 1560 |
| gtaataatta acatgtaatg catgacgtta tttatgagat gggtttttat gattagagtc | 1620 |
| ccgcaattat acatttaata cgcgatagaa acaaaatat agcgcgcaaa ctaggataaa | 1680 |
| ttatcgcgcg cggtgtcatc tatgttacta gatcgcggac cctcatgagc ggagaattaa | 1740 |
| gggagtcacg ttatgacccc cgccgatgac gcgggacaag ccgttttacg tttgaactg | 1800 |
| acagaaccgc aacgaagctt tggcagacaa agtggcagac atactgtccc acaaatgaag | 1860 |
| atggaatctg taaagaaaa cgcgtgaaat aatgcgtctg acaaaggtta ggtcggctgc | 1920 |
| ctttaatcaa taccaaagtg gtccctacca cgatggaaaa actgtgcagt cggtttggct | 1980 |
| ttttctgacg aacaaataag attcgtggcc gacaggtggg ggtccaccat gtgaaggcat | 2040 |
| cttcagactc caataatgga gcaatgacgt aagggcttac gaaataagta agggtagttt | 2100 |
| gggaaatgtc cactcacccg tcagtctata aatacttagc ccctccctca ttgttaaggg | 2160 |

```
agcaaaatct cagagagata gtcctagaga gagaaagaga gcaagtagcc tagaagtgga    2220
tccagctcct tgttggtatg gtgttgatct ggcaagtctc ttggatctca aatgccactg    2280 aacccttttgc cagatcaagt ccataccaca acacgggttt gagctcttca tatgacgatc   2340
gttcaaacat ttggcaataa agtttcttaa gattgaatcc tgttgccggt cttgcgatga    2400
ttatcatata atttctgttg aattacgtta agcatgtaat aattaacatg taatgcatga    2460
cgttatttat gagatgggtt tttatgatta gagtcccgca attatacatt taatacgcga    2520
tagaaaacaa aatatagcgc gcaaactagg ataaattatc gcgcgcggtg tcatctatgt    2580
tactagatcg cggaccgaag cttgcatgcc tgcaggtcga ctctagagga tccggagcca    2640
agtctcataa acgccattgt ggaagaaagt cttgagttgg tggtaatgta acagagtagt    2700
aagaacagag aagagagaga gtgtgagata catgaattgt cgggcaacaa aaatcctgaa    2760 catcttatttt tagcaaagag aaagagttcc gagtctgtag cagaagagtg aggagaaatt    2820
taagctcttg gacttgtgaa ttgttccgcc tcttgaatac ttcttcaatc ctcatatatt    2880
cttcttctat gttacctgaa aaccggcatt taatctcgcg ggtttattcc ggttcaacat    2940 ttttttttgtt ttgagttatt atctgggctt aataacgcag gcctgaaata aattcaaggc   3000
ccaactgttt ttttttttaa gaagttgctg ttaaaaaaaa aaaagggaa ttaacaacaa     3060 caacaaaaaa agataaagaa aataataaca attactttaa ttgtagacta aaaaaacata    3120
gattttatca tgaaaaaaag agaaaagaaa taaaaacttg gatcaaaaaa aaaacataca    3180
gatcttctaa ttattaactt ttcttaaaaa ttaggtcctt tttcccaaca attaggttta    3240
gagttttgga attaaaccaa aaagattgtt ctaaaaaata ctcaaatttg gtagataagt    3300
ttccttattt taattagtca atggtagata ctttttttttc ttttctttat tagagtagat    3360 tagaatctttt tatgccaagt attgataaat taaatcaaga agataaacta tcataatcaa    3420
catgaaatta aaagaaaaat ctcatatata gtattagtat tctctatata tattatgatt    3480
gcttattctt aatgggttgg gttaaccaag acatagtctt aatggaaaga atcttttttg    3540
aactttttcc ttattgatta aattcttcta tagaaaagaa agaaattatt tgaggaaaag    3600
tatatacaaa aagaaaaata gaaaaatgtc agtgaagcag atgtaatgga tgacctaatc    3660
caaccaccac cataggatgt ttctacttga gtcggtcttt taaaaacgca cggtggaaaa    3720
tatgacacgt atcatatgat tccttccttt agtttcgtga taataatcct caactgatat    3780
cttccttttt ttgttttggc taaagatatt ttattctcat taatagaaaa gacggttttg    3840
ggcttttggt ttgcgatata aagaagacct tcgtgtggaa gataataatt catcctttcg    3900 tcttttttctg actcttcaat ctctcccaaa gcctaaagcg atctctgcaa atctctcgcg    3960
actctctctt tcaaggtata ttttctgatt cttttttgttt ttgattcgta tctgatctcc    4020 aattttttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200 ttttttgtgtt ttcttttgttc gattctctct gttttaggtt tcttatgttt agatccgttt    4260
ctctttggtg ttgtttttgat ttctcttacg gcttttgatt tggtatatgt tcgctgattg    4320
gtttctactt gttctattgt tttatttcag gtggatccca ccatgtctcc ggagaggaga    4380
ccagttgaga ttaggccagc tacagcagct gatatggccg cggttgtgta tatcgttaac    4440
cattacattg agacgtctac agtgaacttt aggacagagc cacaaacacc acaagagtgg    4500
```

```
attgatgatc tagagaggtt gcaagataga tacccttggt tggttgctga ggttgagggt    4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac     5280
cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctgataat     5520
gtttttgcg ccgacatcat aacggttctg gcaaatattc tgaaatgagc tgttgacaat     5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gacctttgg aaacttcggc ttcccctgga     5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata cgcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc ggggatctg gctcgcggcg     6480
gacgcacgac gccggggcga gaccataggc gatctcctaa atcaatagta gctgtaacct    6540
cgaagcgttt cacttgtaac aacgattgag aattttttgtc ataaaattga aatacttggt    6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaacacgttc ttccttgtcga tgcgacgtc gctatgcggc    6780
atcttattat tgaatacctt acgatccacg ccttcaaagt gaccgcggta gccgacagca    6840
cccagttcac aagagtactc tcttccgcga cggtcgatgt cgtggttgtt gatctagatt    6900
```

```
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga tttatcgct aagccgttca gtatcagaga gtttctagca cgcattcggg     7080
ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttctttga cgcggacgtg caggtttcgc    7440
acgggggac gatggcagcc tgagccaatt cccagatccc cgaggaatcg gcgtgagcgg     7500
tcgcaaacca tccggcccgg tacaaatcgg cgcggcgctg ggtgatgacc tggtggagaa    7560
gttgaaggcc gcgcaggccg cccagcggca acgcatcgag gcagaagcac gccccggtga    7620
atcgtggcaa gcggccgctg atcgaatccg caaagaatcc cggcaaccgc cggcagccgg    7680
tgcgccgtcg attaggaagc cgcccaaggg cgacgagcaa ccagattttt tcgttccgat    7740
gctctatgac gtgggcaccc gcgatagtcg cagcatcatg gacgtggccg ttttccgtct    7800
gtcgaagcgt gaccgacgag ctggcgaggt gatccgctac gagcttccag acgggcacgt    7860
agaggtttcc gcagggccgg ccggcatggc cagtgtgtgg gattacgacc tggtactgat    7920
ggcggttttcc catctaaccg aatccatgaa ccgataccgg gaagggaagg gagacaagcc   7980
cggccgcgtg ttccgtccac acgttgcgga cgtactcaag ttctgccggc gagccgatgg    8040
cggaaagcag aaagacgacc tggtagaaac ctgcattcgg ttaaacacca cgcacgttgc    8100
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattacttt tgatcgatcc cggcatcggc cgttttctct accgcctggc     8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760
cgatttttcc gcctaaaact ctttaaaact tattaaaact cttaaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacggccag gcaatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccga ttggtgattt tgaacttttg ctttgccacg gaacggtctg cgttgtcggg    9180
aagatgcgtg atctgatcct tcaactcagc aaaagttcga tttattcaac aaagccgccg    9240
```

```
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tattttgaa  aaagccgttt ctgtaatgaa ggagaaaact caccgaggca gttccatagg    9420
atggcaagat cctggtatcg gtctgcgatt ccgactcgtc caacatcaat acaacctatt    9480
aatttcccct cgtcaaaaat aaggttatca agtgagaaat caccatgagt gacgactgaa    9540
tccggtgaga atggcaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca gaatcagg     9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc   10020
ggtgtaggtc gttcgctcca agctgggctg tgtgcacgaa ccccccgttc agcccgaccg   10080
ctgcgcctta tccggtaact atcgtcttga gtccaacccg gtaagacacg acttatcgcc   10140
actggcagca gccactggta acaggattag cagagcgagg tatgtaggcg gtgctacaga   10200
gttcttgaag tggtggccta actacggcta cactagaaga acagtatttg gtatctgcgc   10260
tctgctgaag ccagttacct tcggaaaaag agttggtagc tcttgatccg gcaaacaaac   10320
caccgctggt agcggtggtt tttttgtttg caagcagcag attacgcgca gaaaaaaagg   10380
atctcaagaa gatcctttga tcttttctac ggggtctgac gctcagtgga acgaaaactc   10440
acgttaaggg attttggtca tgagattatc aaaaaggatc ttcacctaga tccttttgat   10500
ccggaatta                                                           10509

<210> SEQ ID NO 40
<211> LENGTH: 10509
<212> TYPE: DNA
<213> ORGANISM: Artificial Sequence
<220> FEATURE:
<223> OTHER INFORMATION: pKS52 (amiR0458)

<400> SEQUENCE: 40
ggaattaatt cctgtggttg gcatgcacat acaaatggac gaacggataa accttttcac      60
gcccttttaa atatccgatt attctaataa acgctcttt  ctcttaggtt tacccgccaa     120
tatatcctgt caaacactga tagtttaaac tgaaggcggg aaacgacaat ctgatcatga     180
gcggagaatt aagggagtca cgttatgacc cccgccgatg acgcgggaca agccgttta     240
cgtttggaac tgacagaacc gcaacgctgc aggaattggc cgcagcggcc atttaaatca     300
attgggcgcg tacgtagcac tagtgaattc cggacccaag cttggcaga  caaagtggca     360
gacatactgt cccacaaatg aagatggaat ctgtaaaaga aaacgcgtga ataatgcgt      420
ctgacaaagg ttaggtcggc tgcctttaat caataccaaa gtggtcccta ccacgatgga     480
aaaactgtgc agtcgtttg  gcttttttctg acgaacaaat aagattcgtg ccgacaggt     540
gggggtccac catgtgaagg catcttcaga ctccaataat ggagcaatga cgtaagggct     600
tacgaaataa gtaagggtag tttgggaaat gtccactcac ccgtcagtct ataaatactt     660
agcccctccc tcattgttaa gggagcaaaa tctcagagag atagtcctag agagagaaag     720
agagcaagta gcctagaagt ggatctccac catggcccag tccaagcacg gcctgaccaa     780
```

```
ggagatgacc atgaagtacc gcatggaggg ctgcgtggac ggccacaagt tcgtgatcac    840
cggcgagggc atcggctacc ccttcaaggg caagcaggcc atcaacctgt gcgtggtgga    900
gggcggcccc ttgcccttcg ccgaggacat cttgtccgcc gccttcatgt acggcaaccg    960
cgtgttcacc gagtacccc aggacatcgt cgactacttc aagaactcct gccccgccgg   1020
ctacacctgg gaccgctcct tcctgttcga ggacggcgcc gtgtgcatct gcaacgccga   1080
catcaccgtg agcgtggagg agaactgcat gtaccacgag tccaagttct acggcgtgaa   1140
cttccccgcc gacggccccg tgatgaagaa gatgaccgac aactgggagc cctcctgcga   1200
gaagatcatc cccgtgccca gcagggcat cttgaagggc gacgtgagca tgtacctgct   1260
gctgaaggac ggtggccgct tgcgctgcca gttcgacacc gtgtacaagg ccaagtccgt   1320
gccccgcaag atgcccgact ggcacttcat ccagcacaag ctgacccgcg aggaccgcag   1380
cgacgccaag aaccagaagt ggcacctgac cgagcacgcc atcgcctccg gctccgcctt   1440
gccctgctct agatccccga atttcccga tcgttcaaac atttggcaat aaagtttctt   1500
aagattgaat cctgttgccg gtcttgcgat gattatcata taatttctgt tgaattacgt   1560
taagcatgta ataattaaca tgtaatgcat gacgttattt atgagatggg ttttatgat   1620 tagagtcccg caattataca tttaatacgc gatagaaaac aaaatatagc gcgcaaacta   1680
ggataaatta tcgcgcgcgg tgtcatctat gttactagat cgcggaccct catgagcgga   1740
gaattaaggg agtcacgtta tgaccccgc cgatgacgcg gacaagccg ttttacgttt   1800 ggaactgaca gaaccgcaac gaagctttgg cagacaaagt ggcagacata ctgtcccaca   1860
aatgaagatg gaatctgtaa aagaaaacgc gtgaaataat gcgtctgaca aaggttaggt   1920
cggctgcctt taatcaatac caaagtggtc cctaccacga tggaaaaact gtgcagtcgg   1980
tttggctttt tctgacgaac aaataagatt cgtggccgac aggtggggt ccaccatgtg   2040 aaggcatctt cagactccaa taatggagca atgacgtaag ggcttacgaa ataagtaagg   2100
gtagtttggg aaatgtccac tcacccgtca gtctataaat acttagcccc tccctcattg   2160
ttaagggagc aaaatctcag agagatagtc ctagagagag aaagagagca agtgagcctag  2220 aagtggatcc agctccttgt tgggatcttg ttgatctggc aagtctcttg gatctcaaat   2280
gccactgaac cctttgccag atcaacaaga tcccacaaca cgggtttgag ctcttcatat   2340
gacgatcgtt caaacatttg gcaataaagt ttcttaagat tgaatcctgt tgccggtctt   2400
gcgatgatta tcatataatt tctgttgaat tacgttaagc atgtaataat taacatgtaa   2460
tgcatgacgt tatttatgag atgggttttt atgattagag tcccgcaatt atacatttaa   2520
tacgcgatag aaaacaaaat atagcgcgca aactaggata aattatcgcg cgcggtgtca   2580
tctatgttac tagatcgcgg accgaagctt gcatgcctgc aggtcgactc tagaggatcc   2640
ggagccaagt ctcataaacg ccattgtgga agaaagtctt gagttggtgg taatgtaaca   2700
gagtagtaag aacagagaag agagagagtg tgagatacat gaattgtcgg gcaacaaaaa   2760
tcctgaacat cttattttag caaagagaaa gagttccgag tctgtagcag aagagtgagg   2820
agaaatttaa gctcttggac ttgtgaattg ttccgcctct tgaatacttc ttcaatcctc   2880
atatattctt cttctatgtt acctgaaaac cggcatttaa tctcgcgggt ttattccggt   2940
tcaacatttt ttttgttttg agttattatc tgggcttaat aacgcaggcc tgaaataaat   3000
tcaaggccca actgtttttt tttttaagaa gttgctgtta aaaaaaaaaa aagggaatta   3060
acaacaacaa caaaaaaaga taagaaaat aataacaatt actttaattg tagactaaaa   3120
```

```
aaacatagat tttatcatga aaaaagaga aagaaataa aaacttggat caaaaaaaa      3180 acatacagat cttctaatta ttaacttttc ttaaaaatta ggtccttttt cccaacaatt    3240
aggtttagag ttttggaatt aaaccaaaaa gattgttcta aaaatactc aaatttggta    3300 gataagtttc cttattttaa ttagtcaatg gtagatactt ttttttcttt tctttattag   3360
agtagattag aatcttttat gccaagtatt gataaattaa atcaagaaga taaactatca   3420
taatcaacat gaaattaaaa gaaaaatctc atatatagta ttagtattct ctatatatat   3480
tatgattgct tattcttaat gggttgggtt aaccaagaca tagtcttaat ggaaagaatc   3540 tttttttgaac tttttcctta ttgattaaat tcttctatag aaaagaaaga aattatttga  3600
ggaaaagtat atacaaaaag aaaaatagaa aaatgtcagt gaagcagatg taatggatga   3660
cctaatccaa ccaccaccat aggatgtttc tacttgagtc ggtcttttaa aaacgcacgg   3720
tggaaaatat gacacgtatc atatgattcc ttcctttagt ttcgtgataa taatcctcaa   3780
ctgatatctt cctttttttg ttttggctaa agatattta ttctcattaa tagaaaagac    3840
ggttttgggc ttttggtttg cgatataaag aagaccttcg tgtggaagat aataattcat   3900
cctttcgtct ttttctgact cttcaatctc tcccaaagcc taaagcgatc tctgcaaatc   3960
tctcgcgact ctctctttca aggtatattt tctgattctt tttgtttttg attcgtatct   4020
gatctccaat ttttgttatg tggattattg aatcttttgt ataaattgct tttgacaata   4080
ttgttcgttt cgtcaatcca gcttctaaat tttgtcctga ttactaagat atcgattcgt   4140
agtgtttaca tctgtgtaat ttcttgcttg attgtgaaat taggattttc aaggacgatc   4200
tattcaattt ttgtgttttc tttgttcgat tctctctgtt ttaggtttct tatgtttaga   4260
tccgtttctc tttggtgttg ttttgatttc tcttacggct tttgatttgg tatatgttcg   4320
ctgattggtt tctacttgtt ctattgtttt atttcaggtg gatcccacca tgtctccgga   4380
gaggagacca gttgagatta ggccagctac agcagctgat atggccgcgg tttgtgatat   4440
cgttaaccat tacattgaga cgtctacagt gaactttagg acagagccac aaacaccaca   4500
agagtggatt gatgatctag agaggttgca agatagatac ccttggttgg ttgctgaggt   4560
tgagggtgtt gtggctggta ttgcttacgc tgggccctgg aaggctagga acgcttacga   4620
ttggacagtt gagagtactg tttacgtgtc acataggcat caaaggttgg gcctaggatc   4680
tacattgtac acacatttgc ttaagtctat ggaggcgcaa ggttttaagt ctgtggttgc   4740
tgttataggc cttccaaacg atccatctgt taggttgcat gaggctttgg atacacagc    4800 ccggggtaca ttgcgcgcag ctggatacaa gcatggtgga tggcatgatg ttggtttttg   4860
gcaaagggat tttgagttgc cagctcctcc aaggccagtt aggccagtta cccagatatg   4920
agtcgagctc tagatccccg aatttccccg atcgttcaaa catttggcaa taaagtttct   4980
taagattgaa tcctgttgcc ggtcttgcga tgattatcat ataatttctg ttgaattacg   5040
ttaagcatgt aataattaac atgtaatgca tgacgttatt tatgagatgg gtttttatga   5100
ttagagtccc gcaattatac atttaatacg cgatagaaaa caaatatag cgcgcaaact   5160 aggataaatt atcgcgcgcg gtgtcatcta tgttactaga tcgggaattg ggtaccatgc   5220 ccggcggcc agcatggccg tatccgcaat gtgttattaa gttgtctaag cgtcaatttg    5280
tttacaccac aatatatcct gccaccagcc agccaacagc tccccgaccg gcagctcggc   5340
acaaaatcac cactcgatac aggcagccca tcagaattaa ttctcatgtt tgacagctta   5400
tcatcgactg cacggtgcac caatgcttct ggcgtcaggc agccatcgga agctgtggta   5460
tggctgtgca ggtcgtaaat cactgcataa ttcgtgtcgc tcaaggcgca ctcccgttct   5520
```

```
ggataatgtt ttttgcgccg acatcataac ggttctggca aatattctga aatgagctgt    5580
tgacaattaa tcatccggct cgtataatgt gtggaattgt gagcggataa caatttcaca    5640
caggaaacag accatgaggg aagcgttgat cgccgaagta tcgactcaac tatcagaggt    5700
agttggcgtc atcgagcgcc atctcgaacc gacgttgctg gccgtacatt tgtacggctc    5760
cgcagtggat ggcggcctga agccacacag tgatattgat ttgctggtta cggtgaccgt    5820
aaggcttgat gaaacaacgc ggcgagcttt gatcaacgac cttttggaaa cttcggcttc    5880
ccctggagag agcgagattc tccgcgctgt agaagtcacc attgttgtgc acgacgacat    5940
cattccgtgg cgttatccag ctaagcgcga actgcaattt ggagaatggc agcgcaatga    6000
cattcttgca ggtatcttcg agccagccac gatcgacatt gatctggcta tcttgctgac    6060
aaaagcaaga gaacatagcg ttgccttggt aggtccagcg gcggaggaac tctttgatcc    6120
ggttcctgaa caggatctat ttgaggcgct aaatgaaacc ttaacgctat ggaactcgcc    6180
gcccgactgg gctggcgatg agcgaaatgt agtgcttacg ttgtcccgca tttggtacag    6240
cgcagtaacc ggcaaaatcg cgccgaagga tgtcgctgcc gactgggcaa tggagcgcct    6300
gccggcccag tatcagcccg tcatacttga agctaggcag gcttatcttg gacaagaaga    6360
tcgcttggcc tcgcgcgcag atcagttgga agaatttgtt cactacgtga aaggcgagat    6420
caccaaagta gtcggcaaat aaagctctag tggatctccg tacccccggg ggatctggct    6480
cgcggcggac gcacgacgcc ggggcgagac cataggcgat ctcctaaatc aatagtagct    6540
gtaacctcga agcgtttcac ttgtaacaac gattgagaat ttttgtcata aaattgaaat    6600
acttggttcg cattttttgtc atccgcggtc agccgcaatt ctgacgaact gcccatttag    6660
ctggagatga ttgtacatcc ttcacgtgaa aatttctcaa gcgctgtgaa caagggttca    6720 gatttttagat tgaaaggtga gccgttgaaa cacgttcttc ttgtcgatga cgacgtcgct    6780
atgcggcatc ttattattga ataccttacg atccacgcct tcaaagtgac cgcggtagcc    6840
gacagcaccc agttcacaag agtactctct tccgcgacgg tcgatgtcgt ggttgttgat    6900
ctagatttag gtcgtgaaga tgggctcgag atcgttcgta atctggcggc aaagtctgat    6960
attccaatca taattatcag tggcgaccgc cttgaggaga cggataaagt tgttgcactc    7020
gagctaggag caagtgattt tatcgctaag ccgttcagta tcagagagtt tctagcacgc    7080 attcggggttg ccttgcgcgt gcgccccaac gttgtccgct ccaaagaccg acggtctttt    7140
tgttttactg actggacact taatctcagg caacgtcgct tgatgtccga agctggcggt    7200
gaggtgaaac ttacggcagg tgagttcaat cttctcctcg cgtttttaga gaacccccgc    7260
gacgttctat cgcgcgagca acttctcatt gccagtcgag tacgcgacga ggaggtttat    7320
gacaggagta tagatgttct cattttgagg ctgccgcca aacttgaggc agatccgtca    7380
agccctcaac tgataaaaac agcaagaggt gccggttatt tctttgacgc ggacgtgcag    7440
gtttcgcacg gggggacgat ggcagcctga gccaattccc agatccccga ggaatcggcg    7500
tgagcggtcg caaaccatcc ggcccggtac aaatcggcgc ggcgctgggt gatgacctgg    7560
tggagaagtt gaaggccgcg caggccgccc agcggcaacg catcgaggca gaagcacgcc    7620
ccggtgaatc gtggcaagcg gccgctgatc gaatccgcaa agaatcccgg caaccgccgg    7680
cagccggtgc gccgtcgatt aggaagccgc ccaagggcga cgagcaacca gattttttcg    7740
ttccgatgct ctatgacgtg gcacccgcg atagtcgcag catcatggac gtggccgttt    7800
tccgtctgtc gaagcgtgac cgacgagctg gcgaggtgat ccgctacgag cttccagacg    7860
```

-continued

```
ggcacgtaga ggtttccgca gggccggccg gcatggccag tgtgtgggat tacgacctgg   7920
tactgatggc ggtttcccat ctaaccgaat ccatgaaccg ataccgggaa gggaagggag   7980
acaagcccgg ccgcgtgttc cgtccacacg ttgcggacgt actcaagttc tgccggcgag   8040
ccgatggcga aaagcagaaa gacgacctgg tagaaacctg cattcggtta aacaccacgc   8100
acgttgccat gcagcgtacg aagaaggcca agaacggccg cctggtgacg gtatccgagg   8160
gtgaagcctt gattagccgc tacaagatcg taaagagcga aacccggcgg ccggagtaca   8220
tcgagatcga gctagctgat tggatgtacc gcgagatcac agaaggcaag aacccggacg   8280
tgctgacggt tcaccccgat tactttttga tcgatcccgg catcggccgt tttctctacc   8340
gcctggcacg ccgcgccgca ggcaaggcag aagccagatg gttgttcaag acgatctacg   8400
aacgcagtgg cagcgccgga gagttcaaga agttctgttt caccgtgcgc aagctgatcg   8460
ggtcaaatga cctgccggag tacgatttga aggaggaggc ggggcaggct ggcccgatcc   8520
tagtcatgcg ctaccgcaac ctgatcgagg gcgaagcatc cgccggttcc taatgtacgg   8580
agcagatgct agggcaaatt gccctagcag gggaaaaagg tcgaaaaggt ctctttcctg   8640
tggatagcac gtacattggg aacccaaagc cgtacattgg gaaccggaac ccgtacattg   8700
ggaacccaaa gccgtacatt gggaaccggt cacacatgta agtgactgat ataaaagaga   8760
aaaaaggcga ttttccgcc taaaactctt taaaacttat taaaactctt aaaacccgcc   8820
tggcctgtgc ataactgtct ggccagcgca cagccgaaga gctgcaaaaa gcgcctaccc   8880
ttcggtcgct cgctcccta cgccccgccg cttcgcgtcg gcctatcgcg gccgctggcc   8940
gctcaaaaat ggctggccta cggccaggca atctaccagg gcgcggacaa gccgcgccgt   9000
cgccactcga ccgccggcgc tgaggtctgc ctcgtgaaga aggtgttgct gactcatacc   9060
aggcctgaat cgccccatca tccagccaga aagtgaggga gccacggttg atgagagctt   9120
tgttgtaggt ggaccagttg gtgattttga acttttgctt tgccacggaa cggtctgcgt   9180
tgtcgggaag atgcgtgatc tgatccttca actcagcaaa agttcgattt attcaacaaa   9240
gccgccgtcc cgtcaagtca gcgtaatgct ctgccagtgt tacaaccaat taaccaattc   9300
tgattagaaa aactcatcga gcatcaaatg aaactgcaat ttattcatat caggattatc   9360
aataccatat ttttgaaaaa gccgtttctg taatgaagga gaaaactcac cgaggcagtt   9420
ccataggatg gcaagatcct ggtatcggtc tgcgattccg actcgtccaa catcaataca   9480
acctattaat ttcccctcgt caaaaataag gttatcaagt gagaaatcac catgagtgac   9540
gactgaatcc ggtgagaatg gcaaaagctc tgcattaatg aatcggccaa cgcgcgggga   9600
gaggcggttt gcgtattggg cgctcttccg cttcctcgct cactgactcg ctgcgctcgg   9660
tcgttcggct gcggcgagcg gtatcagctc actcaaaggc ggtaatacgg ttatccacag   9720
aatcagggga taacgcagga aagaacatgt gagcaaaagg ccagcaaaag gccaggaacc   9780
gtaaaaaggc cgcgttgctg gcgttttttcc ataggctccg ccccctgac gagcatcaca   9840 aaaatcgacg ctcaagtcag aggtggcgaa acccgacagg actataaaga taccaggcgt   9900
ttccccctgg aagctccctc gtgcgctctc ctgttccgac cctgccgctt accggatacc   9960
tgtccgcctt tctcccttcg ggaagcgtgg cgctttctca tagctcacgc tgtaggtatc   10020
tcagttcggt gtaggtcgtt cgctccaagc tgggctgtgt gcacgaaccc cccgttcagc   10080
ccgaccgctg cgccttatcc ggtaactatc gtcttgagtc aacccggta agacacgact   10140 tatcgccact ggcagcagcc actggtaaca ggattagcag agcgaggtat gtaggcggtg   10200
ctacagagtt cttgaagtgg tggcctaact acggctacac tagaagaaca gtatttggta   10260
```

-continued

```
tctgcgctct gctgaagcca gttaccttcg gaaaaagagt tggtagctct tgatccggca   10320
aacaaaccac cgctggtagc ggtggttttt ttgtttgcaa gcagcagatt acgcgcagaa   10380
aaaaaggatc tcaagaagat cctttgatct tttctacggg gtctgacgct cagtggaacg   10440
aaaactcacg ttaagggatt ttggtcatga gattatcaaa aaggatcttc acctagatcc   10500
ttttgatcc                                                           10509
```

<210> SEQ ID NO 41
<211> LENGTH: 10509
<212> TYPE: DNA
<213> ORGANISM: Artificial Sequence
<220> FEATURE:
<223> OTHER INFORMATION: pKS108 (amiR0483)

<400> SEQUENCE: 41

```
attcctgtgg ttggcatgca catacaaatg gacgaacgga taaaccttttt cacgcccttt     60 taaatatccg attattctaa taaacgctct tttctcttag gtttaccgc caatatatcc     120 tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccatttaaa tcaattgggc    300
gcgtacgtag cactagtgaa ttccggaccc aagctttggc agacaaagtg gcagacatac    360
tgtcccacaa atgaagatgg aatctgtaaa agaaaacgcg tgaaataatg cgtctgacaa    420
aggttaggtc ggctgccttt aatcaatacc aaagtggtcc ctaccacgat ggaaaaactg    480
tgcagtcggt ttggcttttt ctgacgaaca ataagattc gtggccgaca ggtgggggtc    540
caccatgtga aggcatcttc agactccaat aatggagcaa tgacgtaagg gcttacgaaa    600
taagtaaggg tagtttggga aatgtccact cacccgtcag tctataaata cttagcccct    660
ccctcattgt taagggagca aaatctcaga gagatagtcc tagagagaga aagagagcaa    720
gtagcctaga agtggatctc caccatggcc cagtccaagc acggcctgac caaggagatg    780
accatgaagt accgcatgga gggctgcgtg gacggccaca gttcgtgat caccggcgag    840 ggcatcggct accccttcaa gggcaagcag gccatcaacc tgtgcgtggt ggagggcggc    900
cccttgccct cgccgagga catcttgtcc gccgccttca tgtacggcaa ccgcgtgttc    960
accgagtacc cccaggacat cgtcgactac ttcaagaact cctgccccgc cggctacacc    1020
tgggaccgct ccttcctgtt cgaggacggc gccgtgtgca tctgcaacgc cgacatcacc    1080
gtgagcgtgg aggagaactg catgtaccac gagtccaagt tctacggcgt gaacttcccc    1140
gccgacggcc ccgtgatgaa gaagatgacc gacaactggg agccctcctg cgagaagatc    1200
atccccgtgc ccaagcaggg catcttgaag gcgacgtga gcatgtacct gctgctgaag    1260
gacggtggcc gcttgcgctg ccagttcgac accgtgtaca aggccaagtc cgtgccccgc    1320
aagatgcccg actggcactt catccagcac aagctgaccc gcgaggaccg cagcgacgcc    1380
aagaaccaga gtggcacct gaccgagcac gccatcgcct ccggctccgc cttgccctgc    1440
tctagatccc cgaatttccc cgatcgttca acatttggc aataaagttt cttaagattg    1500
aatcctgttg ccggtcttgc gatgattatc atataatttc tgttgaatta cgttaagcat    1560
gtaataatta acatgtaatg catgacgtta tttatgagat gggtttttat gattagagtc    1620
ccgcaattat acatttaata cgcgatagaa aacaaaatat agcgcgcaaa ctaggataaa    1680
ttatcgcgcg cggtgtcatc tatgttacta gatcgcggac cctcatgagc ggagaattaa    1740
```

```
gggagtcacg ttatgacccc cgccgatgac gcgggacaag ccgttttacg tttggaactg   1800
acagaaccgc aacgaagctt tggcagacaa agtggcagac atactgtccc acaaatgaag   1860
atggaatctg taaaagaaaa cgcgtgaaat aatgcgtctg acaaaggtta ggtcggctgc   1920
ctttaatcaa taccaaagtg gtccctacca cgatggaaaa actgtgcagt cggtttggct   1980
ttttctgacg aacaaataag attcgtggcc gacaggtggg ggtccaccat gtgaaggcat   2040
cttcagactc caataatgga gcaatgacgt aagggcttac gaaataagta agggtagttt   2100
gggaaatgtc cactcacccg tcagtctata atacttagc ccctccctca ttgttaaggg    2160
agcaaaatct cagagagata gtcctagaga gagaaagaga gcaagtagcc tagaagtgga   2220
tccagctcct tgttgtcaga ttgttgatct ggcaagtctc ttggatctca aatgccactg   2280 aacccctttgc cagatcaagt atctgacaca acacggggttt gagctcttca tatgacgatc  2340
gttcaaacat ttggcaataa agtttcttaa gattgaatcc tgttgccggt cttgcgatga   2400
ttatcatata atttctgttg aattacgtta agcatgtaat aattaacatg taatgcatga   2460
cgttatttat gagatgggtt tttatgatta gagtcccgca attatacatt taatacgcga   2520
tagaaaacaa aatatagcgc gcaaactagg ataaattatc gcgcgcggtg tcatctatgt   2580
tactagatcg cggaccgaag cttgcatgcc tgcaggtcga ctctagagga tccggagcca   2640
agtctcataa acgccattgt ggaagaaagt cttgagttgg tggtaatgta acagagtagt   2700
aagaacagaa aagagagaga gtgtgagata catgaattgt cgggcaacaa aaatcctgaa   2760
catcttattt tagcaaagag aaagagttcc gagtctgtag cagaagagtg aggagaaatt   2820
taagctcttg gacttgtgaa ttgttccgcc tcttgaatac ttcttcaatc ctcatatatt   2880
cttcttctat gttacctgaa aaccggcatt taatctcgcg ggtttattcc ggttcaacat   2940
tttttttgtt ttgagttatt atctgggctt aataacgcag gcctgaaata aattcaaggc   3000
ccaactgttt ttttttttaa gaagttgctg ttaaaaaaaa aaaagggaa ttaacaacaa    3060 caacaaaaaa agataaagaa aataataaca attactttaa ttgtagacta aaaaaacata   3120 gatttttatca tgaaaaaaag agaaagaaa taaaaacttg gatcaaaaaa aaaacataca    3180
gatcttctaa ttattaactt tcttaaaaa ttaggtcctt tttcccaaca attaggttta    3240
gagttttgga attaaaccaa aaagattgtt ctaaaaaata ctcaaatttg gtagataagt   3300
ttccttattt taattagtca atggtagata ctttttttc ttttctttat tagagtagat    3360
tagaatcttt tatgccaagt attgataaat taaatcaaga agataaacta tcataatcaa   3420
catgaaatta aaagaaaaat ctcatatata gtattagtat tctctatata tattatgatt   3480
gcttattctt aatgggttgg gttaaccaag acatagtctt aatggaaaga atcttttttg   3540 aacttttttcc ttattgatta aattcttcta tagaaaagaa agaaattatt tgaggaaaag  3600
tatatacaaa aagaaaaata gaaaaatgtc agtgaagcag atgtaatgga tgacctaatc   3660
caaccaccac cataggatgt ttctacttga gtcggtcttt taaaaacgca cggtggaaaa   3720
tatgacacgt atcatatgat tccttccttt agtttcgtga taataatcct caactgatat   3780 cttcctttt ttgttttggc taaagatatt ttattctcat taatagaaaa gacggtttg     3840 ggcttttggt ttgcgatata aagaagacct tcgtgtggaa gataataatt catccttcg    3900 tcttttttctg actcttcaat ctctcccaaa gcctaaagcg atctctgcaa atctctcgcg   3960
actctctctt tcaaggtata ttttctgatt ctttttgttt ttgattcgta tctgatctcc   4020 aattttttgtt atgtggatta ttgaatcttt tgtataaatt gctttttgaca atattgttcg  4080 tttcgtcaat ccagcttcta aattttgtcc tgattactaa gatatcgatt cgtagtgttt   4140
```

```
acatctgtgt aatttcttgc ttgattgtga aattaggatt ttcaaggacg atctattcaa    4200 ttttgtgtt ttctttgttc gattctctct gttttaggtt tcttatgttt agatccgttt    4260
ctctttggtg ttgttttgat ttctcttacg gcttttgatt tggtatatgt tcgctgattg    4320
gtttctactt gttctattgt tttatttcag gtggatccca ccatgtctcc ggagaggaga    4380
ccagttgaga ttaggccagc tacagcagct gatatggccg cggtttgtga tatcgttaac    4440
cattacattg agacgtctac agtgaacttt aggacagagc cacaaacacc acaagagtgg    4500
attgatgatc tagagaggtt gcaagataga tacccttggt tggttgctga ggttgagggt    4560 gttgtgctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccggggt    4800
acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac    5280 cacaatatat cctgccacca gccagccaac agctcccga ccgcagctc ggcacaaaat    5340 caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520 gtttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
```

```
gacgcacgac gccggggcga gaccataggc gatctcctaa atcaatagta gctgtaacct    6540
cgaagcgttt cacttgtaac aacgattgag aattttttgtc ataaaattga aatacttggt   6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaacacgttc ttcttgtcga tgacgacgtc gctatgcggc    6780
atcttattat tgaataccct acgatccacg ccttcaaagt gaccgcggta gccgacagca    6840
cccagttcac aagagtactc tcttccgcga cggtcgatgt cgtggttgtt gatctagatt    6900
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga ttttatcgct aagccgttca gtatcagaga gtttctagca cgcattcggg    7080
ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttctttga cgcggacgtg caggtttcgc    7440 acgggggac gatggcagcc tgagccaatt cccagatccc cgaggaatcg gcgtgagcgg    7500
tcgcaaacca tccggcccgg tacaaatcgg cgcggcgctg ggtgatgacc tggtggagaa    7560
gttgaaggcc gcgcaggccg cccagcggca acgcatcgag gcagaagcac gccccggtga    7620
atcgtggcaa gcggccgctg atcgaatccg caaagaatcc cggcaaccgc cggcagccgg    7680
tgcgccgtcg attaggaagc cgcccaaggg cgacgagcaa ccagattttt tcgttccgat    7740
gctctatgac gtgggcaccc gcgatagtcg cagcatcatg gacgtggccg ttttccgtct    7800
gtcgaagcgt gaccgacgag ctggcgaggt gatccgctac gagcttccag acgggcacgt    7860 agaggttttcc gcagggccgg ccggcatggc cagtgtgtgg gattacgacc tggtactgat    7920 ggcggttttcc catctaaccg aatccatgaa ccgataccgg gaagggaagg gagacaagcc    7980
cggccgcgtg ttccgtccac acgttgcgga cgtactcaag ttctgccggc gagccgatgg    8040
cggaaagcag aaagacgacc tggtagaaac ctgcattcgg ttaaacacca cgcacgttgc    8100
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccgc aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760 cgattttttcc gcctaaaact cttttaaaact tattaaaact cttaaaaccc gcctggcctg    8820
tgcataactg tctggccagc gcacagccga agagctgcaa aaagcgccta cccttcggtc    8880
```

-continued

```
gctgcgctcc ctacgccccg ccgcttcgcg tcggcctatc gcggccgctg gccgctcaaa      8940
aatggctggc ctacgccagc gcaatctacc agggcgcgga caagccgcgc cgtcgccact      9000
cgaccgccgg cgctgaggtc tgcctcgtga agaaggtgtt gctgactcat accaggcctg      9060
aatcgcccca tcatccagcc agaaagtgag ggagccacgg ttgatgagag ctttgttgta      9120
ggtggaccag ttggtgattt tgaacttttg ctttgccacg gaacggtctg cgttgtcggg      9180
aagatgcgtg atctgatcct tcaactcagc aaaagttcga tttattcaac aaagccgccg      9240
tcccgtcaag tcagcgtaat gctctgccag tgttacaacc aattaaccaa ttctgattag      9300
aaaaactcat cgagcatcaa atgaaactgc aatttattca tatcaggatt atcaatacca      9360 tattttgaa aaagccgttt ctgtaatgaa ggagaaaact caccgaggca gttccatagg       9420
atggcaagat cctggtatcg gtctgcgatt ccgactcgtc caacatcaat acaacctatt      9480
aatttcccct cgtcaaaaat aaggttatca agtgagaaat caccatgagt gacgactgaa      9540
tccggtgaga atggcaaaag ctctgcatta atgaatcggc caacgcgcgg ggagaggcgg      9600
tttgcgtatt gggcgctctt ccgcttcctc gctcactgac tcgctgcgct cggtcgttcg      9660
gctgcggcga gcggtatcag ctcactcaaa ggcggtaata cggttatcca cagaatcagg      9720
ggataacgca ggaaagaaca tgtgagcaaa aggccagcaa aaggccagga accgtaaaaa      9780
ggccgcgttg ctggcgtttt tccataggct ccgcccccct gacgagcatc acaaaaatcg      9840
acgctcaagt cagaggtggc gaaacccgac aggactataa agataccagg cgtttccccc      9900
tggaagctcc ctcgtgcgct ctcctgttcc gaccctgccg cttaccggat acctgtccgc      9960
ctttctccct tcgggaagcg tggcgctttc tcatagctca cgctgtaggt atctcagttc     10020
ggtgtaggtc gttcgctcca agctgggctg tgtgcacgaa ccccccgttc agcccgaccg     10080
ctgcgcctta tccggtaact atcgtcttga gtccaacccg gtaagacacg acttatcgcc     10140
actggcagca gccactggta acaggattag cagagcgagg tatgtaggcg gtgctacaga     10200
gttcttgaag tggtggccta actacggcta cactagaaga acagtatttg gtatctgcgc     10260
tctgctgaag ccagttacct tcggaaaaag agttggtagc tcttgatccg gcaaacaaac     10320
caccgctggt agcggtggtt tttttgtttg caagcagcag attacgcgca gaaaaaaagg     10380
atctcaagaa gatcctttga tcttttctac ggggtctgac gctcagtgga acgaaaactc     10440
acgttaaggg attttggtca tgagattatc aaaaaggatc ttcacctaga tccttttgat     10500
ccggaatta                                                             10509
```

<210> SEQ ID NO 42
<211> LENGTH: 10509
<212> TYPE: DNA
<213> ORGANISM: Artificial Sequence
<220> FEATURE:
<223> OTHER INFORMATION: pKS109 (amiR0514)

<400> SEQUENCE: 42

```
attcctgtgg ttggcatgca catacaaatg gacgaacgga taaacctttt cacgcccttt       60
taaatatccg attattctaa taaacgctct tttctcttag gtttaccgc caatatatcc       120 tgtcaaacac tgatagttta aactgaaggc gggaaacgac aatctgatca tgagcggaga      180
attaagggag tcacgttatg accccgccg atgacgcggg acaagccgtt ttacgtttgg       240
aactgacaga accgcaacgc tgcaggaatt ggccgcagcg gccatttaaa tcaattgggc      300
gcgtacgtag cactagtgaa ttccggaccc aagctttggc agacaaagtg gcagacatac      360
```

-continued

```
tgtcccacaa atgaagatgg aatctgtaaa agaaaacgcg tgaaataatg cgtctgacaa      420
aggttaggtc ggctgccttt aatcaatacc aaagtggtcc ctaccacgat ggaaaaactg      480
tgcagtcggt ttggcttttt ctgacgaaca aataagattc gtggccgaca ggtggggtc       540 caccatgtga aggcatcttc agactccaat aatggagcaa tgacgtaagg cttacgaaa       600 taagtaaggg tagtttggga atgtccact cacccgtcag tctataaata cttagcccct       660
ccctcattgt aagggagca aaatctcaga gagatagtcc tagagagaga aagagagcaa       720
gtagcctaga agtggatctc caccatggcc cagtccaagc acggcctgac caaggagatg     780
accatgaagt accgcatgga gggctgcgtg gacggccaca agttcgtgat caccggcgag     840
ggcatcggct accccttcaa gggcaagcag gccatcaacc tgtgcgtggt ggagggcggc     900
cccttgccct cgccgagga catcttgtcc gccgccttca tgtacggcaa ccgcgtgttc      960
accgagtacc cccaggacat cgtcgactac ttcaagaact cctgccccgc cggctacacc    1020
tgggaccgct ccttcctgtt cgaggacggc gccgtgtgca tctgcaacgc cgacatcacc    1080
gtgagcgtgg aggagaactg catgtaccac gagtccaagt tctacggcgt gaacttcccc    1140
gccgacggcc ccgtgatgaa gaagatgacc gacaactggg agccctcctg cgagaagatc    1200
atccccgtgc ccaagcaggg catcttgaag gcgacgtga gcatgtacct gctgctgaag     1260
gacggtggcc gcttgcgctg ccagttcgac accgtgtaca aggccaagtc cgtgccccgc    1320
aagatgcccg actggcactt catccagcac aagctgaccc gcgaggaccg cagcgacgcc    1380
aagaaccaga gtggcacct  gaccgagcac gccatcgcct ccggctccgc cttgccctgc    1440
tctagatccc cgaatttccc cgatcgttca aacatttggc aataaagttt cttaagattg    1500
aatcctgttg ccggtcttgc gatgattatc atataatttc tgttgaatta cgttaagcat    1560
gtaataatta acatgtaatg catgacgtta tttatgagat gggtttttat gattagagtc    1620
ccgcaattat acatttaata cgcgatagaa acaaaatat agcgcgcaaa ctaggataaa     1680
ttatcgcgcg cggtgtcatc tatgttacta gatcgcggac cctcatgagc ggagaattaa    1740
gggagtcacg ttatgacccc cgccgatgac gcgggacaag ccgttttacg tttggaactg    1800
acagaaccgc aacgaagctt tggcagacaa agtggcagac atactgtccc acaaatgaag    1860
atggaatctg taaagaaaaa cgcgtgaaat aatgcgtctg acaaaggtta ggtcggctgc    1920
ctttaatcaa taccaaagtg gtccctacca cgatggaaaa actgtgcagt cggtttggct    1980
ttttctgacg aacaaataag attcgtggcc gacaggtggg ggtccaccat gtgaaggcat    2040
cttcagactc caataatgga gcaatgacgt aagggcttac gaaataagta agggtagttt    2100
gggaaatgtc cactcacccg tcagtctata atacttagc ccctcctca ttgttaaggg      2160 agcaaaatct cagagagata gtcctagaga gagaaagaga gcaagtagcc tagaagtgga    2220
tccagctcct tgttgtcgtg atgttgatct ggcaagtctc ttggatctca atgccactg     2280 aacccttggc cagatcaagt tcacgacaca acacggggttt gagctcttca tatgacgatc    2340
gttcaaacat ttggcaataa agtttcttaa gattgaatcc tgttgccggt cttgcgatga    2400
ttatcatata atttctgttg aattacgtta agcatgtaat aattaacatg taatgcatga    2460
cgttatttat gagatgggtt tttatgatta gagtcccgca attatacatt taatacgcga    2520
tagaaaacaa aatatagcgc gcaaactagg ataaattatc gcgcgcggtg tcatctatgt    2580
tactagatcg cggaccgaag cttgcatgcc tgcaggtcga ctctagagga tccggagcca    2640
agtctcataa acgccattgt ggaagaaagt cttgagttgg tggtaatgta acagagtagt    2700
aagaacagag aagagagaga gtgtgagata catgaattgt cgggcaacaa aaatcctgaa    2760
```

```
catcttattt tagcaaagag aaagagttcc gagtctgtag cagaagagtg aggagaaatt   2820
taagctcttg gacttgtgaa ttgttccgcc tcttgaatac ttcttcaatc ctcatatatt   2880
cttcttctat gttacctgaa aaccggcatt taatctcgcg ggtttattcc ggttcaacat   2940
tttttttgtt ttgagttatt atctgggctt aataacgcag gcctgaaata aattcaaggc   3000
ccaactgttt ttttttttaa gaagttgctg ttaaaaaaaa aaaagggaa ttaacaacaa    3060 caacaaaaaa agataaagaa aataataaca attactttaa ttgtagacta aaaaaacata   3120
gattttatca tgaaaaaaag agaaaagaaa taaaaacttg gatcaaaaaa aaaacataca   3180
gatcttctaa ttattaactt ttcttaaaaa ttaggtcctt tttcccaaca attaggttta   3240
gagttttgga attaaaccaa aaagattgtt ctaaaaaata ctcaaatttg gtagataagt   3300
ttccttattt taattagtca atggtagata cttttttttc ttttctttat tagagtagat   3360
tagaatcttt tatgccaagt attgataaat taaatcaaga agataaaacta tcataatcaa   3420 catgaaatta aaagaaaaat ctcatatata gtattagtat tctctatata tattatgatt   3480
gcttattctt aatgggttgg gttaaccaag acatagtctt aatggaaaga atcttttttg   3540
aactttttcc ttattgatta aattcttcta tagaaaagaa agaaattatt tgaggaaaag   3600
tatatacaaa aagaaaaata gaaaaatgtc agtgaagcag atgtaatgga tgacctaatc   3660
caaccaccac cataggatgt ttctacttga gtcggtcttt taaaaacgca cggtggaaaa   3720
tatgacacgt atcatatgat tccttccttt agtttcgtga taataatcct caactgatat   3780 cttcctttt ttgttttggc taaagatatt ttattctcat taatagaaaa gacggttttg   3840
ggcttttggt ttgcgatata aagaagacct tcgtgtggaa gataataatt catcctttcg   3900 tcttttctg actcttcaat ctctcccaaa gcctaaagcg atctctgcaa atctctcgcg   3960
actctctctt tcaaggtata ttttctgatt cttttttgttt ttgattcgta tctgatctcc   4020 aattttgtt atgtggatta ttgaatcttt tgtataaatt gcttttgaca atattgttcg    4080
tttcgtcaat ccagcttcta aattttgtcc tgattactaa gatatcgatt cgtagtgttt   4140
acatctgtgt aatttcttgc ttgattgtga aattaggatt ttcaaggacg atctattcaa   4200
tttttgtgtt ttcttgttc gattctctct gtttaggtt tcttatgttt agatccgttt     4260
ctctttggtg ttgttttgat ttctcttacg gcttttgatt tggtatatgt tcgctgattg   4320
gtttctactt gttctattgt tttatttcag gtggatccca ccatgtctcc ggagaggaga   4380
ccagttgaga ttaggccagc tacagcagct gatatggccg cggtttgtga tatcgttaac   4440
cattacattg agacgtctac agtgaacttt aggacagagc cacaaacacc acaagagtgg   4500
attgatgatc tagagaggtt gcaagataga taccccttggt tggttgctga ggttgagggt   4560
gttgtggctg gtattgctta cgctgggccc tggaaggcta ggaacgctta cgattggaca   4620
gttgagagta ctgtttacgt gtcacatagg catcaaaggt tgggcctagg atctacattg   4680
tacacacatt tgcttaagtc tatggaggcg caaggtttta agtctgtggt tgctgttata   4740
ggccttccaa acgatccatc tgttaggttg catgaggctt tgggatacac agcccggggt   4800
acattgcgcg cagctggata caagcatggt ggatggcatg atgttggttt ttggcaaagg   4860
gattttgagt tgccagctcc tccaaggcca gttaggccag ttacccagat atgagtcgag   4920
ctctagatcc ccgaatttcc ccgatcgttc aaacatttgg caataaagtt tcttaagatt   4980
gaatcctgtt gccggtcttg cgatgattat catataattt ctgttgaatt acgttaagca   5040
tgtaataatt aacatgtaat gcatgacgtt atttatgaga tgggttttta tgattagagt   5100
```

```
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat aagttgtct aagcgtcaat ttgtttacac     5280
cacaatatat cctgccacca gccagccaac agctccccga ccggcagctc ggcacaaaat    5340
caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
gacgcacgac gccggggcga gaccataggc gatctcctaa atcaatagta gctgtaacct    6540
cgaagcgttt cacttgtaac aacgattgag aattttttgtc ataaaattga aatacttggt    6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaaacacgtt cttcttgtcga tgacgacgtc gctatgcggc    6780
atcttattat tgaatacctt acgatccacg ccttcaaagt gaccgcggta gccgacagca    6840
cccagttcac aagagtactc tcttccgcga cggtcgatgt cgtggttgtt gatctagatt    6900
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga ttttatcgct aagccgttca gtatcagaga gtttctagca cgcattcggg    7080
ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttcttga cgcggacgtg caggtttcgc    7440 acgggggggac gatggcagcc tgagccaatt cccagatccc cgaggaatcg gcgtgagcgg    7500
```

-continued

| | |
|---|---|
| tcgcaaacca tccggcccgg tacaaatcgg cgcggcgctg ggtgatgacc tggtggagaa | 7560 |
| gttgaaggcc gcgcaggccg cccagcggca acgcatcgag gcagaagcac gccccggtga | 7620 |
| atcgtggcaa gcggccgctg atcgaatccg caaagaatcc cggcaaccgc cggcagccgg | 7680 |
| tgcgccgtcg attaggaagc cgcccaaggg cgacgagcaa ccagattttt tcgttccgat | 7740 |
| gctctatgac gtgggcaccc gcgatagtcg cagcatcatg gacgtggccg ttttccgtct | 7800 |
| gtcgaagcgt gaccgacgag ctggcgaggt gatccgctac gagcttccag acgggcacgt | 7860 |
| agaggtttcc gcagggccgg ccggcatggc cagtgtgtgg gattacgacc tggtactgat | 7920 |
| ggcggttttcc catctaaccg aatccatgaa ccgataccgg gaagggaagg gagacaagcc | 7980 |
| cggccgcgtg ttccgtccac acgttgcgga cgtactcaag ttctgccggc gagccgatgg | 8040 |
| cggaaagcag aaagacgacc tggtagaaac ctgcattcgg ttaaacacca cgcacgttgc | 8100 |
| catgcagcgt acgaagaagg ccaagaacgg ccgcctggtg acggtatccg agggtgaagc | 8160 |
| cttgattagc cgctacaaga tcgtaaagag cgaaaccggg cggccggagt acatcgagat | 8220 |
| cgagctagct gattggatgt accgcgagat cacagaaggc aagaaccgg acgtgctgac | 8280 |
| ggttcacccc gattacttt tgatcgatcc cggcatcggc cgttttctct accgcctggc | 8340 |
| acgccgcgcc gcaggcaagg cagaagccag atggttgttc aagacgatct acgaacgcag | 8400 |
| tggcagcgcc ggagagttca agaagttctg tttcaccgtg cgcaagctga tcgggtcaaa | 8460 |
| tgacctgccg gagtacgatt tgaaggagga ggcggggcag gctggcccga tcctagtcat | 8520 |
| gcgctaccgc aacctgatcg agggcgaagc atccgccggt tcctaatgta cggagcagat | 8580 |
| gctagggcaa attgccctag caggggaaaa aggtcgaaaa ggtctctttc ctgtggatag | 8640 |
| cacgtacatt gggaacccaa agccgtacat tgggaaccgg aacccgtaca ttgggaaccc | 8700 |
| aaagccgtac attgggaacc ggtcacacat gtaagtgact gatataaaag agaaaaaagg | 8760 |
| cgattttttcc gcctaaaact ctttaaaact tattaaaact cttaaaaccc gcctggcctg | 8820 |
| tgcataactg tctggccagc gcacagccga agagctgcaa aaagcgccta cccttcggtc | 8880 |
| gctgcgctcc ctacgccccg ccgcttcgcg tcggcctatc gcggccgctg gccgctcaaa | 8940 |
| aatggctggc ctacggccag gcaatctacc agggcgcgga caagccgcgc cgtcgccact | 9000 |
| cgaccgccgg cgctgaggtc tgcctcgtga agaaggtgtt gctgactcat accaggcctg | 9060 |
| aatcgcccca tcatccagcc agaaagtgag ggagccacgg ttgatgagag ctttgttgta | 9120 |
| ggtggaccag ttggtgattt tgaacttttg ctttgccacg gaacggtctg cgttgtcggg | 9180 |
| aagatgcgtg atctgatcct tcaactcagc aaaagttcga tttattcaac aaagccgccg | 9240 |
| tcccgtcaag tcagcgtaat gctctgccag tgttacaacc aattaaccaa ttctgattag | 9300 |
| aaaaactcat cgagcatcaa atgaaactgc aatttattca tatcaggatt atcaatacca | 9360 |
| tatttttgaa aaagccgttt ctgtaatgaa ggagaaaact caccgaggca gttccatagg | 9420 |
| atggcaagat cctggtatcg gtctgcgatt ccgactcgtc caacatcaat acaacctatt | 9480 |
| aatttcccct cgtcaaaaat aaggttatca agtgagaaat caccatgagt gacgactgaa | 9540 |
| tccggtgaga atggcaaaag ctctgcatta atgaatcggc caacgcgcgg ggagaggcgg | 9600 |
| tttgcgtatt gggcgctctt ccgcttcctc gctcactgac tcgctgcgct cggtcgttcg | 9660 |
| gctgcggcga gcggtatcag ctcactcaaa ggcggtaata cggttatcca cagaatcagg | 9720 |
| ggataacgca ggaaagaaca tgtgagcaaa aggccagcaa aaggccagga accgtaaaaa | 9780 |
| ggccgcgttg ctggcgtttt tccataggct ccgcccccct gacgagcatc acaaaaatcg | 9840 |

| | |
|---|---|
| acgctcaagt cagaggtggc gaaacccgac aggactataa agataccagg cgtttccccc | 9900 |
| tggaagctcc ctcgtgcgct ctcctgttcc gaccctgccg cttaccggat acctgtccgc | 9960 |
| cttctccct tcgggaagcg tggcgctttc tcatagctca cgctgtaggt atctcagttc | 10020 |
| ggtgtaggtc gttcgctcca agctgggctg tgtgcacgaa ccccccgttc agcccgaccg | 10080 |
| ctgcgcctta tccggtaact atcgtcttga gtccaacccg gtaagacacg acttatcgcc | 10140 |
| actggcagca gccactggta acaggattag cagagcgagg tatgtaggcg gtgctacaga | 10200 |
| gttcttgaag tggtggccta actacggcta cactagaaga acagtatttg gtatctgcgc | 10260 |
| tctgctgaag ccagttacct tcggaaaaag agttggtagc tcttgatccg gcaaacaaac | 10320 |
| caccgctggt agcggtggtt ttttttgtttg caagcagcag attacgcgca gaaaaaagg | 10380 |
| atctcaagaa gatcctttga tcttttctac ggggtctgac gctcagtgga acgaaaactc | 10440 |
| acgttaaggg attttggtca tgagattatc aaaaaggatc ttcacctaga tccttttgat | 10500 |
| ccggaatta | 10509 |

<210> SEQ ID NO 43
<211> LENGTH: 10509
<212> TYPE: DNA
<213> ORGANISM: Artificial Sequence
<220> FEATURE:
<223> OTHER INFORMATION: pKS53 (amiR0531)

<400> SEQUENCE: 43

| | |
|---|---|
| aagggaatta acaacaacaa caaaaaaaga taaagaaaat aataacaatt actttaattg | 60 |
| tagactaaaa aaacatagat tttatcatga aaaaagaga aaagaaataa aaacttggat | 120 |
| caaaaaaaaa acatacagat cttctaatta ttaacttttc ttaaaaatta ggtccttttt | 180 |
| cccaacaatt aggtttagag ttttggaatt aaaccaaaaa gattgttcta aaaaatactc | 240 |
| aaatttggta gataagtttc cttatttttaa ttagtcaatg gtagatactt ttttttcttt | 300 |
| tctttattag agtagattag aatcttttat gccaagtatt gataaattaa atcaagaaga | 360 |
| taaactatca taatcaacat gaaattaaaa gaaaaatctc atatatagta ttagtattct | 420 |
| ctatatatat tatgattgct tattcttaat gggttgggtt aaccaagaca tagtcttaat | 480 |
| ggaaagaatc ttttttgaac ttttttcctta ttgattaaat tcttctatag aaaagaaaga | 540 |
| aattatttga ggaaaagtat atacaaaaag aaaaatagaa aaatgtcagt gaagcagatg | 600 |
| taatggatga cctaatccaa ccaccaccat aggatgtttc tacttgagtc ggtcttttaa | 660 |
| aaacgcacgg tggaaaatat gacacgtatc atatgattcc ttcctttagt ttcgtgataa | 720 |
| taatcctcaa ctgatatctt cctttttttg ttttggctaa agatatttta ttctcattaa | 780 |
| tagaaaagac ggttttgggc ttttggtttg cgatataaag aagaccttcg tgtggaagat | 840 |
| aataattcat cctttcgtct ttttctgact cttcaatctc tcccaaagcc taaagcgatc | 900 |
| tctgcaaatc tctcgcgact ctctctttca aggtatattt tctgattctt tttgtttttg | 960 |
| attcgtatct gatctccaat ttttgttatg tggattattg aatcttttgt ataaattgct | 1020 |
| tttgacaata ttgttcgttt cgtcaatcca gcttctaaat tttgtcctga ttactaagat | 1080 |
| atcgattcgt agtgtttaca tctgtgtaat ttcttgcttg attgtgaaat taggattttc | 1140 |
| aaggacgatc tattcaattt ttgtgttttc tttgttcgat tctctctgtt ttaggtttct | 1200 |
| tatgtttaga tccgtttctc tttggtgttg ttttgatttc tcttacggct tttgatttgg | 1260 |
| tatatgttcg ctgattggtt tctacttgtt ctattgtttt atttcaggtg gatcccacca | 1320 |
| tgtctccgga gaggagacca gttgagatta ggccagctac agcagctgat atggccgcgg | 1380 |

```
tttgtgatat cgttaaccat tacattgaga cgtctacagt gaactttagg acagagccac    1440
aaacaccaca agagtggatt gatgatctag agaggttgca agatagatac ccttggttgg    1500
ttgctgaggt tgagggtgtt gtggctggta ttgcttacgc tgggccctgg aaggctagga    1560
acgcttacga ttggacagtt gagagtactg tttacgtgtc acataggcat caaaggttgg    1620
gcctaggatc tacattgtac acacatttgc ttaagtctat ggaggcgcaa ggttttaagt    1680
ctgtggttgc tgttataggc cttccaaacg atccatctgt taggttgcat gaggctttgg    1740
gatacacagc ccggggtaca ttgcgcgcag ctggatacaa gcatggtgga tggcatgatg    1800
ttggtttttg gcaaagggat tttgagttgc cagctcctcc aaggccagtt aggccagtta    1860
cccagatatg agtcgagctc tagatccccg aatttccccg atcgttcaaa catttggcaa    1920
taaagtttct taagattgaa tcctgttgcc ggtcttgcga tgattatcat ataatttctg    1980
ttgaattacg ttaagcatgt aataattaac atgtaatgca tgacgttatt tatgagatgg    2040 gttttttatga ttagagtccc gcaattatac atttaatacg cgatagaaaa caaaatatag    2100
cgcgcaaact aggataaatt atcgcgcgcg gtgtcatcta tgttactaga tcgggaattg    2160
ggtaccatgc ccggcgcggcc agcatggccg tatccgcaat gtgttattaa gttgtctaag    2220
cgtcaatttg tttacaccac aatatatcct gccaccagcc agccaacagc tccccgaccg    2280
gcagctcggc acaaaatcac cactcgatac aggcagccca tcagaattaa ttctcatgtt    2340
tgacagctta tcatcgactg cacggtgcac caatgcttct ggcgtcaggc agccatcgga    2400
agctgtggta tggctgtgca ggtcgtaaat cactgcataa ttcgtgtcgc tcaaggcgca    2460
ctcccgttct ggataatgtt ttttgcgccg acatcataac ggttctggca aatattctga    2520
aatgagctgt tgacaattaa tcatccggct cgtataatgt gtggaattgt gagcggataa    2580
caatttcaca caggaaacag accatgaggg aagcgttgat cgccgaagta tcgactcaac    2640
tatcagaggt agttggcgtc atcgagcgcc atctcgaacc gacgttgctg gccgtacatt    2700
tgtacggctc cgcagtggat ggcggcctga agccacacag tgatattgat ttgctggtta    2760
cggtgaccgt aaggcttgat gaaacaacgc ggcgagcttt gatcaacgac cttttggaaa    2820
cttcggcttc ccctggagag agcgagattc tccgcgctgt agaagtcacc attgttgtgc    2880
acgacgacat cattccgtgg cgttatccag ctaagcgcga actgcaattt ggagaatggc    2940
agcgcaatga cattcttgca ggtatcttcg agccagccac gatcgacatt gatctggcta    3000
tcttgctgac aaaagcaaga gaacatagcg ttgccttggt aggtccagcg gcggaggaac    3060
tctttgatcc ggttcctgaa caggatctat ttgaggcgct aaatgaaacc ttaacgctat    3120
ggaactcgcc gcccgactgg gctggcgatg agcgaaatgt agtgcttacg ttgtcccgca    3180
tttggtacag cgcagtaacc ggcaaaatcg cgccgaagga tgtcgctgcc gactgggcaa    3240
tggagcgcct gccggcccag tatcagcccg tcatacttga agctaggcag gcttatcttg    3300
gacaagaaga tcgcttggcc tcgcgcgcag atcagttgga agaatttgtt cactacgtga    3360
aaggcgagat caccaaagta gtcggcaaat aaagctctag tggatctccg tacccccggg    3420
ggatctggct cgcggcggac gcacgacgcc gggcgagac cataggcgat ctcctaaatc    3480
aatagtagct gtaacctcga agcgtttcac ttgtaacaac gattgagaat ttttgtcata    3540
aaattgaaat acttggttcg catttttgtc atccgcggtc agccgcaatt ctgacgaact    3600
gcccatttag ctggagatga ttgtacatcc ttcacgtgaa aatttctcaa gcgctgtgaa    3660
caagggttca gattttagat tgaaaggtga gccgttgaaa cacgttcttc ttgtcgatga    3720
```

```
cgacgtcgct atgcggcatc ttattattga ataccttacg atccacgcct tcaaagtgac    3780
cgcggtagcc gacagcaccc agttcacaag agtactctct tccgcgacgg tcgatgtcgt    3840
ggttgttgat ctagatttag gtcgtgaaga tgggctcgag atcgttcgta atctggcggc    3900
aaagtctgat attccaatca taattatcag tggcgaccgc cttgaggaga cggataaagt    3960
tgttgcactc gagctaggag caagtgattt tatcgctaag ccgttcagta tcagagagtt    4020
tctagcacgc attcgggttg ccttgcgcgt gcgcccaac gttgtccgct ccaaagaccg    4080
acggtctttt tgttttactg actggacact taatctcagg caacgtcgct tgatgtccga    4140
agctggcggt gaggtgaaac ttacggcagg tgagttcaat cttctcctcg cgttttttaga   4200
gaaaccccgc gacgttctat cgcgcgagca acttctcatt gccagtcgag tacgcgacga    4260
ggaggtttat gacaggagta tagatgttct cattttgagg ctgcgccgca aacttgaggc    4320
agatccgtca agccctcaac tgataaaaac agcaagaggt gccggttatt tctttgacgc    4380
ggacgtgcag gtttcgcacg gggggacgat ggcagcctga gccaattccc agatccccga    4440
ggaatcggcg tgagcggtcg caaaccatcc ggcccggtac aaatcggcgc ggcgctgggt    4500
gatgacctgg tggagaagtt gaaggccgcg caggccgccc agcggcaacg catcgaggca    4560
gaagcacgcc ccggtgaatc gtggcaagcg gccgctgatc gaatccgcaa gaatcccgg     4620
caaccgccgg cagccggtgc gccgtcgatt aggaagccgc caagggcga cgagcaacca    4680
gatttttcg ttccgatgct ctatgacgtg gcaccgcg atagtcgcag catcatggac       4740
gtggccgttt tccgtctgtc gaagcgtgac cgacgagctg gcgaggtgat ccgctacgag    4800
cttccagacg ggcacgtaga ggtttccgca gggccggccg gcatggccag tgtgtgggat    4860
tacgacctgg tactgatggc ggtttcccat ctaaccgaat ccatgaaccg ataccgggaa    4920
gggaagggag acaagcccgg ccgcgtgttc cgtccacacg ttgcggacgt actcaagttc    4980
tgccggcgag ccgatggcgg aaagcagaaa gacgacctgg tagaaacctg cattcggtta    5040
aacaccacgc acgttgccat gcagcgtacg aagaaggcca agaacggccg cctggtgacg    5100
gtatccgagg gtgaagcctt gattagccgc tacaagatcg taaagagcga accgggcgg    5160
ccggagtaca tcgagatcga gctagctgat tggatgtacc gcgagatcac agaaggcaag    5220
aacccggacg tgctgacggt tcaccccgat tactttttga tcgatcccgg catcggccgt    5280
tttctctacc gcctggcacg ccgcgccgca ggcaaggcag aagccagatg gttgttcaag    5340
acgatctacg aacgcagtgg cagcgccgga gagttcaaga agttctgttt caccgtgcgc    5400
aagctgatcg ggtcaaatga cctgccggag tacgatttga aggaggaggc ggggcaggct    5460
ggcccgatcc tagtcatgcg ctaccgcaac ctgatcgagg gcgaagcatc cgccggttcc    5520
taatgtacgg agcagatgct agggcaaatt gccctagcag gggaaaaagg tcgaaaaggt    5580
ctctttcctg tggatagcac gtacattggg aacccaaagc cgtacattgg gaaccggaac    5640
ccgtacattg ggaacccaaa gccgtacatt gggaaccggt cacacatgta agtgactgat    5700
ataaagaga aaaaaggcga ttttttccgcc taaaactctt taaaacttat taaaactctt    5760
aaaacccgcc tggcctgtgc ataactgtct ggccagcgca cagccgaaga gctgcaaaaa    5820
gcgcctaccc ttcggtcgct gcgctcccta cgccccgccg cttcgcgtcg gcctatcgcg    5880
gccgctggcc gctcaaaaat ggctggccta cggccaggca atctaccagg gcgcggacaa    5940
gccgcgccgt cgccactcga ccgccggcgc tgaggtctgc ctcgtgaaga aggtgttgct    6000
gactcatacc aggcctgaat cgccccatca tccagccaga aagtgaggga gccacggttg    6060
atgagagctt tgttgtaggt ggaccagttg gtgattttga acttttgctt tgccacggaa    6120
```

```
cggtctgcgt tgtcgggaag atgcgtgatc tgatccttca actcagcaaa agttcgattt    6180
attcaacaaa gccgccgtcc cgtcaagtca gcgtaatgct ctgccagtgt tacaaccaat    6240
taaccaattc tgattagaaa aactcatcga gcatcaaatg aaactgcaat ttattcatat    6300
caggattatc aataccatat ttttgaaaaa gccgtttctg taatgaagga gaaaactcac    6360
cgaggcagtt ccataggatg gcaagatcct ggtatcggtc tgcgattccg actcgtccaa    6420
catcaataca acctattaat ttcccctcgt caaaaataag gttatcaagt gagaaatcac    6480
catgagtgac gactgaatcc ggtgagaatg gcaaaagctc tgcattaatg aatcggccaa    6540
cgcgcgggga gaggcggttt gcgtattggg cgctcttccg cttcctcgct cactgactcg    6600
ctgcgctcgg tcgttcggct gcggcgagcg gtatcagctc actcaaaggc ggtaatacgg    6660
ttatccacag aatcagggga taacgcagga aagaacatgt gagcaaaagg ccagcaaaag    6720
gccaggaacc gtaaaaaggc cgcgttgctg gcgtttttcc ataggctccg ccccccctgac   6780 gagcatcaca aaaatcgacg ctcaagtcag aggtggcgaa acccgacagg actataaaga    6840
taccaggcgt ttccccctgg aagctccctc gtgcgctctc ctgttccgac cctgccgctt    6900
accggatacc tgtccgcctt tctcccttcg ggaagcgtgg cgctttctca tagctcacgc    6960
tgtaggtatc tcagttcggt gtaggtcgtt cgctccaagc tgggctgtgt gcacgaaccc    7020
cccgttcagc ccgaccgctg cgccttatcc ggtaactatc gtcttgagtc caacccggta    7080
agacacgact tatcgccact ggcagcagcc actggtaaca ggattagcag agcgaggtat    7140
gtaggcggtg ctacagagtt cttgaagtgg tggcctaact acggctacac tagaagaaca    7200
gtatttggta tctgcgctct gctgaagcca gttaccttcg aaaaagagt tggtagctct     7260 tgatccggca aacaaaccac cgctggtagc ggtggttttt ttgtttgcaa gcagcagatt    7320
acgcgcagaa aaaaaggatc tcaagaagat cctttgatct ttctacgg gtctgacgct      7380 cagtggaacg aaaactcacg ttaagggatt ttggtcatga gattatcaaa aaggatcttc    7440
acctagatcc ttttgatccg gaattaattc ctgtggttgg catgcacata caaatggacg    7500
aacggataaa ccttttcacg cccttttaaa tatccgatta ttctaataaa cgctcttttc    7560
tcttaggttt acccgccaat atatcctgtc aaacactgat agtttaaact gaaggcggga    7620
aacgacaatc tgatcatgag cggagaatta agggagtcac gttatgaccc ccgccgatga    7680
cgcgggacaa gccgttttac gtttggaact gacagaaccg caacgctgca ggaattggcc    7740
gcagcggcca tttaaatcaa ttgggcgcgt acgtagcact agtgaattcc ggacccaagc    7800
tttggcagac aaagtggcag acatactgtc ccacaaatga agatggaatc tgtaaaagaa    7860
aacgcgtgaa ataatgcgtc tgacaaaggt taggtcggct gcctttaatc aataccaaag    7920
tggtccctac cacgatggaa aaactgtgca gtcggtttgg cttttctga cgaacaaata     7980 agattcgtgg ccgacaggtg ggggtccacc atgtgaaggc atcttcagac tccaataatg    8040
gagcaatgac gtaagggctt acgaaataag taagggtagt tgggaaatg tccactcacc     8100 cgtcagtcta taaatactta gcccctccct cattgttaag ggagcaaaat ctcagagaga    8160
tagtcctaga gagagaaaga gagcaagtag cctagaagtg gatctccacc atggcccagt    8220
ccaagcacgg cctgaccaag gagatgacca tgaagtaccg catggagggc tgcgtggacg    8280
gccacaagtt cgtgatcacc ggcgagggca tcggctaccc cttcaagggc aagcaggcca    8340
tcaacctgtg cgtggtggag ggcggcccct gcccttcgc cgaggacatc ttgtccgccg     8400
ccttcatgta cggcaaccgc gtgttcaccg agtaccccca ggacatcgtc gactacttca    8460
```

```
agaactcctg ccccgccggc tacacctggg accgctcctt cctgttcgag gacggcgccg    8520
tgtgcatctg caacgccgac atcaccgtga gcgtggagga gaactgcatg taccacgagt    8580
ccaagttcta cggcgtgaac ttccccgccg acggccccgt gatgaagaag atgaccgaca    8640
actgggagcc ctcctgcgag aagatcatcc ccgtgcccaa gcagggcatc ttgaagggcg    8700
acgtgagcat gtacctgctg ctgaaggacg gtggccgctt gcgctgccag ttcgacaccg    8760
tgtacaaggc caagtccgtg ccccgcaaga tgcccgactg gcacttcatc cagcacaagc    8820
tgacccgcga ggaccgcagc gacgccaaga accagaagtg gcacctgacc gagcacgcca    8880
tcgcctccgg ctccgccttg ccctgctcta gatccccgaa tttccccgat cgttcaaaca    8940
tttggcaata aagtttctta agattgaatc ctgttgccgg tcttgcgatg attatcatat    9000
aatttctgtt gaattacgtt aagcatgtaa taattaacat gtaatgcatg acgttattta    9060
tgagatgggt ttttatgatt agagtcccgc aattatacat ttaatacgcg atagaaaaca    9120
aaatatagcg cgcaaactag gataaattat cgcgcgcggt gtcatctatg ttactagatc    9180 gcggacccte atgagcggag aattaaggga gtcacgttat gaccccgcc gatgacgcgg    9240 gacaagccgt tttacgtttg gaactgacag aaccgcaacg aagctttggc agacaaagtg    9300
gcagacatac tgtcccacaa atgaagatgg aatctgtaaa agaaaacgcg tgaaataatg    9360
cgtctgacaa aggttaggtc ggctgccttt aatcaatacc aaagtggtcc ctaccacgat    9420
ggaaaaactg tgcagtcggt ttggcttttt ctgacgaaca aataagattc gtggccgaca    9480
ggtgggggtc caccatgtga aggcatcttc agactccaat aatggagcaa tgacgtaagg    9540
gcttacgaaa taagtaaggg tagtttggga aatgtccact cacccgtcag tctataaata    9600
cttagcccct ccctcattgt taagggagca aaatctcaga gagatagtcc tagagagaga    9660
aagagagcaa gtagcctaga agtggatcca gctccttgtt gtcttcgtgt tgatctggca    9720
agtctcttgg atctcaaatg ccactgaacc ctttgccaga tcaagtcgaa gacacaacac    9780
gggtttgagc tcttcatatg acgatcgttc aaacatttgg caataaagtt tcttaagatt    9840
gaatcctgtt gccggtcttg cgatgattat catataattt ctgttgaatt acgttaagca    9900
tgtaataatt aacatgtaat gcatgacgtt atttatgaga tgggttttta tgattagagt    9960
cccgcaatta tacatttaat acgcgataga aacaaaata tagcgcgcaa actaggataa    10020
attatcgcgc gcggtgtcat ctatgttact agatcgcgga ccgaagcttg catgcctgca    10080
ggtcgactct agaggatccg gagccaagtc tcataaacgc cattgtggaa gaaagtcttg    10140
agttggtggt aatgtaacag agtagtaaga acagagaaga gagagagtgt gagatacatg    10200
aattgtcggg caacaaaaat cctgaacatc ttattttagc aaagagaaag agttccgagt    10260
ctgtagcaga agagtgagga gaaatttaag ctcttggact tgtgaattgt tccgcctctt    10320
gaatacttct tcaatcctca tatattcttc ttctatgtta cctgaaaacc ggcatttaat    10380
ctcgcgggtt tattccggtt caacattttt tttgttttga gttattatct gggcttaata    10440
acgcaggcct gaaataaatt caaggcccaa ctgtttttttt ttttaagaag ttgctgttaa    10500
aaaaaaaaa                                                             10509
```

<210> SEQ ID NO 44
<211> LENGTH: 10509
<212> TYPE: DNA
<213> ORGANISM: Artificial Sequence
<220> FEATURE:
<223> OTHER INFORMATION: pKS51 (amiR0569)

<400> SEQUENCE: 44

```
ggaattaatt cctgtggttg gcatgcacat acaaatggac gaacggataa acctttcac    60
gcccttttaa atatccgatt attctaataa acgctctttt ctcttaggtt tacccgccaa  120
tatatcctgt caaacactga tagtttaaac tgaaggcggg aaacgacaat ctgatcatga  180
gcggagaatt aagggagtca cgttatgacc cccgccgatg acgcgggaca agccgtttta  240
cgtttggaac tgacagaacc gcaacgctgc aggaattggc cgcagcggcc atttaaatca  300
attgggcgcg tacgtagcac tagtgaattc cggacccaag cttttggcaga caaagtggca  360
gacatactgt cccacaaatg aagatggaat ctgtaaaaga aaacgcgtga ataatgcgt   420
ctgacaaagg ttaggtcggc tgcctttaat caataccaaa gtggtcccta ccacgatgga  480
aaaactgtgc agtcggtttg cttttctg acgaacaaat aagattcgtg ccgacaggt    540
gggggtccac catgtgaagg catcttcaga ctccaataat ggagcaatga cgtaagggct  600
tacgaaataa gtaagggtag tttgggaaat gtccactcac ccgtcagtct ataaatactt  660
agcccctccc tcattgttaa gggagcaaaa tctcagagag atagtcctag agagagaaag  720
agagcaagta gcctagaagt ggatctccac catggcccag tccaagcacg gcctgaccaa  780
ggagatgacc atgaagtacc gcatggaggg ctgcgtggac ggccacaagt tcgtgatcac  840
cggcgagggc atcggctacc ccttcaaggg caagcaggcc atcaacctgt gcgtggtgga  900
gggcggcccc ttgcccttcg ccgaggacat cttgtccgcc gccttcatgt acggcaaccg  960
cgtgttcacc gagtaccccc aggacatcgt cgactacttc aagaactcct gccccgccgg 1020
ctacacctgg gaccgctcct tcctgttcga ggacggcgcc gtgtgcatct gcaacgccga 1080
catcaccgtg agcgtggagg agaactgcat gtaccacgag tccaagttct acggcgtgaa 1140
cttccccgcc gacggccccg tgatgaagaa gatgaccgac aactgggagc cctcctgcga 1200
gaagatcatc cccgtgccca gcagggcat cttgaagggc gacgtgagca tgtacctgct 1260
gctgaaggac ggtggccgct tgcgctgcca gttcgacacc gtgtacaagg ccaagtccgt 1320
gccccgcaag atgcccgact ggcacttcat ccagcacaag ctgacccgcg aggaccgcag 1380
cgacgccaag aaccagaagt ggcacctgac cgagcacgcc atcgcctccg gctccgcctt 1440
gccctgctct agatccccga atttccccga tcgttcaaac atttggcaat aaagtttctt 1500
aagattgaat cctgttgccg gtcttgcgat gattatcata taatttctgt tgaattacgt 1560
taagcatgta ataattaaca tgtaatgcat gacgttattt atgagatggg ttttttatgat 1620
tagagtcccg caattataca tttaatacgc gatagaaaac aaaatatagc gcgcaaacta 1680
ggataaatta tcgcgcgcgg tgtcatctat gttactagat cgcggaccct catgagcgga 1740
gaattaaggg agtcacgtta tgaccccgc cgatgacgcg gacaagccg tttttacgttt 1800
ggaactgaca gaaccgcaac gaagctttgg cagacaaagt ggcagacata ctgtcccaca 1860
aatgaagatg gaatctgtaa aagaaaacgc gtgaaataat gcgtctgaca aaggttaggt 1920
cggctgcctt taatcaatac caaagtggtc cctaccacga tggaaaaact gtgcagtcgg 1980
tttggctttt tctgacgaac aaataagatt cgtggccgac aggtgggggt ccaccatgtg 2040
aaggcatctt cagactccaa taatggagca atgacgtaag gcttacgaa ataagtaagg 2100
gtagtttggg aaatgtccac tcacccgtca gtctataaat acttagcccc tcctcattg  2160
ttaagggagc aaaatctcag agagatagtc ctagagagag aaagagagca agtagcctag 2220
aagtggatcc agctccttgt tgtgtgattg ttgatctggc aagtctcttg gatctcaaat 2280
gccactgaac ccttttgccag atcaacaatc acacacaaca cgggtttgag ctcttcatat 2340
```

| | |
|---|---|
| gacgatcgtt caaacatttg gcaataaagt ttcttaagat tgaatcctgt tgccggtctt | 2400 |
| gcgatgatta tcatataatt tctgttgaat tacgttaagc atgtaataat taacatgtaa | 2460 |
| tgcatgacgt tatttatgag atgggttttt atgattagag tcccgcaatt atacatttaa | 2520 |
| tacgcgatag aaaacaaaat atagcgcgca aactaggata aattatcgcg cgcggtgtca | 2580 |
| tctatgttac tagatcgcgg accgaagctt gcatgcctgc aggtcgactc tagaggatcc | 2640 |
| ggagccaagt ctcataaacg ccattgtgga agaaagtctt gagttggtgg taatgtaaca | 2700 |
| gagtagtaag aacagagaag agagagagtg tgagatacat gaattgtcgg gcaacaaaaa | 2760 |
| tcctgaacat cttatttag caaagagaaa gagttccgag tctgtagcag aagagtgagg | 2820 |
| agaaatttaa gctcttggac ttgtgaattg ttccgcctct tgaatacttc ttcaatcctc | 2880 |
| atatattctt cttctatgtt acctgaaaac cggcatttaa tctcgcgggt ttattccggt | 2940 |
| tcaacatttt ttttgttttg agttattatc tgggcttaat aacgcaggcc tgaaataaat | 3000 |
| tcaaggccca actgtttttt ttttaagaa gttgctgtta aaaaaaaaa aagggaatta | 3060 |
| acaacaacaa caaaaaaga taagaaaat aataacaatt actttaattg tagactaaaa | 3120 |
| aaacatagat tttatcatga aaaaagaga aagaaataa aaacttggat caaaaaaaaa | 3180 |
| acatacagat cttctaatta ttaactttc ttaaaaatta ggtccttttt cccaacaatt | 3240 |
| aggtttagag ttttggaatt aaaccaaaaa gattgttcta aaaaatactc aaatttggta | 3300 |
| gataagtttc cttattttaa ttagtcaatg gtagatactt ttttttcttt tctttattag | 3360 |
| agtagattag aatcttttat gccaagtatt gataaattaa atcaagaaga taaactatca | 3420 |
| taatcaacat gaaattaaaa gaaaaatctc atatatagta ttagtattct ctatatatat | 3480 |
| tatgattgct tattcttaat gggttgggtt aaccaagaca tagtcttaat ggaaagaatc | 3540 |
| tttttgaac tttttcctta ttgattaaat tcttctatag aaaagaaaga aattatttga | 3600 |
| ggaaagtat atacaaaaag aaaaatagaa aaatgtcagt gaagcagatg taatggatga | 3660 |
| cctaatccaa ccaccaccat aggatgtttc tacttgagtc ggtctttaa aaacgcacgg | 3720 |
| tggaaaatat gacacgtatc atatgattcc ttcctttagt ttcgtgataa taatcctcaa | 3780 |
| ctgatatctt cctttttg ttttggctaa agatattta ttctcattaa tagaaaagac | 3840 |
| ggttttgggc ttttggtttg cgatataaag aagaccttcg tgtggaagat aataattcat | 3900 |
| cctttcgtct ttttctgact cttcaatctc tcccaaagcc taaagcgatc tctgcaaatc | 3960 |
| tctcgcgact ctctctttca aggtatattt tctgattctt tttgtttttg attcgtatct | 4020 |
| gatctccaat ttttgttatg tggattattg aatcttttgt ataaattgct tttgacaata | 4080 |
| ttgttcgttt cgtcaatcca gcttctaaat tttgtcctga ttactaagat atcgattcgt | 4140 |
| agtgtttaca tctgtgtaat ttcttgcttg attgtgaaat taggattttc aaggacgatc | 4200 |
| tattcaattt ttgtgttttc tttgttcgat tctctctgtt ttaggtttct tatgtttaga | 4260 |
| tccgtttctc tttggtgttg ttttgattc tcttacggct tttgatttgg tatatgttcg | 4320 |
| ctgattggtt tctacttgtt ctattgtttt atttcaggtg gatcccacca tgtctccgga | 4380 |
| gaggagacca gttgagatta ggccagctac agcagctgat atggccgcgg tttgtgatat | 4440 |
| cgttaaccat tacattgaga cgtctacagt gaactttagg acagagccac aaacaccaca | 4500 |
| agagtggatt gatgatctag agaggttgca agatagatac ccttggttgg ttgctgaggt | 4560 |
| tgagggtgtt gtggctggta ttgcttacgc tgggccctgg aaggctagga acgcttacga | 4620 |
| ttggacagtt gagagtactg tttacgtgtc acataggcat caaaggttgg gcctaggatc | 4680 |
| tacattgtac acacatttgc ttaagtctat ggaggcgcaa ggttttaagt ctgtggttgc | 4740 |

```
tgttataggc cttccaaacg atccatctgt taggttgcat gaggctttgg gatacacagc   4800
ccggggtaca ttgcgcgcag ctggatacaa gcatggtgga tggcatgatg ttggtttttg   4860
gcaaagggat tttgagttgc cagctcctcc aaggccagtt aggccagtta cccagatatg   4920
agtcgagctc tagatccccg aatttccccg atcgttcaaa catttggcaa taaagtttct   4980
taagattgaa tcctgttgcc ggtcttgcga tgattatcat ataatttctg ttgaattacg   5040
ttaagcatgt aataattaac atgtaatgca tgacgttatt tatgagatgg gttttatga    5100
ttagagtccc gcaattatac atttaatacg cgatagaaaa caaatatag cgcgcaaact    5160
aggataaatt atcgcgcgcg gtgtcatcta tgttactaga tcgggaattg ggtaccatgc   5220
ccgggcggcc agcatggccg tatccgcaat gtgttattaa gttgtctaag cgtcaatttg   5280
tttacaccac aatatatcct gccaccagcc agcaacagc tccccgaccg gcagctcggc    5340
acaaaatcac cactcgatac aggcagccca tcagaattaa ttctcatgtt tgacagctta   5400
tcatcgactg cacggtgcac caatgcttct ggcgtcaggc agccatcgga agctgtggta   5460
tggctgtgca ggtcgtaaat cactgcataa ttcgtgtcgc tcaaggcgca ctcccgttct   5520
ggataatgtt ttttgcgccg acatcataac ggttctggca aatattctga atgagctgt    5580
tgacaattaa tcatccggct cgtataatgt gtggaattgt gagcggataa caatttcaca   5640
caggaaacag accatgaggg aagcgttgat cgccgaagta tcgactcaac tatcagaggt   5700
agttggcgtc atcgagcgcc atctcgaacc gacgttgctg gccgtacatt tgtacggctc   5760
cgcagtggat ggcggcctga agccacacag tgatattgat ttgctggtta cggtgaccgt   5820
aaggcttgat gaaacaacgc ggcgagcttt gatcaacgac cttttggaaa cttcggcttc   5880
ccctggagag agcgagattc tccgcgctgt agaagtcacc attgttgtgc acgacgacat   5940
cattccgtgg cgttatccag ctaagcgcga actgcaattt ggagaatggc agcgcaatga   6000
cattcttgca ggtatcttcg agccagccac gatcgacatt gatctggcta tcttgctgac   6060
aaaagcaaga gaacatagcg ttgccttggt aggtccagcg gcggaggaac tctttgatcc   6120
ggttcctgaa caggatctat ttgaggcgct aaatgaaacc ttaacgctat ggaactcgcc   6180
gcccgactgg gctggcgatg agcgaaatgt agtgcttacg ttgtcccgca tttggtacag   6240
cgcagtaacc ggcaaaatcg cgccgaagga tgtcgctgcc gactgggcaa tggagcgcct   6300
gccggcccag tatcagcccg tcatacttga agctaggcag gcttatcttg acaagaaga   6360
tcgcttggcc tcgcgcgcag atcagttgga agaatttgtt cactacgtga aaggcgagat   6420
caccaaagta gtcggcaaat aaagctctag tggatctccg taccccgg g gatctggct    6480
cgcggcggac gcacgacgcc ggggcgagac cataggcgat ctcctaaatc aatagtagct   6540
gtaacctcga agcgtttcac ttgtaacaac gattgagaat ttttgtcata aaattgaaat   6600
acttggttcg cattttttgtc atccgcggtc agccgcaatt ctgacgaact gcccatttag   6660
ctggagatga ttgtacatcc ttcacgtgaa aatttctcaa gcgctgtgaa caagggttca   6720
gatttagat tgaaaggtga gccgttgaaa cacgttcttc ttgtcgatga cgacgtcgct    6780
atgcggcatc ttattattga ataccttacg atccacgcct tcaaagtgac cgcggtagcc   6840
gacagcaccc agttcacaag agtactctct tccgcgacgg tcgatgtcgt ggttgttgat   6900
ctagatttag gtcgtgaaga tgggctcgag atcgttcgta atctggcggc aaagtctgat   6960
attccaatca taattatcag tggcgaccgc cttgaggaga cggataaagt tgttgcactc   7020
gagctaggag caagtgattt tatcgctaag ccgttcagta tcagagagtt tctagcacgc   7080
```

```
attcgggttg ccttgcgcgt gcgccccaac gttgtccgct ccaaagaccg acggtctttt    7140
tgttttactg actggacact taatctcagg caacgtcgct tgatgtccga agctggcggt    7200
gaggtgaaac ttacggcagg tgagttcaat cttctcctcg cgttttagga gaaacccgc    7260 gacgttctat cgcgcgagca acttctcatt gccagtcgag tacgcgacga ggaggtttat    7320
gacaggagta tagatgttct cattttgagg ctgcgccgca aacttgaggc agatccgtca    7380
agccctcaac tgataaaaac agcaagaggt gccggttatt tctttgacgc ggacgtgcag    7440
gtttcgcacg ggggacgat ggcagcctga gccaattccc agatccccga ggaatcggcg    7500
tgagcggtcg caaaccatcc ggcccggtac aaatcggcgc ggcgctgggt gatgacctgg    7560
tggagaagtt gaaggccgcg caggccgccc agcggcaacg catcgaggca gaagcacgcc    7620
ccggtgaatc gtggcaagcg gccgctgatc gaatccgcaa agaatcccgg caaccgccgg    7680
cagccggtgc gccgtcgatt aggaagccgc ccaagggcga cgagcaacca gattttttcg    7740
ttccgatgct ctatgacgtg ggcacccgcg atagtcgcag catcatggac gtggccgttt    7800
tccgtctgtc gaagcgtgac cgacgagctg gcgaggtgat ccgctacgag cttccagacg    7860
ggcacgtaga ggtttccgca gggccggccg gcatggccag tgtgtgggat tacgacctgg    7920
tactgatggc ggtttcccat ctaaccgaat ccatgaaccg ataccgggaa gggaagggag    7980
acaagcccgg ccgcgtgttc cgtccacacg ttgcggacgt actcaagttc tgccggcgag    8040
ccgatggcgg aaagcagaaa gacgacctgg tagaaacctg cattcggtta aacaccacgc    8100
acgttgccat gcagcgtacg aagaaggcca agaacggccg cctggtgacg gtatccgagg    8160
gtgaagcctt gattagccgc tacaagatcg taaagagcga aaccgggcgg ccggagtaca    8220
tcgagatcga gctagctgat tggatgtacc gcgagatcac agaaggcaag aacccggacg    8280
tgctgacggt tcaccccgat tacttttga tcgatcccgg catcggccgt tttctctacc    8340
gcctggcacg ccgcgccgca ggcaaggcag aagccagatg gttgttcaag acgatctacg    8400
aacgcagtgg cagcgccgga gagttcaaga agttctgttt caccgtgcgc aagctgatcg    8460
ggtcaaatga cctgccggag tacgatttga aggaggaggc ggggcaggct ggcccgatcc    8520
tagtcatgcg ctaccgcaac ctgatcgagg gcgaagcatc cgccggttcc taatgtacgg    8580
agcagatgct agggcaaatt gccctagcag gggaaaaagg tcgaaaaggt ctctttcctg    8640
tggatagcac gtacattggg aacccaaagc cgtacattgg gaaccggaac ccgtacattg    8700
ggaacccaaa gccgtacatt gggaaccggt cacacatgta agtgactgat ataaaagaga    8760
aaaaaggcga ttttttccgcc taaaactctt taaaacttat taaaactctt aaaacccgcc    8820
tggcctgtgc ataactgtct ggccagcgca cagccgaaga gctgcaaaaa gcgcctaccc    8880
ttcggtcgct gcgctcccta cgccccgccg cttcgcgtcg gcctatcgcg gccgctggcc    8940
gctcaaaaat ggctggccta cggccaggca atctaccagg gcgcggacaa gccgcgccgt    9000
cgccactcga ccgccggcgc tgaggtctgc ctcgtgaaga aggtgttgct gactcatacc    9060
aggcctgaat cgccccatca tccagccaga aagtgaggga gccacggttg atgagagctt    9120
tgttgtaggt ggaccagttg gtgattttga acttttgctt tgccacggaa cggtctgcgt    9180
tgtcgggaag atgcgtgatc tgatccttca actcagcaaa agttcgattt attcaacaaa    9240
gccgccgtcc cgtcaagtca gcgtaatgct ctgccagtgt tacaaccaat taaccaattc    9300
tgattagaaa aactcatcga gcatcaaatg aaactgcaat ttattcatat caggattatc    9360
aataccatat ttttgaaaaa gccgtttctg taatgaagga gaaaactcac cgaggcagtt    9420
ccataggatg caagatcct ggtatcggtc tgcgattccg actcgtccaa catcaataca    9480
```

```
acctattaat ttccctcgt caaaaataag gttatcaagt gagaaatcac catgagtgac    9540
gactgaatcc ggtgagaatg gcaaaagctc tgcattaatg aatcggccaa cgcgcgggga    9600
gaggcggttt gcgtattggg cgctcttccg cttcctcgct cactgactcg ctgcgctcgg    9660
tcgttcggct gcggcgagcg gtatcagctc actcaaaggc ggtaatacgg ttatccacag    9720
aatcagggga taacgcagga agaacatgt gagcaaaagg ccagcaaaag gccaggaacc    9780
gtaaaaaggc cgcgttgctg gcgttttcc ataggctccg ccccctgac gagcatcaca    9840
aaaatcgacg ctcaagtcag aggtggcgaa acccgacagg actataaaga taccaggcgt    9900
ttccccctgg aagctccctc gtgcgctctc ctgttccgac cctgccgctt accggatacc    9960
tgtccgcctt tctcccttcg ggaagcgtgg cgctttctca tagctcacgc tgtaggtatc   10020
tcagttcggt gtaggtcgtt cgctccaagc tgggctgtgt gcacgaaccc cccgttcagc   10080
ccgaccgctg cgccttatcc ggtaactatc gtcttgagtc aacccggta agacacgact   10140
tatcgccact ggcagcagcc actggtaaca ggattagcag agcgaggtat gtaggcggtg   10200
ctacagagtt cttgaagtgg tggcctaact acggctacac tagaagaaca gtatttggta   10260
tctgcgctct gctgaagcca gttaccttcg gaaaaagagt tggtagctct tgatccggca   10320
aacaaaccac cgctggtagc ggtggttttt tgtttgcaa gcagcagatt acgcgcagaa   10380
aaaaaggatc tcaagaagat cctttgatct tttctacggg gtctgacgct cagtggaacg   10440
aaaactcacg ttaagggatt ttggtcatga gattatcaaa aaggatcttc acctagatcc   10500
ttttgatcc                                                            10509

<210> SEQ ID NO 45
<211> LENGTH: 10509
<212> TYPE: DNA
<213> ORGANISM: Artificial Sequence
<220> FEATURE:
<223> OTHER INFORMATION: pKS104 (aMIR164-rps23-1)

<400> SEQUENCE: 45
attcctgtgg ttggcatgca catacaaatg gacgaacgga taaaccttt cacgcccttt      60
taaatatccg attattctaa taaacgctct tttctcttag gtttaccccgc caatatatcc    120
tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccatttaaa tcaattgggc     300
gcgtacgtag cactagtgaa ttccggaccc aagctttggc agacaaagtg gcagacatac     360
tgtcccacaa atgaagatgg aatctgtaaa agaaacgcg tgaaataatg cgtctgacaa     420
aggttaggtc ggctgccttt aatcaatacc aaagtggtcc ctaccacgat ggaaaaactg     480
tgcagtcggt ttggcttttt ctgacgaaca aataagattc gtggccgaca ggtgggggtc     540
caccatgtga aggcatcttc agactccaat aatggagcaa tgacgtaagg gcttacgaaa     600
taagtaaggg tagtttggga aatgtccact cacccgtcag tctataaata cttagcccct    660
ccctcattgt taagggagca aaatctcaga gagatagtcc tagagagaga aagagagcaa     720
gtagcctaga agtggatctc caccatggcc cagtccaagc acggcctgac caaggagatg     780
accatgaagt accgcatgga gggctgcgtg gacggccaca gttcgtgat caccggcgag     840
ggcatcggct accccttcaa gggcaagcag gccatcaacc tgtgcgtggt ggagggcggc     900
ccctttgccct tcgccgagga catcttgtcc gccgccttca tgtacggcaa ccgcgtgttc     960
```

-continued

```
accgagtacc cccaggacat cgtcgactac ttcaagaact cctgccccgc cggctacacc      1020
tgggaccgct ccttcctgtt cgaggacggc gccgtgtgca tctgcaacgc cgacatcacc      1080
gtgagcgtgg aggagaactg catgtaccac gagtccaagt tctacggcgt gaacttcccc      1140
gccgacggcc ccgtgatgaa gaagatgacc gacaactggg agccctcctg cgagaagatc      1200
atccccgtgc ccaagcaggg catcttgaag ggcgacgtga gcatgtacct gctgctgaag      1260
gacggtggcc gcttgcgctg ccagttcgac accgtgtaca aggccaagtc cgtgccccgc      1320
aagatgcccg actggcactt catccagcac aagctgaccc gcgaggaccg cagcgacgcc      1380
aagaaccaga gtggcaccct gaccgagcac gccatcgcct ccggctccgc cttgccctgc      1440
tctagatccc cgaatttccc cgatcgttca acatttggc  aataaagttt cttaagattg      1500
aatcctgttg ccggtcttgc gatgattatc atataatttc tgttgaatta cgttaagcat      1560
gtaataatta acatgtaatg catgacgtta tttatgagat gggtttttat gattagagtc      1620
ccgcaattat acatttaata cgcgataaga aacaaaatat agcgcgcaaa ctaggataaa      1680
ttatcgcgcg cggtgtcatc tatgttacta gatcgcggac cctcatgagc ggagaattaa      1740
gggagtcacg ttatgacccc cgccgatgac gcgggacaag ccgttttacg tttggaactg      1800
acagaaccga aacgaagctt tggcagacaa agtggcagac atactgtccc acaaatgaag      1860
atggaatctg taaagaaaaa cgcgtgaaat aatgcgtctg acaaaggtta ggtcggctgc      1920
ctttaatcaa taccaaagtg gtccctacca cgatggaaaa actgtgcagt cggtttggct      1980
ttttctgacg aacaaataag attcgtggcc gacaggtggg ggtccaccat gtgaaggcat      2040
cttcagactc caataatgga gcaatgacgt aagggcttac gaaataagta agggtagttt      2100
gggaaatgtc cactcacccg tcagtctata aatacttagc ccctccctca ttgttaaggg      2160
agcaaaatct cagagagata gtcctagaga gagaaagaga gcaagtagcc tagaagtgga      2220
tccagctcct tgtttctcgg aaattgcgct tccaagtctc ttggatctca aatgccactg      2280
aaccctttgg aagcgcaaaa tccgagaaca acacgggttt gagctcttca tatgacgatc      2340
gttcaaacat ttggcaataa agtttcttaa gattgaatcc tgttgccggt cttgcgatga      2400
ttatcatata atttctgttg aattacgtta agcatgtaat aattaacatg taatgcatga      2460
cgttatttat gagatgggtt tttatgatta gagtcccgca attatacatt taatacgcga      2520
tagaaaacaa aatatagcgc gcaaactagg ataaattatc gcgcgcggtg tcatctatgt      2580
tactagatcg cggaccgaag cttgcatgcc tgcaggtcga ctctagagga tccggagcca      2640
agtctcataa acgccattgt ggaagaaagt cttgagttgg tggtaatgta acagagtagt      2700
aagaacagag aagagagaga gtgtgagata catgaattgt cgggcaacaa aaatcctgaa      2760
catcttattt tagcaaagag aaagagttcc gagtctgtag cagaagagtg aggagaaatt      2820
taagctcttg gacttgtgaa ttgttccgcc tcttgaatac ttcttcaatc ctcatatatt      2880
cttcttctat gttacctgaa aaccggcatt aatctcgcg  ggtttattcc ggttcaacat      2940 ttttttttgtt ttgagttatt atctgggctt aataacgcag gcctgaaata aattcaaggc      3000
ccaactgttt tttttttttaa gaagttgctg ttaaaaaaaa aaaagggaa  ttaacaacaa      3060 caacaaaaaa agataaagaa aataataaca attactttaa ttgtagacta aaaaaacata      3120
gattttatca tgaaaaaaag agaaagaaa  taaaaacttg gatcaaaaaa aaaacataca      3180
gatcttctaa ttattaactt ttcttaaaaa ttaggtcctt tttcccaaca attaggttta      3240
gagttttgga attaaaccaa aaagattgtt ctaaaaaata ctcaaatttg gtagataagt      3300
ttccttattt taattagtca atggtagata ctttttttttc ttttctttat tagagtagat      3360
```

```
tagaatctttt tatgccaagt attgataaat taaatcaaga agataaaacta tcataatcaa    3420 catgaaatta aagaaaaat  ctcatatata gtattagtat tctctatata tattatgatt    3480
gcttattctt aatgggttgg gttaaccaag acatagtctt aatggaaaga atcttttttg    3540 aacttttttcc ttattgatta aattcttcta tagaaaagaa agaaattatt tgaggaaaag    3600
tatatacaaa aagaaaaata gaaaatgtc  agtgaagcag atgtaatgga tgacctaatc    3660
caaccaccac cataggatgt ttctacttga gtcggtcttt taaaaacgca cggtggaaaa    3720
tatgacacgt atcatatgat tccttccttt agtttcgtga taataatcct caactgatat    3780
cttccttttt ttgttttggc taaagatatt ttattctcat taatagaaaa gacggttttg    3840
ggcttttggt ttgcgatata aagaagacct tcgtgtggaa gataataatt catcctttcg    3900 tcttttttctg actcttcaat ctctcccaaa gcctaaagcg atctctgcaa atctctcgcg    3960
actctctctt tcaaggtata ttttctgatt ctttttgttt ttgattcgta tctgatctcc    4020 aattttttgtt atgtggatta ttgaatcttt tgtataaatt gcttttgaca atattgttcg    4080
tttcgtcaat ccagcttcta aattttgtcc tgattactaa gatatcgatt cgtagtgttt    4140
acatctgtgt aatttcttgc ttgattgtga aattaggatt ttcaaggacg atctattcaa    4200
tttttgtgtt ttctttgttc gattctctct gttttaggtt tcttatgttt agatccgttt    4260
ctctttggtg ttgttttgat ttctcttacg gcttttgatt tggtatatgt tcgctgattg    4320
gtttctactt gttctattgt tttatttcag gtggatccca ccatgtctcc ggagaggaga    4380
ccagttgaga ttaggccagc tacagcagct gatatggccg cggtttgtga tatcgttaac    4440
cattacattg agacgtctac agtgaacttt aggacagagc cacaaacacc acaagagtgg    4500
attgatgatc tagagaggtt gcaagataga taccccttggt tggttgctga ggttgagggt    4560
gttgtggctg gtattgctta cgctgggccc tggaaggcta ggaacgctta cgattggaca    4620
gttgagagta ctgtttacgt gtcacatagg catcaaaggt tgggcctagg atctacattg    4680
tacacacatt tgcttaagtc tatggaggcg caaggtttta agtctgtggt tgctgttata    4740
ggccttccaa acgatccatc tgttaggttg catgaggctt tgggatacac agcccgggt    4800 acattgcgcg cagctggata caagcatggt ggatggcatg atgttggttt ttggcaaagg    4860
gattttgagt tgccagctcc tccaaggcca gttaggccag ttacccagat atgagtcgag    4920
ctctagatcc ccgaatttcc ccgatcgttc aaacatttgg caataaagtt tcttaagatt    4980
gaatcctgtt gccggtcttg cgatgattat catataattt ctgttgaatt acgttaagca    5040
tgtaataatt aacatgtaat gcatgacgtt atttatgaga tgggttttta tgattagagt    5100
cccgcaatta tacatttaat acgcgataga aaacaaaata tagcgcgcaa actaggataa    5160
attatcgcgc gcggtgtcat ctatgttact agatcgggaa ttgggtacca tgcccgggcg    5220
gccagcatgg ccgtatccgc aatgtgttat taagttgtct aagcgtcaat tgtttacac    5280 cacaatatat cctgccacca gccagccaac agctccccga ccgcagctc  ggcacaaaat    5340 caccactcga tacaggcagc ccatcagaat taattctcat gtttgacagc ttatcatcga    5400
ctgcacggtg caccaatgct tctggcgtca ggcagccatc ggaagctgtg gtatggctgt    5460
gcaggtcgta aatcactgca taattcgtgt cgctcaaggc gcactcccgt tctggataat    5520
gttttttgcg ccgacatcat aacggttctg gcaaatattc tgaaatgagc tgttgacaat    5580
taatcatccg gctcgtataa tgtgtggaat tgtgagcgga taacaatttc acacaggaaa    5640
cagaccatga gggaagcgtt gatcgccgaa gtatcgactc aactatcaga ggtagttggc    5700
```

```
gtcatcgagc gccatctcga accgacgttg ctggccgtac atttgtacgg ctccgcagtg    5760
gatggcggcc tgaagccaca cagtgatatt gatttgctgg ttacggtgac cgtaaggctt    5820
gatgaaacaa cgcggcgagc tttgatcaac gaccttttgg aaacttcggc ttcccctgga    5880
gagagcgaga ttctccgcgc tgtagaagtc accattgttg tgcacgacga catcattccg    5940
tggcgttatc cagctaagcg cgaactgcaa tttggagaat ggcagcgcaa tgacattctt    6000
gcaggtatct tcgagccagc cacgatcgac attgatctgg ctatcttgct gacaaaagca    6060
agagaacata gcgttgcctt ggtaggtcca gcggcggagg aactctttga tccggttcct    6120
gaacaggatc tatttgaggc gctaaatgaa accttaacgc tatggaactc gccgcccgac    6180
tgggctggcg atgagcgaaa tgtagtgctt acgttgtccc gcatttggta cagcgcagta    6240
accggcaaaa tcgcgccgaa ggatgtcgct gccgactggg caatggagcg cctgccggcc    6300
cagtatcagc ccgtcatact tgaagctagg caggcttatc ttggacaaga agatcgcttg    6360
gcctcgcgcg cagatcagtt ggaagaattt gttcactacg tgaaaggcga gatcaccaaa    6420
gtagtcggca aataaagctc tagtggatct ccgtaccccc gggggatctg gctcgcggcg    6480
gacgcacgac gccggggcga gaccataggc gatctcctaa atcaatagta gctgtaacct    6540
cgaagcgttt cacttgtaac aacgattgag aattttttgtc ataaaattga aatacttggt    6600
tcgcattttt gtcatccgcg gtcagccgca attctgacga actgcccatt tagctggaga    6660
tgattgtaca tccttcacgt gaaaatttct caagcgctgt gaacaagggt tcagatttta    6720
gattgaaagg tgagccgttg aaacacgttc ttcttgtcga tgacgacgtc gctatgcggc    6780
atcttattat tgaataccctt acgatccacg ccttcaaagt gaccgcggta gccgacagca    6840
cccagttcac aagagtactc tcttccgcga cggtcgatgt cgtggttgtt gatctagatt    6900
taggtcgtga agatgggctc gagatcgttc gtaatctggc ggcaaagtct gatattccaa    6960
tcataattat cagtggcgac cgccttgagg agacggataa agttgttgca ctcgagctag    7020
gagcaagtga ttttatcgct aagccgttca gtatcagaga gtttctagca cgcattcggg    7080
ttgccttgcg cgtgcgcccc aacgttgtcc gctccaaaga ccgacggtct ttttgtttta    7140
ctgactggac acttaatctc aggcaacgtc gcttgatgtc cgaagctggc ggtgaggtga    7200
aacttacggc aggtgagttc aatcttctcc tcgcgttttt agagaaaccc cgcgacgttc    7260
tatcgcgcga gcaacttctc attgccagtc gagtacgcga cgaggaggtt tatgacagga    7320
gtatagatgt tctcattttg aggctgcgcc gcaaacttga ggcagatccg tcaagccctc    7380
aactgataaa aacagcaaga ggtgccggtt atttctttga cgcggacgtg caggtttcgc    7440 acgggggac gatggcagcc tgagccaatt cccagatccc cgaggaatcg gcgtgagcgg    7500
tcgcaaacca tccggcccgg tacaaatcgg cgcggcgctg ggtgatgacc tggtggagaa    7560
gttgaaggcc gcgcaggccg cccagcggca acgcatcgag gcagaagcac gccccggtga    7620
atcgtggcaa gcggccgctg atcgaatccg caaagaatcc cggcaaccgc cggcagccgg    7680
tgcgccgtcg attaggaagc cgcccaaggg cgacgagcaa ccagattttt tcgttccgat    7740
gctctatgac gtgggcaccc gcgatagtcg cagcatcatg gacgtggccg ttttccgtct    7800
gtcgaagcgt gaccgacgag ctggcgaggt gatccgctac gagcttccag acgggcacgt    7860
agaggtttcc gcagggccgg ccggcatggc cagtgtgtgg gattacgacc tggtactgat    7920 ggcggttttcc catctaaccg aatccatgaa ccgataccgg gaaggaaagg gagacaagcc    7980
cggccgcgtg ttccgtccac acgttgcgga cgtactcaag ttctgccggc gagccgatgg    8040
cggaaagcag aaagacgacc tggtagaaac ctgcattcgg ttaaacacca cgcacgttgc    8100
```

```
catgcagcgt acgaagaagg ccaagaacgg ccgcctggtg acggtatccg agggtgaagc    8160
cttgattagc cgctacaaga tcgtaaagag cgaaaccggg cggccggagt acatcgagat    8220
cgagctagct gattggatgt accgcgagat cacagaaggc aagaacccgg acgtgctgac    8280
ggttcacccc gattactttt tgatcgatcc cggcatcggc cgttttctct accgcctggc    8340
acgccgcgcc gcaggcaagg cagaagccag atggttgttc aagacgatct acgaacgcag    8400
tggcagcgcc ggagagttca agaagttctg tttcaccgtg cgcaagctga tcgggtcaaa    8460
tgacctgccg gagtacgatt tgaaggagga ggcggggcag gctggcccga tcctagtcat    8520
gcgctaccga aacctgatcg agggcgaagc atccgccggt tcctaatgta cggagcagat    8580
gctagggcaa attgccctag caggggaaaa aggtcgaaaa ggtctctttc ctgtggatag    8640
cacgtacatt gggaacccaa agccgtacat tgggaaccgg aacccgtaca ttgggaaccc    8700
aaagccgtac attgggaacc ggtcacacat gtaagtgact gatataaaag agaaaaaagg    8760
cgatttttcc gcctaaaact ctttaaaact tattaaaact cttaaaaccc gcctggcctg    8820
tgcataactg tctggccagc gcacagccga agagctgcaa aaagcgccta cccttcggtc    8880
gctgcgctcc ctacgccccg ccgcttcgcg tcggcctatc gcggccgctg gccgctcaaa    8940
aatggctggc ctacggccag gcaatctacc agggcgcgga caagccgcgc cgtcgccact    9000
cgaccgccgg cgctgaggtc tgcctcgtga agaaggtgtt gctgactcat accaggcctg    9060
aatcgcccca tcatccagcc agaaagtgag ggagccacgg ttgatgagag ctttgttgta    9120
ggtggaccag ttggtgattt tgaacttttg ctttgccacg gaacggtctg cgttgtcggg    9180
aagatgcgtg atctgatcct tcaactcagc aaaagttcga tttattcaac aaagccgccg    9240
tcccgtcaag tcagcgtaat gctctgccag tgttacaacc aattaaccaa ttctgattag    9300
aaaaactcat cgagcatcaa atgaaactgc aatttattca tatcaggatt atcaatacca    9360
tatttttgaa aaagccgttt ctgtaatgaa ggagaaaact caccgaggca gttccatagg    9420
atggcaagat cctggtatcg gtctgcgatt ccgactcgtc aacatcaat acaacctatt    9480 aatttcccct cgtcaaaaat aaggttatca agtgagaaat caccatgagt gacgactgaa    9540
tccggtgaga atgcaaaaag ctctgcatta atgaatcggc caacgcgcgg ggagaggcgg    9600
tttgcgtatt gggcgctctt ccgcttcctc gctcactgac tcgctgcgct cggtcgttcg    9660
gctgcggcga gcggtatcag ctcactcaaa ggcggtaata cggttatcca cagaatcagg    9720
ggataacgca ggaaagaaca tgtgagcaaa aggccagcaa aaggccagga accgtaaaaa    9780
ggccgcgttg ctggcgtttt tccataggct ccgcccccct gacgagcatc acaaaaatcg    9840
acgctcaagt cagaggtggc gaaacccgac aggactataa agataccagg cgtttccccc    9900
tggaagctcc ctcgtgcgct ctcctgttcc gaccctgccg cttaccggat acctgtccgc    9960
ctttctccct tcgggaagcg tggcgctttc tcatagctca cgctgtaggt atctcagttc   10020
ggtgtaggtc gttcgctcca agctgggctg tgtgcacgaa ccccccgttc agcccgaccg   10080
ctgcgcctta tccggtaact atcgtcttga gtccaacccg gtaagacacg acttatcgcc   10140
actggcagca gccactggta acaggattag cagagcgagg tatgtaggcg gtgctacaga   10200
gttcttgaag tggtggccta actacggcta cactagaaga acagtatttg gtatctgcgc   10260
tctgctgaag ccagttacct tcggaaaaag agttggtagc tcttgatccg gcaaacaaac   10320
caccgctggt agcggtggtt tttttgtttg caagcagcag attacgcgca gaaaaaaagg   10380
atctcaagaa gatcctttga tcttttctac ggggtctgac gctcagtgga acgaaaactc   10440
```

-continued

```
acgttaaggg attttggtca tgagattatc aaaaaggatc ttcacctaga tccttttgat    10500
ccggaatta                                                            10509
```

<210> SEQ ID NO 46
<211> LENGTH: 9634
<212> TYPE: DNA
<213> ORGANISM: Artificial Sequence
<220> FEATURE:
<223> OTHER INFORMATION: Control vector 15312 (empty)

<400> SEQUENCE: 46

```
aattcctgtg gttggcatgc acatacaaat ggacgaacgg ataaaccttt tcacgccctt      60
ttaaatatcc gattattcta ataaacgctc ttttctctta ggtttacccg ccaatatatc     120
ctgtcaaaca ctgatagttt aaactgaagg cgggaaacga caatctgatc atgagcggag     180
aattaaggga gtcacgttat gacccccgcc gatgacgcgg gacaagccgt tttacgtttg     240
gaactgacag aaccgcaacg ctgcaggaat tggccgcagc ggccatttaa atcaattggg     300
cgcgtacgta gcactagtga attccggacc caagctttgg cagacaaagt ggcagacata     360
ctgtcccaca aatgaagatg gaatctgtaa agaaaacgc gtgaaataat gcgtctgaca     420
aaggttaggt cggctgcctt taatcaatac caaagtggtc cctaccacga tggaaaaact     480
gtgcagtcgg tttggctttt tctgacgaac aaataagatt cgtggccgac aggtggggt     540 ccaccatgtg aaggcatctt cagactccaa taatggagca atgacgtaag gcttacgaa     600 ataagtaagg gtagtttggg aaatgtccac tcacccgtca gtctataaat acttagcccc     660
tccctcattg ttaagggagc aaaatctcag agagatagtc ctagagagag aaagagagca     720
agtagcctag aagtggatct ccaccatggc ccagtccaag cacggcctga ccaaggagat     780
gaccatgaag taccgcatgg agggctgcgt ggacggccac aagttcgtga tcaccggcga     840
gggcatcggc tacccttca agggcaagca ggccatcaac ctgtgcgtgg tgagggcgg     900 cccccttgccc ttcgccgagg acatcttgtc cgccgcctc atgtacgca accgcgtgtt     960 caccgagtac ccccaggaca tcgtcgacta cttcaagaac tcctgccccg ccggctacac    1020 ctgggaccg tccttcctgt tcgaggacgg cgccgtgtgc atctgcaacg ccgacatcac    1080
cgtgagcgtg gaggagaact gcatgtacca cgagtccaag ttctacggcg tgaacttccc    1140
cgccgacggc cccgtgatga agaagatgac cgacaactgg gagccctcct gcgagaagat    1200
catccccgtg cccaagcagg gcatcttgaa gggcgacgtg agcatgtacc tgctgctgaa    1260
ggacggtggc cgcttgcgct gccagttcga caccgtgtac aaggccaagt ccgtgccccg    1320
caagatgccc gactggcact tcatccagca caagctgacc cgcgaggacc gcagcgacgc    1380
caagaaccag aagtggcacc tgaccgagca cgccatcgcc tccggctccg ccttgccctg    1440
ctctagatcc ccgaatttcc ccgatcgttc aaacatttgg caataaagtt tcttaagatt    1500
gaatcctgtt gccggtcttg cgatgattat catataattt ctgttgaatt acgttaagca    1560
tgtaataatt aacatgtaat gcatgacgtt atttatgaga tgggttttta tgattagagt    1620
cccgcaatta tacatttaat acgcgataga aaacaaaata tagcgcgcaa actaggataa    1680
attatcgcgc gcggtgtcat ctatgttact agatcgcgga ccgaagcttg catgcctgca    1740
ggtcgactct agaggatccg gagccaagtc tcataaacgc cattgtggaa gaaagtcttg    1800
agttggtggt aatgtaacag agtagtaaga acagagaaga gagagagtgt gagatacatg    1860
aattgtcggg caacaaaaat cctgaacatc ttatttagc aaagagaaag agttccgagt    1920
ctgtagcaga agagtgagga gaaatttaag ctcttggact tgtgaattgt tccgcctctt    1980
```

```
gaatacttct tcaatcctca tatattcttc ttctatgtta cctgaaaacc ggcatttaat    2040
ctcgcgggtt tattccggtt caacattttt tttgttttga gttattatct gggcttaata    2100
acgcaggcct gaaataaatt caaggcccaa ctgttttttt ttttaagaag ttgctgttaa    2160
aaaaaaaaaa agggaattaa caacaacaac aaaaaaagat aaagaaaata ataacaatta    2220
ctttaattgt agactaaaaa aacatagatt ttatcatgaa aaaagagaa aagaaataaa     2280 aacttggatc aaaaaaaaaa catacagatc ttctaattat taacttttct taaaaattag    2340 gtccttttc ccaacaatta ggtttagagt tttggaatta aaccaaaaag attgttctaa     2400
aaaatactca aatttggtag ataagtttcc ttattttaat tagtcaatgg tagatacttt    2460 ttttttctttt ctttattaga gtagattaga atcttttatg ccaagtattg ataaattaaa   2520
tcaagaagat aaactatcat aatcaacatg aaattaaaag aaaaatctca tatatagtat    2580
tagtattctc tatatatatt atgattgctt attcttaatg ggttgggtta accaagacat    2640
agtcttaatg gaaagaatct tttttgaact ttttccttat tgattaaatt cttctataga    2700
aaagaaagaa attatttgag gaaaagtata tacaaaaaga aaaatagaaa aatgtcagtg    2760
aagcagatgt aatggatgac ctaatccaac caccaccata ggatgtttct acttgagtcg    2820
gtcttttaaa aacgcacggt ggaaaatatg acacgtatca tatgattcct tcctttagtt    2880
tcgtgataat aatcctcaac tgatatcttc cttttttgt tttggctaaa gatattttat     2940
tctcattaat agaaaagacg gttttgggct tttggtttgc gatataaaga agaccttcgt    3000
gtggaagata taattcatc ctttcgtctt tttctgactc ttcaatctct cccaaagcct      3060
aaagcgatct ctgcaaatct ctcgcgactc tctctttcaa ggtatatttt ctgattcttt    3120 ttgttttga ttcgtatctg atctccaatt tttgttatgt ggattattga atcttttgta      3180
taaattgctt ttgacaatat tgttcgtttc gtcaatccag cttctaaatt ttgtcctgat    3240
tactaagata tcgattcgta gtgtttacat ctgtgtaatt tcttgcttga ttgtgaaatt    3300
aggattttca aggacgatct attcaatttt tgtgttttct ttgttcgatt ctctctgttt    3360
taggtttctt atgtttagat ccgtttctct ttggtgttgt tttgatttct cttacggctt    3420
ttgatttggt atatgttcgc tgattggttt ctacttgttc tattgtttta tttcaggtgg    3480
atcccaccat gtctccggag aggagaccag ttgagattag gccagctaca gcagctgata    3540
tggccgcggt ttgtgatatc gttaaccatt acattgagac gtctacagtg aactttagga    3600
cagagccaca acaccacaa gagtggattg atgatctaga gaggttgcaa gatagatacc      3660
cttggttggt tgctgaggtt gagggtgttg tggctggtat tgcttacgct gggccctgga    3720
aggctaggaa cgcttacgat tggacagttg agagtactgt ttacgtgtca cataggcatc    3780
aaaggttggg cctaggatct acattgtaca cacatttgct taagtctatg gaggcgcaag    3840
gttttaagtc tgtggttgct gttataggcc ttccaaacga tccatctgtt aggttgcatg    3900
aggctttggg atacacagcc cggggtacat tgcgcgcagc tggatacaag catggtggat    3960
ggcatgatgt tggttttttgg caaagggatt ttgagttgcc agctcctcca aggccagtta   4020
ggccagttac ccagatatga gtcgagctct agatccccga atttcccga tcgttcaaac     4080 atttggcaat aaagtttctt aagattgaat cctgttgccg tcttgcgat gattatcata      4140 taatttctgt tgaattacgt taagcatgta ataattaaca tgtaatgcat gacgttatttt   4200 atgagatggg ttttttatgat tagagtcccg caattataca tttaatacgc gatagaaaac   4260
aaaatatagc gcgcaaacta ggataaatta tcgcgcgcgg tgtcatctat gttactagat    4320
```

```
cgggaattgg gtaccatgcc cgggcggcca gcatggccgt atccgcaatg tgttattaag    4380
ttgtctaagc gtcaatttgt ttacaccaca atatatcctg ccaccagcca gccaacagct    4440
ccccgaccgg cagctcggca caaaatcacc actcgataca ggcagcccat cagaattaat    4500
tctcatgttt gacagcttat catcgactgc acggtgcacc aatgcttctg cgtcaggca    4560 gccatcggaa gctgtggtat ggctgtgcag gtcgtaaatc actgcataat tcgtgtcgct    4620
caaggcgcac tcccgttctg gataatgttt tttgcgccga catcataacg gttctggcaa    4680
atattctgaa atgagctgtt gacaattaat catccggctc gtataatgtg tggaattgtg    4740
agcggataac aatttcacac aggaaacaga ccatgaggga agcgttgatc gccgaagtat    4800
cgactcaact atcagaggta gttggcgtca tcgagcgcca tctcgaaccg acgttgctgg    4860
ccgtacattt gtacggctcc gcagtggatg gcggcctgaa gccacacagt gatattgatt    4920
tgctggttac ggtgaccgta aggcttgatg aaacaacgcg gcgagctttg atcaacgacc    4980
ttttggaaac ttcggcttcc cctggagaga gcgagattct ccgcgctgta gaagtcacca    5040
ttgttgtgca cgacgacatc attccgtggc gttatccagc taagcgcgaa ctgcaatttg    5100
gagaatggca gcgcaatgac attcttgcag gtatcttcga gccagccacg atcgacattg    5160
atctggctat cttgctgaca aaagcaagag aacatagcgt tgccttggta ggtccagcgg    5220
cggaggaact cttttgatccg gttcctgaac aggatctatt tgaggcgcta aatgaaacct    5280
taacgctatg gaactcgccg cccgactggg ctggcgatga gcgaaatgta gtgcttacgt    5340
tgtcccgcat ttggtacagc gcagtaaccg gcaaaatcgc gccgaaggat gtcgctgccg    5400
actgggcaat ggagcgcctg ccggcccagt atcagcccgt catacttgaa gctaggcagg    5460
cttatcttgg acaagaagat cgcttggcct cgcgcgcaga tcagttggaa gaatttgttc    5520
actacgtgaa aggcgagatc accaaagtag tcggcaaata agctctagt ggatctccgt    5580 acccccgggg gatctggctc gcggcggacg cacgacgccg gggcgagacc ataggcgatc    5640
tcctaaatca atagtagctg taacctcgaa gcgtttcact tgtaacaacg attgagaatt    5700
tttgtcataa aattgaaata cttggttcgc attttttgtca tccgcggtca gccgcaattc    5760
tgacgaactg cccattttagc tggagatgat tgtacatcct tcacgtgaaa atttctcaag    5820
cgctgtgaac aagggttcag attttagatt gaaaggtgag ccgttgaaac acgttcttct    5880
tgtcgatgac gacgtcgcta tgcggcatct tattattgaa taccttacga tccacgcctt    5940
caaagtgacc gcggtagccg acagcaccca gttcacaaga gtactctctt ccgcgacggt    6000
cgatgtcgtg gttgttgatc tagatttagg tcgtgaagat gggctcgaga tcgttcgtaa    6060
tctggcggca aagtctgata ttccaatcat aattatcagt ggcgaccgcc ttgaggagac    6120
ggataaagtt gttgcactcg agctaggagc aagtgatttt atcgctaagc cgttcagtat    6180
cagagagttt ctagcacgca ttcgggttgc cttgcgcgtg cgcccaacg ttgtccgctc    6240 caaagaccga cggtcttttt gttttactga ctggacactt aatctcaggc aacgtcgctt    6300
gatgtccgaa gctggcggtg aggtgaaact acggcaggt gagttcaatc ttctcctcgc    6360 gttttttagag aaaccccgcg acgttctatc gcgcgagcaa cttctcattg ccagtcgagt    6420
acgcgacgag gaggtttatg acaggagtat agatgttctc atttttgaggc tgcgccgcaa    6480 acttgaggca gatccgtcaa gccctcaact gataaaaaca gcaagaggtg ccggttattt    6540
ctttgacgcg gacgtgcagg tttcgcacgg gggacgatg gcagcctgag ccaattccca    6600
gatccccgag gaatcggcgt gagcggtcgc aaaccatccg gcccggtaca aatcggcgcg    6660
gcgctgggtg atgacctggt ggagaagttg aaggccgcgc aggccgccca gcggcaacgc    6720
```

```
atcgaggcag aagcacgccc cggtgaatcg tggcaagcgg ccgctgatcg aatccgcaaa    6780
gaatcccggc aaccgccggc agccggtgcg ccgtcgatta ggaagccgcc caagggcgac    6840
gagcaaccag attttttcgt tccgatgctc tatgacgtgg gcaccgcgca tagtcgcagc    6900
atcatggacg tggccgtttt ccgtctgtcg aagcgtgacc gacgagctgg cgaggtgatc    6960
cgctacgagc ttccagacgg gcacgtagag gtttccgcag ggccggccgg catggccagt    7020
gtgtgggatt acgacctggt actgatggcg gtttcccatc taaccgaatc catgaaccga    7080
taccgggaag ggaagggaga caagcccggc cgcgtgttcc gtccacacgt tgcggacgta    7140
ctcaagttct gccggcgagc cgatggcgga aagcagaaag acgacctggt agaaacctgc    7200
attcggttaa acaccacgca cgttgccatg cagcgtacga agaaggccaa gaacggccgc    7260
ctggtgacgg tatccgaggg tgaagccttg attagccgct acaagatcgt aaagagcgaa    7320
accgggcggc cggagtacat cgagatcgag ctagctgatt ggatgtaccg cgagatcaca    7380
gaaggcaaga acccgacgt gctgacggtt caccccgatt acttttttgat cgatcccggc    7440
atcggccgtt ttctctaccg cctggcacgc cgcgccgcag gcaaggcaga agccagatgg    7500
ttgttcaaga cgatctacga acgcagtggc agcgccggag agttcaagaa gttctgtttc    7560
accgtgcgca agctgatcgg gtcaaatgac ctgccggagt acgatttgaa ggaggaggcg    7620
gggcaggctg gcccgatcct agtcatgcgc taccgcaacc tgatcgaggg cgaagcatcc    7680
gccggttcct aatgtacgga gcagatgcta gggcaaattg ccctagcagg ggaaaaggt    7740
cgaaaaggtc tctttcctgt ggatagcacg tacattggga acccaaagcc gtacattggg    7800
aaccggaacc cgtacattgg gaacccaaag ccgtacattg gaaccggtc acacatgtaa    7860
gtgactgata taaagagaa aaaggcgat ttttccgcct aaaactcttt aaaacttatt    7920
aaaactctta aaacccgcct ggcctgtgca taactgtctg gccagcgcac agccgaagag    7980
ctgcaaaaag cgcctaccct tcggtcgctg cgctccctac gccccgccgc ttcgcgtcgg    8040
cctatcgcgg ccgctggccg ctcaaaaatg gctggcctac ggccaggcaa tctaccaggg    8100
cgcggacaag ccgcgccgtc gccactcgac cgccggcgct gaggtctgcc tcgtgaagaa    8160
ggtgttgctg actcatacca ggcctgaatc gccccatcat ccagccagaa agtgagggag    8220
ccacggttga tgagagcttt gttgtaggtg gaccagttgg tgattttgaa cttttgcttt    8280
gccacggaac ggtctgcgtt gtcgggaaga tgcgtgatct gatccttcaa ctcagcaaaa    8340
gttcgattta ttcaacaaag ccgccgtccc gtcaagtcag cgtaatgctc tgccagtgtt    8400
acaaccaatt aaccaattct gattagaaaa actcatcgag catcaaatga aactgcaatt    8460
tattcatatc aggattatca ataccatatt tttgaaaaag ccgtttctgt aatgaaggag    8520
aaaactcacc gaggcagttc cataggatgg caagatcctg gtatcggtct gcgattccga    8580
ctcgtccaac atcaatacaa cctattaatt tcccctcgtc aaaaataagg ttatcaagtg    8640
agaaatcacc atgagtgacg actgaatccg gtgagaatgg caaaagctct gcattaatga    8700
atcggccaac gcgcgggag aggcggtttg cgtattgggc gctcttccgc ttcctcgctc    8760
actgactcgc tgcgctcggt cgttcggctg cggcgagcgg tatcagctca ctcaaaggcg    8820
gtaatacggt tatccacaga atcaggggat aacgcaggaa agaacatgtg agcaaaaggc    8880
cagcaaaagg ccaggaaccg taaaaaggcc gcgttgctgg cgttttccca taggctccgc    8940
cccccctgacg agcatcacaa aaatcgacgc tcaagtcaga ggtggcgaaa cccgacagga    9000
ctataaagat accaggcgtt tcccccctgga agctccctcg tgcgctctcc tgttccgacc    9060
```

| | |
|---|---|
| ctgccgctta ccggatacct gtccgccttt ctcccttcgg aagcgtggc gctttctcat | 9120 |
| agctcacgct gtaggtatct cagttcggtg taggtcgttc gctccaagct gggctgtgtg | 9180 |
| cacgaaccccc ccgttcagcc cgaccgctgc gccttatccg gtaactatcg tcttgagtcc | 9240 |
| aacccggtaa gacacgactt atcgccactg gcagcagcca ctggtaacag gattagcaga | 9300 |
| gcgaggtatg taggcggtgc tacagagttc ttgaagtggt ggcctaacta cggctacact | 9360 |
| agaagaacag tatttggtat ctgcgctctg ctgaagccag ttaccttcgg aaaaagagtt | 9420 |
| ggtagctctt gatccggcaa acaaaccacc gctggtagcg gtggtttttt tgtttgcaag | 9480 |
| cagcagatta cgcgcagaaa aaaggatct caagaagatc ctttgatctt ttctacgggg | 9540 |
| tctgacgctc agtggaacga aaactcacgt taagggattt tggtcatgag attatcaaaa | 9600 |
| aggatcttca cctagatcct tttgatccgg aatt | 9634 |

```
<210> SEQ ID NO 47
<211> LENGTH: 21
<212> TYPE: RNA
<213> ORGANISM: Artificial Sequence
<220> FEATURE:
<223> OTHER INFORMATION: SCN siRNA Random Seed Sequence
<220> FEATURE:
<221> NAME/KEY: misc_feature
<222> LOCATION: (2)..(2)
<223> OTHER INFORMATION: N2 is A or G
<220> FEATURE:
<221> NAME/KEY: misc_feature
<222> LOCATION: (3)..(3)
<223> OTHER INFORMATION: N3 is A, G, or U
<220> FEATURE:
<221> NAME/KEY: misc_feature
<222> LOCATION: (4)..(4)
<223> OTHER INFORMATION: N4 is C or G
<220> FEATURE:
<221> NAME/KEY: misc_feature
<222> LOCATION: (5)..(5)
<223> OTHER INFORMATION: N5 is A, G, or U
<220> FEATURE:
<221> NAME/KEY: misc_feature
<222> LOCATION: (6)..(6)
<223> OTHER INFORMATION: N6 is G or U
<220> FEATURE:
<221> NAME/KEY: misc_feature
<222> LOCATION: (7)..(7)
<223> OTHER INFORMATION: N7 is A, C, or G
<220> FEATURE:
<221> NAME/KEY: misc_feature
<222> LOCATION: (8)..(8)
<223> OTHER INFORMATION: N8 is A, G, or U

<400> SEQUENCE: 47
unnnnnnnug uugaucuggu u                                             21

<210> SEQ ID NO 48
<211> LENGTH: 21
<212> TYPE: RNA
<213> ORGANISM: Artificial Sequence
<220> FEATURE:
<223> OTHER INFORMATION: SCN siRNA Defined Seed Sequence

<400> SEQUENCE: 48
urdsdkvdug uugaucuggu u                                             21

<210> SEQ ID NO 49
<211> LENGTH: 21
<212> TYPE: RNA
<213> ORGANISM: Artificial Sequence
<220> FEATURE:
<223> OTHER INFORMATION: SCN siRNA Selected Seed Sequence
```

<400> SEQUENCE: 49
urdbdkvdug uugaucuggu u                                                    21

<210> SEQ ID NO 50
<211> LENGTH: 21
<212> TYPE: RNA
<213> ORGANISM: Artificial Sequence
<220> FEATURE:
<223> OTHER INFORMATION: CRW siRNA Random Seed Sequence
<220> FEATURE:
<221> NAME/KEY: misc_feature
<222> LOCATION: (2)..(2)
<223> OTHER INFORMATION: N2 is A, C, G, or U
<220> FEATURE:
<221> NAME/KEY: misc_feature
<222> LOCATION: (3)..(3)
<223> OTHER INFORMATION: N3 is A, G, or U
<220> FEATURE:
<221> NAME/KEY: misc_feature
<222> LOCATION: (4)..(4)
<223> OTHER INFORMATION: N4 is A, C, G, or U
<220> FEATURE:
<221> NAME/KEY: misc_feature
<222> LOCATION: (5)..(5)
<223> OTHER INFORMATION: N5 is A or U
<220> FEATURE:
<221> NAME/KEY: misc_feature
<222> LOCATION: (6)..(6)
<223> OTHER INFORMATION: N6 is A, G, or U
<220> FEATURE:
<221> NAME/KEY: misc_feature
<222> LOCATION: (7)..(7)
<223> OTHER INFORMATION: N7 is A, C, G, or U
<220> FEATURE:
<221> NAME/KEY: misc_feature
<222> LOCATION: (8)..(8)
<223> OTHER INFORMATION: N8 is A, C, G, or U

<400> SEQUENCE: 50
unnnnnnnua uccggauucu u                                                    21

<210> SEQ ID NO 51
<211> LENGTH: 21
<212> TYPE: RNA
<213> ORGANISM: Artificial Sequence
<220> FEATURE:
<223> OTHER INFORMATION: CRW siRNA Defined Seed Sequence
<220> FEATURE:
<221> NAME/KEY: misc_feature
<222> LOCATION: (2)..(2)
<223> OTHER INFORMATION: N2 is A, C, G, or U
<220> FEATURE:
<221> NAME/KEY: misc_feature
<222> LOCATION: (4)..(4)
<223> OTHER INFORMATION: N4 is A, C, G, or U
<220> FEATURE:
<221> NAME/KEY: misc_feature
<222> LOCATION: (7)..(7)
<223> OTHER INFORMATION: N7 is A, C, G, or U
<220> FEATURE:
<221> NAME/KEY: misc_feature
<222> LOCATION: (8)..(8)
<223> OTHER INFORMATION: N8 is A, C, G, or U

<400> SEQUENCE: 51
undnwdnnua uccggauucu u                                                    21

<210> SEQ ID NO 52
<211> LENGTH: 2690
<212> TYPE: DNA
<213> ORGANISM: Glycine max

```
<400> SEQUENCE: 52
atggaatcct gcaattgtat tgacccacaa gtgccagctg atgacttatt gatgaaatac      60
caatatatct ctgatttctt cattgcccett gcttatttct caatccctt ggagcttatc     120
tactttgtta agaaatcagc agtatttcca tatagatggg tccttgttca gtttggtgct    180
tttatagttt tatgtggagc aacacatcta attaatttat ggacctttag aattcattca    240
agaactgtgg ctgttgtaat gaccactgct aaggttttaa ctgctgtggt atcatgtgca    300
actgccctca tgctggtaca tattattcct gatttattaa gtgttaaaac tagggaatta    360
ttagaaactg gtcgacatgt taggatgttg actcatgaga ttagaagcac tcttgataga    420
cacacaatat tgaaaacgac tcttgttgaa ttaggtagaa ctttggcact agaggaatgt    480
gcgttatgga tgccaacacg aactggtttg gagcttcaac tctcttacac attgcgacag    540
cagaacccag ttggatacac agtacccatt catcttcctg ttatcaatca agtatttagt    600
aacaacaggg cagtaaaaat ttcacctaat tgtccagttg ctagattacg accttatgct    660
ggaaaataca tgcctggggc agtagtagct gttcgagttc ctctcctaca tctttctaat    720
ttccaaatat atgattggcc tgaggtttca acaagaagtt atgctttgat ggttttgatg    780
cttccatcag atagtgctag acaatggcat gtgcacgagt tagaactggt tgaggtagtt    840
gctgaccagg tagctgttgc tcttttcacat gctgcaatct tagaagagtc aatgagggca    900
agggatcagc tcatcgagca gaatgttgca ttagatctag caagaagaga agcagaaact    960
gcaattcgtg ctcgtaatga cttcttggca gttatgaacc atgagatgag aactcccatg   1020
catgcagtta ttgcactctc ttcattacta caggaaacag atttgacagc tgagcaacga   1080
ctgatggtgg agacaatatt gaaaagcagc aatttgttgg ctaccctcat caatgacgtt   1140
ttggatcttt cacggcttga agatggcagt cttcaacttg aagcagcaac atttaacctc   1200
cattctttgt tcagagaggt gaaatttcat gccaaatcct gatatttaat catattagtc   1260
cgacttctag ctaatgatct tgagtttctc taaaagcttg atgttgatct gttatcctga   1320
ttgcaggtcc ttaacttgat taagcctgtt gcatctgtta aaaagttatc actcacttca   1380
catgtagcct cagatttgcc aatgtatgcc attggtgatg aaaaacgtct catgcaaact   1440
attctgaatg ttgttggtaa tgctgtgaag ttctcaaaag agggttgcat ttccatcact   1500
gctttcgttg caaagcctga atcctttaga gatgctagaa ttcctgactt tcttccagtg   1560
ccaagtgata accactttta tttgcgagta caggtttgtt tcttcaagct tagttaataa   1620
tcttcttcct tgtggtattg tgtcctctgt tatctgacta caatgatgga atttaatttt   1680
ttactcatca taggtaaaag attcaggatc aggaattaat ccacaagata tcccgaagtt   1740
attcactaag tttgcacaaa accaatcgtt aacaacaaga atcctgctg gaagtggact    1800
tggcctggca atttgtagga ggtactatat tcttgtatgt ttactgtctt aactaggatg   1860
tgaagcacag ttatttatat gctattcctt ggaacattgc aaaattggaa tcaggttctt   1920
tttagaattc ctatttgaga tttttcagtt gattatgtac tgttttctta aattgtgagc   1980
aggtttgtaa atcttatgga aggacatatt tgggttgaaa gcgaaggtat tgataaagga   2040
tgtacagtca cttttattgt aaaacttgga atcccagacc gatcaaatga atttaagcta   2100
ccttttgtac ctaaagtacc gggaaatcat ggatctacaa actttgctgg gctcaaagtt   2160
cttgtcacgg atgacaatgg gtcagttgca taggctttat ttttgtacct tctgttctga   2220
tatatgtttc tatatcattt acttactaag taaaacatta gaattttggg atagcataca   2280
aaagcaaact taggttgttt acttataact gattgtgaaa cttgtactgt agggttagca   2340
```

```
ggacagtaac aaagggactt cttatgcatt taggatgtga tgtaaccaca gcaagctcaa    2400
gtgaagaatg tctgcgtgtt gtttctctgg aacatgaagt ggtcttcatg gatgtgattg    2460
tgccagggtt agatggttat gaacttgcaa tccgtataca tgaaaagttt actaaacatc    2520
aagatagacc actaatagtt gctcttactg gaaacaccaa aaaggtaaca aaagaaaact    2580
gtatgagggt tggtatggat ggccttatat tgaaacctgt ttctgttgac aaaatgaggg    2640 gtgtttatc agaactattg gagtgccgag ttctgttcga aactgtttaa               2690
```

\<210\> SEQ ID NO 53
\<211\> LENGTH: 20
\<212\> TYPE: RNA
\<213\> ORGANISM: Glyciine max

\<400\> SEQUENCE: 53

```
agaccgauca aaugaauuua                                                  20
```

\<210\> SEQ ID NO 54
\<211\> LENGTH: 20
\<212\> TYPE: RNA
\<213\> ORGANISM: Glycine max

\<400\> SEQUENCE: 54

```
uggaagugga cuuggccugg                                                  20
```

\<210\> SEQ ID NO 55
\<211\> LENGTH: 21
\<212\> TYPE: RNA
\<213\> ORGANISM: Artificial Sequence
\<220\> FEATURE:
\<223\> OTHER INFORMATION: amiRNA0097*

\<400\> SEQUENCE: 55

```
acauucaagu ugaacuagac c                                                21
```

\<210\> SEQ ID NO 56
\<211\> LENGTH: 21
\<212\> TYPE: RNA
\<213\> ORGANISM: Artificial Sequence
\<220\> FEATURE:
\<223\> OTHER INFORMATION: amiRNA0145*

\<400\> SEQUENCE: 56

```
acaucgaacu ugaacuagac c                                                21
```

\<210\> SEQ ID NO 57
\<211\> LENGTH: 21
\<212\> TYPE: RNA
\<213\> ORGANISM: Glycine max

\<400\> SEQUENCE: 57

```
ugcgaguaca gguaaaagau u                                                21
```

\<210\> SEQ ID NO 58
\<211\> LENGTH: 25
\<212\> TYPE: RNA
\<213\> ORGANISM: Glycine max

\<400\> SEQUENCE: 58

```
ggccugaggu uucaacaaga aguua                                            25
```

\<210\> SEQ ID NO 59

```
<211> LENGTH: 21
<212> TYPE: RNA
<213> ORGANISM: Artificial Sequence
<220> FEATURE:
<223> OTHER INFORMATION: siRNA0043*

<400> SEQUENCE: 59
acggucuagu uguuauucaa u                                          21

<210> SEQ ID NO 60
<211> LENGTH: 21
<212> TYPE: RNA
<213> ORGANISM: Artificial Sequence
<220> FEATURE:
<223> OTHER INFORMATION: siRNA0046*

<400> SEQUENCE: 60
acggucuagu uguucuucaa u                                          21
```

SMALL INTERFERING RNAS WITH TARGET-SPECIFIC SEED SEQUENCES

RELATED APPLICATION INFORMATION

This application claims priority under 35 U.S.C. §371 from PCT Application No. PCT/US2012/025004, filed Feb. 14, 2012, which claims the benefit of U.S. Provisional Application No. 61/442,765, filed Feb. 14, 2011, the disclosures of which are incorporated by reference herein in their entirety.

FIELD OF THE INVENTION

The invention relates to methods for designing small interfering RNAs (siRNAs) based upon enrichment of target-specific siRNA sequences, siRNAs produced thereby, and methods for using the same. More particularly, the invention relates to small interfering RNAs having activity against pests or pathogens and their use in plants.

BACKGROUND

In the past decade, RNA interference (RNAi) has been described and characterized in organisms as diverse as plants, fungi, nematodes, hydra, and humans. Zamore and Haley (2005) *Science* 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) *Trends Genet.* 15, 358-363.

RNA interference occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes. Most plant miRNAs show extensive base pairing to, and guide cleavage of their target mRNAs. Jones-Rhoades et al. (2006) *Annu. Rev. Plant Biol.* 57, 19-53; Llave et al. (2002) *Proc. Natl. Acad. Sci. USA* 97, 13401-13406. In other instances, interfering RNAs may bind to target RNA molecules having imperfect complementarity, causing translational repression without mRNA degradation. The majority of the animal miRNAs studied so far appear to function in this manner.

Based upon the role of miRNAs as endogenous regulators of gene expression, substantial efforts have been made toward the design of miRNAs for targeted regulation of gene expression. For example, pre-miRNAs can be designed by replacing both the 21-nucleotide mature miRNA sequence and the complementary sequence (i.e., the miRNA* strand or miRNA star strand), with engineered or synthetic 21-nucleotide sequences. Such artificial pre-miRNAs have sequences identical to those of the natural pre-miRNAs except in the region encoding the mature miRNA and the star strand. By this method, artificial miRNAs (amiRNA) have been designed that can target and silence specific mRNA transcripts with complementary sequences.

Within miRNA sequences, highly conserved regions of 6-7 nucleotides, which are called seed sequences, are responsible for base pairing with a target gene/RNA. The seed sequences are positioned at nucleotides 2-7 or 2-8 by linear counting from the 5'-end of the miRNA molecule, while the remaining nucleotides are called non-seed sequences. miRNAs that are members of a same miRNA family (i.e., miRNAs with the same sequence at nucleotides 2-8) share the same predicted mRNA targets. See Bartel (2009) *Cell* 136, 215-233.

Given their role in sequence-specific gene regulation, siRNAs are envisioned to have many applications, including studies of gene function, development of therapies for conditions associated with aberrant protein expression or accumulation, and methods for conferring desirable traits, including in plants. To meet this need, the invention provides methods for efficient design of target-specific siRNAs, siRNA libraries, and siRNA molecules produced thereby, and methods for using the same.

SUMMARY

The invention described herein is a method of preparing a library of small interfering RNAs (siRNAs), siRNAs produced thereby, and uses thereof.

One aspect of the invention is a method of preparing a library of small interfering RNAs (siRNAs) comprising synthesizing a plurality of RNA molecules, wherein each RNA molecule comprises (a) a seed sequence comprising random nucleotides, and (b) a non-seed sequence comprising designated nucleotides.

Another aspect of the invention is a method of preparing a library of small interfering RNAs (siRNAs) comprising synthesizing a plurality of RNA molecules, wherein each RNA molecule comprises (a) a seed sequence comprising nucleotides representative of one or more microRNA seed sequences of a target organism or an organism related to the target organism, and (b) a non-seed sequence comprising designated nucleotides.

Another aspect of the invention is a method for preparing a library of small interfering RNAs (siRNAs), further comprising the steps of: (a) excluding RNA molecules comprising one or more nucleotides within the seed sequence, which occur at low frequency at corresponding positions of microRNA sequences of a target organism or an organism related to a target organism; (b) excluding RNA molecules comprising a homonucleotide quadruplet within the seed sequence; and/or (c) excluding RNA molecules comprising a seed sequence having greater GC content at positions 1-9 than the GC content at positions 11-19.

Another aspect of the invention is a siRNA library comprising a plurality of RNA molecules, wherein each RNA molecule comprises (a) a seed sequence comprising random nucleotides, and (b) a non-seed sequence comprising designated nucleotides. Another aspect of the invention is a siRNA library comprising a plurality of RNA molecules, wherein each RNA molecule comprises (a) a seed sequence comprising nucleotides representative of one or more microRNA seed sequences of a target organism or an organism related to the target organism, and (b) a non-seed sequence. In one aspect, the siRNA library is an in silico siRNA library.

Another aspect of the invention comprises a siRNA library wherein the non-seed sequence comprises a consensus microRNA sequence from a plant pest or pathogen or from an organism related to a plant pest or pathogen. One aspect of the invention is a siRNA library, wherein the non-seed sequence comprises nucleotides occupying positions 1, and 9-19 of SEQ ID NO: 47. Another aspect of the invention is a siRNA library, wherein the non-seed sequence comprises nucleotides occupying positions 1, and 9-19 of SEQ ID NO: 50. Another aspect of the invention is a siRNA library, wherein the non-seed sequence further comprises one or more nucleotide substitutions to improve microRNA stability.

Another aspect of the invention is a siRNA library, which excludes: (a) RNA molecules comprising one or more nucleotides within the seed sequence, which occur at low frequency at corresponding positions of microRNA sequences of a target organism or an organism related to a target organism; (b) RNA molecules comprising a homonucleotide quadruplet within the seed sequence; and/or (c) RNA molecules comprising a seed sequence having greater GC content at positions 1-9 than at positions 11-19.

Another aspect of the invention is a siRNA library, which excludes RNA molecules comprising a seed sequence complementary to a host nucleic acid. An additional aspect of the invention is a siRNA library, which comprises a seed sequence of residues 2-8 of SEQ ID NO: 49. Another aspect of the invention is a siRNA library, which comprises a seed sequence of residues 2-8 of SEQ ID NO: 51.

Another aspect of the invention is a siRNA molecule comprising (a) a seed sequence comprising nucleotides representative of one or more microRNA seed sequences of a target organism or an organism related to the target organism, and (b) a non-seed sequence. Another aspect of the invention is a siRNA molecule which comprises at least about 19 nucleotides, and wherein the seed sequence comprises 6-8 nucleotides. One aspect of the invention is a siRNA molecule, which comprises 21 nucleotides, wherein the seed sequence comprises nucleotides occupying positions 2-8 of the RNA molecule, and wherein the non-seed sequence comprises nucleotides occupying positions 1 and 9-21 of the RNA molecule.

Another aspect of the invention is a siRNA molecule, wherein the non-seed sequence comprises a consensus microRNA sequence.

Another aspect of the invention is a siRNA molecule, wherein the non-seed sequence comprises a consensus microRNA sequence from a plant pest or pathogen, or from an organism related to a plant pest or pathogen. One aspect of the invention is a siRNA molecule, wherein the non-seed sequence comprises nucleotides occupying positions 1, and 9-19 of SEQ ID NO: 49.

Another aspect of the invention is a siRNA molecule, wherein the non-seed sequence comprises nucleotides occupying positions 1, and 9-19 of SEQ ID NO: 51. Another aspect of the invention is a siRNA molecule, wherein the non-seed sequence further comprises one or more nucleotide substitutions to improve microRNA stability.

Another aspect of the invention is a siRNA molecule, which comprises a seed sequence of residues 2-8 of SEQ ID NO: 49. Another aspect of the invention is a siRNA molecule, which comprises a seed sequence of residues 2-8 of SEQ ID NO: 48. A further aspect of the invention is a siRNA molecule which comprises a seed sequence of residues 2-8 of any one of SEQ ID NOs: 1-14. An additional aspect of the invention is a siRNA molecule, which comprises a seed sequence of residues 2-8 of SEQ ID NO: 51.

Another aspect of the invention is a siRNA molecule, which comprises the nucleotide sequence of any one of SEQ ID NOs: 1-14. Another aspect of the invention is a siRNA molecule, which comprises the nucleotide sequence of SEQ ID NO: 51.

Another aspect of the invention is an artificial RNA molecule comprising the siRNA molecule, which comprises the nucleotide sequence of any one of SEQ ID NOs: 16-29. A further aspect of the invention is an artificial RNA molecule comprising the siRNA molecule, which comprises the nucleotide sequence of SEQ ID NO: 51.

Another aspect of the invention is a vector comprising the siRNA molecule, which comprises the nucleotide sequence of any one of SEQ ID NOs: 31-44. An additional aspect of the invention is a vector comprising the siRNA molecule, which comprises the nucleotide sequence of SEQ ID NO: 51

Another aspect of the invention is a transgenic plant, or part thereof, comprising the siRNA molecule of any one of SEQ ID NOs: 1-51. In one aspect, the transgenic plant is *Glycine max*. In another aspect, the transgenic plant is *Zea mays*.

Another aspect of the invention is a plant product comprising the siRNA molecule of any one of SEQ ID NOs: 1-51. A further aspect of the invention is a commodity product comprising the siRNA of any one of SEQ ID NOs: 1-51.

Another aspect of the invention is a method of identifying a siRNA that confers a desirable phenotypic outcome in a target organism comprising: (a) contacting the target organism with a siRNA molecule of a siRNA library; and (b) correlating the siRNA treatment of (a) with the desirable phenotypic outcome. Another aspect of the invention is a method of identifying a siRNA that confers resistance to soybean cyst nematode comprising: (a) contacting soybean cyst nematode with a siRNA molecule of a siRNA library; and (b) correlating the siRNA treatment of (a) with soybean resistance to soybean cyst nematode infection. A further aspect of the invention is a method of identifying a siRNA that confers resistance to corn rootworm: (a) contacting corn rootworm with a siRNA molecule of a siRNA library; and (b) correlating the siRNA treatment of (a) with corn resistance to corn rootworm infection.

Another aspect of the invention is a method of conferring nematode resistance to a plant comprising expressing in the plant a nucleic acid comprising a siRNA of SEQ ID NOs: 1-14, whereby the plant is nematode resistant. Another aspect of the invention is a method of conferring insect resistance to a plant comprising expressing in the plant a nucleic acid comprising a siRNA of SEQ ID NO: 51, whereby the plant is insect resistant.

Another aspect of the invention is a method of reducing nematode infectivity to a plant comprising contacting the nematode with a nucleic acid comprising a siRNA of SEQ ID NOs: 1-14, whereby nematode infectivity is reduced. Another aspect of the invention is a method of reducing insect infectivity to a plant comprising contacting the insect with a nucleic acid comprising a siRNA of SEQ ID NO: 51, whereby insect infectivity is reduced.

An aspect of the invention is a method of reducing risk of nematode infection in a plant comprising expressing in the plant a nucleic acid comprising a siRNA of SEQ ID NOs: 1-14, whereby risk of nematode infection is reduced. Another aspect of the invention is a method of reducing risk of nematode infection in a plant comprising expressing in the plant a nucleic acid comprising a siRNA of SEQ ID NO: 51, whereby risk of insect infection is reduced.

Another aspect of the invention is a method of providing a grower with a means controlling nematode pests comprising supplying seed to a grower, wherein the seed comprises a nucleic acid comprising a siRNA of SEQ ID NOs: 1-14. A further aspect of the invention is a method of providing a grower with a means controlling insect pests comprising supplying seed to a grower, wherein the seed comprises a nucleic acid comprising a siRNA of SEQ ID NO: 51.

Another aspect of the invention is a siRNA molecule that targets both a nematode gene and an endogenous plant gene related to a nematode-resistant plant phenotype.

Another aspect of the invention is a transgenic plant, or part thereof, having a reduced level of expression of a ethylene response gene compared to a non-transgenic plant of the same species, wherein the transgenic plant comprises an siRNA that suppresses the expression of a pest nematode gene, and wherein the transgenic plant has a greater tolerance to infection by the nematode pest than would be expected from the reduced level of expression of the ethylene response gene or the suppression of the nematode gene alone.

Another aspect of the invention is a method of enhancing resistance of a plant, or part thereof, to infection by a nematode pest, comprising introducing into the plant, or part thereof, a nucleic acid comprising a siRNA molecule that suppresses the expression of a nematode gene thereby reducing the ability of the nematode to infect the plant, or part thereof, wherein the plant, or part thereof, additionally has a reduced level of expression of an ethylene response gene compared to a plant, or part thereof, of the same species without the siRNA molecule, whereby the plant, or part thereof, comprising the siRNA has a greater resistance to infection by the nematode than would be expected from the suppression of the nematode gene or the suppression of the ethylene response gene alone.

BRIEF DESCRIPTION OF THE SEQUENCES

The Sequence Listing provides disclosure of siRNAs and amiRNAs of the following sequences that are specific aspects of the invention.

SEQ ID NOs: 1-15 are the nucleic acid sequences of siRNAs, which are also listed in Table 8, below.

SEQ ID NOs: 16-30 are the nucleic acid sequences of amiRNAs, which are also listed in Table 9, below.

SEQ ID NOs: 31-45 are the nucleic acid sequences of amiRNAs in expression vectors, which are also listed in Table 10, below. SEQ ID NO: 46 is the empty expression vector control.

SEQ ID NO: 47, 5'-UNNNNNNNUGUUGAUCUG-GUU-3', is the sequence of a siRNA containing a random seed sequence and a non-seed sequence that is a consensus of *C. elegans* miRNAs, as described in Example 1, below.

SEQ ID NO: 48, 5'-URDSDKVDUGUUGAUCUGGUU-3', encompasses the sequences of all siRNAs in the enriched library, prepared as described in Example 1, below.

SEQ ID NO: 49, 5'-URDBDKVDUGUUGAUCUG-GUU-3', encompasses the sequences for siRNAs having activity against soybean cyst nematode, as described in Example 4, below.

SEQ ID NO: 50, 5'-UNNNNNNNUAUCCG-GAUUCUU-3', is the sequence of a siRNA containing a random seed sequence and a non-seed sequence that is a consensus of *Tribolium castaneum* miRNAs, as described in Example 6, below.

SEQ ID NO: 51, 5'-UNDNWDNNUAUCCG-GAUUCUU-3', encompasses the sequences of all siRNAs in the enriched library, prepared as described in Example 6, below.

SEQ ID NO: 52 is the nucleotide sequence of a soybean ETR1 nucleic acid (gma-ETR1), GenBank accession number EF210138.

SEQ ID NO: 53 is the nucleotide sequence comprising the mRNA portion of a soybean ETR1 that binds to siRNA0097 and siRNA0145.

SEQ ID NO: 54 is the nucleotide sequence comprising the mRNA portion of a soybean ETR1 that binds to siRNA0097* and siRNA0145*.

SEQ ID NO: 55 is the nucleotide sequence of siRNA0097*.

SEQ ID NO: 56 is the nucleotide sequence of siRNA0145*.

SEQ ID NO: 57 is the nucleotide sequence describing the mRNA sequence of a soybean ETR1 that has low complementarity to amiRNA0043*.

SEQ ID NO: 58 is the nucleotide sequence describing the mRNA sequence of a soybean ETR1 that has low complementarity to amiRNA0046*.

SEQ ID NO: 59 is the nucleotide sequence of siRNA0043*.

SEQ ID NO: 60 is the nucleotide sequence of siRNA0046*.

DETAILED DESCRIPTION

The invention provides methods for preparing a library of small interfering RNAs (siRNAs), libraries produced by the methods, and individual siRNA molecules. As described herein, the library design includes enrichment of siRNAs having target-specific sequences. The libraries are useful for selecting one or more siRNAs that elicit a desired phenotype when contacted with a target organism. Also provided are siRNAs produced thereby and methods for using the same.
siRNA Molecules The invention disclosed herein provides a strategy for the design of siRNAs having activity in a target organism. Also provided are siRNAs produced thereby, which have utility for numerous applications, as described herein below. The scope of the invention is not limited to nucleic acids or libraries comprising siRNAs for which specific sequences are disclosed herein. Rather, sequences from any organism, both known and presently unknown, can be used to design siRNAs according to the disclosed methods.

The term "RNA" includes any molecule comprising at least one ribonucleotide residue, including those possessing one or more natural ribonucleotides of the following bases: adenine, cytosine, guanine, and uracil; abbreviated A, C, G, and U, respectively, modified ribonucleotides, and non-ribonucleotides. "Ribonucleotide" means a nucleotide with a hydroxyl group at the 2' position of the D-ribofuranose moiety.

As used herein, the terms and phrases "RNA," "RNA molecule(s)," and "RNA sequence(s)," are used interchangeably to refer to RNA that mediates RNA interference. These terms and phrases include single-stranded RNA, double-stranded RNA, isolated RNA, partially purified RNA, essentially pure RNA, synthetic RNA, recombinant RNA, intracellular RNA, and RNA that differs from naturally occurring RNA by the addition, deletion, substitution, and/or alteration of one or more nucleotides. "mRNA" refers to messenger RNA, which is RNA produced by transcription.

An "interfering RNA" (e.g., siRNA and miRNA) is a RNA molecule capable of post-transcriptional gene silencing or suppression, RNA silencing, and/or decreasing gene expression. Interfering RNAs affect sequence-specific, post-transcriptional gene silencing in animals and plants by base pairing to the mRNA sequence of a target nucleic acid. Thus, the siRNA is at least partially complementary to the silenced gene. The partially complementary siRNA may include one or more mismatches, bulges, internal loops, and/or non-Watson-Crick base pairs (i.e., G-U wobble base pairs).

The terms "silencing" and "suppression" are used interchangeably to generally describe substantial and measurable reductions of the amount of mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene refers to a gene that is subject to silencing or suppression of the mRNA encoded by the gene.

The descriptions "small interfering RNA" and "siRNA" are used interchangeably herein to describe a synthetic or non-natural interfering RNA. The terms "miRNA" or "microRNA" generally refer to natural or endogenous interfering RNAs. As used herein, "miRNA" refers to interfering RNAs that have been or will be processed in vitro or in vivo from a pre-microRNA precursor to form the active interfering RNA. Both siRNAs and miRNAs are RNA molecules of about 19-24 nucleotides, although shorter or longer siRNAs/miRNAs, e.g., between 18 and 26 nucleotides in length, may also be useful. siRNAs or miRNAs may be single stranded or double stranded.

microRNAs are encoded by genes that are transcribed but not translated into protein (non-coding DNA), although some miRNAs are encoded by sequences that overlap protein-coding genes. miRNAs are processed from primary transcripts known as pri-miRNAs to short stem-loop structures called pre-miRNAs that are further processed creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-Watson-Crick base pairs (i.e., G-U wobble base pairs), and other features are frequently observed in pre-miRNAs and such characteristics are thought to be important for processing. Mature miRNA molecules are partially complementary to one or more messenger RNA molecules, and they function to regulate gene expression. siRNAs of the invention have structural and functional properties of endogenous miRNAs (e.g., gene silencing and suppressive functions). Thus, in various aspects of the invention, siRNAs of the invention can be processed from a portion of a precursor transcript that, optionally, folds into a stable hairpin (i.e., a duplex) or a stem-loop structure.

The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism but not in a non-target organism, such as a host organism (the organism expressing or producing the miRNA) or a consumer of the host organism. Consequently, "target-specific siRNAs or amiRNAs" only produce phenotypes in target organisms and do not produce phenotypes in non-target organisms.

In one aspect of the invention, a siRNA molecule comprises (a) a seed sequence comprising nucleotides representative of one or more microRNA seed sequences of a target organism or an organism related to the target organism, or a consensus sequence thereof, and (b) a non-seed sequence. Such siRNA molecules comprise at least about 19 nucleotides, wherein the seed sequence comprises 6-7 nucleotides.

The description "seed sequence," as used herein, refers to a region of a siRNA molecule that is at least partially complementary to a target gene or RNA. As used herein, the seed sequence consists of 6-7 nucleotides beginning at the second residue from the 5'-end of a siRNA (e.g., nucleotides 2-7 or 2-8, as numbered linearly from the 5'-end of a siRNA). The seed sequences are the most highly conserved regions among metazoan miRNAs, and miRNAs with the same sequence at nucleotides 2-8 share the same predicted mRNA targets. See Bartel (2009) *Cell* 136, 215-233.

In one aspect of the invention, nucleotides within the seed sequence are based upon the frequency at which particular nucleotides are observed in miRNA seed sequences of a "target organism," i.e., an organism in which a siRNA of the invention is intended to be functional for gene silencing. Similarly, nucleotides within the seed sequence may be based upon the frequency at which particular nucleotides are observed in miRNA seed sequences of an "organism related to a target organism." In this context, "related" means relative phylogenic closeness between and among organisms, whether evolutionary relationships are determined by phenotypic traits, molecular markers, and/or variation in rates of speciation and/or extinction, or sequence identity or similarity. The degree of relation may be in some aspects, closely related through phylogeny, such as sharing the same genus or family. In other aspects, the degree of phylogenic relation may be distant, such as sharing only the same phylum or class. In other aspects, there may be no phylogenic relation to target an organism but the non-seed sequence may be "related" to the target organism through sequence homology, similarity, or identity. The consensus non-seed sequence can also be prepared from non-seed sequences from the target organism and/or from one or more organisms related to the target organism. As used herein, any organism that contains nucleic acids capable of interacting with seed sequences of the invention disclosed herein is a "target" organism.

The nucleotides of the seed sequence may be further selected based upon observed frequencies at each position in naturally occurring miRNAs, for example, by excluding those nucleotides that are observed at a low frequency. A low frequency can comprise an observed incidence of less than about 50% among a population of naturally occurring miRNAs, or less than about 45%, or less than about 40%, or less than about 35%, or less than about 30%, or less than about 25%, or less than about 20%, or less than about 15%, or less than about 10%, or less than about 5%.

The seed sequence may alternatively comprise a consensus of two or more miRNA seed sequences of a target organism and/or an organism related to the target organism. See also Example 1. The phrase "consensus sequence," as used herein, refers to a nucleotide sequence wherein each nucleotide represents the most frequently observed nucleotide at a particular position in the sequence when similar or related sequences are compared to each other as described herein for determining the similarity or identity (see below). As used herein, the consensus sequence of a siRNA, or part thereof, refers to either a selected group of siRNAs or all siRNAs that are conserved within an organism, species, genus, family, order, class, phylum, kingdom, or domain.

The term "consensus" also encompasses structural elements known or predicted from the sequence, or from analogous or homologous sequences, such as duplexes, mismatches, budges, G-U wobble base pairs, loops, hairpins, tetraloops, inter alia, which are observed in pri-mRNA, pre-miRNA, miRNA, or siRNA sequences that are thought to be important for miRNA processing. See, e.g., Saxena et al. (2003) *J. Biol. Chem.* 278, 44312-44319.

Representative siRNA seed sequences of the invention include residues 2-8 of SEQ ID NO: 48, which is a degenerate consensus sequence, the degeneracy based upon the frequency of nucleotides observed at the same positions in naturally occurring miRNAs of *C. elegans*. Additional representative seed sequences include residues 2-8 of any one of SEQ ID NOs: 1-14, and residues 2-8 of SEQ ID NO: 49, which is a consensus of the seed sequences of SEQ ID NOs: 1-14. In addition, SEQ ID NO: 51, is a degenerate consensus sequence, the degeneracy based upon the frequency of nucleotides observed at the same positions in naturally occurring miRNAs of *Tribolium castaneum*.

The description "non-seed sequence," as used herein, refers to all sequences of a siRNA or miRNA that are not the seed sequence. For a 21-nucleotide siRNA, the non-seed sequence comprises linear nucleotides 1 and 8-21 or 1 and 9-21, depending on whether the seed sequence consists of 6 nucleotides (e.g., positions 2-7) or 7 nucleotides (e.g., positions 2-8). In one aspect of the invention, the non-seed sequence comprises a naturally occurring miRNA non-seed sequence. In another aspect of the invention, the non-seed sequence comprises a consensus microRNA non-seed sequence, i.e., a consensus of miRNA non-seed sequences. Such a consensus may be prepared from two or more miRNA non-seed sequences, for example, three miRNA sequences, or four miRNA sequences, or five miRNA sequences, or six miRNA sequences, or seven miRNA sequences, or eight miRNA sequences, or nine miRNA sequences, or ten miRNA sequences, or twenty miRNA sequences, or thirty miRNA sequences, or forty miRNA sequences, or fifty miRNA sequences, or more. One skilled in the art understands techniques and computational tools for making such alignments and can readily prepare consensus sequences using any number of miRNA sequences.

In one aspect of the invention, the miRNA non-seed sequence or consensus of miRNA non-seed sequences comprises a consensus of non-seed sequences from a target organism, i.e., an organism in which a siRNA of the invention is intended to be functional for gene silencing. Similarly, the consensus of miRNA non-seed sequences can comprise a consensus of non-seed sequences related to the target organism. In this context, "related" means relative phylogenic closeness between or among organisms, as described herein above with respect to design of seed sequences.

In another aspect of the invention, the non-seed sequence is partially or completely synthetic, i.e., a non-naturally occurring sequence that shows desired functional properties as determined by modeling or empirically. For example, the non-seed sequence can comprise one or more nucleotide substitutions relative to a naturally occurring miRNA sequence, a siRNA sequence, or a miRNA/siRNA consensus sequence to improve siRNA stability, such as 3'-terminal uridines or deoxythymidine. See Example 1.

For example, where the target organism is a plant parasitic nematode, a useful non-seed sequence can comprise a consensus of miRNA non-seed sequences of the model nematode *Caenorhabditis elegans*. A representative non-seed sequence having these properties is set forth as nucleotides 1 and 9-19 of SEQ ID NO: 47. See Example 1. As another example, where the target organism is a plant parasitic nematode, other useful seed sequences include consensus sequences of miRNA non-seed sequences of one or more of the nematodes identified in Table 6. As a further example, where the target organism is an insect pest, a useful non-seed sequence can comprise consensus of miRNA non-seed sequences of the organism *Tribolium castaneum*. A representative non-seed sequence having these properties is set forth as nucleotides 1 and 9-19 of SEQ ID NO: 50. See Example 6.

Representative siRNAs of the invention include SEQ ID NOs: 1-14, which were obtained from the siRNA library described in Example 1. Additional siRNA molecules of the invention include molecules of siRNA libraries produced by the methods described herein below.

The invention also provides "artificial microRNAs" or "amiRNAs," which are non-naturally occurring nucleic acid sequences that are capable of expressing siRNA molecules. In one aspect of the invention, the sequence of the *Glycine max* miRNA precursor gma-MIR164 was used as the starting sequence or backbone for designing an artificial microRNA targeting nematodes that will be expressed in a plant host. The design of this artificial microRNA for use in soybeans is described in U.S. Provisional Application 61/421,275 and a similar approach for use of amiRNAs in *Arabidopsis thaliana* is described by Schwab et al. (2006) *Plant Cell* 18, 1121-1133, both of which are incorporated herein by reference in their entirety. Representative amiRNAs of the invention include amiRNAs comprising a siRNA of any one of SEQ ID NOs: 1-14, for example, the amiRNAs set forth as SEQ ID NOs: 16-29.

The above-described siRNAs, or seed or non-seed sequences therein, or precursors thereof (e.g., pri-miRNA and pre-miRNA), may be further altered by the addition, deletion, substitution, and/or alteration of one or more nucleotides to introduce variation; to modify specificity; to alter complementarity; to introduce or remove secondary structural elements such as mismatches, bulges, loops, single-stranded regions, double-stranded regions, overhangs, or other motifs; to enhance or maintain the capability of the RNA to be processed in a RISC complex in vitro or in vivo; to improve the stability of the RNA molecule in vitro or in vivo (i.e., the ability of the RNA molecule to be maintained without being degraded by nucleases and/or its ability to fold into stable secondary or tertiary structures); and/or to enhance the ability to hybridize to a target gene/RNA.

Nucleic acids that share a substantial degree of complementarity will form stable interactions with each other, for example, by matching base pairs. The terms "complementary" or "complementarity" refer to the specific base pairing of nucleotide bases in nucleic acids. The phrase "perfect complementarity," as used herein, refers to complete (100%) base paring within a contiguous region of nucleic acid, such as between a seed sequence in a siRNA and its complementary sequence in a target gene/RNA, as described herein. "Partial complementarity" or "partially complementary" indicates that two sequences can base pair with one another, although the complementarity is not 100%. As used herein, the phrase "sequence complementary to a sequence" is used to describe a nucleotide sequence capable of base pairing with another sequence, although the complementarity may not be 100%.

Alternatively stated, the phrase "sequence complementary to a sequence" with respect to two nucleotide sequences indicates that the two-nucleotide sequences have sufficient complementarity and have the natural tendency to interact with each other to form a double stranded molecule. Two nucleotide sequences can form stable interactions with each other within a wide range of sequence complementarities. Nucleotide sequences with high degrees of complementarity are generally stronger and/or more stable than ones with low degrees of complementarity. Different strengths of interactions may be required for different processes. For example, the strength of interaction for the purpose of forming a stable nucleotide sequence duplex in vitro may be different from that for the purpose of forming a stable interaction between a siRNA and a binding sequence in vivo. The strength of interaction can be readily determined experimentally or predicted with appropriate software by a person skilled in the art.

The terms "hybridize" or "hybridization," as used herein, refer to the ability of a nucleic acid sequence or molecule to base pair with a complementary sequence and form a duplex nucleic acid structure. Hybridization can be used to test whether two polynucleotides are substantially complementary to each other and to measure how stable the interaction is.

Polynucleotides that share a sufficient degree of complementarity will hybridize to each other under various hybridization conditions. Consequently, polynucleotides that share a high degree of complementarity thus form strong stable interactions and will hybridize to each other under stringent hybridization conditions. "Stringent hybridization conditions" are well known in the art, as described in Sambrook et al. (1989) Molecular Cloning: A Laboratory Manual, Second Edition, Cold Spring Harbor Laboratory, Cold Spring Harbor, N.Y. An exemplary stringent hybridization condition comprises hybridization in 6× sodium chloride/sodium citrate (SSC) at about 45° C., followed by one or more washes in 0.2×SSC and 0.1% SDS at 50-65° C.

"Homologous," "homology," "identical," and "identity," as used herein, refers to comparisons among nucleic acid sequences. When referring to nucleic acid molecules, "homology," "similarity," "identity," or "percent identity," refers to the percentage of the nucleotides of a particular nucleic acid sequence that have been matched to similar or identical nucleotide sequences by a sequence analysis program. Sequence "identity" or "similarity," as known in the art, is the relationship between two or more polynucleotide sequences, as determined by comparing the sequences. In the art, identity also means the degree of sequence relatedness between polynucleotide sequences, as determined by the match between such sequences. To determine the percent identity or similarity of two nucleic acid sequences, the sequences are aligned for optimal comparison purposes (i.e., gaps can be introduced in the sequence of a first nucleic acid sequence for optimal alignment with a second nucleic acid sequence). The nucleotides at corresponding nucleotide positions are then compared. When a position in the first sequence is occupied by the same or similar nucleotide as the corresponding position in the second sequence, then the molecules are identical or similar at that position, respectively. The percent identity or similarity between the two sequences is a function of the number of identical or similar positions shared by the sequences (i.e., the percentage (%) identity is number of identical positions divided by the total number of positions (e.g., overlapping positions)×100). Two sequences that share 100% sequence identity are identical. Two sequences that share less than 100% identity, but greater than 50% identity, are similar. Sequences with less than 50% identity are dissimilar.

Both identity and similarity can be readily calculated. Methods commonly employed to determine identity or similarity between sequences include, but are not limited to those disclosed in Carillo et al. (1988) SIAM J. Applied Math. 48, 1073. A non-limiting example of a mathematical algorithm utilized for the comparison of two sequences is the algorithm of Karlin et al. (1990) Proc. Natl. Acad. Sci. USA 87, 2264-2268, modified as in Karlin et al. (1993) Proc. Natl. Acad. Sci. USA 90, 5873-5877. Such an algorithm is incorporated into the NBLAST and XBLAST programs of Altschul et al. (1990) J. Mol. Biol. 215, 403-410. To obtain gapped alignments for comparison purposes, Gapped BLAST can be utilized as described in Altschul et al. (1997) Nucleic Acids Res., 25: 3389-3402. Alternatively, PSI-Blast can be used to perform an iterated search that detects distant relationships between molecules. When utilizing BLAST, Gapped BLAST, and PSI-Blast programs, the default parameters of the respective programs (e.g., XBLAST and NBLAST) can be used. Additionally, the FASTA method can also be used. See Altschul et al. (1990) J. Mol. Biol. 215, 403-410. Another example of a mathematical algorithm useful for the comparison of sequences is the algorithm of Myers et al. (1988) CABIOS 4, 11-17. The percent identity between two sequences can also determined using the algorithm of Needleman and Wunsch (1970) J. Mol. Biol. 48, 443-453. Another algorithm for calculating the percent identity between two sequences is determined using the local homology method. Smith and Waterman (1981) J. Mol. Biol., 147, 195-197. Optimal alignments may be produced by inserting gaps to maximize the number of matches.

The invention provides methods for attenuating or inhibiting gene expression in a cell using small interfering RNA (siRNA). The siRNA contains a nucleotide sequence that hybridizes under physiologic conditions of the cell to the nucleotide sequence of at least a portion of the target mRNA of the gene to be inhibited (i.e., the target gene). The methods described herein do not require 100% sequence identity or complementarity between the siRNA and the target gene. By utilizing bioinformatic tools, the sequence can contain mismatching pairs of nucleotides. Thus, the methods of the invention have the advantage of being able to tolerate some sequence variations that might be expected due to genetic mutation, strain polymorphism, or evolutionary divergence.

Without being bound by theory, it is believed that plants transformed according to the invention transcribe an RNA molecule(s) with a region homologous to and a region complementary to the pest target gene, and wherein the transcript(s) form a double stranded RNA molecule (dsRNA). The plant recognizes the dsRNA as a potential foreign substance (e.g., a substance of viral origin). The dicer enzyme of the plant cuts the double stranded RNA into pieces of single-stranded RNA of about 23 nucleotides in length, called small interfering RNAs (siRNAs). These siRNAs are consumed by invading pests that have entered the plant via the digestion of plant cells (e.g., cutin). Once absorbed, the siRNAs can be incorporated into the pest's RNA-induced silencing complexes. The RISC complex can then digest the mRNA of the pest's homologous gene limiting the pest's ability to harm the plant.

siRNA Libraries

A plurality of the above-described siRNA molecules, i.e., two or more siRNAs, may be used to prepare a siRNA library. Based upon the target-specific design of the siRNA molecules, such libraries provide an efficient means for screening for desirable phenotypes in a target organism.

Thus, in one aspect of the invention, a method of preparing a library of small interfering RNAs (siRNAs) comprises synthesizing a plurality of RNA molecules, wherein each RNA molecule comprises (a) a seed sequence comprising random nucleotides, and (b) a non-seed sequence comprising designated nucleotides. In another aspect of the invention, a method of preparing a library of small interfering RNAs (siRNAs) comprises synthesizing a plurality of RNA molecules, wherein each RNA molecule comprises (a) a seed sequence comprising nucleotides representative of one or more microRNA seed sequences of a target organism or an organism related to the target organism, and (b) a non-seed sequence comprising designated nucleotides.

According to the disclosed methods, libraries may be prepared by actual synthesis of each of the plurality of the siRNA molecules, which can be accomplished using techniques as known in the art, including automated chemical synthesis, optionally using a mixture of nucleotides to create a randomized sequence. The invention also encompasses in silico preparation of a library, i.e., using computational techniques to generate sequences of each of the plurality of siRNA molecules. In many instances, in silico library preparation will be useful for initial steps in library preparation, including steps for exclusion of siRNA molecules to thereby enrich for target-specific sequences, as described further below.

In one aspect of the invention, a siRNA library comprises siRNA molecules, wherein each molecule contains a randomized seed sequence, i.e., every possible combination of the four standard ribonucleosides (i.e., adenosine, cytidine, guanosine, and uridine) is stochastically represented at each position within the randomized seed sequence. In other aspects of the invention, preparation of a siRNA library involves one or more steps to exclude siRNA molecules with low complexity and/or low specificity.

For example, in some aspects of the invention, a method of preparing a library can further comprise (a) excluding RNA molecules comprising one or more nucleotides within the seed sequence, which occur at low frequency at corresponding positions of microRNA sequences of a target organism or an organism related to a target organism; (b) excluding RNA molecules comprising a homonucleotide quadruplet within the seed sequence; and/or (c) excluding RNA molecules comprising a seed sequence having greater GC content at positions 1-9 than the GC content of the non-seed sequence at positions 11-19.

The description of nucleotides that occur at low frequency in miRNAs of a target organism refers to an observed incidence of less than about 50% among a population of naturally occurring miRNAs, or less than about 45%, or less than about 40%, or less than about 35%, or less than about 30%, or less than about 25%, or less than about 20%, or less than about 15%, or less than about 10%, or less than about 5%.

Alternatively stated, siRNAs of the library may be maintained if the siRNA contains nucleotides within the seed sequence that are observed at a threshold level among naturally occurring miRNAs. Such threshold level may be varied as desired, with a higher threshold being generally correlated with increased target specificity. For example, a threshold level may be at least about 1%, or greater frequency at which a nucleotide is observed among naturally occurring miRNAs, or about 5% or greater, or about 10% or greater, or about 20% or greater, or about 30% or greater, or about 40% or greater, or about 50% or greater, or about 60% or greater, or about 70% or greater, or about 80% or greater, or about 90% or greater, or about 95% or greater. In a particular aspect of the invention, the frequency threshold refers to a nucleotide that occurs at a corresponding position in a seed sequence greater than about 20% compared to a consensus of seed sequences surveyed from the *C. elegans* genome. See Example 1. In another aspect of the invention, the frequency threshold refers to a nucleotide that occurs at a corresponding position in a seed sequence greater than about 20% compared to a consensus of seed sequences surveyed from the *Tribolium castaneum* genome. See Example 6.

A "homonucleotide quadruplet" refers to the same nucleotide being repeated four times in succession, such as AAAA, within a seed sequence.

The "GC-content" (or guanosine-cytidine content) of a sequence refers to the percentage of bases in a nucleic acid molecule or sequence or specific region of a sequence that are either guanosine or cytidine. For example, when a seed sequence has at least about 60%, at least about 50%, or at least about 40%, or at least about 30%, or at least about 20%, or at least about 10%, or at least about 5%, or at least about 1% GC-content and likewise, the non-seed sequence has at most about 40%, at most about 50%, or at most about 60%, or at most about 70%, or at most about 80%, or at most about 90%, or at most about 95%, or at most about 99% GC-content, respectively.

Alternatively or in addition, a method of preparing a library can further comprise a step of excluding RNA molecules complementary to a host nucleic acid. In this way, the siRNA molecules of the library will not include siRNAs likely to be functional for gene silencing in a host organism.

A "host" is an organism that is intended for expression or production of a siRNA. In one aspect of the invention, a host organism is the same as a target organism, i.e., the siRNA is expressed or produced in the same organism in which it is intended to be functional. In another aspect of the invention, the host organism serves as a carrier of the siRNA to a target organism. As one example, a host organism can comprise a plant, wherein the target organism is a pest or pathogen of the plant. In particular aspects of the invention, the host organism is *Glycine max*.

In other aspects of the invention, the host organism is *Zea mays*.

siRNA libraries of the invention include siRNA molecules as described herein. Accordingly, the seed and non-seed sequences of siRNA molecules within the library can comprise the target-specific seed and non-seed sequences, including consensus sequences, as described herein above. The scope of the invention is not limited to a library comprising siRNAs for which specific sequences are disclosed herein. Rather, sequences from any organism, both known and presently unknown, can be used to prepare target-specific siRNAs according to the disclosed methods, as described further herein below.

Additional Compositions Comprising siRNAs

The invention also provides nucleic acids comprising the disclosed siRNAs, artificial miRNAs, and siRNA libraries. Such nucleic acids are generally useful for production or expression of the siRNAs in a manner that they can contact target nucleic acids, i.e., nucleic acids to be regulated by the siRNA.

In the context of the invention, the phrase "nucleic acid" or term "nucleotides" refers to oligonucleotides and polynucleotides such as ribonucleic acid (RNA) and deoxyribonucleic acid (DNA). The phrase nucleic acid should also be understood to include, as applicable, single-stranded (such as sense or antisense) and double-stranded polynucleotides.

Nucleic acids according to the invention may be partially or wholly synthetic, and may be isolated and/or purified (i.e., from their natural environment), in substantially pure or homogeneous form, or free or substantially free of other nucleic acid.

Representative nucleic acids comprising siRNAs of the invention include expression constructs and vectors. The term "expression construct" refers to a nucleic acid suitable for expression or production in a cell. The term "vector" refers to a nucleic acid molecule (plasmid, virus, bacteriophage, artificial, heterologous, or cut DNA molecule) that can be used to deliver a heterologous or natural polynucleotide of the invention into a host cell.

Vectors are capable of being replicated and contain cloning sites for introduction of a foreign polynucleotide.

Those skilled in the art are readily able to prepare expression constructs and vectors of the invention disclosed herein and recombinantly express the same. For further details see, e.g., Sambrook et al. (1989) Molecular Cloning: A Laboratory Manual, Second Edition, Cold Spring Harbor Laboratory, Cold Spring Harbor, N.Y. Such applicable techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992.

Specific expression techniques and vectors previously used with wide success upon plants are described by Bevan, *Nucl. Acids Res.* (1984) 12, 8711-8721, and Guerineau and Mullineaux, (1993) "Plant transformation and expression vectors," *Plant Molecular Biology* Labfax (Croy RRD, ed.) Oxford, BIOS Scientific Publishers, 121-148.

Expression constructs include a promoter operably linked to a nucleic acid comprising a siRNA, for example, an artificial microRNA, as described herein above. Useful promoters include constitutive promoters, promoters that direct spatially and temporally regulated expression (e.g., tissue-specific and developmental stage-specific promoters), and inducible promoters. Expression constructs may also include enhancers of gene expression as known in the art.

Tissue-preferred promoters can be utilized to target enhanced expression of a sequence of interest within a particular plant tissue. Tissue-preferred promoters include Yamamoto et al. (1997) *Plant J.* 12, 255-265; Kawamata et al. (1997) *Plant Cell Physiol.* 38, 792-803; Hansen et al. (1997) *Mol. Gen. Genet.* 254, 337-343; Russell et al. (1997) *Transgenic Res.* 6, 157-168; Rinehart et al. (1996) *Plant Physiol.* 112, 1331-1341; Van Camp et al. (1996) *Plant Physiol.* 112, 525-535; Canevascini et al. (1996) *Plant Physiol.* 112, 513-524; Yamamoto et al. (1994) *Plant Cell Physiol.* 35, 773-778; Lam (1994) *Results Probl. Cell Differ.* 20, 181-196; Orozco et al. (1993) *Plant Mol. Biol.* 23, 1129-1138; Matsuoka et al. (1993) *Proc Natl. Acad. Sci. USA* 90, 9586-9590; and Guevara-Garcia et al. (1993) *Plant J.* 4, 495-505. Such promoters can be modified, if necessary, for weak expression.

Leaf-preferred promoters are known in the art. See, e.g., Yamamoto et al. (1997) *Plant J.* 12, 255-265; Kwon et al. (1994) *Plant Physiol.* 105, 357-67; Yamamoto et al. (1994) *Plant Cell Physiol.* 35, 773-778; Gotor et al. (1993) *Plant J.* 3, 509-18; Orozco et al. (1993) *Plant Mol. Biol.* 23, 1129-1138; and Matsuoka et al. (1993) *Proc. Natl. Acad. Sci. USA* 90, 9586-9590. In addition, the promoters of cab and rubisco can also be used. See, e.g., Simpson et al. (1958) *EMBO J.* 4, 2723-2729 and Timko et al. (1988) *Nature* 318, 57-58.

Root-preferred promoters are known and can be selected from the many available from the literature or isolated de novo from various compatible species. See, e.g., Hire et al. (1992) *Plant Mol. Biol.* 20, 207-218 (soybean root-specific glutamine synthetase gene); Keller and Baumgartner (1991) *Plant Cell* 3, 1051-1061 (root specific control element in the GRP 1.8 gene of French bean); Sanger et al. (1990) *Plant Mol. Biol.* 14, 433-443 (root specific promoter of the mannopine synthase (MAS) gene of *Agrobacterium tumefaciens*); and Miao et al. (1991) *Plant Cell* 3, 11-22 (i.e., a full-length cDNA clone encoding cytosolic glutamine synthetase (GS), which is expressed in roots and root nodules of soybean). See also Bogusz et al. (1990) *Plant Cell* 2, 633-641, where two root-specific promoters isolated from hemoglobin genes from the nitrogen-fixing non legume *Parasponia andersonii* and the related non-nitrogen fixing non legume *Trema tomentosa* are described. The promoters of these genes were linked to a 13-glucuronidase reporter gene and introduced into both the non-legume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes*. See *Plant Science* (Limerick) 79, 69-76. They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene. See *EMBO J.* 8 343-350. The TR1' gene, fused to nptII (neomycin phosphotransferase II) showed similar characteristics. Additional root-preferred promoters include the VfENOD-GRP3 gene promoter and rolB promoter. See also Kuster et al. (1995) *Plant Mol. Biol.* 29, 759-772; Capana et al. (1994) *Plant Mol. Biol.* 25, 681-691. See also U.S. Pat. Nos. 5,837,876; 5,750,386; 5,633,363; 5,459, 252; 5,401,836; 5,110,732; and 5,023,179. The phaseolin gene is described by Murai et al. (1983) *Science* 23, 476-482, and Sengopta-Gopalen et al. (1988) *Proc. Natl. Acad. Sci. USA* 82, 3320-3324.

In some aspects, it will be beneficial to express siRNAs of the invention using an inducible promoter, such as from a pest or pathogen-inducible promoter. Such promoters include those from pathogenesis-related proteins (PR proteins), which are induced following infection by a pathogen; e.g., PR proteins, SAR proteins, $\beta$-1,3-glucanase, chitinase, etc. See, e.g., Redolfi et al. (1983) *Neth. J. Plant Pathol.* 89:245-254; Uknes et al. (1992) *Plant Cell* 4, 645-656; and Van Loon (1985) *Plant Mol. Virol.* 4, 111-116. See also PCT International Publication No. WO 99/43819.

Promoters that are expressed locally at or near the site of pest infection are particularly of interest. See, e.g., Marineau et al. (1987) *Plant Mol. Biol.* 9, 335-342; Matton et al. (1989) *Molecular Plant-Microbe Interactions* 2, 325-331; Somsisch et al. (1986) *Proc. Natl. Acad. Sci. USA* 83, 2427-2430; Somsisch et al. (1988) *Mol. Gen. Genet.* 2, 93-98; and Yang (1996) *Proc. Natl. Acad. Sci. USA* 93, 14972-14977. See also, Chen et al. (1996) *Plant J.* 10, 955-966; Zhang et al. (1994) *Proc. Natl. Acad. Sci. USA* 91, 2507-2511; Warner et al. (1993) *Plant J.* 3, 191-201; Siebertz et al. (1989) *Plant Cell* 1, 961-968; U.S. Pat. No. 5,750,386 (nematode-inducible); Cordero et al. (1992) *Physiol. Mol. Plant. Path.* 41, 189-200, and the references cited therein.

Additionally, as pests or pathogens enter host plants through wounds or insect damage, a wound-inducible promoter may be used in the constructs of the invention. Such wound-inducible promoters include potato proteinase inhibitor (pin /I) gene (Ryan (1990) *Ann. Rev. Phytopath.* 28, 425-449; Duan et al. (1996) *Nature Biotech.* 14, 494-498); wun1 and wun2, U.S. Pat. No. 5,428,148; win1 and wing (Stanford et al. (1989) *Mol. Gen. Genet.* 215, 200-208); *systemin* (McGurl et al. (1992) *Science* 225, 1570-1573); WIP1 (Rohmeier et al. (1993) *Plant Mol. Biol.* 22, 783-792; Eckelkamp et al. (1993) *FEBS Lett.* 323, 73-76); and the MPI gene (Corderok et al. (1994) *Plant J.* 6, 141-150). Accumulation of metallocarboxypeptidase-inhibitor protein has been reported in leaves of wounded potato plants (Graham et al. (1981) *Biochem. Biophys. Res. Comm.* 101, 1164-1170). Other studies have focused on genes inducibly regulated in response to environmental stress or stimuli such as increased salinity, drought, and pathogen wounding (Graham et al. (1985) *J. Biol. Chem.* 260, 6555-6560; Graham et al. (1985) *J. Biol. Chem.* 260, 6561-6564; Smith et al. (1986) *Planta* 168, 94-100). Other plant genes can be induced by methyl jasmonate, elicitors, heat-shock, anaerobic stress, or herbicide safeners.

U.S. Pat. Nos. 5,589,622 and 5,824,876 describe the identification of plant genes expressed specifically in or adjacent to the feeding site of the plant after attachment by a nematode. The promoters of these plant target genes can then be used to direct the specific expression of detrimental amiRNA to the pest target gene.

In addition to the above-identified promoters, U.S. Patent Application Publication Numbers 2004/0016025, 2007/0056055, 2008/0120750, 2009/0183283, and U.S. Pat. Nos. 7,550,578 and 7,615,624 describe a variety of promoters from *Oryza sativa* and *Arabidopsis thaliana*, which may also be used for expression of siRNAs as described herein. The particular promoter sequences of the just named patent documents, and disclosure regarding use of such promoters, are incorporated by reference herein.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. It is understood that some promoters that show preferential targeting of expression in target tissues may also exhibit "leaky" expression in non-preferential targeted tissues. One example may be a promoter whose expression profile shows preferential expression in maize seed however also exhibits strong expression in mature leaf tissue. Methods for identifying and characterizing promoter regions in plant genomic DNA include, for example, those described in the following references: Jordano et al. (1989) *Plant Cell* 1, 855-866; Bustos et al. (1989) *Plant Cell* 1, 839-854; Green et al. (1988) *EMBO J.* 7, 4035-4044; Meier et al. (1991) *Plant Cell* 3, 309-316; and Zhang et al. (1996) *Plant Physiol.* 110, 1069-1079.

Promoters active in photosynthetic tissue in order to drive transcription in green tissues such as leaves and stems are of particular interest for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35, 773-778), the Cab-1 gene promoter from wheat (Fejes et al. (1990) *Plant Mol. Biol.* 15, 921-932), the Cab-1 promoter from spinach (Lubberstedt et al. (1994) *Plant Physiol.* 104, 997-1006), the cab1R promoter from rice (Luan et al. (1992) Plant Cell 4, 971-981), the pyruvate orthophosphate dikinase (PPDK) promoter from maize (Matsuoka et al. (1993) *Proc. Natl. Acad. Sci. USA* 90, 9586-9590), the tobacco Lhcb1*2 promoter (Cerdan et al. (1997) *Plant Mol. Biol.* 33, 245-255), the *Arabidopsis thaliana* SUC2 sucrose-$H^+$ symporter promoter (Truernit et al. (1995) Planta 196, 564-570), and thylakoid membrane protein promoters from spinach (psaD, psaF, psaE, PC, FNR, atpC, atpD, cab, rbcS. Other promoters that drive transcription in stems, leafs, and green tissue are described in U.S. Patent Publication No. 2007/0006346.

Any of the above-described promoters, or other known promoters, may be used to express siRNAs of the invention. One skilled in the art is readily able to select a promoter as appropriate for a particular application.

The expression constructs and vectors of the invention may be used to prepare compositions for conferring traits to a target or host organism, as described herein below. In one aspect of the invention, such a composition is a nematicidal composition comprising a siRNA comprising nucleotides 2-8 of any one of SEQ ID NOs: 1-14, for example, a siRNA comprising the sequence set forth SEQ ID NOs: 1-14. Compositions for conferring traits may also include two or more siRNAs.

Target Organisms

A target organism is an organism in which siRNAs of the invention are intended to be functional, i.e., to mediate gene silencing or suppression. In one aspect of the invention, a target organism is also a host organism, as described herein below. In other aspects of the invention, a target organism is separate and distinct from a host organism that serves as a source of the siRNA to be functional in the target organism.

The terms "targeting" or "target(s)," as used herein, refer to the ability of siRNA molecules to form base pairs with a complementary mRNA molecule in a particular organism to thereby result in gene silencing or suppression. Such an organism is referred to as the target organism. A "target nucleic acid" or "target sequence" is a nucleic acid sequence or molecule from or in a target organism. Target sequence also implies a nucleic acid sequence that is selected for suppression and is not limited to polynucleotides encoding polypeptides. The target sequence typically comprises a sequence that is substantially or fully complementary to the siRNA. The target sequence includes, but is not limited to, RNA, DNA, or other polynucleotide comprising the target sequence.

In one aspect of the invention, "target organisms" are plant pests or pathogens whose damage to the plant can be reduced or eliminated according to the invention. Representative plant pests and pathogens include insects, nematodes, fungi, bacteria, viruses, and parasitic plants such as striga, dodder, and mistletoe. Insect pests that may be targeted according to the invention include without limitation chewing, sucking, and boring insects that belong, for example, to the non-limiting Orders *Coleoptera, Diptera, Hemiptera, Heteroptera, Homoptera, Hymenoptera, Lepidoptera,* and *Orthoptera*. Non-limiting examples of such insect pests are shown in Table 1. Non-limiting examples of nematodes that may be targeted in accordance with the invention include those set forth in Table 2. Non-limiting examples of fungi, mildews, and rusts that may be targeted in accordance with the invention include those set forth in Table 3. Non-limiting examples of bacteria are shown in Table 4. Non-limiting examples of plant viruses that may be targeted are shown in Table 5.

TABLE 1

Target Pests - Insects

Lepidoptera

*Ostrinia nubilalis*, European corn borer
*Helicoverpa zea*, corn earworm
*Spodoptera exigua*, beet armyworm
*Spodoptera frugiperda*, fall armyworm
*Diatraea grandiosella*, Southwestern corn borer
*Elasmopalpus lignosellus*, lesser cornstalk borer
*Papaipema nebris*, stalk borer
*Pseudaletia unipuncta*, common armyworm
*Agrotis ipsilon*, black cutworm
*Striacosta albicosta*, Western bean cutworm
*Spodoptera ornithogalli*, yellowstriped armyworm
*Spodoptera praefica*, western yellowstriped armyworm
*Spodoptera eridania*, southern armyworm
*Spodoptera eridania*, southern armyworm
*Peridroma saucia*, variegated cutworm
*Papaipema nebris*, stalk borer
*Trichoplusia ni*, cabbage looper
*Keiferia lycopersicella*, tomato pinworm
*Manduca sexta*, tobacco hornworm
*Manduca quinquemaculata*, tomato hornworm
*Artogeia rapae*, imported cabbageworm
*Pieris brassicae*, cabbage butterfly
*Trichoplusia ni*, cabbage looper
*Plutella xylostella*, diamondback moth
*Spodoptera exigua*, beet armyworm
*Agrotis segetum*, common cutworm
*Phthorimaea operculella*, potato tuberworm
*Plutella xylostella*, diamondback moth
*Diatraea saccharalis*, sugarcane borer
*Crymodes devastator*, glassy cutworm
*Feltia ducens*, dingy cutworm
*Agrotis gladiaria*, claybacked cutworm
*Plathypena scabra*, Green cloverworm
*Pseudoplusia includes*, Soybean looper
*Anticarsia gemmatalis*, Velvetbean caterpillar
Coleoptera

*Diabrotica barberi*, northern corn rootworm
*Diabrotica undecimpunctata*, southern corn rootworm
*Diabrotica virgifera*, Western corn rootworm
*Sitophilus zeamais*, maize weevil
*Leptinotarsa decemlineata*, Colorado potato beetle
*Epitrix hirtipennis*, tobacco flea beetle
*Phyllotreta cruciferae*, crucifer flea beetle
*Phyllotreta pusilla*, western black flea beetle TABLE 1-continued Target Pests - Insects

*Anthonomus eugenii*, pepper weevil
*Leptinotarsa decemlineata*, Colorado potato beetle
*Epitrix cucumeris*, potato flea beetle
*Hemicrepidus memnonius*, wireworms
*Melanpotus* spp., wireworms
*Ceutorhychus assimilis*, cabbage seedpod weevil
*Phyllotreta cruciferae*, crucifer flea beetle
*Melanolus* spp., *Aeolus mellillus*, wireworm
*Aeolus mancus*, wheat wireworm
*Horistonotus uhlerii*, sand wireworm
*Sphenophorus maidis*, maize billbug
*Sphenophorus zeae*, timothy bilibug
*Sphenophorus parvulus*, bluegrass billbug
*Sphenophorus callosus*, southern corn billbug
*Phyllophaga* spp., white grubs
*Chaetocnema pulicaria*, corn flea beetle
*Popillia japonica*, Japanese beetle
*Epilachna varivestis*, Mexican bean beetle
*Cerotoma trifurcate*, Bean leaf beetle
*Epicauta pestifera*, *Epicauta lemniscata*, Blister beetles
Homoptera

*Rhopalosiphum maidis*, corn leaf aphid
*Anuraphis maidiradicis*, corn root aphid
*Myzus persicae*, green peach aphid
*Macrosiphum euphorbiae*, potato aphid
*Trileurodes vaporariorum*, greenhouse whitefly
*Bemisia tabaci*, sweetpotato whitefly
*Bemisia argentifolii*, silverleaf whitefly
*Brevicoryne brassicae*, cabbage aphid
*Myzus persicae*, green peach aphid
*Empoasca fabae*, potato leafhopper
*Paratrioza cockerelli*, potato psyllid
*Bemisia argentifolii*, silverleaf whitefly
*Bemisia tabaci*, sweetpotato whitefly
*Cavariella aegopodii*, carrot aphid
*Brevicoryne brassicae*, cabbage aphid
*Saccharosydne saccharivora*, West Indian canefly
*Sipha flava*, yellow sugarcane aphid
*Spissistilus festinus*, Threecornered alfalfa hopper
Hemiptera

*Lygus lineolaris*, *Lygus hesperus*, *Lygus rugulipennis*, lygus bug
*Acrosternum hilare*, green stink bug
*Euschistus servus*, brown stick bug
*Blissus leucopterus leucopterus*, chinch bug
Diptera

*Liriomyza trifolii*, leafminer
*Liriomyza sativae*, vegetable leafminer
*Scrobipalpula absoluta*, tomato leafminer
*Delia platura*, seedcorn maggot
*Delia brassicae*, cabbage maggot
*Delia radicum*, cabbage root fly
*Psilia rosae*, carrot rust fly
*Tetanops myopaeformis*, sugarbeet root maggot
Orthoptera

*Melanoplus differentialis*, Differential grasshopper
*Melanoplus femurrubrum*, Redlegged grasshopper
*Melanoplus bivittatus*, Twostriped grasshopper

TABLE 2

Target Pests - Parasitic Nematodes

| Disease | Causative Agent |
| --- | --- |
| Awl | *Dolichoderus* spp., *D. heterocephalus* |
| Bulb and stem (Europe) | *Ditylenchus dipsaci* |
| Burrowing | *Radopholus similes R. similis* |
| Cyst | *Heterodera avenae*, *H. zeae*, *H. schachti*; *Globodera rostochiensis*, *G. pallida*, and *G. tabacum*; *Heterodera trifolii*, *H. medicaginis*, *H. ciceri*, *H. mediterranea*, *H. cyperi*, |

TABLE 2-continued

Target Pests - Parasitic Nematodes

| Disease | Causative Agent |
|---|---|
|  | H. salixophila, H. zeae, H. goettingiana, H. riparia, H. humuli, H. latipons, H. sorghi, H. fici, H. litoralis, and H. turcomanica; Punctodera chalcoensis |
| Dagger | Xiphinema spp., X. americanum, X. Mediterraneum |
| False root-knot | Nacobbus dorsalis |
| Lance, Columbia | Hoplolaimus Columbus |
| Lance | Hoplolaimus spp., H. galeatus |
| Lesion | Pratylenchus spp., P. brachyurus, P. coffeae P. crenatus, P. hexincisus, P. neglectus, P. penetrans, P. scribneri, P. magnica, P. neglectus, P. thornei, P. vulnus, P. zeae |
| Needle | Longidorus spp., L. breviannulatus |
| Ring | Criconemella spp., C. ornata |
| Root-knot | Meloidogyne spp., M. arenaria, M. chitwoodi, M. artiellia, M. fallax, M. hapla, M. javanica, M. incognita, M. microtyla, M. partityla, M. panyuensis, M. paranaensis |
| Spiral | Helicotylenchus spp. |
| Sting | Belonolaimus spp., B. longicaudatus |
| Stubby-root | Paratrichodorus spp., P. christiei, P. minor, Quinisulcius acutus, Trichodorus spp. |
| Stunt | Tylenchorhynchus dubius |
| Others | Hirschmanniella species, Pratylenchoid magnicauda |

TABLE 3

Target Pathogens - Fungi

| Disease | Causative Agent |
|---|---|
| Brown stripe downy mildew | Sclerophthora rayssiae var. zeae |
| Crazy top downy mildew | Sclerophthora macrospora = S. macrospora |
| Green ear downy mildew | Sclerospora graminicola |
| Java downy mildew | Peronosclerospora maydis = Sclerospora maydis |
| Philippine downy mildew | Peronosclerospora philippinensis = Sclerospora philippinensis |
| Sorghum downy mildew | Peronosclerospora sorghi = Sclerospora sorghi |
| Spontaneum downy mildew | Peronosclerospora spontanea = Sclerospora spontanea |
| Sugarcane downy mildew | Peronosclerospora sacchari = Sclerospora sacchari |
| Dry ear rot (cob, kernel and stalk rot) | Nigrospora oryzae (teleomorph: Khuskia oryzae) |
| Ear rots, minor | Aspergillus glaucus, A. niger, Aspergillus spp., Cunninghamella sp., Curvularia pallescens, Doratomyces stemonitis = Cephalotrichum stemonitis, Fusarium culmorum, Gonatobotrys simplex, Pithomyces maydicus, Rhizopus microsporus, R. stolonifer = R. nigricans, Scopulariopsis brumptii |
| Ergot (horse's tooth, diente del caballo) | Claviceps gigantea (anamorph: Sphacelia sp.) |
| Eyespot | Aureobasidium zeae = Kabatiella zeae |
| Fusarium ear and stalk rot | Fusarium subglutinans = F. moniliforme var. subglutinans |
| Fusarium kernel, root and stalk rot, seed rot and seedling blight | Fusarium moniliforme (teleomorph: Gibberella fujikuroi) |
| Fusarium stalk rot, seedling root rot | Fusarium avenaceum (teleomorph: Gibberella avenacea) |
| Gibberella ear and stalk rot | Gibberella zeae (anamorph: Fusarium graminearum) |
| Gray ear rot | Botryosphaeria zeae = Physalospora zeae (anamorph: Macrophoma zeae) |
| Gray leaf spot (Cercospora leaf spot) | Cercospora sorghi = C. sorghi var. maydis, C. zeae-maydis |
| Helminthosporium root rot | Exserohilum pedicellatum = Helminthosporium pedicellatum (teleomorph: Setosphaeria) |
| Hormodendrum ear rot (Cladosporium rot) | Cladosporium cladosporioides = Hormodendrum cladosporioides, C. herbarum (teleomorph: Mycosphaerella tassiana) |
| Hyalothyridium leaf spot | Hyalothyridium maydis |
| Late wilt | Cephalosporium maydis |
| Leaf spots, minor | Alternaria alternata, Ascochyta maydis, A. tritici, A. zeicola, Bipolaris victoriae = Helminthosporium victoriae (teleomorph: Cochliobolus victoriae), C. sativus (anamorph: Bipolaris sorokiniana = H. sorokinianum = H. sativum), Epicoccum nigrum, Exserohilum prolatum = Drechslera prolata (teleomorph: Setosphaeria prolata) Graphium penicillioides, Leptosphaeria maydis, Leptothyrium zeae, Ophiosphaerella herpotricha, (anamorph: Scolecosporiella sp.), Paraphaeosphaeria michotii, Phoma sp., Septoria zeae, S. zeicola, S. zeina |
| Northern corn leaf blight | Exserohilum turcicum = Helminthosporium turcicum, Setosphaeria turcica |
| Northern corn leaf spot | Cochliobolus carbonum |
| Helminthosporium ear rot (race 1) | Bipolaris zeicola = Helminthosporium carbonum |
| Penicillium ear rot (blue eye, blue mold) | Penicillium spp., P. chrysogenum, P. expansum, P. oxalicum |
| Phaeocytostroma stalk rot and root rot | Phaeocytostroma ambiguum, Phaeocytosporella zeae |
| Phaeosphaeria leaf spot | Phaeosphaeria maydis, Sphaerulina maydis |
| Physalospora ear rot | Botryosphaeria Botryosphaeria festucae = Physalospora zeicola, (anamorph: Diplodia frumenti) |
| Purple leaf sheath | Hemiparasitic bacteria and fungi |
| Pyrenochaeta stalk rot and root rot | Phoma terrestris, Pyrenochaeta terrestris |
| Pythium root rot | Pythium spp., P. arrhenomanes, P. graminicola |
| Pythium stalk rot | Pythium aphanidermatum = P. butleri L. |
| Red kernel disease (ear mold, leaf and seed rot) | Epicoccum nigrum |
| Rhizoctonia ear rot | Rhizoctonia zeae (teleomorph: Waitea circinata) |
| Rhizoctonia root rot and stalk rot | Rhizoctonia solani, Rhizoctonia zeae |
| Root rots, minor | Alternaria alternata, Cercospora sorghi, Dictochaeta fertilis, Fusarium acuminatum (teleomorph: Gibberella acuminata), F. equiseti (teleomorph: G. intricans), F. oxysporum, F. pallidoroseum, F. poae, F. roseum, F. cyanogena, (anamorph: F. sulphureum), Microdochium bolleyi, Mucor sp., Periconia circinata, Phytophthora cactorum, P. drechsleri, P. nicotianae var. parasitica, Rhizopus arrhizus |
| Rostratum leaf spot (leaf disease, ear and stalk rot) | Setosphaeria rostrata, Helminthosporium (anamorph: Exserohilum rostratum = Helminthosporium rostratum) |
| Rust, common corn | Puccinia sorghi |
| Rust, southern corn | Puccinia polysora |
| Rust, tropical corn | Physopella pallescens, P. zeae = Angiospora zeae |
| Sclerotium ear rot (southern blight) | Sclerotium rolfsii (teleomorph: Athelia rolfsii) |
| Seed rot-seedling blight | Bipolaris sorokiniana, B. zeicola = Helminthosporium carbonum, Diplodia maydis, Exserohilum pedicellatum, Exserohilum turcicum = Helminthosporium turcicum, Fusarium avenaceum, F. culmorum, F. moniliforme, Gibberella zeae (anamorph: F. graminearum), Macrophomina phaseolina, |

TABLE 3-continued

Target Pathogens - Fungi

| Disease | Causative Agent |
|---|---|
| | *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M. rubber* |
| Smut, common | *Ustilago zeae* = *U. maydis* |
| Smut, false | *Ustilaginoidea virens* |
| Smut, head | *Sphacelotheca reiliana* = *Sporisorium holci-sorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium episphaeria*, *F. merismoides*, *F. oxysporum*, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |
| Tar spot | *Phyllachora maydis* |
| *Trichoderma* ear rot and root rot | *Trichoderma viride* = *T. lignorum* (teleomorph: *Hypocrea* sp.) |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |
| Anthracnose leaf blight and stalk rot | *Colletotrichum graminicola* anthracnose (teleomorph: *Glomerella graminicola*), *Glomerella tucumanensis* (anamorph: *Glomerella falcatum*) |
| *Aspergillus* ear and kernel rot | *Aspergillus flavus* |
| Banded leaf and sheath spot | *Rhizoctonia solani* = *Rhizoctonia microsclerotia* (teleomorph: *Thanatephorus cucumeris*) |
| Black bundle disease | *Acremonium strictum* = *Cephalosporium acremonium* |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitialis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or leaf streak | *Stenocarpella macrospora* = *Diplodia macrospore* |
| Corn common rust | *Puccinia sorghi* |
| Corn southern rust | *Puccinia polysora* |
| Corn tropical rust | *Physopella pallescens*, *P. zeae* = *Angiospora zeae* |
| Oat crown rust | *Puccinia coronata* |
| Oat stem Rust | *Puccinia graminis* |
| Stem rust | *Puccinia graminis* = *P. graminis* f. sp. *secalis* |
| Leaf (brown) rust | *Puccinia recondita* (anamorph: *Aecidium clematitis*) |
| Sugarcane common rust | *Puccinia melanocephala* = *P. eriantha* |
| Wheat leaf (brown) rust | *Puccinia triticina* = *P. Recondita* f. Sp. *tritici* = *P. tritici-duri* |
| Wheat stem (black) rust | *Puccinia graminis* = *P. graminis* f. sp. *tritici* |
| Wheat stripe (yellow) rust | *Puccinia striiformis* (anamorph: *P. uredoglumarum*) |
| Bean rust | *Uromyces appendiculatus* |
| Cotton rust | *Puccinia schedonnardi* |
| Cotton southwestern rust | *Puccinia cacabata* |
| Cotton tropical rust | *Phakopsora gossypii* |
| Peanut rust | *Puccinia arachidis* |
| Potato common rust | *Puccinia pittieriana* |
| Potato deforming rust | *Aecidium cantensis* |
| Soybean rust | *Phakopsora pachyrhizi* |

TABLE 4

Target Pathogens - Bacteria

| Disease | Causative Agent |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *Zeae* |
| Bacterial stripe | *Pseudomonas andropogonis* |
| Chocolate spot | *Pseudomonas syringae* pv. *Coronafaciens* |
| Goss's bacterial wilt blight (leaf freckles and wilt) | *Clavibacter michiganensis* subsp. *nebraskensis* = *Cornebacterium michiganense* pv. *Nebraskense* |
| Holcus spot | *Pseudomonas syringae* pv. *Syringae* |
| Purple leaf sheath | Hemiparasitic bacteria + (See Table 3) |
| Seed rot-seedling blight | *Bacillus subtilis* |
| Stewart's disease (bacterial wilt) | *Pantoea stewartii* = *Erwinia stewartii* |
| Corn stunt (Mesa Central or Rio Grande stunt) | *Achapparramiento*, stunt, *Spiroplasma kunkelii* |

TABLE 5

Target Pests - Viruses

| | |
|---|---|
| Alfamoviruses: Bromoviridae | Alfalfa mosaic alfamovirus |
| Alphacrypto-viruses: Partitiviridae | Alfalfa 1 alphacryptovirus, Beet 1 alphacryptovirus, Beet 2 alphacryptovirus, Beet 3 alphacryptovirus, Carnation 1 alphacryptovirus, Carrot temperate 1 alphacryptovirus, Carrot temperate 3 alphacryptovirus, Carrot temperate 4 alphacryptovirus, Cocksfoot alphacryptovirus, Hop trefoil 1 alphacryptovirus, Hop trefoil 3 alphacryptovirus, Radish yellow edge alphacryptovirus, Ryegrass alphacryptovirus, Spinach temperate alphacryptovirus, Vicia alphacryptovirus, White clover 1 alphacryptovirus, White clover 3 alphacryptovirus |
| Badnaviruses | Banana streak badnavirus, Cacao swollen shoot badnavirus, Canna yellow mottle badnavirus, Commelina yellow mottle badnavirus, Dioscorea bacilliform badnavirus, Kalanchoe top-spotting badnavirus, Rice tungro bacilliform badnavirus, Schefflera ringspot badnavirus, Sugarcane bacilliform badnavirus |
| Betacryptoviruses: Partitiviridae | Carrot temperate 2 betacryptovirus, Hop trefoil 2 betacryptovirus, Red clover 2 betacryptovirus, White clover 2 betacryptovirus |

TABLE 5-continued

Target Pests - Viruses

| | |
|---|---|
| Bigeminiviruses: Geminiviridae | Abutilon mosaic bigeminivirus, Ageratum yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomate bigeminivirus, Cotton leaf crumple bigeminivirus, Cotton leaf curl bigeminivirus, Croton yellow vein mosaic bigeminivirus, Dolichos yellow mosaic bigeminivirus, Euphorbia mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigeminivirus, Rhynchosia mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus, Watermelon curly mottle bigeminivirus |
| Bromoviruses: Bromoviridae | Broad bean mottle bromovirus, Brome mosaic bromovirus, Cassia yellow blotch bromovirus, Cowpea chlorotic mottle bromovirus, Melandrium yellow fleck bromovirus, Spring beauty latent bromovirus |
| Bymoviruses: Potyviridae | Barley mild mosaic bymovirus, Barley yellow mosaic bymovirus, Oat mosaic bymovirus, Rice necrosis mosaic bymovirus, Wheat spindle streak mosaic bymovirus, Wheat yellow mosaic bymovirus |
| Capilloviruses | Apple stem grooving capillovirus, Cherry A capillovirus, Citrus tatter leaf capillovirus, Lilac chlorotic leafspot capillovirus |
| Carlaviruses | Blueberry scorch carlavirus, Cactus 2 carlavirus, Caper latent carlavirus, Carnation latent carlavirus, Chrysanthemum B carlavirus, Dandelion latent carlavirus, Elderberry carlavirus, Fig S carlavirus, Helenium S carlavirus, Honeysuckle latent carlavirus, Hop American latent carlavirus, Hop latent carlavirus, Hop mosaic carlavirus, Kalanchoe latent carlavirus, Lilac mottle carlavirus, Lily symptomless carlavirus, Mulberry latent carlavirus, Muskmelon vein necrosis carlavirus, Nerine latent carlavirus, Passiflora latent carlavirus, Pea streak carlavirus, Poplar mosaic carlavirus, Potato M carlavirus, Potato S carlavirus, Red clover vein mosaic carlavirus, Shallot latent carlavirus, Strawberry pseudo mild yellow edge carlavirus |
| Carmoviruses: Tombusviridae | Bean mild mosaic carmovirus, Cardamine chlorotic fleck carmovirus, Carnation mottle carmovirus, Cucumber leaf spot carmovirus, Cucumber soil-borne carmovirus, Galinsoga mosaic carmovirus, Hibiscus chlorotic ringspot carmovirus, Melon necrotic spot carmovirus, Pelargonium flower break carmovirus, Turnip crinkle carmovirus |
| Caulimoviruses | Blueberry red ringspot caulimovirus, Carnation etched ring caulimovirus, Cauliflower mosaic caulimovirus, Dahlia mosaic caulimovirus, Figwort mosaic caulimovirus, Horseradish latent caulimovirus, Mirabilis mosaic caulimovirus, Peanut chlorotic streak caulimovirus, Soybean chlorotic mottle caulimovirus, Sweet potato caulimovirus, Thistle mottle caulimovirus |
| Closteroviruses | Beet yellow stunt closterovirus, Beet yellows closterovirus, Broad bean severe chlorosis closterovirus, Burdock yellows closterovirus, Carnation necrotic fleck closterovirus, Citrus tristeza closterovirus, Clover yellows closterovirus, Grapevine stem pitting associated closterovirus, Wheat yellow leaf closterovirus |
| Comoviruses: Comoviridae | Bean pod mottle comovirus, Bean rugose mosaic comovirus, Broad bean stain comovirus, Broad bean true mosaic comovirus, Cowpea mosaic comovirus, Cowpea severe mosaic comovirus, Glycine mosaic comovirus, Pea mild mosaic comovirus, Potato Andean mottle comovirus, Quail pea mosaic comovirus, Radish mosaic comovirus, Red clover mottle comovirus, Squash mosaic comovirus, Ullucus C comovirus |
| Cucumoviruses: Bromoviridae | Cucumber mosaic cucumovirus, Peanut stunt cucumovirus, Tomato aspermy cucumovirus |
| Cytorhabdo- viruses: Rhabdoviridae | Barley yellow striate mosaic cytorhabdovirus, Broad bean yellow vein cytorhabdovirus, Broccoli necrotic yellows cytorhabdovirus, Cereal northern mosaic cytorhabdovirus, Festuca leaf streak cytorhabdovirus, Lettuce necrotic yellows cytorhabdovirus, Sonchus cytorhabdovirus, Strawberry crinkle cytorhabdovirus |
| Dianthoviruses | Carnation ringspot dianthovirus, Red clover necrotic mosaic dianthovirus, Sweet clover necrotic mosaic dianthovirus |
| Enamoviruses | Pea enation mosaic enamovirus |
| Fijiviruses: Reoviridae | Maize rough dwarf fijivirus, Oat sterile dwarf fijivirus, Pangola stunt fijivirus, Rice black-streaked dwarf fijivirus, Sugarcane Fiji disease fijivirus |
| Furoviruses | Beet necrotic yellow vein furovirus, Beet soil-borne furovirus, Broad bean necrosis furovirus, Oat golden stripe furovirus, Peanut clump furovirus, Potato mop-top furovirus, Sorghum chlorotic spot furovirus, Wheat soil-borne mosaic furovirus |
| Hordeiviruses | Anthoxanthum latent blanching hordeivirus, Barley stripe mosaic hordeivirus, Lychnis ringspot hordeivirus, Poa semilatent hordeivirus |
| Hybrigemini- viruses: Geminiviridae | Beet curly top hybrigeminivirus, Tomato pseudo curly top hybrigeminivirus |
| Idaeoviruses | Raspberry bushy dwarf idaeovirus |
| Ilarviruses: Bromoviridae | Apple mosaic ilarvirus, Asparagus 2 ilarvirus, Blueberry necrotic shock ilarvirus, Citrus leaf rugose ilarvirus, Citrus variegation ilarvirus, Elm mottle ilarvirus, Humulus japonicus ilarvirus, Hydrangea mosaic ilarvirus, Lilac ring mottle ilarvirus, Parietaria mottle ilarvirus, Plum American line pattern ilarvirus, Prune dwarf ilarvirus, Prunus necrotic ringspot ilarvirus, Spinach latent ilarvirus, Tobacco streak ilarvirus, Tulare apple mosaic ilarvirus |
| Ipomoviruses: Potyviridae | Sweet potato mild mottle ipomovirus, Sweet potato yellow dwarf ipomovirus |
| Luteovirus | Barley yellow dwarf luteovirus, Bean leaf roll luteovirus, Beet mild yellowing luteovirus, Beet western yellows luteovirus, Carrot red leaf luteovirus, Groundnut rosette assistor luteovirus, Potato leafroll luteovirus, Solanum yellows luteovirus, Soybean dwarf luteovirus, Soybean Indonesian dwarf luteovirus, Strawberry mild yellow edge luteovirus, Subterranean clover red leaf luteovirus, Tobacco necrotic dwarf luteovirus |
| Machlomoviruses | Maize chlorotic mottle machlomovirus |
| Macluravirus | Maclura mosaic macluravirus, Narcissus latent macluravirus |
| Marafiviruses | Bermuda grass etched-line marafivirus, Maize rayado fino marafivirus, Oat blue dwarf marafivirus |
| Monogemini- viruses: Geminiviridae | Chloris striate mosaic monogeminivirus, Digitaria striate mosaic monogeminivirus, Digitaria streak monogeminivirus, Maize streak monogeminivirus, Miscanthus streak monogeminivirus, Panicum streak monogeminivirus, Paspalum striate mosaic monogeminivirus, Sugarcane streak monogeminivirus, Tobacco yellow dwarf monogeminivirus, Wheat dwarf monogeminivirus |
| Nanaviruses | Banana bunchy top nanavirus, Coconut foliar decay nanavirus, Faba bean necrotic yellows nanavirus, Milk vetch dwarf nanavirus, Subterranean clover stunt nanavirus |
| Necroviruses | Tobacco necrosis necrovirus, Carnation yellow stripe necrovirus, Lisianthus necrosis necrovirus |
| Nepoviruses: Comoviridae | Arabis mosaic nepovirus, Arracacha A nepovirus, Artichoke Italian latent nepovirus, Artichoke yellow ringspot nepovirus, Blueberry leaf mottle nepovirus, Cacao necrosis nepovirus, Cassava green mottle nepovirus, Cherry leaf roll nepovirus, Cherry rasp leaf nepovirus, Chicory yellow mottle nepovirus, Crimson clover latent nepovirus, Cycas necrotic stunt nepovirus, Grapevine Bulgarian latent nepovirus, |

TABLE 5-continued

Target Pests - Viruses

| | |
|---|---|
| | Grapevine chrome mosaic nepovirus, Grapevine fanleaf nepovirus, Hibiscus latent ringspot nepovirus, Lucerne Australian latent nepovirus, Mulberry ringspot nepovirus, Myrobalan latent ringspot nepovirus, Olive latent ringspot nepovirus, Peach rosette mosaic nepovirus, Potato black ringspot nepovirus, Potato U nepovirus, Raspberry ringspot nepovirus, Tobacco ringspot nepovirus, Tomato black ring nepovirus, Tomato ringspot nepovirus |
| Nucleorhabdo-viruses: Rhabdoviridae | Carrot latent nucleorhabdovirus, Coriander feathery red vein nucleorhabdovirus, Cow parsnip mosaic nucleorhabdovirus, Cynodon chlorotic streak nucleorhabdovirus, Datura yellow vein nucleorhabdovirus, Eggplant mottled dwarf nucleorhabdovirus, Maize mosaic nucleorhabdovirus, Pittosporum vein yellowing nucleorhabdovirus, Potato yellow dwarf nucleorhabdovirus, Sonchus yellow net nucleorhabdovirus, Sowthistle yellow vein nucleorhabdovirus, Tomato vein clearing nucleorhabdovirus, Wheat American striate mosaic nucleorhabdovirus |
| Oryzaviruses: Reoviridae | Echinochloa ragged stunt oryzavirus, Rice ragged stunt oryzavirus |
| Ourmiaviruse | Cassava Ivorian bacilliform ourmiavirus, Epirus cherry ourmiavirus, Melon Ourmia ourmiavirus, Pelargonium zonate spot ourmiavirus |
| Phytoreoviruses: Reoviridae | Clover wound tumor phytoreovirus, Rice dwarf phytoreovirus, Rice gall dwarf phytoreovirus, Rice bunchy stunt phytoreovirus, Sweet potato phytoreovirus |
| Potexviruses | Asparagus 3 potexvirus, Cactus X potexvirus, Cassava X potexvirus, Chicory X potexvirus, Clover yellow mosaic potexvirus, Commelina X potexvirus, Cymbidium mosaic potexvirus, Daphne X potexvirus, Foxtail mosaic potexvirus, Hydrangea ringspot potexvirus, Lily X potexvirus, Narcissus mosaic potexvirus, Nerine X potexvirus, Papaya mosaic potexvirus, Pepino mosaic potexvirus, Plantago asiatica mosaic potexvirus, Plantain X potexvirus, Potato aucuba mosaic potexvirus, Potato X potexvirus, Tulip X potexvirus, Viola mottle potexvirus, White clover mosaic potexvirus |
| Potyviruses: Potyviridae | Alstroemeria mosaic potyvirus, Amaranthus leaf mottle potyvirus, Araujia mosaic potyvirus, Arracacha Y potyvirus, Artichoke latent potyvirus, Asparagus 1 potyvirus, Banana bract mosaic potyvirus, Bean common mosaic necrosis potyvirus, Bean common mosaic potyvirus, Bean yellow mosaic potyvirus, Beet mosaic potyvirus, Bidens mosaic potyvirus, Bidens mottle potyvirus, Cardamom mosaic potyvirus, Carnation vein mottle potyvirus, Carrot thin leaf potyvirus, Cassava brown streak potyvirus, Cassia yellow spot potyvirus, Celery mosaic potyvirus, Chickpea bushy dwarf potyvirus, Chickpea distortion mosaic potyvirus, Clover yellow vein potyvirus, Commelina diffusa potyvirus, Commelina mosaic potyvirus, Cowpea green vein-banding potyvirus, Cowpea Moroccan aphid-borne mosaic potyvirus, Cowpea rugose mosaic potyvirus, Crinum mosaic potyvirus, Daphne Y potyvirus, Dasheen mosaic potyvirus, Datura Colombian potyvirus, Datura distortion mosaic potyvirus, Datura necrosis potyvirus, Datura shoestring potyvirus, Dendrobium mosaic potyvirus, Desmodium mosaic potyvirus, Dioscorea alata potyvirus, Dioscorea green banding mosaic potyvirus, Eggplant green mosaic potyvirus, Euphorbia ringspot potyvirus, Freesia mosaic potyvirus, Groundnut eyespot potyvirus, Guar symptomless potyvirus, Guinea grass mosaic potyvirus, Helenium Y potyvirus, Henbane mosaic potyvirus, Hippeastrum mosaic potyvirus, Hyacinth mosaic potyvirus, Iris fulva mosaic potyvirus, Iris mild mosaic potyvirus, Iris severe mosaic potyvirus, Johnsongrass mosaic potyvirus, Kennedya Y potyvirus, Leek yellow stripe potyvirus, Lettuce mosaic potyvirus, Lily mottle potyvirus, Maize dwarf mosaic potyvirus, Malva vein clearing potyvirus, Marigold mottle potyvirus, Narcissus yellow stripe potyvirus, |
| | Nerine potyvirus, Onion yellow dwarf potyvirus, Ornithogalum mosaic potyvirus, Papaya ringspot potyvirus, Parsnip mosaic potyvirus, Passiflora ringspot potyvirus, Passiflora South African potyvirus, Passionfruit woodiness potyvirus, Patchouli mosaic potyvirus, Pea mosaic potyvirus, Pea seed-borne mosaic potyvirus, Peanut green mosaic potyvirus, Peanut mottle potyvirus, Pepper Indian mottle potyvirus, Pepper mottle potyvirus, Pepper severe mosaic potyvirus, Pepper veinal mottle potyvirus, Plum pox potyvirus, Pokeweed mosaic potyvirus, Potato A potyvirus, Potato V potyvirus, Potato Y potyvirus, Primula mosaic potyvirus, Ranunculus mottle potyvirus, Sorghum mosaic potyvirus, Soybean mosaic potyvirus, Statice Y potyvirus, Sugarcane mosaic potyvirus, Sweet potato feathery mottle potyvirus, Sweet potato G potyvirus, Swordbean distortion mosaic potyvirus, Tamarillo mosaic potyvirus, Telfairia mosaic potyvirus, Tobacco etch potyvirus, Tobacco vein-banding mosaic potyvirus, Tobacco vein mottling potyvirus, Tobacco wilt potyvirus, Tomato Peru potyvirus, Tradescantia-Zebrina potyvirus, Tropaeolum 1 potyvirus, Tropaeolum 2 potyvirus, Tuberose potyvirus, Tulip band-breaking potyvirus, Tulip breaking potyvirus, Tulip chlorotic blotch potyvirus, Turnip mosaic potyvirus, Ullucus mosaic potyvirus, Vallota mosaic potyvirus, Vanilla mosaic potyvirus, Vanilla necrosis potyvirus, Voandzeia distortion mosaic potyvirus, Watermelon mosaic 1 potyvirus, Watermelon mosaic 2 potyvirus, Wild potato mosaic potyvirus, Wisteria vein mosaic potyvirus, Yam mosaic potyvirus, Zucchini yellow fleck potyvirus, Zucchini yellow mosaic potyvirus |
| Rymoviruses: Potyviridae Agropyron mosaic rymovirus | Hordeum mosaic rymovirus, Oat necrotic mottle rymovirus, Ryegrass mosaic rymovirus, Wheat streak mosaic rymovirus |
| Satellite RNAs | Arabis mosaic satellite RNA, Chicory yellow mottle satellite RNA, Cucumber mosaic satellite RNA, Grapevine fanleaf satellite RNA, Strawberry latent ringspot satellite RNA, Tobacco ringspot satellite RNA, Tomato black ring satellite RNA, Velvet tobacco mottle satellite RNA |
| Satelliviruses | Maize white line mosaic satellivirus, Panicum mosaic satellivirus, Tobacco mosaic satellivirus, Tobacco necrosis satellivirus |
| Sequiviruses: Sequiviridae | Dandelion yellow mosaic sequivirus, Parsnip yellow fleck sequivirus |
| Sobemoviruses | Bean southern mosaic sobemovirus, Blueberry shoestring sobemovirus, Cocksfoot mottle sobemovirus, Lucerne transient streak sobemovirus, Rice yellow mottle sobemovirus, Rottboellia yellow mottle sobemovirus, Solanum nodiflorum mottle sobemovirus, Sowbane mosaic sobemovirus, Subterranean clover mottle sobemovirus, Turnip rosette sobemovirus, Velvet tobacco mottle sobemovirus |
| Tenuiviruses | Maize stripe tenuivirus, Rice grassy stunt tenuivirus, Rice hoja blanca tenuivirus, Rice stripe tenuivirus |
| Tobamoviruses | Cucumber green mottle mosaic tobamovirus, Frangipani mosaic tobamovirus, Kyuri green mottle mosaic tobamovirus, Odontoglossum ringspot tobamovirus, Paprika mild mottle tobamovirus, Pepper mild mottle tobamovirus, Ribgrass mosaic tobamovirus, Opuntia Sammons' tobamovirus, Sunn-hemp mosaic tobamovirus, Tobacco mild green mosaic tobamovirus, Tobacco mosaic tobamovirus, Tomato mosaic tobamovirus, Ullucus mild mottle tobamovirus |
| Tobraviruses | Pea early browning tobravirus, Pepper ringspot tobravirus, Tobacco rattle tobravirus |
| Tombusviruses: Tombusviridae | Artichoke mottled crinkle tombusvirus, Carnation Italian ringspot tombusvirus, Cucumber necrosis tombusvirus, Cymbidium ringspot tombusvirus, Eggplant mottled crinkle tombusvirus, Grapevine Algerian latent tombusvirus, Lato River tombusvirus, |

TABLE 5-continued

Target Pests - Viruses

| | |
|---|---|
| | Neckar River tombusvirus, Pelargonium leaf curl tombusvirus, Pepper Moroccan tombusvirus, Petunia asteroid mosaic tombusvirus, Tomato bushy stunt tombusvirus |
| Tospoviruses: Bunyaviridae | Impatiens necrotic spot tospovirus, Peanut yellow spot tospovirus, Tomato spotted wilt tospovirus |
| Trichoviruses | Apple chlorotic leaf spot trichovirus, Heracleum latent trichovirus, Potato T trichovirus |
| Tymoviruses | Abelia latent tymovirus, Belladonna mottle tymovirus, Cacao yellow mosaic tymovirus, Clitoria yellow vein tymovirus, Desmodium yellow mottle tymovirus, Dulcamara mottle tymovirus, Eggplant mosaic tymovirus, Erysimum latent tymovirus, Kennedya yellow mosaic tymovirus, Melon rugose mosaic tymovirus, Okra mosaic tymovirus, Ononis yellow mosaic tymovirus, Passionfruit yellow mosaic tymovirus, Physalis mosaic tymovirus, Plantago mottle tymovirus, Potato Andean latent tymovirus, Scrophularia mottle tymovirus, Turnip yellow mosaic tymovirus, Voandzeia necrotic mosaic tymovirus, Wild cucumber mosaic tymovirus |
| Umbraviruses | Bean yellow vein banding umbravirus, Carrot mottle mimic umbravirus, Carrot mottle umbravirus, Carrot mottle mimic umbravirus, Groundnut rosette umbravirus, Lettuce speckles mottle umbravirus, Tobacco mottle umbravirus |
| Varicosaviruses | Freesia leaf necrosis varicosavirus, Lettuce big-vein varicosavirus, Tobacco stunt varicosavirus |
| Waikaviruses: Sequiviridae | Anthriscus yellows waikavirus, Maize chlorotic dwarf waikavirus, Rice tungro spherical waikavirus |
| Putative Ungrouped Viruses | Alsike clover vein mosaic virus, Alstroemeria streak potyvirus, Amaranthus mosaic potyvirus, Amazon lily mosaic potyvirus, Anthoxanthum mosaic potyvirus, Apple stem pitting virus, Aquilegia potyvirus, Asclepias rhabdovirus, Atropa belladonna rhabdovirus, Barley mosaic virus, Barley yellow streak mosaic virus, Beet distortion mosaic virus, Beet leaf curl rhabdovirus, Beet western yellows ST9-associated RNA virus, Black raspberry necrosis virus, Bramble yellow mosaic potyvirus, Brinjal mild mosaic potyvirus, Broad bean B virus, Broad bean V potyvirus, Broad bean yellow ringspot virus, Bryonia mottle potyvirus, Burdock mosaic virus, Burdock mottle virus, Callistephus chinensis chlorosis rhabdovirus, Canary reed mosaic potyvirus, Canavalia maritima mosaic potyvirus, Carnation rhabdovirus, Carrot mosaic potyvirus, Cassava symptomless rhabdovirus, Cassia mosaic virus, Cassia ringspot virus, Celery yellow mosaic potyvirus, Celery yellow net virus, Cereal flame chlorosis virus, Chickpea filiform potyvirus, Chilli veinal mottle potyvirus, Chrysanthemum spot potyvirus, Chrysanthemum vein chlorosis rhabdovirus, Citrus leprosis rhabdovirus, Citrus ringspot virus, Clover mild mosaic virus, Cocksfoot streak potyvirus, Colocasia bobone disease rhabdovirus, Cucumber toad-skin rhabdovirus, Cucumber vein yellowing virus, Cypripedium calceolus potyvirus, Datura innoxia Hungarian mosaic potyvirus, Dioscorea trifida potyvirus, Dock mottling mosaic potyvirus, Dodonaea yellows-associated virus, Eggplant severe mottle potyvirus, Euonymus fasciation rhabdovirus, Euonymus rhabdovirus, Fern potyvirus, Fig potyvirus, Gerbera symptomless rhabdovirus, Grapevine fleck virus, Grapevine stunt virus, Guar top necrosis virus, Habenaria mosaic potyvirus, Holcus lanatus yellowing rhabdovirus, Holcus streak potyvirus, Iris germanica leaf stripe rhabdovirus, Iris Japanese necrotic ring virus, Isachne mosaic potyvirus, Kalanchoe isometric virus, Kenaf vein-clearing rhabdovirus, Launaea mosaic potyvirus, Lupin yellow vein rhabdovirus, Maize eyespot virus, Maize line virus, Maize mottle/chlorotic stunt virus, Maize white line mosaic virus, Malvastrum mottle virus, Melilotus mosaic potyvirus, Melon vein-banding mosaic potyvirus, Melothria mottle potyvirus, Mimosa mosaic virus, Mung bean mottle potyvirus, Narcissus degeneration potyvirus, Narcissus late season yellows potyvirus, Nerine Y potyvirus, Nothoscordum mosaic potyvirus, Oak ringspot virus, Orchid fleck rhabdovirus, Palm mosaic potyvirus, Parsley green mottle potyvirus, Parsley rhabdovirus, Parsnip leafcurl virus, Passionfruit Sri Lankan mottle potyvirus, Passionfruit vein-clearing rhabdovirus, Patchouli mottle rhabdovirus, Pea stem necrosis virus, Peanut top paralysis potyvirus, Peanut veinal chlorosis rhabdovirus, Pecteilis mosaic potyvirus, Pepper mild mosaic potyvirus, Perilla mottle potyvirus, Pigeonpea proliferation rhabdovirus, Pigeonpea sterility mosaic virus, Plantain 7 potyvirus, Plantain mottle rhabdovirus, Pleioblastus chino potyvirus, Poplar decline potyvirus, Primula mottle potyvirus, Purple granadilla mosaic virus, Ranunculus repens symptomless rhabdovirus, Rice yellow stunt virus, Saintpaulia leaf necrosis rhabdovirus, Sambucus vein clearing rhabdovirus, Sarracenia purpurea rhabdovirus, Shamrock chlorotic ringspot potyvirus, Soybean mild mosaic virus, Soybean rhabdovirus, Soybean spherical virus, Soybean yellow vein virus, Soybean Z potyvirus, Strawberry latent C rhabdovirus, Strawberry mottle virus, Strawberry pallidosis virus, Sunflower mosaic potyvirus, Sweet potato latent potyvirus, Teasel mosaic potyvirus, Thimbleberry ringspot virus, Tomato mild mottle potyvirus, Trichosanthes mottle potyvirus, Tulip halo necrosis virus, Tulip mosaic virus, Turnip vein-clearing virus, Urd bean leaf crinkle virus, Vigna sinensis mosaic rhabdovirus, Watercress yellow spot virus, Watermelon Moroccan mosaic potyvirus, Wheat chlorotic spot rhabdovirus, White bryony potyvirus, Wineberry latent virus, Zinnia mild mottle potyvirus, Zoysia mosaic potyvirus |

A "non-target organism(s)," as used herein, is/are any organism(s) other than the target organism(s). Where the target organism and host organism differ, a non-target organism can comprise a host organism and organisms that consume the host organism or otherwise contact siRNAs expressed in a host organism. The target-specific design of siRNAs, as described herein, provides that such siRNAs have little or no gene silencing activity in non-target organisms.

Host Organisms

A "host" or "host organism" as used herein refers to an organism that expresses or produces siRNA. The host organism may transiently or stably express the siRNA. A host organism may be a transgenic organism. In one aspect of the invention, a host organism is the same as a target organism, i.e., the siRNA is expressed in the same organism in which it is intended to be functional. In another aspect of the invention, the host organism serves as a carrier of the siRNA to a target organism. As one non-limiting example, a host organism is a plant, wherein the target organism is a pest or pathogen of the plant. In another example, the host organism may be a food source for a target organism.

A "host nucleic acid" is a nucleic acid from or in a host organism, for example, a nucleic acid from or in a plant or plant part.

The term "expression," as used herein with regard to siRNA or miRNA refers to transcription of a siRNA/miRNA nucleotide sequence driven by its promoter. Expression as used herein also includes the production of siRNAs or miRNAs from larger RNA transcripts. As such, a host organism may express a RNA that is processed to produce or express one or more siRNAs or miRNAs.

Plants useful as host organisms include any of various photosynthetic, eukaryotic, multicellular organisms of the kingdom Plantae, including both monocots and dicots. The term "plant" includes reference to whole plants, plant parts, plant organs, plant tissues, plant cells, seeds, and progeny of the same. Plant cells include, without limitation, cells from seeds, suspension cultures, embryos, meristematic regions, callus tissue, leaves, roots, shoots, gametophytes, sporophytes, pollen, and microspores. Plant also refers to plants or plant parts that stably or transiently express a gene product, including a siRNA.

A "plant part" is any portion of a plant regardless of whether it is isolated or attached to an intact plant. The phrase "plant part" includes differentiated and undifferentiated tissues including, but not limited to the following: roots, stems, shoots, leaves, pollen, seeds, tumor tissue, and various forms of cells and culture (e.g., single cells, protoplasts, embryos, and callus tissue). The plant tissue may be in plant or in a plant organ, tissue, or cell culture. Plant parts also include plant products, such as grains, seeds, fruits, and nuts or commodity products.

A "plant product" refers to an agricultural or commercial product created from a plant, plant part, or seed. Non-limiting examples of plant products include flowers, pollen, leaves, vines, stalks, fruits, vegetables, cucurbits, roots, tubers, cones, pods, seeds, beans, grains, kernels, and hulls.

Some plant products are processed and thus become "commodity products." As used herein, "commodity products" include, but are not limited to, whole or processed seeds, beans, grains, kernels, hulls, meals, grits, flours, sugars, starches, protein concentrates, protein, lipids, carbohydrates, nucleic acids, metabolites, chlorophylls, waxes, oils, extracts, juices, concentrates, liquids, syrups, feed, silage, fiber, wood, pulp, paper, pigments, natural products, toxins, or other food or product produced from plants.

Commodity products containing one or more of the nucleotide sequences of the invention, or produced from a transformed plant, recombinant plant, or seed containing one or more of the nucleotide sequences of the invention are specifically contemplated as aspects of the invention as a means of identifying or detecting the source of the plant product or commodity. Such aspects are referred to herein as "biological samples." The identification or detection of one or more of the nucleotide sequences of the invention in one or more biological samples is de facto evidence that the plant product or commodity product comprises a plant or plant part of the invention disclosed herein.

As used herein, "a nucleotide sequence of the invention" comprises the siRNAs, miRNAs, or constructs thereof as disclosed herein. Such nucleotide sequences of the invention can be used to identify plants, plant products, or commodity products containing one or more of the nucleotide sequence of the invention using any number of techniques known to those having skill in the art such as through PCR-based methods, southern blotting, northern blotting, or microarray analyses. In this particular aspect, the functionality of nucleotide sequence of the invention (i.e., siRNA or miRNA) is immaterial and the presence of the nucleotide sequence in the plant or plant product serves to specifically identify or detect the source of the plant part, plant product, or commodity.

Representative host plants include soybean (*Glycine max*), corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), tobacco (*Nicotiana tabacum*), potato (*Solanum tuberosum*), peanuts (*Arachis hypogaea*), cotton (*Gossypium hirsutum*), sweet potato (*Ipomoea batatas*), cassava (*Manihot esculenta*), coffee (*Coffea* ssp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), papaya (*Carica papaya*), cashew (*Anacardium occidental*), macadamia (*Macadamia integrifolia*), almond (*Prunus amygdalus*), sugar beets (*Beta vulgaris*), oats, barley, vegetables, ornamentals, and conifers.

Additional host plants of the invention are crop plants, for example, cereals and pulses, maize, wheat, potatoes, tapioca, rice, sorghum, millet, cassava, barley, pea, and other root, tuber, or seed crops. Important seed crops for the invention are oil-seed rape, sugar beet, maize, sunflower, soybean, and sorghum. Horticultural plants to which the invention may be applied may include lettuce, endive, and vegetable *brassica* including cabbage, broccoli, and cauliflower, and carnations, geraniums, petunias, and begonias. The invention may be applied to tobacco, cucurbits, carrot, strawberry, sunflower, tomato, pepper, chrysanthemum, poplar, eucalyptus, and pine. Optionally, plants of the invention include grain seeds, such as corn, wheat, barley, rice, sorghum, rye, etc. Optionally, plants of the invention include oil-seed plants. Oil seed plants include canola, cotton, soybean, safflower, sunflower, *brassica*, maize, alfalfa, palm, coconut, etc. Optionally, plants of the invention include leguminous plants. Leguminous plants include beans and peas. Beans include guar, locust bean, fenugreek, soybean, garden beans, cowpea, mung bean, lima bean, fava bean, lentils, chickpea, etc. Host plants useful in the invention are row crops and broadcast crops. Non-limiting examples of useful row crops are corn, soybeans, cotton, amaranth, vegetables, rice, sorghum, wheat, milo, barley, sunflower, durum, and oats. Non-limiting examples of useful broadcast crops are sunflower, millet, rice, sorghum, wheat, milo, barley, durum, and oats. Host plants useful in the invention are monocots and dicots. Non-limiting examples of useful monocots are rice, corn, wheat, palm trees, turf grasses, barley, and oats. Non-limiting examples of useful dicots are soybean, cotton, alfalfa, canola, flax, tomato, sugar beet, sunflower, potato, tobacco, corn, wheat, rice, lettuce, celery, cucumber, carrot, and cauliflower, grape, and turf grasses. Host plants useful in the invention include plants cultivated for aesthetic or olfactory benefits. Non-limiting examples include flowering plants, trees, grasses, shade plants, and flowering and non-flowering ornamental plants. Host plants useful in the invention include plants cultivated for nutritional value, fibers, wood, and industrial products.

One skilled in the art will recognize the wide variety of host cells that can be transformed with the vectors according to the invention disclosed herein. Non-limiting examples of such cells are those in embryogenic tissue, callus tissue types I, II, and III, hypocotyl, meristem, root tissue, tissues for expression in phloem, and the like.

Almost all plant tissues may be transformed during dedifferentiation using appropriate techniques described herein. Recipient cell targets include, but are not limited to, meristem cells, Type I, Type II, and Type III callus, immature embryos, and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like.

Those cells that are capable of proliferating as callus also are recipient cells for genetic transformation. Techniques for transforming immature embryos and subsequent regeneration of fertile transgenic plants are well known in the art. Direct transformation of immature embryos obviates the need for long-term development of recipient cell cultures. Pollen, as well as its precursor cells, microspores, may be capable of functioning as recipient cells for genetic transformation, or as vectors to carry foreign DNA for incorporation during fertilization. Direct pollen transformation obviates the need for cell culture.

Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a completely transformed plant. In fact, it is proposed that embryogenic suspension cultures may be an in vitro meristematic cell system, retaining ability for continued cell division in an undifferentiated state, controlled by the media environment.

Wide varieties of techniques are available for introducing siRNAs of the invention into a host under conditions that allow for stable maintenance and expression of the siRNA. The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Transformation protocols as well as protocols for introducing heterologous nucleic acids into plants may vary depending on the type of plant or plant cell, i.e., monocot or dicot, targeted for transformation. Suitable methods of introducing the DNA construct include microinjection (Crossway et al. (1986) *Biotechniques* 4, 320-334; and U.S. Pat. No. 6,300,543); sexual crossing, electroporation (Riggs et al. (1986) *Proc. Natl. Acad. Sci. USA* 83, 5602-5606); *Agrobacterium*-mediated transformation (Townsend et al., U.S. Pat. Nos. 5,563,055 and 5,981,840); direct gene transfer (Paszkowski et al. (1984) *EMBO J.* 3, 2717-2722); and ballistic particle acceleration (see, e.g., Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6, 923-926). See also Weissinger et al. (1988) *Ann. Rev. Genet.* 22, 421-477; Sanford et al. (1987) *Particulate Science and Technology* 5, 27-37 (onion); Christou et al. (1988) *Plant Physiol.* 87, 671-674 (soybean); Finer and McMullen (1991) *In Vitro Cell Dev. Biol.* 27P, 175-182 (soybean); Singh et al. (1998) *Theor. Appl. Genet.* 96, 319-324 (soybean); Datta et al. (1990) *Biotechnology* 8, 736-740 (rice); Klein et al. (1988) *Proc. Natl. Acad. Sci. USA* 85, 4305-4309 (maize); Klein et al. (1988) *Biotechnology* 6, 559-563 (maize); Tomes, U.S. Pat. No. 5,240,855; Buising et al., U.S. Pat. Nos. 5,322,783 and 5,324,646; Klein et al. (1988) *Plant Physiol.* 91, 440-444 (maize); Fromm et al. (1990) *Biotechnology* 8, 833-839 (maize); Hooykaas-Van Slogteren et al. (1984) *Nature* 311, 763-764; Bowen et al., U.S. Pat. No. 5,736,369 (cereals); Bytebier et al. (1987) *Proc. Natl. Acad. Sci. USA* 84, 5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9, 415-418 and Kaeppler et al. (1992) *Theor. Appl. Genet.* 84, 560-566 (whisker-mediated transformation); D'Halluin et al. (1992) *Plant Cell* 4, 1495-1505 (electroporation); Li et al. (1993) *Plant Cell Reports* 12, 250-255 and Christou and Ford (1995) *Annals of Botany* 75, 407-413 (rice); Osjoda et al. (1996) *Nature Biotechnology* 14, 745-750 (maize via *Agrobacterium tumefaciens*); U.S. Pat. No. 5,736,369 (meristem transformation); and U.S. Pat. Nos. 5,302,523 and 5,464,765 (whiskers technology).

Nucleic acids of the invention may be introduced into plants by contacting plants with a virus or viral nucleic acids. Generally, such methods involve incorporating an expression construct of the invention within a viral DNA or RNA molecule. Further, it is recognized that useful promoters encompass promoters utilized for transcription by viral RNA polymerases. Methods for introducing expression constructs into plants and expressing a protein encoded therein, involving viral DNA or RNA molecules, are known in the art. See, e.g., U.S. Pat. Nos. 5,889,191; 5,889,190; 5,866,785; 5,589,367; and 5,316,931.

DNA constructs containing siRNAs may be integrated of the into the host cell genome according to conventional methods, e.g., by homologous recombination or other methods of integration, including targeted integration at a particular host chromosomal site.

In other aspects of the invention, transient expression may be desired. In those cases, standard transient transformation techniques may be used, such as viral transformation methods, and microinjection of DNA or RNA, as well other methods well known in the art.

The cells from the plants that have stably incorporated the nucleotide sequence may be grown into plants in accordance with conventional techniques. See, e.g., McCormick et al. (1986) *Plant Cell Reports* 5, 81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited, and then seeds are harvested to ensure expression of the desired phenotypic characteristic has been achieved.

Initial identification and selection of cells and/or plants comprising siRNA expression constructs may be facilitated by the use of marker genes. Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as well as markers that facilitate screening, such as visual markers. Selectable markers include genes carrying resistance to an antibiotic such as spectinomycin, (e.g., the aada gene, Svab et al. (1990) *Plant Mol. Biol.* 14, 197); streptomycin, (Jones et al. (1987) *Mol. Gen. Genet.* 210, 86); kanamycin (e.g., nptII, Fraley et al. (1983) *Proc. Natl. Acad. Sci. USA* 80, 4803); hygromycin (e.g., HPT, Vanden Elzen et al. (1985) *Plant Mol. Biol.* 5, 299); gentamycin (Hayford et al. (1988) *Plant Physiol.* 86, 1216); phleomycin, zeocin, or bleomycin (Hille et al. (1986) *Plant Mol. Biol.* 7, 171); or resistance to a herbicide such as phosphinothricin (bar gene); or sulfonylurea (acetolactate synthase (ALS)) (Charest et al. (1990) *Plant Cell Rep.* 8, 643); genes that fulfill a growth requirement on an incomplete media such as HIS3, LEU2, URA3, LYS2, and TRP1 genes in yeast; and other such genes known in the art. Negative selectable markers include cytosine deaminase (codA) (Stougaard (1993) *Plant J.* 3, 755-761); tms2 (DePicker et al. (1988) *Plant Cell Rep.* 7, 63-66); nitrate reductase (Nussame et al. (1991) *Plant J.* 1, 267-274), SU1 (O'Keefe et al. (1994) *Plant Physiol.* 105, 473-482); aux-2 from the Ti plasmid of *Agrobacterium*; and thymidine kinase. Screenable markers include fluorescent proteins such as green fluorescent protein (GFP) (Chalfie et al. (1994) *Science* 263, 802; U.S. Pat. No. 6,146,826; U.S. Pat. No. 5,491,084; and PCT International Publication No. WO 97/41228); reporter enzymes such as 13-glucuronidase (GUS) (Jefferson R. A. (1987) *Plant Mol. Biol. Rep.* 5, 387, U.S. Pat. No. 5,599,670, and U.S. Pat. No. 5,432,081), 13-galactosidase (lacZ); alkaline phosphatase (AP); glutathione S-transferase (GST) and luciferase (U.S. Pat. No. 5,674,713; and Ow et al. (1986) *Science* 234: 856-859), visual markers like anthocyanins such as CRC (Ludwig et al. (1990) *Science* 247: 449-450) R gene family (e.g., Lc, P, S); A, C, R-nj, body and/or eye color genes in *Drosophila*, coat color genes in mammalian systems, and others known in the art.

One or more markers may be used in order to select and screen for targeting of a siRNA to a particular genomic locus, which is also referred to as site-specific integration. One common strategy for site-specific integration involves using a promoterless selectable marker. Since the selectable marker lacks a promoter, random integration events generally do not lead to transcription of the gene. Gene targeting events will put the selectable marker under control of a promoter at the target site. Gene targeting events are identified by selection for expression of the selectable marker. Another common strategy utilizes a positive-negative selection scheme. This scheme utilizes two selectable markers, one that confers resistance ($R^+$) coupled with one that confers sensitivity ($S^+$), each with a promoter. When a heterologous nucleic acid containing the two markers is randomly inserted, the resulting phenotype is $R^+/S^+$. When a gene-targeting event is generated, the two markers are uncoupled and the resulting phenotype is $R^+/S^-$. Examples of using positive-negative selection are found in Thykjer et al. (1997) *Plant Mol. Biol.* 35, 523-530; and PCT International Publication No. WO 01/66717.

While various transformation methods are taught herein as separate methods, the skilled artisan will readily recognize that certain methods can be used in combination to enhance the efficiency of the transformation process. Non-limiting examples of such methods include bombardment with *Agrobacterium*-coated microparticles (EP486234) or microprojectile bombardment to induce wounding followed by co-cultivation with *Agrobacterium* (EP486233).

Direct delivery can also be used to transform hosts according to the invention disclosed herein. By way of non-limiting example, such direct delivery methods include polyethylene glycol treatment, electroporation, liposome mediated DNA uptake or the vortexing method. See, e.g., Freeman et al. (1984) *Plant Cell Physiol.* 29, 1353 and Kindle, (1990) *Proc. Natl. Acad. Sci. USA* 87, 1228. One form of direct DNA delivery is direct gene transfer into protoplasts from embryogenic cell suspension cultures. See Lazzeri and Lorz (1988) *Advances in Cell Culture*, Vol. 6, Academic Press, p. 291; OziasAkins and Lorz (1984) *Trends in Biotechnology* 2, 119.

The skilled artisan is aware of certain challenges of genotype-dependent transformation arising from low regeneration potential of cereals. Accordingly, in one embodiment of the invention, transformation is accomplished by a genotype-independent transformation approach based on the pollination pathway. Ohta (1986) *Proc. Natl. Acad. Sci. USA* 83, 715-719. In maize, high efficiency genetic transformation can be achieved by a mixture of pollen and exogenous DNA. Luo and Wu (1989) *Plant Mol. Biol. Rep.* 7, 69-77. Maize can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

Transformation of tomato and melon with heterologous polynucleotides according to the invention can be accomplished into intact plants via pollination pathway. See Chesnokov, et al. (1999) USSR Patent No. 1708849; Bulletin of the USSR Patents, No. 4; Chesnokov and Korol (1993); Genetika USSR, 29, 1345-1355. The procedures of genetic transformation based on the pollination-fecundation pathway include: (i) employment of a mixture (paste) of the pollen and transforming DNA; (ii) delivery of the alien DNA into the pollen tube, after pollination; and (iii) microparticle bombardment of microspores or pollen grains.

In one aspect of the invention, plants hosts are transformed using *Agrobacterium* technology (e.g., *A. tumefaciens* and *A. rhizogenes*). *Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, e.g., the methods described by Lloyd et al. (1986) *Science* 234, 464-466; Horsch et al. (1987) "*Agrobacterium*-mediated transformation of plants," *Plant Biology* Alan R. Liss, NY pp 317-329; and Wang (2006) *Agrobacterium* protocols, Vol. 2, Humana Press, Totowa N.J. and U.S. Pat. No. 5,563,055.

*Agrobacterium*-mediated transformation can efficiently be used with dicotyledonous host plants of the invention including, by way of non-limiting example, *Arabidopsis*, corn, soybean, cotton, canola, tobacco, tomato, and potato.

*Agrobacterium*-mediated transformation is also applicable to nearly all monocotyledonous plants of the invention. By non-limiting example, such monocotyledonous plant technologies are adaptable to rice, wheat, and barley. See, e.g., Hiei et al. (1994) *Plant J.* 6, 271-282; Zhang et al. (1997) *Mol. Biotechnol.* 8, 223-231; Ishida et al. (1996) *Nat. Biotechnol.* 14, 745-750; McCormac et al. (1998) *Euphytica* 99, 17-25, Tingay S. et al. (1997) *Plant J.* 11, 1369-1376; and U.S. Pat. No. 5,591,616.

*Agrobacterium*-mediated transformation can be accomplished with cultured isolated protoplasts or by transformation of intact cells or tissues. *Agrobacterium*-mediated transformation in dicotyledons facilitates the delivery of larger pieces of heterologous nucleic acid as compared with other transformation methods such as particle bombardment, electroporation, polyethylene glycol-mediated transformation methods, and the like. In addition, *Agrobacterium*-mediated transformation appears to result in relatively few gene rearrangements and more typically results in the integration of low numbers of gene copies into the plant chromosome.

Modern *Agrobacterium* transformation vectors are capable of replication in *E. coli* as well as *Agrobacterium*, allowing for convenient manipulations as described. Klee et al. (1987) *Ann. Rev. Plant Physiology* 38, 467-486. Moreover, recent technological advances in vectors for *Agrobacterium*-mediated gene transfer have improved the arrangement of genes and restriction sites in the vectors to facilitate the construction of vectors capable of expressing various polypeptide-coding genes. The vectors described by Horsch et al. have convenient multi-linker regions flanked by a promoter and a polyadenylation site for direct expression of inserted polypeptide coding genes and are suitable for present purposes. Horsch et al. (1987) "*Agrobacterium*-mediated transformation of plants," *Plant Biology* Alan R. Liss, NY pp 317-329. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

When *Agrobacteria* are used to transform plant cells according to the invention, nucleic acids to be inserted can be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation).

Binary vectors can replicate themselves both in *E. coli* and in *Agrobacteria*. Such vectors can comprise a selection marker gene and a linker or polylinker, which are framed by the right and left T-DNA border regions. They can be transformed directly into *Agrobacteria*. Holsters et al. (1978) *Mol. Gen. Genet.* 163, 181-187. The *Agrobacterium* used as host cell can comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted nucleic acids.

Methods of Conferring Desirable Traits

The invention further provides methods of identifying a siRNA that confers a desirable phenotypic outcome in a target organism. In one aspect of the invention, the method comprises (a) contacting a target organism with a siRNA molecule of a siRNA library as described herein; and (b) correlating the siRNA treatment of (a) with a desirable phenotypic outcome. For example, siRNAs that confer resistance to soybean cyst nematode were identified by (a) contacting soybean cyst nematode with a siRNA molecule of a siRNA library of the invention; and (b) correlating the siRNA treatment of (a) with soybean resistance to soybean cyst nematode infection. See Examples 2 and 4.

The phrase "correlating the siRNA treatment" as used herein, refers to the process of measuring the effects of contacting a target organism with a siRNA molecule and determining whether a desirable phenotypic outcome has been achieved in the target organism by means of such siRNA treatment. In general, correlation of a siRNA treatment is measured relative to a control treatment.

For example, transgenic soybean hairy roots expressing siRNAs were contacted with soybean cyst nematodes (SCN). The number of SCN cysts formed in multiple independent, biologically replicated experiments were determined and compared to controls that did not express siRNAs. Statistically significant reductions in the number of cysts formed were observed during the experiments compared with controls. Consequently, the siRNA expression correlated with reduced infectivity of SCN, i.e., soybean resistance to SCN infection. See Examples 2 and 4.

As used herein, the terms "contacting" and "administering," or phrase "contact with" are used interchangeably, and refer to a process by which the siRNAs or miRNAs of the invention are delivered or administered to target organisms, in order to inhibit expression of a gene in the target organisms. Contacting describes physical proximity of siRNAs or miRNAs and the target organism so that they interact. The siRNAs or miRNAs may be administered or delivered in any number of ways, including, but not limited to, direct introduction into a cell (i.e., intracellularly); or extracellular introduction into a cavity, interstitial space, or into the circulation of the target organism, oral introduction, the siRNA or miRNA may be introduced by bathing the target organism in a solution containing siRNA or miRNA, or the siRNA or miRNA may be present in a food source. Methods for oral introduction include direct mixing of siRNA or miRNA with a food source of the target organism, as well as engineered approaches in which a species that is used as food is engineered to express a siRNA or miRNA, and then this species is fed to the target organism to be affected. For example, the siRNA or miRNA constructs may be sprayed onto a plant, or the siRNA may be applied to soil in the vicinity of roots, taken up by plant and/or the target organism, or a plant may be genetically engineered to express the siRNA or miRNA in an amount sufficient to kill or adversely affect some or all of the target organisms to which the plant is exposed. Thus, "contacting" refers to any process by which a siRNA or miRNA is administered or delivered to a target organism to thereby inhibit expression of a gene in the target organism.

As used herein, "contacting" also refers to placing a pest, pathogen, or target organism on or near a host plant, or part thereof, such that the pest, pathogen, or target organism has an opportunity to interact with, attack, or infect the plant or plant part, which effectively results in proximity between siRNAs expressed in the host plant and the target organism.

The siRNA may be "contacted" or "administered" to the target in any manner that results in physical proximity of a siRNA and a target nucleic acid permitting interaction. In one aspect of the invention, a siRNA may be expressed within a host organism and then passively diffuse or be actively transported to a target organism. Expression within the host can be transient, or stable, and/or inducible. The siRNA can be expressed as a precursor or inactive form that becomes active within the target organism. Expression in a host may be achieved using any of the expression constructs and vectors described herein.

Other examples of contacting include, but are not limited to, direct introduction into a cell (i.e., intracellularly); extracellular introduction into a cavity, interstitial space, or into the circulation of a target organism; oral introduction; the siRNA may be introduced by bathing or soaking the target organism in a solution containing siRNA. Methods for oral introduction include direct mixing of siRNA with food of a target organism, as well as engineered approaches in which a species that is used as food is engineered to express a siRNA, and then fed to the organism to be affected.

Where the target organism or host organism is a plant, a composition comprising a siRNA may be sprayed onto the plant, or the siRNA may be applied to soil in the vicinity of roots, taken up by the plant and/or target pest or pathogen, or a plant may be modified to express the siRNA.

A host organism expressing a heterologous siRNA is "transgenic." As used herein, the term "transgenic" refers to a host organism, or part or cell thereof, which comprises within its genome a heterologous polynucleotide. A transgenic host organism may be stably transformed or transiently transformed. If the heterologous siRNA is stably integrated within the genome, it is passed on, or heritable, to successive generations. The heterologous siRNA may be integrated into the genome alone or as part of an expression construct. Transgenic is used herein to include any cell, cell line, callus, tissue, plant part or plant, the genotype of which has been altered by the presence of a heterologous nucleic acid including those transgenics initially so altered as well as those created by breeding, sexual crosses, or asexual propagation from the initial transgenic cell.

The phrase "desirable phenotype," as used herein, refers to an intended effect that has been elicited in a target organism and/or host organism as a result of siRNA gene silencing or suppression. The invention provides methods for identifying siRNAs that confer desirable phenotypes. In one aspect of the invention, the method comprises designing siRNAs complementary to target genes whose regulation is known to have a desirable effect. For example, where the target organism is a plant pest or pathogen, the method can comprise designing siRNAs complementary to target genes involved in the development, survival, or pathogenicity of the plant pest or pathogen. In another aspect of the invention, the method comprises empirically identifying siRNAs capable of eliciting a desired phenotype by screening siRNA libraries as described herein. See Examples 2 and 4. In addition, these two general approaches may be combined.

Where the host or target organism is a plant, desirable phenotypes include resistance to a pest or pathogen, resistance to abiotic stress, and improved growth or yield. Where the target organism is a plant pest or pathogen, desirable phenotypes include reduced infectivity, decreased persistence, reduced disease causing ability, or death of the pest.

"Resistance to a target organism," as used herein, refers to the ability of a host organism to withstand or reduce the severity of pest or pathogen distress, infections, or disease. Resistance can be measured by the host's ability to survive pest infection, reduced pest susceptibility, reduced pest burden, increased yields, decreased attrition or death, or other suitable agronomic indicators.

As used herein, the phrases "abiotic stress," "stress," or "stress condition" refer to the exposure of a plant, plant part, plant cell, or the like, to a non-living, i.e., abiotic physical stress, chemical agents, or environmental conditions that can produce adverse effects on metabolism, growth, development, propagation, and/or survival of the plant (collectively "growth"). Abiotic stress can be imposed on a plant, for example, because of environmental factors such as water (e.g., flooding, drought, and dehydration), anaerobic conditions (e.g., a low level of oxygen), abnormal osmotic conditions, salinity or temperature (e.g., hot/heat, cold, freezing, frost), a deficiency of nutrients, exposure to pollutants, or by a exposure to hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during a monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ, plant part, or whole plant. Drought stress can be induced by or associated with the deprivation of water or reduced supply of water to a cell, tissue, organ, or organism. Salinity-induced stress (i.e., salt-stress) can be associated with or induced by a perturbation in the osmotic potential of the intracellular or extracellular environment of a cell.

As used herein, "resistance to abiotic stress," "abiotic stress resistance," or "abiotic stress tolerance" includes, but is not limited to, greater water optimization; greater tolerance to dehydration, water deficit conditions, or drought; better recovery from dehydration, water deficit conditions, or drought; increased root growth; increased lateral root formation; increased root branching; increased surface area of roots; increased root mass; more root hairs; increased nutrient uptake; increased micronutrient uptake; increased metabolic efficiency; greater photosynthetic capacity; more rapid growth rate; greater fruit or seed yield; modified plant architecture; enhanced herbicide resistance; reduced or increased height; reduced or increased branching; enhanced cold and frost tolerance; improved vigor; enhanced color; enhanced health and nutritional characteristics; improved storage; enhanced yield; enhanced salt tolerance; enhanced resistance of wood or plant tissue to decay; enhanced heavy metal tolerance; enhanced sweetness; improved texture; decreased phosphate content; increased germination; improved starch composition; improved flower longevity; production of novel resins; production of novel proteins or peptides; enhanced agronomic traits, or any other agronomically desirable or commercially advantageous traits or characteristics.

The skilled artisan can readily identify pest or pathogen genes to target using the invention disclosed herein. Such a target gene could be any pest gene that serves a direct or indirect role in such a pest's deleterious effects on a host plant. By way of example only, such a gene may be one that serves a role in pest growth, development, replication and reproduction, and invasion or infection.

Target genes for use in the invention may include, for example, those that play important roles in the viability, growth, development, reproduction and infectivity of a particular pest. These target genes may be one or more of any housekeeping genes, transcription factors, or pest- or pathogen-specific genes that provide an observable phenotype, in particular a phenotype that results in the suppression of response to stimuli, movement, feeding, growth, development, reproduction, and infectivity or eventually results in the death of the pest or pathogen.

The genes targeted for suppression can also include those required for essential functions such as DNA replication, RNA transcription, protein synthesis, amino acid biosynthesis, amino acid degradation, nucleotide synthesis, nucleotide degradation, muscle formation, juvenile hormone formation, juvenile hormone regulation, ion regulation and transport, digestive enzyme synthesis, maintenance of cell membrane potential, sperm formation, pheromone synthesis, pheromone sensing, antennae formation, wing formation, leg formation, egg formation, larval maturation, digestive enzyme formation, haemolymph synthesis, haemolymph maintenance, neurotransmission, cell division, energy metabolism, development and differentiation, respiration, and apoptosis.

For example, target genes that are presumed to be effective in producing such phenotypes are similar to those that have been shown to affect the viability, growth, development, mobility, neurological stimulation, muscular function, and reproduction in *C. elegans*, including but not limited to the following phenotypes: (Adl) adult lethal, (Age), (Bli) blistered, (Bmd) body morphology defect, (Ced) Cell death abnormality, (Clr) clear, (Dan DAuer Formation, (Dpy) dumpy, (Egl) egg laying defect, (Emb) embryonic lethal, (Evl) everted vulva, (Fern) feminization of XX and XO animals, (Fgc) Fewer Germ Cells, (Fog) feminization of germline, (Gon) GONad development abnormal, (Gro) slow growth, (Him) high incidence of male progeny, (Hya) HYperActive, (Let) larval lethal, (Lin) lineage abnormal, (Lon) long body, (Lpd), (Lva) larval arrest, (Lvl) larval lethal, (Mab) Male ABnormal, (Mei) Defective meiosis, (Mig) MIGration of cells abnormal, (Mlt) molt defect, (Morphology), (Mut) Mutator, (Muv) MUlti-Vulva, (Oma) Oocyte MAturation defective, (Pat) Paralyzed, Arrested elongation at Two-fold, (Pch) PatCHy coloration, (Pnm) Pronuclear migration alteration in early embryo, (Prl) paralyzed, (Prz) PaRaLyzed, (Pvl) protruding vulva, (Pvu) protruding vulva, (Rde), (Reproductive), (Rol) roller, (Rot) centrosome pair and associated pronuclear rotation abnormal, (Rup) exploded, (Sck) sick, (Sle) Slow embryonic development, (Slu) SLUggish, (Sma) small, (Spd) SpinDle, abnormal embryonic, (Spo) Abnormal embryonic spindle position and orientation, (Step) sterile, (Stp) sterile progeny, (Unc) uncoordinated, (Unclassified), (Vul) vulvaless, (WT), (defect) morphological or behavioral defects.

As further examples, potential Coleoptera target genes include: swelling-dependent chloride channels; glyceraldehyde-3-phosphate dehydrogenase; glucose-6-phosphate 1-dehydrogenase; chitinase; vacuolar ATPase D subunit 1; ADP-ribosylation factor; juvenile hormone esterase; transcription factor IIB; cytosolic juvenile hormone binding protein; actin orthologs; chitinase; α-tubulin; vacuolar ATPase A subunit 2; vacuolar ATPase E; ATP synthase chain A; endoglucanase; ADP/ATP translocase; activating transcription factor; mRNA capping enzyme; apple ATPase2; ribosomal protein L9; ribosomal protein L19; 26S proteosome regulatory subunit p28; chromodomain helicase-DNA-binding protein; and β-tubulin. See U.S. Pat. No. 7,812,219 and Baum et al. (2007) *Nat. Biotech.* 25, 1322-1326, including Table 1 in the supplementary information, all of which are incorporated by reference herein in their entirety.

Additional target genes encode various gene products that, when disrupted, exert a negative effect or observable phenotype in *Drosophila* or in *C. elegans*.

Further target genes in various organisms are listed in Table 6.

TABLE 6

| Pest or Pathogen | Pest Pathogenecity Gene |
|---|---|
| Fungi | Cutinases |
|  | Kinases |
|  | Ribosomal RNAs |
|  | Adhesins |
|  | Elicitins |

TABLE 6-continued

| Pest or Pathogen | Pest Pathogenecity Gene |
|---|---|
| Bacteria | Cutinases |
|  | Macerating enzymes |
|  | Kinases |
|  | Ribosomal RNAs |
|  | Adhesins |
|  | G-proteins |
| Insects | Kinases |
|  | Ribosomal RNAs |
|  | G-proteins |
|  | Moulting factors |
|  | Serine proteases |
|  | Cysteine proteases |
|  | Juvenile hormone esterase |
| Nematodes | Kinases |
|  | Ribosomal RNAs |
|  | G-proteins |
|  | Cuticle collagen proteins |
|  | Cathepsin proteases |
| Viruses | Capsid, coat proteins |
|  | Viral polymerases |
|  | Viral nucleic acid binding proteins |
|  | Viral packaging proteins |
|  | Viral proteases |
|  | Viral proteins, generally |
|  | Viral genomic nucleic acids |

The invention further provides a siRNA molecule that targets both a nematode gene, such as a soybean cyst nematode gene, and an endogenous plant gene related to a nematode-resistant plant phenotype. In one embodiment the siRNA molecule is capable of suppressing expression of the nematode gene and the endogenous plant gene. In another embodiment, the siRNA when expressed in a transgenic plant, or part thereof, confers upon the plant, or part thereof, a level of tolerance to nematode infection that is greater than would be expected from suppression of the nematode gene or the endogenous plant gene alone. In yet another embodiment, the endogenous plant gene is an ethylene response gene. In particular, siRNAs designed to target nematode genes that are also capable of modulating gene silencing of ethylene response (ETR) nucleic acids, such as, ETR1, EIN1, QITR, Q8, TETR, TGETR1, TGETR2 and the like are encompassed by the invention.

A number of ethylene response genes have been characterized. The ETR1 gene from *Arabidopsis*, as well as other plant homologues of ETR1 and ETR2, are considered to be ethylene receptors. (see, e.g., Gamble et al. (1998) *PNAS USA* 95, 7825-7829). The *Arabidospsis* ETR1 protein contains an amino-terminal half with a hydrophobic domain responsible for ethylene binding and membrane localization (Gamble et al. supra). The carboxyl-terminal half of the *Arabidopsis* ETR1 contains domains with homology to histidine kinases and response regulators (Gamble et al., supra).

Ethylene production in plants is involved in a plant's response to multiple biotic and abiotic stresses. Plants carrying mutations in ETR genes have been studied. For example, ethylene insensitive soybean plants with mutations in the ETR1 gene have been found to have increased resistance to some pathogens but reduced resistance to other pathogens (Hoffman et al., (1999) *Plant Physiology* 119, 935-949). In addition, alteration in ethylene sensitivity in soybean has been implicated in tolerance to soybean cyst nematode (Bent et al. 2006. *Crop Science* 46:893-901).

In another embodiment, the ETR1 gene of the invention is a soybean ETR1. In another embodiment, the soybean ETR1 gene comprises SEQ ID NO: 52, or a complement thereof.

In another embodiment, the siRNA molecule that targets a soybean cyst nematode gene and a soybean ETR1 gene comprises SEQ ID NO: 3 (siRNA0097) or SEQ ID NO: 4 (siRNA00145). In yet another embodiment the star strand of the siRNA targets ETR1 and comprises SEQ ID NO: 55 (siRNA0097*) or SEQ ID NO: 56 (siRNA0145*). In yet another embodiment, the mRNA portion of the soybean ETR1 gene that binds to siRNA0097 (SEQ ID NO: 3) and siRNA0145 (SEQ ID NO: 4) comprises SEQ ID NO: 53. In still another embodiment, the mRNA portion of the soybean ETR1 gene that binds siRNA0097* (SEQ ID NO: 55) and siRNA0145* (SEQ ID NO: 56) comprises SEQ ID NO: 54.

In another embodiment, the invention encompasses an siRNA molecule designed to target a gene of a nematode plant pest that when contacted with the nematode pest the nematode pest has decreased capability to infect a plant susceptibile to infection by the nematode, and wherein the siRNA, when expressed in the plant, suppresses expression of an endogenous plant gene, wherein the suppression of the plant gene confers upon the plant resistance to the nematode plant pest. In another embodiment, the endogenous plant gene is an ethylene response gene. In yet another embodiment, the ethylene response gene is a soybean ETR1 gene. In another embodiment, the soybean ETR1 gene comprises SEQ ID NO: 52. In another embodiment, the pest nematode is soybean cyst nematode. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the transgenic plant is suppressed by at least about 30% compared to a wild-type plant of the same species.

In another embodiment, the invention encompasses a siRNA molecule designed to target a gene of a nematode plant pest, wherein the siRNA molecule is capable of suppressing the expression of the nematode gene and an endogenous plant gene, whereby the suppression of the nematode gene and the endogenous plant gene confer upon a transgenic plant or part thereof expressing the siRNA molecule resistance to the nematode. In another embodiment, the endogenous plant gene is an ethylene response gene. In still another embodiment, the transgenic plant or part thereof is a soybean plant or part thereof. In yet another embodiment, the ethylene response gene is a soybean ETR1 gene. In another embodiment, the soybean ETR1 gene comprises SEQ ID NO: 52. In another embodiment, the nematode is soybean cyst nematode. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the transgenic plant or part thereof is suppressed by at least about 30% compared to a non-transgenic plant or part thereof of the same species.

In one embodiment, the invention provides a transgenic plant, or part thereof, having a reduced level of expression of a ethylene response gene compared to a non-transgenic plant, or part thereof, of the same species, wherein the transgenic plant or part thereof comprises an siRNA that suppresses the expression of a nematode pest gene, and wherein the transgenic plant has a greater tolerance to infection by the nematode pest than would be expected from the reduced level of expression of the ethylene response gene or the suppression of the nematode gene alone. In another embodiment, the transgenic plant is a soybean plant.

In another embodiment, the ethylene response gene is a soybean ETR1 gene. In another embodiment, the ETR1 gene comprises SEQ ID NO: 52. In another embodiment, the pest nematode is soybean cyst nematode. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the transgenic plant is reduced by at least about 30%. In yet another embodiment, the greater tolerance to infection by the soybean cyst nematode is measured by the number of cysts on soybean roots. In another embodiment, the number of cysts on the roots is reduced by at least about 52%.

In one embodiment, the invention encompasses a method of conferring nematode pest resistance to a plant, or part thereof, comprising expressing in the plant or part thereof a nucleic acid molecule comprising an siRNA that suppresses the expression of a nematode pest gene, and wherein the plant or part thereof is ethylene-insensitive, whereby the plant or part thereof is resistant to the nematode pest to a greater degree than would be expected from the siRNA or ethylene insensitivity alone. In another embodiment, the plant or part thereof is a soybean plant. In another embodiment, the ethylene-insensitivity is due to the suppression of an ETR1 gene (ethylene response gene). In another embodiment, the ETR1 gene comprises SEQ ID NO: 52. In another embodiment, the nematode pest is soybean cyst nematode. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the plant or part thereof is reduced by at least about 30%. In yet another embodiment, the resistance to infection by the soybean cyst nematode is measured by the number of cysts on soybean roots. In another embodiment, the number of cysts on the roots is reduced by at least about 52%.

In anther embodiment, the invention encompasses a method of enhancing resistance of a plant, or part thereof, to infection by a nematode pest, comprising introducing into the plant, or part thereof, a nucleic acid comprising a siRNA that suppresses the expression of a nematode gene thereby reducing the ability of the nematode to infect the plant, or part thereof, wherein the plant, or part thereof, additionally has a reduced level of expression of an ethylene response gene compared to a plant, or part thereof, of the same species without the siRNA, whereby the plant or part thereof comprising the siRNA has a greater resistance to infection by the nematode than would be expected from the suppression of the nematode gene or the suppression of the ethylene response gene alone. In another embodiment, the plant or part thereof is a soybean plant. In another embodiment, the ethylene response gene is an ETR1 gene. In another embodiment, the ETR1 gene comprises SEQ ID NO: 52. In another embodiment, the nematode pest is soybean cyst nematode. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the plant or part thereof is reduced by at least about 30%. In yet another embodiment, the greater resistance to infection by the soybean cyst nematode is measured by the number of cysts on soybean roots. In another embodiment, the number of cysts on the roots is reduced by at least about 52%.

In still another embodiment, the invention encompasses a method of reducing cyst development on soybean roots susceptible to soybean cyst nematode infection, comprising introducing into cells of a soybean plant or part thereof a nucleic acid molecule comprising a siRNA that when contacted with the soybean cyst nematode causes the soybean cyst nematode to produce a reduced number of cysts on the soybean roots and wherein the soybean plant or part thereof has a reduced level of an ETR1 gene, whereby cyst development on soybean roots is reduced to a greater degree than would be expected from the siRNA contacting the soybean cyst nematode or the reduced expression level of the ETR1 gene alone. In another embodiment, the ETR1 gene comprises SEQ ID NO: 52. In still another embodiment, the siRNA is selected from the group consisting of SEQ ID NO: 3 (siRNA0097), SEQ ID NO: 4 (siRNA0145), SEQ ID NO: 55 (siRNA0097*) and SEQ ID NO: 56 (siRNA0145*). In still another embodiment, the level of expression of the ETR1 gene in the plant or part thereof is reduced by at least about 30%. In another embodiment, the number of cysts on the roots is reduced by at least about 52%.

EXAMPLES

The foregoing description of the aspects, including preferred aspects, of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

Example 1

Soybean Cyst Nematode siRNA Library Design and Construction

A small interfering RNA library was prepared having a partially randomized seed sequence to target mRNAs of a pest or pathogen. The soybean cyst nematode (SCN) was chosen as a target pest for testing this siRNA library.

A 21-nucleotide small interfering RNA library was designed with a randomized seed sequence located at positions 2-8 from the 5'-end, and positions 1, 9-21 were fixed. Since the small RNA was designed to target nematode genes, the non-seed sequence was based on *Caenorhabditis elegans* microRNAs. Bioinformatic analyses of the predicted and known *C. elegans* miRNAs revealed conserved nucleotides at each position of the non-seed region of miRNAs (i.e., positions 1 and 11-19). These nucleotides were selected for the non-seed sequence for the siRNA library. Uridine residues were chosen for positions 20 and 21 in order to increase the stability of the molecule for in vitro screening. The model non-seed sequence generated from the consensus *C. elegans* miRNA is 5'-UNNNNNNNU-GUUGAUCUGGUU-3', (SEQ ID NO: 47) where N indicates a random nucleotide (i.e., either A, C, G, or U) in the seed sequence. A siRNA library of this exemplary sequence consists of $4^7$ (i.e., 4×4×4×4×4×4×4) different RNA molecules, or 16,384 possible sequences.

In order to reduce the complexity of an RNA library (i.e., the number of sequences contained in the library), a subset of sequences were excluded from the library. In particular, the complexity of the siRNA library was reduced by computationally excluding nucleotides that occurred at a particular position in *C. elegans* miRNA seed sequences at lower frequencies. In this example, the frequency threshold was chosen to be 20%. Accordingly, any nucleotide that was determined to occur less than 20% at a particular position in a *C. elegans* seed sequence using bioinformatic analyses was excluded at that particular position. Nucleotides that occurred with a frequency of 20% or greater in *C. elegans* seed sequences were included in the library. Table 7 shows the nucleotides that are frequently observed at each position.

TABLE 7

Nucleotides present in greater than 20% of *C. elegans* miRNA seed sequences

| | Position in miRNA seed sequence | | | | | | |
|---|---|---|---|---|---|---|---|
| | 2 | 3 | 4 | 5 | 6 | 7 | 8 |
| Nucleotide 1 | A | A | C | A | G | A | A |
| Nucleotide 2 | G | G | G | G | U | C | G |
| Nucleotide 3 | — | U | — | U | — | G | U |
| Number of Nucleotides | 2 | 3 | 2 | 3 | 2 | 3 | 3 |
| Motif Seed Sequence | R | D | S | D | K | V | D |

The reduced combination of nucleotides at the 7-positions within the seed sequence was equal to: 2×3×2×3×2×3×3, or 648 possible sequences, which was a 25-fold reduction in complexity.

In addition, RNA sequences were excluded from the library if the resulting small RNA sequence contained homonulceotide quadruplets, such as AAAA. Further, small RNA sequences having a GC-content in positions 1-9 (i.e., position 1 and the seed sequence) greater than the GC-content of positions 11-19 were also excluded. After these two additional parameters were considered, the number of siRNA sequences in the library was reduced to 563 sequences. The siRNA consensus motif is 5'-URDSDKV-DUGUUGAUCUGGUU-3' (SEQ ID NO: 48).

The 563 siRNAs were synthesized as duplexes using standard automated synthesis. In order to enhance the stability, the 3'-residues may be stabilized against nucleolytic degradation, e.g., they consist of purine nucleotides. Alternatively, substitution of pyrimidine nucleotides by modified analogues, e.g., substitution of uridine by 2'-deoxythymidine is tolerated and does not affect the efficiency of RNA interference. siRNAs were synthesized with a dTdT dinucleotide at the 3'-end as an overhang to increase stability and prevent nucleolytic degradation.

Example 2

In vitro Screening

Second stage juveniles (J2s) of soybean cyst nematodes were surface-sterilized in 0.01% $HgCl_2$ and then rinsed in sterile water 3-times before being resuspended in NGM medium (1.7% bacto-agar, 0.25% peptone, 0.3% NaCl, 1 mM $MgSO_4$, 1 mM $CaCl_2$, 25 mM $KH_2PO_4$, pH 6.0) containing 50 mM octopamine and a single siRNA duplex at a concentration of 0.5 mg/mL (ca. 0.4 mM RNA duplex).

A 100 μL aliquot of the soaking solution containing 500 J2s was dispensed into a single well on a 48-well plate, and incubated at 26° C. for 5 days. The J2s were observed daily. A siRNA duplex targeting the *H. glycines* hg-rps23 gene was used as a positive control. As a negative control, soaking solution without siRNA duplex was used.

After 5 days of incubation, the J2s were observed for their activity compared to the controls and then inoculated onto the roots of 4-day old soybean seedlings grown in germination pouches containing water-soaked paper towels. The infected seedlings were cultured in a growth chamber at 26° C. with 16 hour per day lighting for a month.

The number of cysts formed on each plant were counted and compared to the controls. The results indicated that 15 of the 563 duplexes tested reduced the number of SCN cysts on the root to less than 40% of the controls. The sequences of the siRNAs that reduced the SCN cysts are listed in Table 8. The si-rps23-1 siRNA was used as a postitive control because this RNA has been shown to reduce SCN cysts. See PCT Application PCT/US11/064082.

TABLE 8 siRNA sequences reducing the incidence of SCN cysts on soybean seedling roots

| siRNA ID | siRNA Sequence (5'→3') | SEQ ID NO: |
|---|---|---|
| siRNA0043 | UAACUUAUUGUUGAUCUGGUU | 1 |
| siRNA0046 | UAACUUCUUGUUGAUCUGGUU | 2 |
| siRNA0097 | UAAGUUCAUGUUGAUCUGGUU | 3 |
| siRNA0145 | UAGCUUGAUGUUGAUCUGGUU | 4 |
| siRNA0192 | UAGGUUGGUGUUGAUCUGGUU | 5 |
| siRNA0243 | UAUCUUCGUGUUGAUCUGGUU | 6 |
| siRNA0309 | UGACAGGAUGUUGAUCUGGUU | 7 |
| siRNA0382 | UGAGGUCAUGUUGAUCUGGUU | 8 |
| siRNA0423 | UGGUAUGGUGUUGAUCUGGUU | 9 |
| siRNA0458 | UGGGAUCUUGUUGAUCUGGUU | 10 |
| siRNA0483 | UGUCAGAUUGUUGAUCUGGUU | 11 |
| siRNA0514 | UGUCGUGAUGUUGAUCUGGUU | 12 |

TABLE 8-continued siRNA sequences reducing the incidence of SCN cysts on soybean seedling roots

| siRNA ID | siRNA Sequence (5'→3') | SEQ ID NO: |
|---|---|---|
| siRNA0531 | UGUCUUCGUGUUGAUCUGGUU | 13 |
| siRNA0569 | UGUGUGAUUGUUGAUCUGGUU | 14 |
| si-rps23-1 | UUCUCGGAAAUUGCGCUUCUU | 15 |

Example 3

Construction of Target-Specific amiRNAs

The 15 siRNA molecules that reduced the number of SCN cysts on soybean roots were assembled into artificial micro-RNA constructs. Soybean microRNA precursor, gma-MIR164, was used as the backbone of the amiRNA. The miR164/miR164* sequence on this precursor was replaced by siRNA/siRNA* sequence, while the mismatch positions on the miR164/miR164* duplex were maintained in the artificial siRNA/siRNA* sequence by making mutations on the siRNA* passenger strand.

The design of the artificial microRNA (amiRNA) for expression of anti-SCN siRNA in host plant cell follows the literature of Schwab et al., where amiRNAs were designed to target individual genes or groups of endogenous genes in a plant cell. See Schwab et al. (2006) Plant Cell 18, 1121-1133; Alvarez et al. (2006) *Plant Cell* 18, 1134-1151. The soybean miRNA precursor gma-MIR164 was chosen for the backbone of the amiRNAs. Details regarding the assembly of the target-specific artificial microRNA are described in U.S. Provisional Application 61/421,275 filed Dec. 9, 2010, which is incorporated by reference herein in its entirety. The aMIR164-rps23-1 amiRNA was used as a positive control as in the siRNA experiments.

TABLE 9

Target-specific amiRNA sequences

| siRNA ID | amiRNA Sequence (5'→3') | SEQ ID NO: |
|---|---|---|
| amiRNA0043 | AGCTCCTTGTTAACTTATTGTTGATCTGGCAAGTCTCTTGGATC TCAAATGCCACTGAACCCTTTGCCAGATCAAGTATAAGTTACAA CACGGGTTT | 16 |
| amiRNA0046 | AGCTCCTTGTTAACTTCTTGTTGATCTGGCAAGTCTCTTGGATC TCAAATGCCACTGAACCCTTTGCCAGATCAAGTAGAAGTTACAA CACGGGTTT | 17 |
| amiRNA0097 | AGCTCCTTGTTAAGTTCATGTTGATCTGGCAAGTCTCTTGGATC TCAAATGCCACTGAACCCTTTGCCAGATCAAGTTGAACTTACAA CACGGGTTT | 18 |

TABLE 9-continued Target-specific amiRNA sequences

| siRNA ID | amiRNA Sequence (5'→3') | SEQ ID NO: |
|---|---|---|
| amiRNA0145 | AGCTCCTTGTTAGCTTGATGTTGATCTGGCAAGTCTCTTGGATCTCAAATGCCACTGAACCCTTTGCCAGATCAAGTTCAAGCTACAACACGGGTTT | 19 |
| amiRNA0192 | AGCTCCTTGTTAGGTTGGTGTTGATCTGGCAAGTCTCTTGGATCTCAAATGCCACTGAACCCTTTGCCAGATCAAGTCCAACCTACAACACGGGTTT | 20 |
| amiRNA0243 | AGCTCCTTGTTATCTTCGTGTTGATCTGGCAAGTCTCTTGGATCTCAAATGCCACTGAACCCTTTGCCAGATCAAGTCGAAGATACAACACGGGTTT | 21 |
| amiRNA0309 | AGCTCCTTGTTGACAGGATGTTGATCTGGCAAGTCTCTTGGATCTCAAATGCCACTGAACCCTTTGCCAGATCAAGTTCCTGTCACAACACGGGTTT | 22 |
| amiRNA0382 | AGCTCCTTGTTGAGGTCATGTTGATCTGGCAAGTCTCTTGGATCTCAAATGCCACTGAACCCTTTGCCAGATCAAGTTGACCTCACAACACGGGTTT | 23 |
| amiRNA0423 | AGCTCCTTGTTGGTATGGTGTTGATCTGGCAAGTCTCTTGGATCTCAAATGCCACTGAACCCTTTGCCAGATCAAGTCCATACCACAACACGGGTTT | 24 |
| amiRNA0458 | AGCTCCTTGTTGGGATCTTGTTGATCTGGCAAGTCTCTTGGATCTCAAATGCCACTGAACCCTTTGCCAGATCAACAAGATCCCACAACACGGGTTT | 25 |
| amiRNA0483 | AGCTCCTTGTTGTCAGATTGTTGATCTGGCAAGTCTCTTGGATCTCAAATGCCACTGAACCCTTTGCCAGATCAAGTATCTGACACAACACGGGTTT | 26 |
| amiRNA0514 | AGCTCCTTGTTGTCGTGATGTTGATCTGGCAAGTCTCTTGGATCTCAAATGCCACTGAACCCTTTGCCAGATCAAGTTCACGACACAACACGGGTTT | 27 |
| amiRNA0531 | AGCTCCTTGTTGTCTTCGTGTTGATCTGGCAAGTCTCTTGGATCTCAAATGCCACTGAACCCTTTGCCAGATCAAGTCGAAGACACAACACGGGTTT | 28 |
| amiRNA0569 | AGCTCCTTGTTGTGTGATTGTTGATCTGGCAAGTCTCTTGGATCTCAAATGCCACTGAACCCTTTGCCAGATCAACAATCACACACAACACGGGTTT | 29 |
| aMIR164-rps23-1 | AGCTCCTTGTTTCTCGGAAATTGCGCTTCCAAGTCTCTTGGATCTCAAATGCCACTGAACCCTTTGGAAGCGCAAAATCCGAGAACAACACGGGTTT | 30 |

Example 4

In vivo Transgenic Root-SCN Assays

Expression vectors containing target-specific artificial miRNAs were transformed into soybean roots to test their ability to reduce SCN cysts as transgenes. Soybean NAs such as amiRNA0046, amiRNA0569, amiRNA0458, and amiRNA0531 did not significantly reduce the number of SCN cysts compared to the controls, the results do not indicate that these few amiRNAs are ineffective at targeting SCN RNAs. For example, an improved expression strategy that results in a higher level of expression of the siRNA might increase the efficacy of these siRNAs. The assay results for amiRNAs reducing cyst formation in soybean hairy roots are listed in the following tables.

TABLE 10 amiRNA Vector Sequences

| amiRNA ID | Vector ID | SEQ ID NO |
|---|---|---|
| amiRNA0043 | pKS49 | 31 |
| amiRNA0046 | pKS50 | 32 |
| amiRNA0097 | pKS100 | 33 |
| amiRNA0145 | pKS101 | 34 |
| amiRNA0192 | pKS102 | 35 |
| amiRNA0243 | pKS105 | 36 |
| amiRNA0309 | pKS106 | 37 |
| amiRNA0382 | pKS107 | 38 |
| amiRNA0423 | pKS62 | 39 |
| amiRNA0458 | pKS52 | 40 |
| amiRNA0483 | pKS108 | 41 |
| amiRNA0514 | pKS109 | 42 |
| amiRNA0531 | pKS53 | 43 |
| amiRNA0569 | pKS51 | 44 |
| aMIR164-rps23-1 | pKS104 | 45 |
| Vector Control | Empty 15312 | 46 |

TABLE 11

In vivo transgenic root-SCN assay

| Plasmid ID | Gene of Interest | Avg. Cysts | n | Standard error |
|---|---|---|---|---|
| Empty Vector (SEQ ID NO: 46) | None (Negative Control) | 17.7 | 3 | 3.8 |
| pKS104 (SEQ ID NO: 45) | aMIR164-rps23-1 (Positive Control) | 10.4 | 5 | 1.1 |

TABLE 12

In vivo transgenic root-SCN assay

| Plasmid ID | Gene of Interest | Avg. Cysts | n | Standard error |
|---|---|---|---|---|
| Empty Vector (SEQ ID NO: 46) | None (Negative Control) | 34.1 | 7 | 3.2 |
| pKS100 (SEQ ID NO: 33) | siRNA0097 | 11.1 | 11 | 1.2 |
| pKS101 (SEQ ID NO: 34) | siRNA0145 | 16.3 | 16 | 1.8 |
| pKS49 (SEQ ID NO: 31) | siRNA0043 | 21.9 | 8 | 3.3 |
| pKS50 (SEQ ID NO: 32) | siRNA0046 | 32.2 | 5 | 4.4 |

TABLE 13

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 16.5 | 10 | 2.1 |
| pKS105 (SEQ ID NO: 36) | siRNA0243 | 11.6 | 8 | 2.1 |

TABLE 14

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 33.0 | 4 | 4.8 |
| pKS62 (SEQ ID NO: 39) | siRNA0423 | 29.0 | 8 | 4.7 |
| pKS51 (SEQ ID NO: 44) | siRNA0569 | 32.2 | 4 | 5.2 |

TABLE 15

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 25.0 | 5 | 5.4 |
| pKS52 (SEQ ID NO: 40) | siRNA0458 | 26.0 | 6 | 4.0 |
| pKS53 (SEQ ID NO: 43) | siRNA0531 | 21.7 | 3 | 3.5 |

TABLE 16

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 35.6 | 11 | 3.0 |
| pKS108 (SEQ ID NO: 41) | siRNA0483 | 17.5 | 13 | 2.0 |
| pKS109 (SEQ ID NO: 42) | siRNA0514 | 19.5 | 22 | 1.2 |

TABLE 17

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 78.1 | 10 | 6.7 |
| pKS106 (SEQ ID NO: 37) | siRNA0309 | 51.7 | 16 | 7.4 |

TABLE 18

In vivo transgenic root-SCN assay

| Plasmid ID | Gene of interest | Avg. Cysts | n | Standard error |
|---|---|---|---|---|
| Empty Vector (SEQ ID NO: 46) | None (Negative Control) | 154.9 | 7 | 11.0 |
| pKS107 (SEQ ID NO: 38) | siRNA0382 | 106.4 | 14 | 8.7 |

Example 4.1

Dual Activity of amiRNAs

Two of the amiRNAs tested above, amiRNA0097 comprising siRNA0097, and amiRNA0145 comprising siRNA0145 (See Table 12) caused an increase in root growth and proliferation in the transgenic soybean cells in which they were expressed compared to soybean cells expressing the other siRNAs or an empty-vector (negative control), suggesting that siRNA0097 and siRNA01435 are modulating expression of one or more soybean genes in addition to targeting a nematode gene. Although neither strand of any of the siRNAs tested above produced any full-length complementation to any soybean genes when screened in silico against a soybean genome, surprisingly both strands of siRNA0097 and siRNA0145 have significant complementarity to two soybean orthologs of an *Arabidopsis* ethylene response 1 gene (ETR1). Interestingly, ethylene receptor or response genes like ETR1-type genes have been implicated in root proliferation and an increased tolerance to some nematodes in certain plants. In one study, for example, chemically mutagenized soybean plants that were ethylene-insensitive (i.e. mutated ethylene response gene(s)) prodcued about 41% fewer females (cysyts) than wild-type non-mutagenized soybean plants (Bent et al. 2006. Crop Science 46:893-901). To date, it does not appear that any studies have correlated RNA knock-out of an ethylene response gene with nematode resistance.

Results of the siRNA strand complementation analysis are shown in Table 19. Complementation was highest for both strands of amiRNA0097, particularly in the seed sequence (underlined sequence). The amiRNA0097 plus strand has 7 out of 7 matches in the seed sequence to the sopybean ETR1 gene and the amiRNA0097* strand (star strand) has 6 out of 7 matches in the seed sequence. amiRNA0145 plus strand has 5 out of 7 matches and amiRNA0145* star strand has 6 out of 7 matches. Both of these treatments, amiRNA0097 and amiRNA0145 had enhanced reduction of nematode infection (measured by cyst formation) compared to amiRNA0043 that had only 4/7 mtaches to ETR1 and amiRNA0046 that had 5/7 matches to ETR1 but which had a large gap between nucleotide 7 and 8.

TABLE 19

Complementation of siRNAs with Soybean
ETR1-type Genes
Complementation alignment of siRNAs with
ETR1 mRNA

```
gma-ETR1    5'AGACCGAUCAA-AUGAAUUUA3' SEQ ID NO: 53
              | | |||||||  ||||||||||
siRNA0097   3'ACGGUCUAGUUGUACUUGAAU5' SEQ ID NO:  3 gma-ETR1    5'AGACCGAUCAA-AUGAAUUUA3' SEQ ID NO: 53
              | | |||||||  || || |||
siRNA0145   3'ACGGUCUAGUUGUAGUUCGAU5' SEQ ID NO:  4 gma-ETR1      UGCGAGUACAGGUAAAAGAUU   SEQ ID NO: 57
              ||||||   |||    ||| |
siRNA0043*    ACGGUCUAGUUGUUAUUCAAU   SEQ ID NO: 59 gma-ETR1      GGCCUGAGGUUUCAACAAGAAGUUA SEQ ID NO: 58
              ||| ||     | |   ||||||||
siRNA0046*    ACGGUCUAGUUGUU----CUUCAAU SEQ ID NO: 60 gma-ETR1    5'UGGAAG-UGGACUUGGCCUGG3' SEQ ID NO: 54
              || ||| | |||||||| ||||
siRNA0097*  3'ACAUUCAAGUUGAACUAGACC5' SEQ ID NO: 55 gma-ETR1    5'UGGAAG-UGGACUUGGCCUGG3' SEQ ID NO: 54
              || |   ||||||||| ||||
siRNA0145*  3'ACAUCGAACUUGAACUAGACC5' SEQ ID NO: 56
```

In recent years, it has been discovered that the miRNA* strand of some of the miRNA/miRNA* duplexes can also be loaded into the RISC and interfere with the expression of its complementary mRNA target (Kulcheski et al, 2011. BMC Genomics 12:307). Therefore it is possible that the miRNA* can be loaded into the RNA-induced silencing complex (RISC) and used to silence the target mRNA. In addition to the plus strand, both the amiRNA0097* and the amiRNA0145* star strands can form complementary binding with the gma-ETR1 mRNA (see Table 19 above), therefore it is possible that both strands of the amiRNA0097 and amiRNA0145 can down-regulate the expression of the gma-ETR1 gene.

Surprisingly, the results in Table 12 above show that soybean roots expressing the amiRNA0097 and amiRNA0145 had significantly enhanced resistance to cyst formation compared to the soybean roots expressing amiRNA0043, amiRNA0046 and the negative control (evident by the non-overlap of their standard errors). The enhanced reduction in the number of cysts is likely due to siRNA0097 and siRNA0145 having both a direct effect on nematodes, i.e. siRNA0097 and siRNA0145 target a nematode gene and suppress or silence that gene thus reducing the number of cysts the nematode is capable of producing (See Example 2 above), and an indirect effect on nematodes, i.e. siRNA0097 and siRNA0145 also suppress expression of an endogenous plant gene (ETR1) by virtue of their having complementarity to ETR1 mRNA, which in turn confers some resistance to nematode infectivity (production of cysts). The enhanced effect on cyst production then is likely due to the synergistic suppression of a nematode gene and an endogenous plant gene. It is believed that this is the first report of such "direct" and "indirect" effect on nematode infectivity of a single siRNA molecule.

Example 5

Transformation of Plants with siRNAs

The artificial pre-miRNAs, gma-aMIR164-amir0097 and gma-aMIR164-amir0145, comprising the amiRNA0097/amiRNA0097* duplex and the amiRNA0145/amiRNA0145* duplex, respectively (See Example 3), were each cloned into separate binary vectors and named 20111 and 20109, respectively. The 20111 and the 20109 vectors were transformed into soybean.

Transformation of soybean to produce transgenic soybean plants was accomplished using immature seed targets of variety Williams 82 via *A. tumefaciens*-mediated transformation. Explant materials and media recipes were essentially as described in Hwang et al. (PCT International Publication No. WO 08/112,044) and Que et al. (PCT International Publication No. WO 08/112,267), with some variations as noted below. Using this method, genetic elements within the left and right border regions of the transformation plasmid are efficiently transferred and integrated into the genome of the plant cell, while genetic elements outside these border regions are generally not transferred.

Maturing soybean pods were harvested from greenhouse-grown plants, sterilized with diluted bleach solution, and rinsed with sterile water. Immature seeds were then excised from seedpods and rinsed briefly with sterile water. Explants were prepared from sterilized immature seeds essentially as described in Hwang et al. (PCT International Publication No. WO 08/112,044) and infected with *A. tumefaciens* strain EHA101 harboring either vector 20111 or 20109 and allowed to incubate for an additional 30 to 240 minutes. Excess *A. tumefaciens* suspension was removed by aspiration and the explants were moved to plates containing a non-selective co-culture medium. The explants were co-cultured with the remaining *A. tumefaciens* at about 23° C. for about 4 days in the dark and then transferred to recovery and regeneration medium supplemented with an antibiotics mixture consisting of ticarcillin (75 mg/L), cefotaxime (75 mg/L) and vancomycin (75 mg/L) where they are incubated in the dark for seven days.

The explants were then transferred to regeneration medium containing hygromycin B (3 to 6 mg/L) and a mixture of antibiotics consisting of ticarcillin (75 mg/L), cefotaxime (75 mg/L) and vancomycin (75 mg/L) to inhibit and kill A. tumefaciens. Shoot elongation and regeneration was carried out in elongation media containing 2-4 mg/L of hygromycin B. The hygromycin phosphor-transferase (HPT) gene was used as a selectable marker during the transformation process. Regenerated plantlets were transplanted in soil essentially as described (PCT International Publication No. WO 08/112,267) and tested for the presence of HPT and CMP promoter sequences using TaqMan PCR analyses (Ingham et al. (2001) Biotech 31, 132-140). This screen allows for the selection of transgenic events that carry the T-DNA and are free of vector DNA. Plants positive for HPT gene and CMP sequences and negative for the spectinomycin (spec) gene were transferred to the greenhouse for analysis of miRNA expression and seed setting.

When the roots were about 2-3 inches, plants were then transplanted into 1-gallon pots using Fafard #3 soil and 30 grams of incorporated Osmocote Plus 15-9-12 and maintained under standard greenhouse growing conditions for soybean plants.

The leaves of the transgenic soybean events of 20111 and 21019 were sampled to quantitatively determine the expression level of the ETR1 gene using an art recognized quantitative real time polymerase chain reaction (qRT-PCR) (See for example, VanGuilder et al. (2008). Biotechniques 44 (5): 619-626; Udvardi et al. (2008). Plant Cell 20 (7): 1736-1737). The relative amount of ETR1 gene expression in the transgenic events and in wild-type control soybean plants was determined by comparing to the ETR1 level to a different endogenous soybean gene.

Results of the qRT-PCR assays showed that ETR1 expression in the transgenic soybean roots producing siRNA0097 and siRNA0145 was significantly lower compared to the wild-type control soybean roots. The relative amount ETR1 expression level was about 34±5 (N=9, where N is the number of plants) in wild-type soybean roots and about 23±4 (N=14, where N is the number of events) and about 12±1 (N=21, where N is number of events) in the siRNA0145 and siRNA0097 transgenic soybean roots, respectively. Therefore, the siRNA0145 and siRNA0097 transgenic soybean roots had a 33% and a 66% reduction in ETR1 gene expression, respectively, compared to the wild-type soybean roots.

These results correlate with the other results obtained for siRNA0097 and siRNA0145 described above. siRNA0097 and siRNA0145 were designed to target a nematode gene and upon contact of soybean cyst nematode with either siRNA0097 or siRNA0145 the nematode's ability to produce cysts on soybean roots was reduced (See Example 2). Soybean roots expressing siRNA0097 or siRNA0145 had significantly reduced number of cysts when infected with SCN (Example 4) with siRNA0097 having a significantly lower number than siRNA0145. Interestingly, siRNA0097 had the highest complementarity in both strands to a soybean ETR1 gene and soybean roots expressing siRNA0097 had the lowest level of ETR1 gene expression. Bent et al. 2006 (supra) reported about a 41% reduction in cysts in ethylene-insensitive soybean plants with a chemically mutated ETR1 gene. Here, soybean roots expressing an siRNA that directly targets an SCN gene and modulates the expression of an endogenous ETR1 gene had as high as a 68% reduction in the number of cysts, a level that is higher than expected of either the modulation of the nematode gene or the modulation of the ETR1 gene alone.

Although there have been reports of "off-type" effects of dsRNA designed to target a plant pest gene, to date, it appears that no studies have reported the suppression of an endogenous plant gene by an siRNA designed to target a gene of a nematode plant pest whereby the suppression of the plant gene also confers resistance to the same nematode pest. Thus, it is surprising that an siRNA designed to target a nematode gene suppresses the expression of both a nematode gene (direct effect on the nematode) and an endogenous plant gene that in turn interferes with nematode infectivity (indirect effect on nematode). It is further surprising that the modulation of an endogenous plant gene by a siRNA designed to target a nematode gene may be due to both the plus and star strands of the siRNA.

Plants transformed with the vectors are inoculated with J2-stage soybean cyst nematodes (SCN J2). Briefly, 1-week old seedlings of the transgenic T1 generation soybean grown in germination pouches are inoculated with SCN J2 suspension at the level of 750 J2 per plant. One month after nematode inoculation, the number of cysts is determined for the transgenic plants comprising amiRNA expression cassettes and for the null segregants from the same T0 parents.

Example 6

Corn Rootworm siRNA Library Design and Construction

A small interfering RNA library was prepared having a partially randomized seed sequence to indiscriminately target mRNAs of an insect pest. The corn rootworm (CRW) was chosen as a target pest for testing this siRNA library.

A 21-nucleotide small interfering RNA library was designed with a randomized seed sequence located at positions 2-8 from the 5'-end, and positions 1, 9-21 were fixed. Since the small RNA was designed to target insect pest genes, the non-seed sequence was based on microRNAs from a related coleopteran pest insect, Tribolium castaneum. Bioinformatic analyses of the predicted and known T. castaneum miRNAs revealed conserved nucleotides at each position of the non-seed region of miRNAs (i.e., positions 1 and 11-19). These nucleotides were selected for the non-seed sequence for the siRNA library. Uridine residues were chosen for positions 20 and 21 in order to increase the stability of the molecule for in vitro screening. The model non-seed sequence generated from the consensus T. castaneum miRNA is 5'-UNNNNNNNUAUCCGGAUUCUU-3', (SEQ ID NO: 50) where N indicates a random nucleotide (i.e., either A, C, G, or U) in the seed sequence. A siRNA library of this exemplary sequence consists of $4^7$ (i.e., 4×4×4×4×4×4×4) different RNA molecules, or 16,384 possible sequences.

In order to reduce the complexity of an RNA library (i.e., the number of sequences contained in the library), a subset of sequences were excluded from the library. In particular, the complexity of the siRNA library was reduced by computationally excluding nucleotides that occurred at a particular position in T. castaneum miRNA seed sequences at lower frequencies. In this example, the frequency threshold was chosen to be 20%. Accordingly, any nucleotide that was determined to occur less than 20% at a particular position in a T. castaneum seed sequence using bioinformatic analyses was excluded at that particular position. Nucleotides that occurred with a frequency of 20% or greater in *T. castaneum* seed sequences were included in the library. Table 20 shows the nucleotides that are frequently observed at each position.

TABLE 20

Nucleotides present in greater than 20% of *T. castaneum* miRNA seed sequences

| | Position in miRNA seed sequence | | | | | | |
|---|---|---|---|---|---|---|---|
| | 2 | 3 | 4 | 5 | 6 | 7 | 8 |
| Nucleotide 1 | A | A | A | A | A | A | A |
| Nucleotide 2 | C | — | C | — | — | C | C |
| Nucleotide 3 | G | G | G | — | G | G | G |
| Nucleotide 4 | U | U | U | U | U | U | U |
| Number of Nucleotides | 4 | 3 | 4 | 2 | 3 | 4 | 4 |
| Motif Seed Sequence | N | D | N | W | D | N | N |

The reduced combination of nucleotides at the 7-positions within the seed sequence was equal to: 4×3×4×2×3×4×4, or 4608 possible sequences, which was a 3.6-fold reduction in complexity.

In addition, small RNA sequences were excluded from the in silico library if the seed sequence contained homonucleotide quadruplets, such as AAAA. Further, sequences having a GC-content in positions 1-9 (i.e., position 1 and the seed sequence and position 9) greater than the GC-content of positions 11-19 were also excluded. After these two additional parameters were considered, the number of siRNA sequences in the in silico library was reduced to 3899-sequences. The siRNA consensus motif is 5'-UNDNWDN-NUAUCCGGAUUCUU-3' (SEQ ID NO: 51).

The 3899 siRNAs are synthesized as duplexes using standard automated synthesis. In order to enhance the stability, the 3'-residues may be stabilized against nucleolytic degradation, e.g., they consist of purine nucleotides. Alternatively, substitution of pyrimidine nucleotides by modified analogues, e.g., substitution of uridine by 2'-deoxythymidine is tolerated and does not affect the efficiency of RNA interference. siRNAs can also be synthesized with a dTdT dinucleotide at the 3'-end as an overhang to increase stability and prevent nucleolytic degradation.

What is claimed is:

1. A siRNA molecule comprising the nucleotide sequence of any one of SEQ ID NOs: 1-14 and wherein the siRNA molecule reduces the number of soybean cyst nematode cysts on soybean roots.

2. An artificial RNA molecule comprising the siRNA molecule of claim 1, wherein the artificial RNA molecule is encoded by the nucleotide sequence of any one of SEQ ID NOs: 16-29.

3. A vector comprising the siRNA molecule of claim 1, wherein the vector is encoded by the nucleotide sequence of any one of SEQ ID NOs: 31-44.

* * * * *